United States Patent
Rudd et al.

(10) Patent No.: US 11,655,216 B2
(45) Date of Patent: May 23, 2023

(54) ARYL AND HETEROARYL ETHER DERIVATIVES AS LIVER X RECEPTOR BETA AGONISTS, COMPOSITIONS, AND THEIR USE

(71) Applicants: Merck Sharp & Dohme Corp., Rahway, NJ (US); Michael T. Rudd, Collegeville, PA (US); Zhaoyang Meng, Ambler, PA (US); Jenny Wai, Harleysville, PA (US); David Jonathan Bennett, Winchester, MA (US); Edward J. Brnardic, Lansdale, PA (US); Nigel J. Liverton, Harleysville, PA (US); Shawn J. Stachel, Perkasie, PA (US); Yongxin Han, Needham, MA (US); Paul Tempest, Taipei (TW); Jiuxiang Zhu, Shanghai (CN); Xuewang Xu, Shanghai (CN); Bin Zhu, Shanghai (CN)

(72) Inventors: Michael T. Rudd, Collegeville, PA (US); Zhaoyang Meng, Ambler, PA (US); Jenny Wai, Harleysville, PA (US); David Jonathan Bennett, Winchester, MA (US); Edward J. Brnardic, Lansdale, PA (US); Nigel J. Liverton, Harleysville, PA (US); Shawn J. Stachel, Perkasie, PA (US); Yongxin Han, Needham, MA (US); Paul Tempest, Taipei (TW); Jiuxiang Zhu, Shanghai (CN); Xuewang Xu, Shanghai (CN); Bin Zhu, Shanghai (CN)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 16/341,595

(22) PCT Filed: Oct. 9, 2017

(86) PCT No.: PCT/US2017/055690
§ 371 (c)(1),
(2) Date: Apr. 12, 2019

(87) PCT Pub. No.: WO2018/071317
PCT Pub. Date: Apr. 19, 2018

(65) Prior Publication Data
US 2020/0247754 A1   Aug. 6, 2020

(30) Foreign Application Priority Data
Oct. 14, 2016 (WO) ............... PCT/CN2016/102096

(51) Int. Cl.
*C07D 221/20* (2006.01)
*C07D 401/12* (2006.01)
(Continued)

(52) U.S. Cl.
CPC .......... *C07D 221/20* (2013.01); *C07D 211/22* (2013.01); *C07D 401/12* (2013.01);
(Continued)

(58) Field of Classification Search
None
See application file for complete search history.

(56) References Cited

U.S. PATENT DOCUMENTS 9,018,200 B2 * 4/2015 Maletic ............... C07D 413/12
546/214

FOREIGN PATENT DOCUMENTS

EP          2065369 A1   6/2009
WO    2007003962 A2   1/2007
(Continued)

OTHER PUBLICATIONS

Stachel, SJ, Identification and in Vivo Evaluation of Liver X Receptor β-Selective Agonists for the Potential Treatment of Alzheimer's Disease, Journal of Medicinal Chemistry, 2016, 3489-3498, vol. 59, No. 7.

(Continued)

*Primary Examiner* — Po-Chih Chen
(74) *Attorney, Agent, or Firm* — Sylvia A. Ayler; Catherine D. Fitch

(57) ABSTRACT

In its many embodiments, the present invention provides certain substituted aryl and heteroaryl ether compounds of the Formula (I): and pharmaceutically acceptable salts thereof, wherein X, $R^1$, $R^2$, $R^3$, L, $R^4$, $L_1$, Q, and $R^5$ are as defined herein. The novel compounds of the invention, and pharmaceutically acceptable compositions comprising a compound thereof, are useful as Liver X-β receptor (LXRβ) agonists, and may be useful for treating or preventing pathologies related thereto. Such pathologies include, but are not limited to, inflammatory diseases and diseases characterized by defects in cholesterol and lipid metabolism, such as Alzheimer's disease.

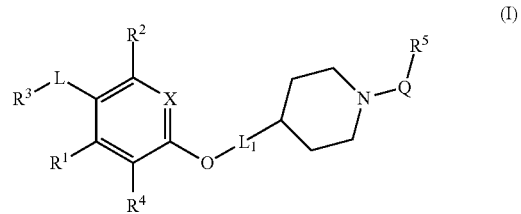

8 Claims, No Drawings

(51) Int. Cl.
    *C07D 417/12*     (2006.01)
    *C07D 405/12*     (2006.01)
    *C07D 211/22*     (2006.01)
    *C07D 401/14*     (2006.01)
    *C07D 417/14*     (2006.01)

(52) U.S. Cl.
    CPC ......... *C07D 401/14* (2013.01); *C07D 405/12* (2013.01); *C07D 417/12* (2013.01); *C07D 417/14* (2013.01)

(56) References Cited

FOREIGN PATENT DOCUMENTS

| WO | 2008101885 | A1 | 8/2008 |
| WO | 2008122787 | A1 | 10/2008 |
| WO | 2010004343 | A1 | 1/2010 |
| WO | 2010004348 | A1 | 1/2010 |
| WO | 2011051282 | A1 | 5/2011 |
| WO | 2011089550 | A1 | 7/2011 |
| WO | 2011151808 | A1 | 12/2011 |
| WO | 2012138845 | A1 | 10/2012 |
| WO | 2013062835 | A1 | 5/2013 |
| WO | WO2013062835 | * | 5/2013 |
| WO | 2017083216 | A1 | 5/2017 |
| WO | 2017083219 | A1 | 5/2017 |
| WO | 2017095758 | A1 | 6/2017 |
| WO | 2018071313 | A1 | 4/2018 |
| WO | 2018071315 | A2 | 4/2018 |

OTHER PUBLICATIONS

Chemical Abstracts Service, Database Accession No. 1204336-55-9 dated Feb. 1, 2010, titled "1-Piperidinecarboxylic acid, 4-[3-[[5-[[[2-hydroxy-1-(hydroxymethyl)ethyl]amino]carbonyl]-6-methyl-2-pyridinyl]oxy]propyl]-,1,1-dimethylethyl ester", 1 page.

International Search Report for PCT/CN2016/102096 dated Jul. 13, 2017, 21 pages.

International Search Report for PCT/US2017/055690 dated Dec. 1, 2017, 10 pages.

Espacenet-CN102105452(A)—Jun. 22, 2011, Substituted Carbinol Compound Having Cyclic Linker, Yuki Yamaguchi, et al., English Translate.

* cited by examiner

ARYL AND HETEROARYL ETHER DERIVATIVES AS LIVER X RECEPTOR BETA AGONISTS, COMPOSITIONS, AND THEIR USE

FIELD OF THE INVENTION

The present invention provides certain aryl and heteroaryl ether compounds of formula (I), and compositions comprising these compounds, as liver X receptor β (LXRβ) agonists, which may be useful for treating or preventing pathologies related thereto. Such pathologies include, but are not limited to, inflammatory diseases and diseases characterized by defects in cholesterol and lipid metabolism, such as Alzheimer's disease.

BACKGROUND OF THE INVENTION

Alzheimer's disease is a common neurodegenerative disease affecting the elderly, resulting in progressive memory impairment, loss of language and visuospatial skills, and behavior deficits. Clinical, genetic, epidemiological and biochemical evidence suggest that dysfunctional cholesterol metabolism is implicated in the pathogenesis of Alzheimer's Disease. Hypercholesterolemia and low levels of high density lipoprotein are well-established risk factors for Alzheimer's Disease. It has been suggested that vascular, genetic and amyloid factors, in combination with diet and lifestyle, contribute to the cause and progression of Alzheimer's Disease. Hooijmans et al, *Eur J Pharmacol* 585 (2008), 176-196.

The liver X receptor (LXR) is a member of the nuclear receptor family of transcription factors, and is a part of the cholesterol regulation pathway. There are two identified isoforms of LXRs. LXRα is found in liver, intestine and in macrophages, while LXRβ is widely expressed in many tissues and is considered a ubiquitous receptor. Typically, the activity of nuclear receptors is controlled by small lipophilic moieties, such as hormones, fatty acids, bile acids, cholesterol precursors and oxysterols. Lala, *Curr Opinions Invest Drugs* 2005, 6:934-943. Cholesterol precursors such as desmosterol and oxysterols are known to bind and activate LXRs.

LXRs have demonstrated a role in the physiological metabolism of lipid and cholesterol, and thus are believed to have an important role in metabolic disorders such as hyperlipidemia and atherosclerosis. Activation of LXRs reduces cholesterol absorption, thereby reducing the ability of the body to take up cholesterol. Consistently, deletion of LXRs in mice leads to impaired cholesterol and bile acid metabolism. See Peet et al, *Cell* 1998, 93(5): 693-704. Activation of LXRs also increase peripheral cholesterol efflux systems, and impact the elimination of cholesterol by regulating cholesterol excretion into bile. See Cao et al, *Drug News Perspect* 20004, 17(1), 35-41.

LXRs also regulate lipid homeostasis in the brain. The connection between metabolic disorders and Alzheimer's Disease suggests that LXRs may have a role in the Alzheimer's disease pathway. Activation of LXRs also inhibit inflammation and pro-inflammatory expression in the body. Zelcer et al, *J Clin Invest* 2006, 116:3 (607-614). Thus, LXRs may serve as targets for the treatment of inflammatory diseases. However, activation of hepatic LXRα is believed to be the underlying cause of liver steatosis and hyperlipidemia associated with dual LXRα/β small agonist molecules developed to date.

LXRs have also been proposed as possible therapeutics to treat a number of cancers e.g. prostate, breast, ovarian, melanoma, pancreas, lung, colon and hematological malignancy (Lin, C-Y and Gustafsson, J-A, (2015) Nature Reviews Cancer 15, 216-224).

LXRβ is the predominant brain isoform. See Song et al, *Ann NY Acad Sci* 195, 761:38-49. LXRβ knockout male mice demonstrated adult-onset motor neuron degeneration. (Andersson et al, *Proc Nat'l Acad Sci USA* 2005, 8; 1902 (1)):3857-3862), and the LXRα and LXRβ double knockout mice develop neurodegenerative changes in brain tissue. (Wang et al, Proc Natl Acad Sci USA. 2002, 99(21):13878-83). Therefore development of selective LXRβ agonists could be a therapeutic approach to neurodegenerative diseases such as AD and avoid the peripheral adverse lipid effects that have been linked to LXRα.

Applicants have now discovered a series of LXRβ selective agonists. Thus, the compounds of the invention, which are selective LXRβ agonists, may be useful in the treatment of Alzheimer's disease, inflammatory diseases, and diseases characterized by defects in cholesterol and lipid metabolism.

SUMMARY OF THE INVENTION

The present invention provides certain aryl and heteroaryl ether compounds, which are collectively or individually referred to herein as "compound(s) of the invention", as described herein. The compounds of the invention are selective agonists of LXRβ, and may be useful for treating or preventing diseases or pathologies related thereto.

In one embodiment, the compounds of the invention have the structural Formula (I):

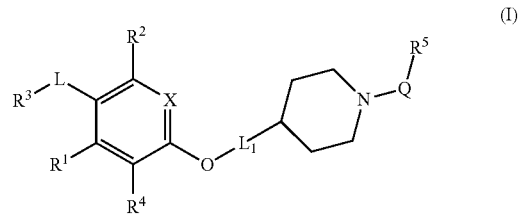

or a pharmaceutically acceptable salt thereof, wherein:
X is CH or N;
$R^1$ is selected from H, methyl, and halogen;
$R^2$ is selected from H, halogen, cyano, cyclopropyl, —$CH_3$, —$CH_2CH_3$, and —$OCH_3$;
$R^4$ is selected from H, halogen, and methyl;
-L- is a divalent moiety selected from —C(O)— and —S(O)$_2$—
$R^3$ is —N($R^{N1}$)($R^{N2}$), wherein:
  $R^{N1}$ is selected from H and —($C_1$-$C_6$)alkyl; and
  $R^{N2}$ is selected from H, cyclopropyl, —OH, halogen, —CN, and —($C_1$-$C_6$)alkyl which is substituted with 1 or 2 groups independently selected from:
    —OH, halogen, —CN,
    optionally substituted phenyl, (wherein said optional substituents on said phenyl are 1 to 3 groups independently selected from OH, CN, —($C_1$-$C_4$)alkyl, —($C_1$-$C_4$)alkoxyl),
    optionally substituted heteroaryl, (wherein said optional substituents on said heteroaryl are 1 to 3 groups independently selected from —($C_1$-$C_6$)alkyl, —($C_1$-$C_4$)alkoxyl, and cyclopropyl), optionally substituted cyclopropyl (wherein said optional substituents on said cyclopropyl are 1 to 3 groups independently selected from —(C₁-C₆)alkyl), and
optionally substituted heterocycloalkyl (wherein said optional substitutents on said heterocycloalkyl are 1 to 3 groups independently selected from halogen, —OH, oxo, CN, and —(C₁-C₆)alkyl,
or, alternatively, $R^{N1}$ and $R^{N2}$ are taken together with the nitrogen atom to which they are shown attached to form a 4-, 5-, or 6-membered fully saturated heterocyclic ring comprising (including the nitrogen atom) 1, 2, or 3 ring heteroatoms selected from N, N-oxide, O, S, and S-oxide,
wherein said heterocyclic ring is unsubstituted or substituted with 1, 2, or 3 substituents independently selected from halogen, —OH, oxo, CN, —(C₁-C₆)alkyl, amino-substituted —(C₁-C₆)alkyl (wherein said amino is 1, 2, or 3 groups independently selected from —NH₂, —N(C₁-C₄alkyl)₂, and —NH(C₁-C₄alkyl)), —O—(C₁-C₆)alkyl, —(C₁-C₆)alkyl-OH, —(C₁-C₆)haloalkyl, —C(O)O—(C₁-C₆)alkyl, cyclopropyl, spirocyclopropyl, —CH₂—NHC(O)O—(C₁-C₆)alkyl, —CH₂—N(CH₃)C(O)O—(C₁-C₆)alkyl, phenyl, benzyl, —NHC(O)-phenyl, heteroaryl, and —(C₁-C₄)alkylheteroaryl, heterocycloalkyl;
-L₁- is a divalent moiety selected from:

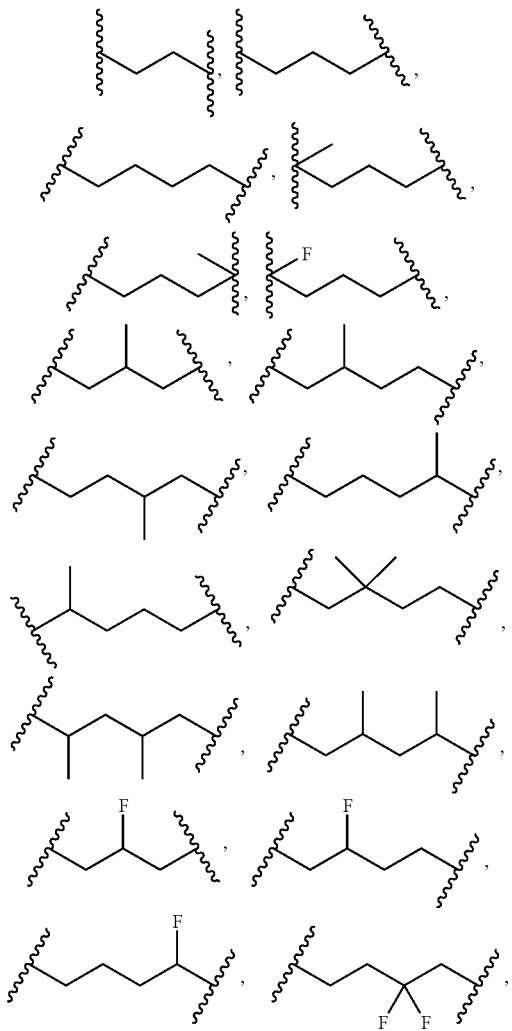

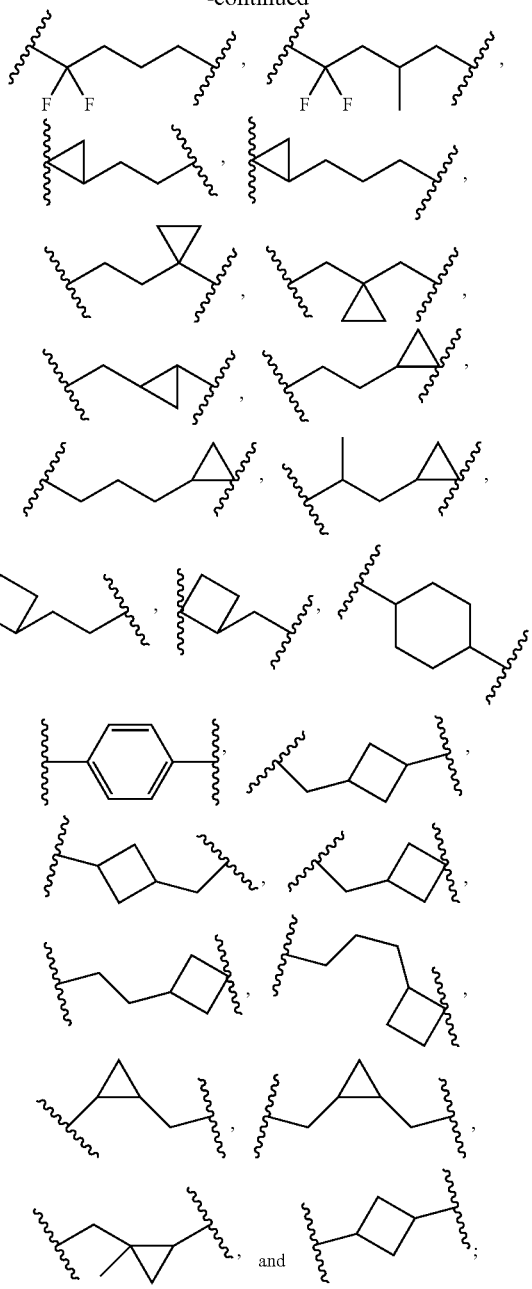

Q is a bond or a divalent moiety selected from —C(O)—, —S(O)₂—, and —C(O)O—; and
$R^5$ is selected from:
—C($R^{5A}$)($R^{5B}$)($R^{5C}$), wherein:
each of $R^{5A}$, $R^{5B}$ and $R^{5C}$ is independently selected from: H, halogen, OH, NH₂, NHCH₃, —(C₁-C₆)alkyl, —(C₁-C₆)haloalkyl, —(C₁-C₆)alkenyl, —(C₁-C₆)alkynyl, —(C₃-C₆)cycloalkyl, —(C₃-C₆)cycloalkyl substituted with —(C₁-C₆)alkyl, —(C₁-C₆)alkenyl, —(C₁-C₆)alkynyl, thiadiazolyl, thienyl, thiazolyl, phenyl, phenyl substituted with from 1 to 3 groups independently selected from halogen, OH, —NH₂, —(C₁-C₆)alkyl, —O—(C₁-C₆)alkyl, cyclopropyl, —O—(C₁-C₆)haloalkyl, —O-cyclopropyl, —C(O)O—(C₁-C₆)alkyl, pyrazolyl, and pyridinyl,

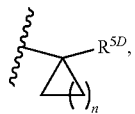

wherein n is an integer from 1 to 4;

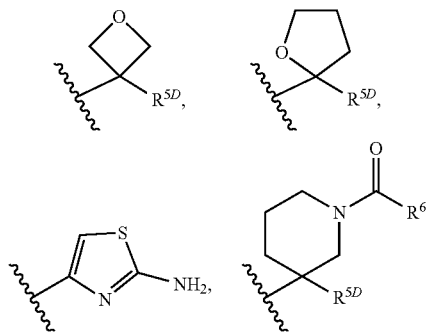

wherein $R^{5D}$ is selected from H, —$(C_1$-$C_6)$alkyl, —$(C_1$-$C_6)$haloalkyl, pyrimidinyl, phenyl, and phenyl which is substituted with from 1 to 3 groups independently selected from OH, halogen, —$(C_1$-$C_6)$alkyl, and —O—$(C_1$-$C_6)$alkyl; and $R^6$ is H or $CH_3$, —O—$(C_1$-$C_6)$alkyl; and phenyl, wherein:

said phenyl is unsubstituted or substituted with 1, 2, or 3 groups independently selected from halogen, CN, —$(C_1$-$C_6)$alkyl, —$(C_1$-$C_6)$haloalkyl, and pyrrolidinyl.

In other embodiments, the invention provides compositions, including pharmaceutical compositions, comprising one or more compounds of the invention (e.g., one compound of the invention) or a pharmaceutically acceptable salt thereof, optionally together with one or more additional therapeutic agents, optionally in an acceptable (e.g., pharmaceutically acceptable) carrier or diluent.

In another embodiment, the invention is directed to methods of treating an inflammatory diseases or a disease characterized by defects in cholesterol or lipid metabolism, in a patient in need thereof by administering to the patient a compound of the invention or a pharmaceutically acceptable salt thereof. Non-limiting examples of such inflammatory diseases and diseases characterized by defects in cholesterol or lipid metabolism are described below.

In another embodiment, the invention provides for the use of a compound of the invention in the manufacture of a medicament for treating an inflammatory disease or a disease characterized by defects in cholesterol or lipid metabolism in a patient in need thereof. Non-limiting examples of such inflammatory diseases and diseases characterized by defects in cholesterol or lipid metabolism are described below.

In another embodiment, the invention is directed to a method of treating cancer in a patient in need thereof comprising administering to the patient a compound of the invention or a pharmaceutically acceptable salt thereof. Such cancers include prostate, breast, ovarian, melanoma, pancreas, lung, colon and hematological malignancy.

In another embodiment, the invention provides for the use of a compound of the invention in the manufacture of a medicament for treating cancer in a patient in need thereof comprising administering to the patient a compound of the invention or a pharmaceutically acceptable salt thereof. Such cancers include prostate, breast, ovarian, melanoma, pancreas, lung, colon and hematological malignancy.

In another embodiment, the invention provides for the use of any of the compounds of the invention for use as a medicament, or in medicine, or in therapy.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I) as described above, and pharmaceutically acceptable salts thereof.

In another embodiment, in Formula (I), X is N.
In another embodiment, in Formula (I), X is CH.

The following alternative embodiments of $R^1$ apply to Formula (I) and also to each of the embodiments described hereinabove.

In another embodiment, in Formula (I), $R^1$ is selected from H, methyl, F, and Cl.

In another embodiment, in Formula (I), $R^1$ is H.

The following alternative embodiments of $R^2$ apply to Formula (I) and also to each of the embodiments and alternative embodiments, and all combinations of embodiments, described hereinabove.

In another embodiment, in Formula (I), $R^2$ is selected from H, Cl, cyano, cyclopropyl, —$CH_3$, and —$OCH_3$.

In another embodiment, in Formula (I), $R^2$ is Cl.
In another embodiment, in Formula (I), $R^2$ is cyano.
In another embodiment, in Formula (I), $R^2$ is cyclopropyl.
In another embodiment, in Formula (I), $R^2$ is $CH_3$.
In another embodiment, in Formula (I), $R^2$ is $OCH_3$.

The following alternative embodiments of $R^4$ apply to Formula (I) and also to each of the embodiments and alternative embodiments, and all combinations of embodiments, described hereinabove.

In another embodiment, in Formula (I), $R^4$ is H, —$CH_3$, or chloro.

The following alternative embodiments of L apply to Formula (I) and also to each of the embodiments and alternative embodiments, and all combinations of embodiments, described hereinabove.

In another embodiment, in Formula (I): L is —C(O)—.

The following alternative embodiments of $R^3$ apply to Formula (I) and also to each of the embodiments and alternative embodiments, and all combinations of embodiments, described hereinabove.

In another embodiment, in Formula (I), $R^3$ is —N($R^{N1}$)($R^{N2}$), wherein:

$R^{N1}$ is selected from H and —$(C_1$-$C_6)$alkyl; and
$R^{N2}$ is selected from H, —$(C_1$-$C_6)$alkyl, cyclopropyl, —O—$(C_1$-$C_6)$alkyl, —OH, halogen, —CN, and —$(C_1$-$C_6)$alkyl which is substituted with 1 or 2 groups independently selected from:
—OH, halogen, —CN,
optionally substituted phenyl, (wherein said optional substitutents on said phenyl are 1 to 3 groups independently selected from OH, CN, —$(C_1$-$C_4)$alkyl, —$(C_1$-$C_4)$alkoxyl), optionally substituted heteroaryl, (wherein said optional substituents on said heteroaryl are 1 to 3 groups independently selected from —($C_1$-$C_6$)alkyl, —($C_1$-$C_4$)alkoxyl, and cyclopropyl), optionally substituted cyclopropyl (wherein said optional substituents on said cyclopropyl are 1 to 3 groups independently selected from —($C_1$-$C_6$)alkyl), and optionally substituted heterocycloalkyl (wherein said optional substitutents on said heterocycloalkyl are 1 to 3 groups independently selected from halogen, —OH, oxo, CN, and —($C_1$-$C_6$)alkyl).

In another embodiment, in Formula (I):

$R^3$ is —N($R^{N1}$)($R^{N2}$), wherein:

$R^{N1}$ is selected from H, methyl, and ethyl; and $R^{N2}$ is H, methyl, ethyl, —O-methyl, —O-ethyl, OH, fluoro, chloro, —CN, substituted methyl, or substituted ethyl, wherein each said substituent is 1 or 2 groups independently selected from:

OH, fluoro, chloro, —CN, optionally substituted phenyl, (wherein said optional substitutents on said phenyl are 1 to 3 groups independently selected from OH, CN, methyl, ethyl, —O-methyl, and —O-ethyl), optionally substituted heteroaryl, (wherein said optional substituents on said heteroaryl are 1 to 3 groups independently selected from methyl, ethyl, —O-methyl, —O-ethyl, and cyclopropyl), optionally substituted cyclopropyl (wherein said optional substituents on said cyclopropyl are 1 to 3 groups independently selected from methyl and ethyl, optionally substituted heterocycloalkyl (wherein said optional substitutents on said heterocycloalkyl are 1 to 3 groups independently selected from halogen, —OH, oxo, CN, methyl, and ethyl, —O-methyl, —O-ethyl, —OH, F, Cl, and —CN).

In each of these embodiments, non-limiting examples of said optionally substituted heteroaryl include: pyridyl, pyrazinyl, furanyl, thienyl, pyrimidinyl, isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, oxindolyl, indolyl, azaindolyl, imidazolyl, thienopyridyl, imidazopyridyl, isoquinolinyl, benzoazaindolyl, and triazinyl. In one embodiment, said optionally substituted heteroaryl is isoxazolyl, oxadiazolyl, or thiazolyl.

In each of these embodiments, non-limiting examples of said optionally substituted heterocycloalkyl include: tetrahydrofuranyl and morpholinyl.

In each of these embodiments, non-limiting examples of said optionally substituted cycloalkyl include cyclopropyl, cyclobutyl, cyclopentyl and cyclohexyl.

In another embodiment, in Formula (I), $R^3$ is —N($R^{N1}$)($R^{N2}$), wherein $R^{N1}$ and $R^{N2}$ are each independently selected from H, methyl, ethyl, n-propyl, i-propyl, —$CH_2CH_2$—OH, cyclopropyl, —$CH_2$-oxadiazolyl, —$CH_2$-triazolyl (wherein said oxadiazolyl and said triazolyl are each optionally substituted with methyl or cyclopropyl). In another such embodiment, L is —C(O)—.

In another embodiment, in Formula (I), and in each of the embodiments and alternative embodiments described hereinabove, L is —C(O)—; and $R^3$ is —N($CH_3$)$_2$ or —NH($CH_3$).

In another embodiment, in Formula (I), $R^3$ is —N($R^{N1}$)($R^{N2}$), wherein:

$R^{N1}$ and $R^{N2}$ are taken together with the nitrogen atom to which they are shown attached to form a 4-, 5-, or 6-membered fully saturated heterocyclic ring comprising (including the nitrogen atom) 1, 2, or 3 ring heteroatoms selected from N, N-oxide, O, S, and S-oxide, wherein said heterocyclic ring is unsubstituted or substituted with 1, 2, or 3 substituents independently selected from halogen, —OH, oxo, CN, —($C_1$-$C_6$)alkyl, aminosubstituted —($C_1$-$C_6$)alkyl (wherein said amino is 1, 2, or 3 groups independently selected from —$NH_2$, —N($C_1$-$C_4$alkyl)$_2$, and —NH($C_1$-$C_4$alkyl)), —O—($C_1$-$C_6$)alkyl, —($C_1$-$C_6$)alkyl-OH, —($C_1$-$C_6$)haloalkyl, —C(O)O—($C_1$-$C_6$)alkyl, cyclopropyl, spirocyclopropyl, —$CH_2$—NHC(O)O—($C_1$-$C_6$)alkyl, —$CH_2$—N($CH_3$)C(O)O—($C_1$-$C_6$)alkyl, phenyl, benzyl, —NHC(O)-phenyl, heteroaryl, and —($C_1$-$C_4$)alkylheteroaryl, heterocycloalkyl;

In the immediately preceding embodiment, non-limiting examples of said unsubstituted or substituted heterocyclic ring include azetidinyl, pyrrolidinyl, piperidinyl, and morpholinyl.

In an alternative of each of the preceding embodiments of $R^3$, L is —C(O)—.

The following alternative embodiments of $R^5$ apply to Formula (I) and also to each of the embodiments and alternative embodiments, and all combinations of embodiments, described hereinabove.

In one embodiment, in Formula (I):

—C($R^{5A}$)($R^{5B}$)($R^{5C}$), wherein:

each of $R^{5A}$, $R^{5B}$ and $R^{5C}$ is independently selected from: H, halogen, OH, $NH_2$, $NHCH_3$, —($C_1$-$C_6$)alkyl, —($C_1$-$C_6$)haloalkyl, —($C_1$-$C_6$)alkenyl, —($C_1$-$C_6$)alkynyl, —($C_3$-$C_6$)cycloalkyl, —($C_3$-$C_6$)cycloalkyl substituted with —($C_1$-$C_6$)alkyl, —($C_1$-$C_6$)alkenyl, —($C_1$-$C_6$)alkynyl, thiadiazolyl, thienyl, thiazolyl, phenyl, phenyl substituted with from 1 to 3 groups independently selected from halogen, OH, —$NH_2$, —($C_1$-$C_6$)alkyl, —O—($C_1$-$C_6$)alkyl, cyclopropyl, —O—($C_1$-$C_6$)haloalkyl, —O-cyclopropyl, —C(O)O—($C_1$-$C_6$)alkyl, pyrazolyl, and pyridinyl.

In an alternative of the immediately preceding embodiment, $R^{5A}$ is OH;

$R^{5B}$ is —($C_1$-$C_3$)fluoroalkyl; and $R^{5C}$ is selected from $NH_2$, $NHCH_3$, —($C_1$-$C_6$)alkyl, —($C_1$-$C_4$)fluoroalkyl, thiadiazolyl, thienyl, thiazolyl, phenyl, (wherein said phenyl substituted with from 1-3 groups independently selected from halogen —($C_1$-$C_6$)alkyl, and —($C_1$-$C_6$)alkoxy), cyclopropyl (wherein said cyclopropyl is optionally substituted with —($C_1$-$C_6$)alkyl), cyclobutyl (wherein said cyclobutyl is optionally substituted with —($C_1$-$C_6$)alkyl), ethenyl, ethynyl, pyrazolyl, and pyridinyl).

In another embodiment, in Formula (I), $R^5$ is

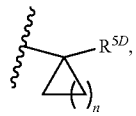

wherein n is an integer from 1 to 4; and $R^{5D}$ is as defined in Formula (I).

In another embodiment, in Formula (I), $R^5$ is

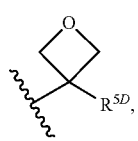

wherein $R^{5D}$ is as defined in Formula (I).

In another embodiment, in Formula (I), $R^5$ is

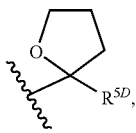

where $R^{5D}$ is as defined in Formula (I). In an alternative of this embodiment, $R^{5D}$ is selected from H, —$(C_1$-$C_6)$alkyl, —$(C_1$-$C_6)$haloalkyl, phenyl, and phenyl substituted with from 1 to 3 groups independently selected from OH, F, Cl, methyl, ethyl, n-propyl, i-propyl, —O-methyl, and —O-ethyl.

In another embodiment, in Formula (I), $R^5$ is

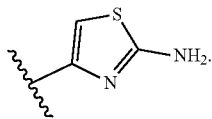 [SMILES: *c1csc(N)n1]

In another embodiment, in Formula (I), $R^5$ is

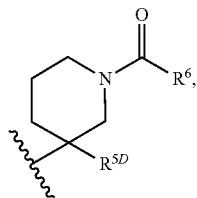

where $R^{5D}$ and $R^6$ are each is as defined in Formula (I). In an alternative of this embodiment, $R^{5D}$ is selected from H, —$(C_1$-$C_6)$alkyl, —$(C_1$-$C_6)$haloalkyl, pyrimidinyl, phenyl, and phenyl substituted with from 1 to 3 groups independently selected from OH, F, Cl, methyl, ethyl, n-propyl, i-propyl, —O-methyl, and —O-ethyl. In another alternative of each of the immediately preceding embodiments, $R^6$ is H. In another alternative of each of the immediately preceding embodiments, $R^6$ is $CH_3$.

In another embodiment, in Formula (I), $R^5$ is phenyl, wherein said phenyl is unsubstituted or substituted with 1, 2, or 3 groups independently selected from halogen, CN, methyl, ethyl, n-propyl, i-propyl, —$(C_1$-$C_4)$haloalkyl, and pyrrolidinyl.

The following alternative embodiments of Q apply to Formula (I) and also to each of the embodiments and alternative embodiments, and all combinations of embodiments, described hereinabove.

In another embodiment, Q is a bond. In another embodiment, Q is —C(O)—. In another embodiment, Q is —S(O)$_2$—. In another embodiment, Q is —C(O)O—.

Specific non-limiting embodiments of compounds of the invention are shown in the examples below. All valences not shown explicitly filled in the pictured example compounds of the invention are assumed to be filled by hydrogen such that all valences are satisfied unless otherwise indicated.

In another embodiment, 1 to 3 carbon atoms of the compounds of the invention may be replaced with 1 to 3 silicon atoms so long as all valence requirements are satisfied.

In another embodiment, there is provided a composition comprising a compound of the invention and a pharmaceutically acceptable carrier or diluent.

In one embodiment, the invention is directed to methods of treating a patient (preferably a human) for inflammatory diseases and diseases characterized by defects in cholesterol or lipid metabolism, by administering to the patient a compound of the invention or a pharmaceutically acceptable salt thereof.

The invention is also directed to the use of a compound of the invention for treating inflammatory diseases and diseases characterized by defects in cholesterol or lipid metabolism, by administering to a patient (preferably a human) a compound of the invention or a pharmaceutically acceptable salt thereof.

The invention is also directed to medicaments or pharmaceutical compositions for treating inflammatory diseases and diseases characterized by defects in cholesterol or lipid metabolism, by administering to a patient (preferably a human) a compound of the invention, or a pharmaceutically acceptable salt thereof, and a pharmaceutically acceptable carrier.

The invention is further directed to a the manufacture of a medicament or a composition for inflammatory diseases and diseases characterized by defects in cholesterol or lipid metabolism, by administering to a patient (preferably a human) a compound of the invention or a pharmaceutically acceptable salt thereof, with one or more pharmaceutically acceptable carriers.

Exemplary inflammatory diseases and diseases characterized by defects in cholesterol or lipid metabolism for which the compounds of the invention are useful include neurodegenerative and neurological diseases, such as Alzheimer's Disease, Neimann-Pick disease type C1, Parkinson's Disease, amyotrophic lateral sclerosis, stroke, age-related macular degeneration, psychiatric disorders such as schizophrenia and depression, and metabolic disorders such as cardiovascular disease, obesity and diabetes.

The present invention is directed to the use of the compounds of the invention as LXRβ agonists in a patient or subject such as a mammal in need of such activity, comprising the administration of an effective amount of the compound. In addition to humans, a variety of other mammals can be treated according to the method of the present invention.

The compounds of the invention may have utility in treating or ameliorating Alzheimer's disease. The compounds may also be useful in treating or ameliorating other inflammatory diseases and diseases characterized by defects in cholesterol and lipid metabolism, such as Neimann-Pick disease type C1, Parkinson's Disease, amyotrophic lateral sclerosis, stroke, age-related macular degeneration, psychiatric disorders such as schizophrenia and depression, and metabolic disorders such as cardiovascular disease, obesity and diabetes.

For example, the compounds of the invention may be useful for the prevention of dementia of the Alzheimer's type, as well as for the treatment of early stage, intermediate stage or late stage dementia of the Alzheimer's type.

Potential cardiovascular conditions or disorders for which the compounds of the invention may be useful include atherosclerosis, hypertension, hyperlipidemia, coronary heart disease, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, vascular complications of diabetes, obesity (including abdominal obesity) and endotoxemia.

The compounds of the invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease.

The compounds of the invention may also be useful for the treatment of Type 2 diabetes, and conditions and disorders related to Type 2 diabetes, such as (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

The compounds of the invention may also have utility in treating certain kinds of cancers which are affected by the LXR mechanism. Such cancers include, but are not limited to, prostate, breast, ovarian, melanoma, pancreas, lung, colon and hematological malignancy. (Lin, C-Y and Gustafsson, J-A, (2015) Nature Reviews Cancer 15, 216-224).

The compounds of the invention may be used in combination with one or more other drugs in the treatment of diseases or conditions for which the compounds of the invention have utility, where the combination of the drugs together are safer or more effective than either drug alone. Additionally, the compounds of the invention may be used in combination with one or more other drugs that treat, prevent, control, ameliorate, or reduce the risk of side effects or toxicity of the compounds of the invention. Such other drugs may be administered, by a route and in an amount commonly used contemporaneously or sequentially with the compounds of the invention. Accordingly, the pharmaceutical compositions of the present invention include those that contain one or more other active ingredients, in addition to the compounds of the invention. The combinations may be administered as part of a unit dosage form combination product, or as a kit or treatment protocol wherein one or more additional drugs are administered in separate dosage forms as part of a treatment regimen.

Examples of combinations of the compounds of the invention include combinations with anti-Alzheimer's Disease agents, for example: other LXRβ agonists; beta-secretase inhibitors including verubecestat (N-[3-[(5R)-3-amino-2,5-dimethyl-1,1-dioxo-6H-1,2,4-thiadiazin-5-yl]-4-fluorophenyl]-5-fluoropyridine-2-carboxamide); alpha 7 nicotinic agonists; ADAM 10 ligands or activators; gamma-secretase inhibitors, such as LY450139 and TAK 070; gamma secretase modulators; tau phosphorylation inhibitors; glycine transport inhibitors; ApoE4 conformational modulators; NR2B antagonists; androgen receptor modulators; blockers of Aβ 15 cortico formation; 5-HT4 agonists, such as PRX-03140; 5-HT6 antagonists, such as xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab; anti-inflammatory compounds such as I-flurbiprofen, nitroflurbiprofen; PPAR gamma agonists, such as pioglitazone and rosiglitazone; CB-1 receptor antagonists or CB-1 receptor inverse agonists; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine and ladostigil; growth hormone secretagogues such as ibutamoren, ibutamoren mesylate, and capromorelin; histamine $H_3$ receptor antagonists; AMPA agonists or AMPA modulators; PDE IV inhibitors; $GABA_A$ inverse agonists; GSK3β inhibitors; neuronal nicotinic agonists; selective M1 agonists; HDAC inhibitors; and microtubule affinity regulating kinase (MARK) ligands; dimebon; or other drugs that affect receptors or enzymes that either increase the efficacy, safety, convenience, or reduce unwanted side effects or toxicity of the compounds of the invention.

Other examples of combinations of the compounds of the invention include combinations with anti-obesity agents such as apolipoprotein-B secretion/microsomal triglyceride transfer protein (apo-B/MTP) inhibitors, 11β-hydroxy steroid dehydrogenase-1 (11β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $β_3$ adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), neuropeptide-Y antagonists (e.g., NPY Y5 receptor antagonists) thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™, available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like.

Other examples of combinations of the compounds of the invention include combinations with antihypertensive agents; anti-inflammatory agents (e.g., COX-2 inhibitors); antidepressants (e.g., fluoxetine hydrochloride (Prozac™)); cognitive improvement agents (e.g., donepezil hydrochloride (Aricept™) and other acetylcholinesterase inhibitors); neuroprotective agents (e.g., memantine); antipsychotic medications (e.g., ziprasidone (Geodon™), risperidone and olanzapine); insulin and insulin analogs (e.g., LysPro insulin); GLP-1 (7-37) (insulinotropin) and GLP-1 (7-36)-$NH_2$; sulfonylureas and analogs thereof: chlorpropamide, glibenclamide, tolbutamide, tolazamide, acetohexamide, Glypizide™, glimepiride, repaglinide, meglitinide; biguanides:

metformin, phenformin, buformin; alpha2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, Avandia™; fatty acid oxidation inhibitors: clomoxir, etomoxir; alpha-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex: fenfluramine; vanadate and vanadium complexes (e.g., Naglivan™) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. Non-limiting examples of HMG-CoA reductase inhibitors include statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; cerivastatin, particularly the sodium salt thereof, and nisvastatin.

The compounds of the invention may also be administered in combination with a naturally occurring compound that acts to lower plasma cholesterol levels. Such naturally occurring compounds are commonly called nutraceuticals and include, for example, garlic extract, Hoodia plant extracts, and niacin.

Other examples of combinations of the compounds of the invention include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, corticotrophi, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be used in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the compounds of the invention may be used in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Other examples of combinations of the compounds of the invention include combinations with agents for the treatment of stroke or stroke recovery. Examples of such second agents for treatment of stroke include, but are not limited to, aspirin, intercellular adhesion molecule (ICAM)-I and LFA-I antagonists including antibodies such as enlimomab (an anti-ICAM-1 monoclonal antibody), and anti-CD18 and anti-CD 1Ia antibodies, human anti-leukocytic antibodies such as Hu23F2G, glycoprotein lib Ilia antagonists such as eptifibatide (INTEGRELIN™), direct thrombin inhibitors, external or local ultrasound, mechanical clot retrieval or inaceration, fibrinolytic agents, neuronal wound healing agents such as basic fibroblast growth factor (e.g., FIBLAST™), neuroprotective agents such as citicoline, magnesium, nalmefene, dizocilpine, nimodipine, lamotrigine, sipatrigine, lubeluzole, mexiletine, clomethiazole, calcium and sodium channel blocking agents, beta-amino-3-hydroxy-5-methylisoxazole-4-proprionic acid antagonist, a serotonin agonist, a transmembrane potassium channel modulator, agents that inhibit astrocyte activation (e.g., ONO 2506), antioxidants (e.g., MCI-186), anti-adhesion monoclonal antibodies and antagonists and antibodies inhibiting platelet aggregation such as argatroban and abciximab (REOPRO™), phenytoin, nitrogen oxides, CNS-protective therapies, free-radical scavengers such as tirilazad, reactive oxygen metabolites, and antioxidants, and other thrombolytic agents than tenecteplase, as defined below, such as, for example, acylated plasminogen-streptokinase activator complex (APSAC), single-chain urokinase-plasminogen activator (scu-PA), thrombin-like enzymes from snake venoms such as ancrod, streptokinase (e.g., SAKSTAR™), urokinase, anistreplase, alteplase, saruplase, reteplase, lanoteplase (SUN-9216; Genetics Institute Inc.), plasmin, a truncated form of plasmin (microplasmin; ThromboGenics Ltd), a direct-acting thrombolytic with non-thrombolytic-related neuroprotective activities, recombinant desmodus rotundus salivary plasminogen activator (rDSPA) alpha-1 (Schering/Teijin Pharmaceuticals), a mutant fibrin-activated human plasminogen (BB 101 53; British Biotech Inc.), staphylokinase, fibrolase, prourokinase (intra-arterial administration directly into M1 or M2 arterial thrombus), monteplase (modified rtPA), pamiteplase, tisokinase, and vampire bat plasminogen activator, a spin-trap agent such as NXY-059 (cerovive), clopidogrel, n-methyl-dextro-aspartic acid receptor blocking agent, an anticonvulsive agent, a caspase 3 inhibitor, ((tert butylimino)methyl) 1,3 (benzenedisulfonate disodium n oxide), ebselen, glutathione peroxidase, norphenazone, rovelizumab, lactacystin beta-lactone, tsukubaenolide, 4 phosphonomethylpipecolic acid, eliprodil, antibodies to ganglioside GMl; and thrombolytic agents, including streptokinase, acylated plasminogen-streptokinase activator complex (APSAC), urokinase, single-chain urokinase-plasminogen activator (scu-PA), thrombin-like enzymes from snake venoms such as ancrod (Bell, W. "Defibrinogenating enzymes" In Colman et al (eds), *Hemostasis and Thrombosis* Lippincott, Philadelphia (1987) p. 886), tPA, and biologically active variants of each of the above.

Other examples of combinations of the compounds of the invention include combinations with agents for the treatment of depression or anxiety, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), alpha-adrenoreceptor antagonists, atypical antidepressants, benzodiazepines, 5-HT$_{1A}$ agonists or antagonists, especially 5-HT$_{1A}$ partial agonists, 20orticotrophin releasing factor (CRF) antagonists, and pharmaceutically acceptable salts thereof.

Other examples of combinations of the compounds of the invention include combinations with agents for the treatment of diabetes or diabetes conditions, including dipeptidyl peptidase IV (DPP-IV) inhibitors (including isoleucine thiazolidide vildagliptin, stigaliptin, and saxagliptin); SGLT inhibitors (e.g., gliflozins such as dapagliflozin, empagliflozin, canagliflozin, ipragliflozin, tofogliflozin, sergliflozin etabonate, remogliflozin etabonate, ertugliflozin, and luseogliflozin/TS-071), insulin sensitizers, including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, tesaglitazar, TAK-559, PPARα agonists, such as fenofibric acid derivatives (gemfibrozil, clofibrate, fenofibrate and bezafibrate), and selective PPAR gamma modulators (SPPARγM's); (ii) biguanides such as metformin and phenformin, and (iii) protein tyrosine phosphatase-1B (PTP-1B) inhibitors; insulin or insulin mimetics; sulfonylureas and other insulin secretagogues, such as tolbutamide, glyburide, glipizide, glimepiride, and meglitinides, such as nateglinide and repaglinide; α-glucosidase inhibitors (such as acarbose and miglitol); glucagon receptor antagonists; GLP-1, GLP-1 analogues or mimetics, and GLP-1 receptor agonists, such as exendin-4 (exenatide), liraglutide; GIP and GIP mimetics and GIP receptor agonists; PACAP, PACAP mimetics, and PACAP receptor agonists; cholesterol lowering agents; PPAR delta agonists; antiobesity agents; ileal bile acid transporter inhibitors; agents intended for use in inflammatory conditions such as aspirin, non-steroidal anti-inflammatory drugs (NSAIDs), glucocorticoids, azulfidine, and selective cyclooxygenase-2 (COX-2) inhibitors; antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers; glucokinase activators (GKAs); inhibitors of 11-β-hydroxysteroid dehydrogenase type 1; inhibitors of cholesteryl ester transfer protein (CETP), such as torcetrapib; and inhibitors of fructose 1,6-bisphosphatase.

The subject or patient to whom the compounds of the invention is administered is generally a human being, male or female, in whom LXRβ agonism is desired, but may also encompass other mammals, such as dogs, cats, mice, rats, cattle, horses, sheep, rabbits, monkeys, chimpanzees or other apes or primates, for which treatment of the above noted disorders is desired.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, and they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to 10 carbon atoms. "Lower alkyl" means a straight or branched alkyl group comprising 1 to 4 carbon atoms. Branched means that one or more lower alkyl groups such as methyl, ethyl or propyl, are attached to a linear alkyl chain or to the same methyl group. Non-limiting examples of suitable alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halo group defined above.

"Alkenyl" means an aliphatic hydrocarbon group containing at least one carbon-carbon double bond and which may be straight or branched and comprising 2 to 10 carbon atoms in the straight or branched chain. Branched means that one or more lower alkyl groups such as methyl, ethyl propyl, ethenyl or propenyl are attached to a linear or branched alkenyl chain. "Lower alkenyl" means 2 to 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising 2 to 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means 2 to 4 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein ═O replaces two available hydrogens on the same carbon atom (i.e., heterocyclyl includes rings having a carbonyl group in the ring). (Such ═O groups may be referred to herein as "oxo", further described below.) As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected from N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

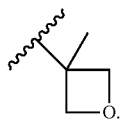

"Oxo" is defined as a oxygen atom that is double bonded to a ring carbon in a cycloalkyl, cycloalkenyl, heterocyclyl, heterocyclenyl, or other ring described herein, e.g.,

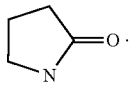

It should be noted that in hetero-atom containing ring systems of this invention, there are no hydroxyl groups on carbon atoms adjacent to a N, O or S, as well as there are no N or S groups on carbon adjacent to another heteroatom.

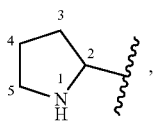

there is no —OH attached directly to carbons marked 2 and 5.

"Alkoxy" means an —O-alkyl group in which the alkyl group is as previously described. Non-limiting examples of alkoxy groups include methoxy, ethoxy, n-propoxy, iso-propoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^6$ in —N($R^6$)$_2$, or a variable appears more than once in a structure presented herein, the variables can be the same or different.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the formula or by the name.

The line ———, as a bond generally indicates a mixture of, or either of, the possible isomers, e.g., containing (R)- and (S)-stereochemistry. For example:

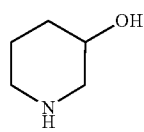

means

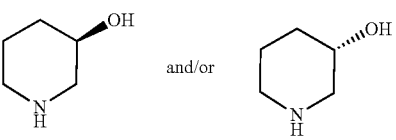

The wavy line ∿∿∿, as used herein, indicates a point of attachment to the rest of the compound. Lines drawn into the ring systems, such as, for example:

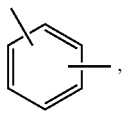

indicate that the indicated line (bond) may be attached to any of the substitutable ring carbon atoms.

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

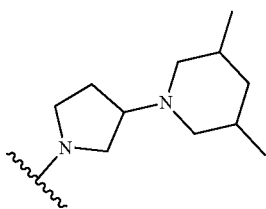 [SMILES: *N1CCC(N2CC(C)CC(C)C2)C1]

represents

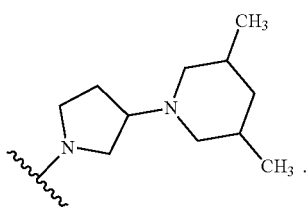 [SMILES: *N1CCC(N2CC(C)CC(C)C2)C1]

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from 0.001 to 500 mg/kg of body weight/day of the compound of the invention. In one embodiment, the dosage is from 0.01 to 25 mg/kg of body weight/day of a compound of the invention, or a pharmaceutically acceptable salt or solvate of said compound. In another embodiment, the quantity of active compound in a unit dose of preparation may be varied or adjusted from 1 mg to 100 mg, preferably from 1 mg to 50 mg, more preferably from 1 mg to 25 mg, according to the particular application. In another embodiment, a typical recommended daily dosage regimen for oral administration can range from 1 mg/day to 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comprising one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

The compounds of the invention can be made according to procedures that will be apparent to those of ordinary skill in the art. Several methods for preparing the compounds of this invention are illustrated in the Schemes and examples herein. Starting materials are available commercially or are made according to procedures known in the art or as illustrated herein. The following examples are provided so that the invention might be more fully understood. These examples are illustrative only and should not be construed as limiting the scope of the invention.

General Scheme A outlines a method for preparing compounds Af the type A-3. A suitably acylated amino alcohol (A-1) can be reacted with hydroxy-aryl F-2 to form A-3.

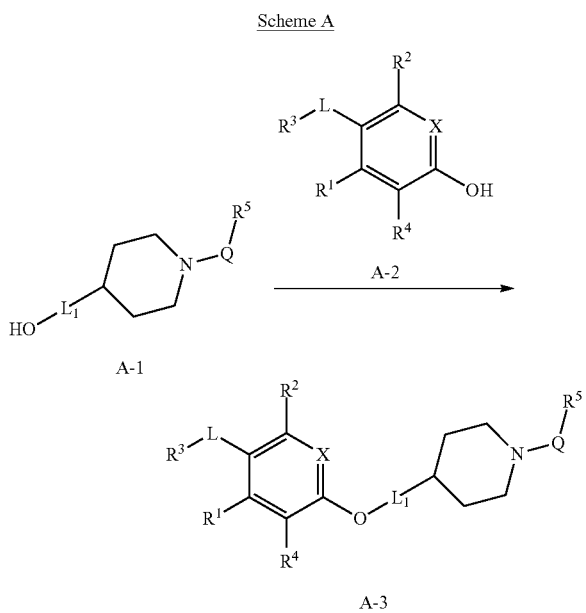

General Scheme B outlines a method for preparing compounds of the type B-4/B-5. A suitably protected amino alcohol (B-1) can be reacted with hydroxy-aryl A-2 to form B-2. Following deprotection, coupling with appropriate carboxylic acids or sulfonyl chlorides yields B-4/B-5.

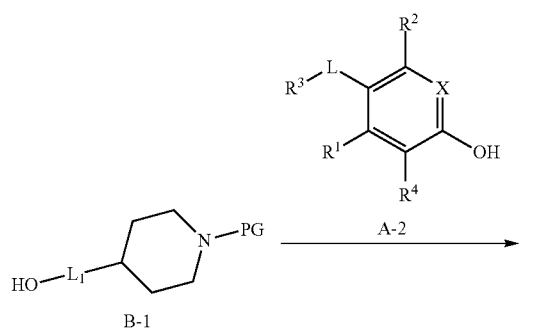

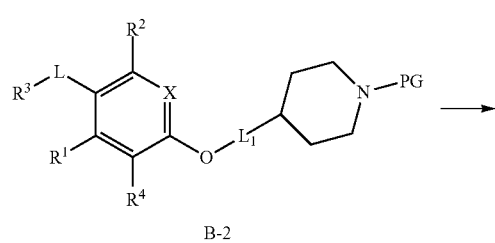

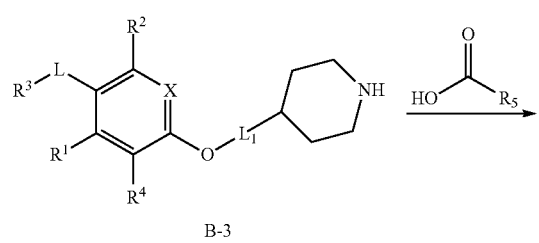

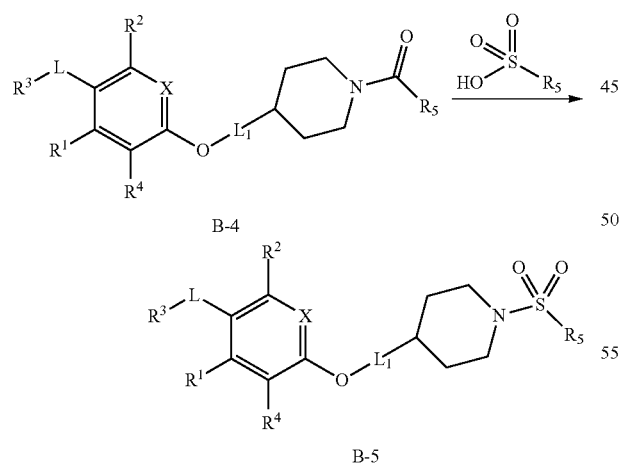

Scheme C

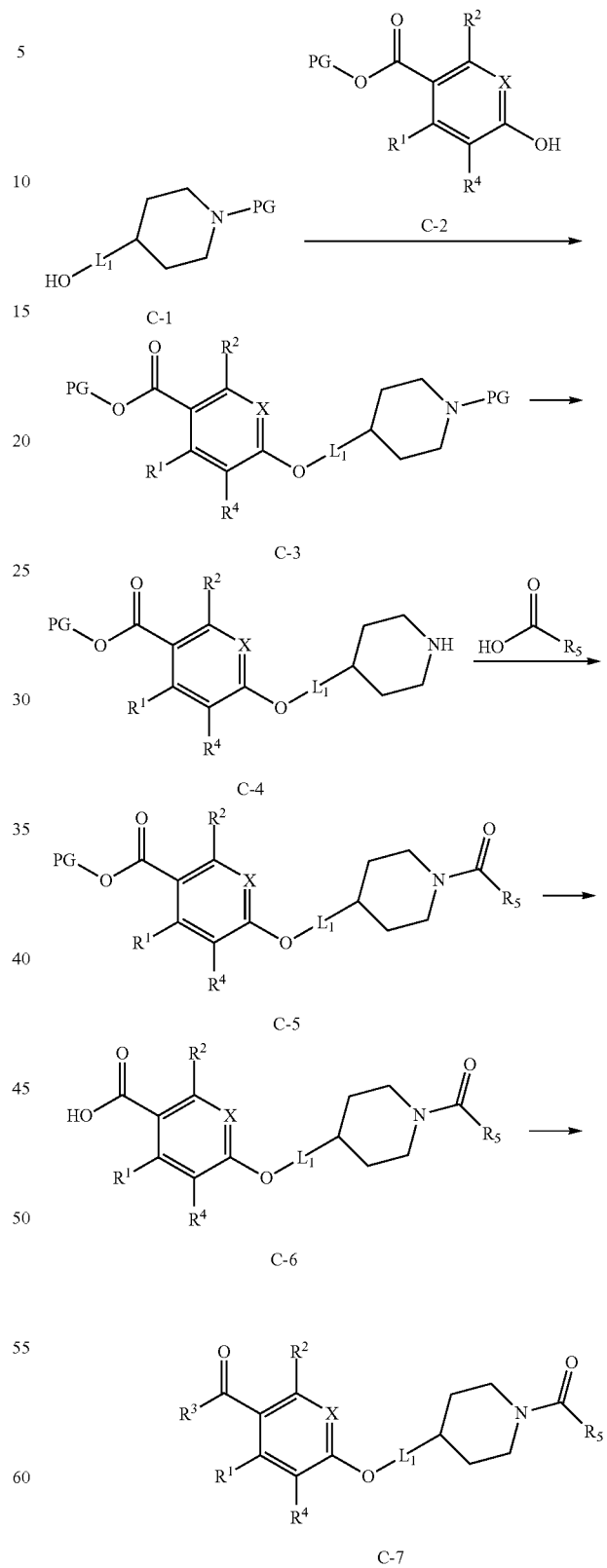

General Scheme C outlines a method for preparing compounds of the type C-7. A suitably protected amino alcohol (C-1) can be reacted with hydroxy-aryl C-2 to form C-3. Following deprotection, coupling with appropriate carboxylic acids yields C-5. Hydrolysis and coupling to appropriate amines yield C-7.

General Scheme D outlines a method for preparing compounds of the type D-4. A suitably activated alcohol (D-1)

can be reacted with hydroxy-aryl A-2 to form D-2. Following deprotection, coupling with appropriate carboxylic acids yields D-4.

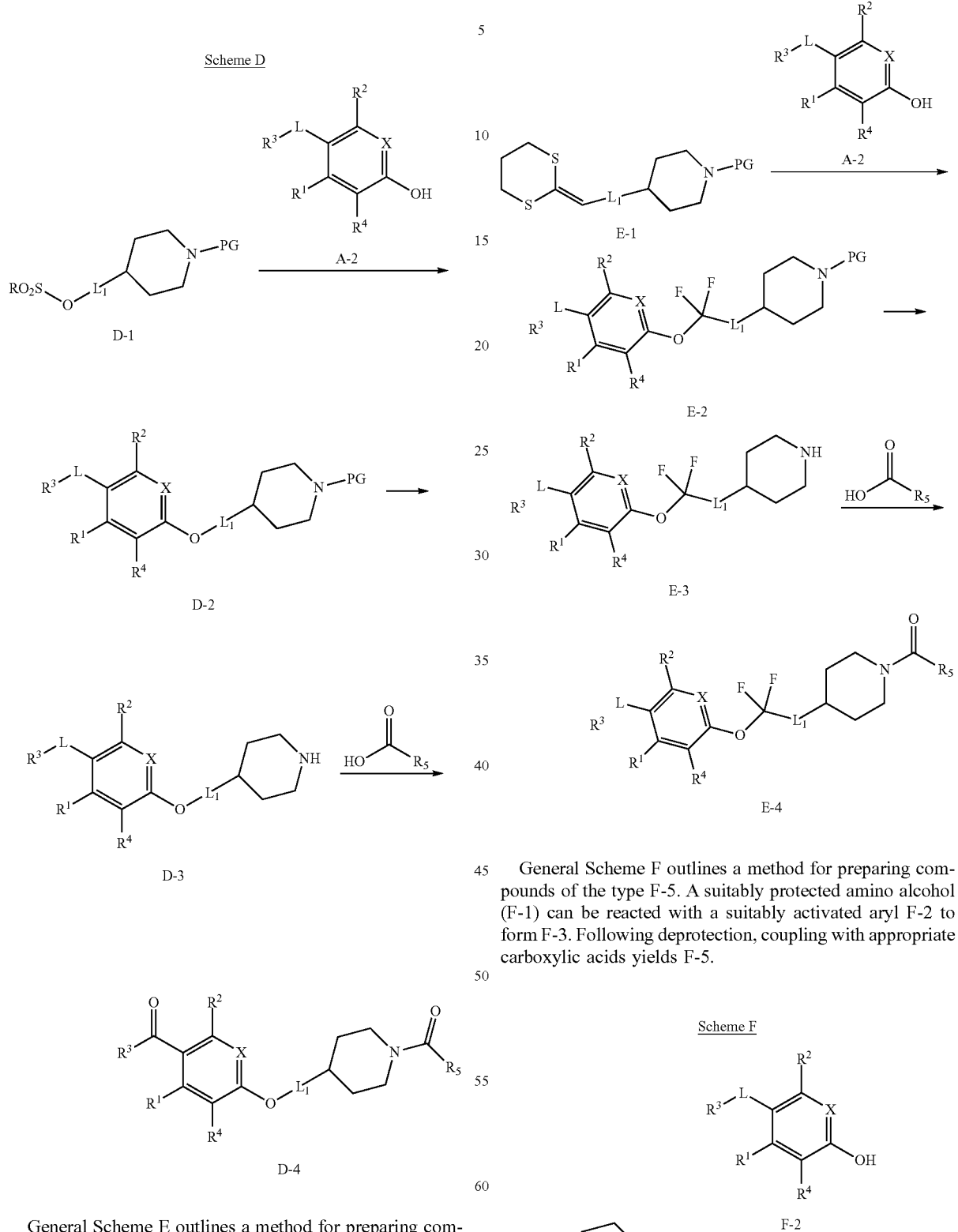

General Scheme E outlines a method for preparing compounds of the type E-5. A suitably protected amino dithiane (E-1) can be reacted with hydroxy-aryl A-2 to form E-3. Following deprotection, coupling with appropriate carboxylic acids yields E-4.

General Scheme F outlines a method for preparing compounds of the type F-5. A suitably protected amino alcohol (F-1) can be reacted with a suitably activated aryl F-2 to form F-3. Following deprotection, coupling with appropriate carboxylic acids yields F-5.

Scheme F

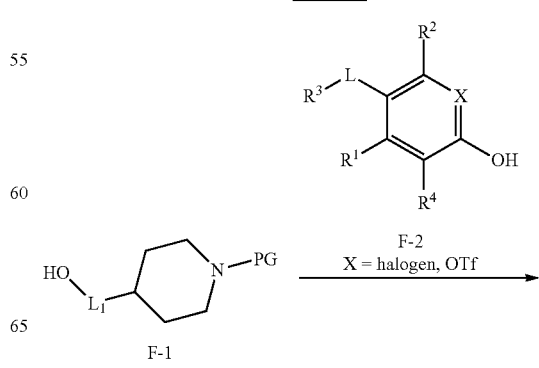

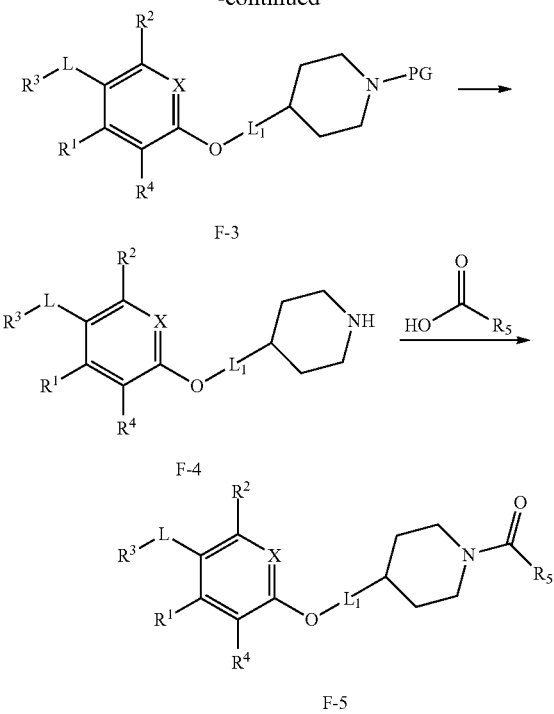

F-3

F-4

F-5

List of Abbreviations
BOP (benzotriazol-1-yloxy)tris(dimethylamino)phosphonium hexafluorophosphate
Br₂BH-SMe₂ dibromoborane-methylsulfide complex
CDI N,N'-carbonyldiimidazole
Cs₂CO₃ cesium carbonate
DCC N,N'-dicyclohexylcarbodiimide
DCE dichloroethane
DCM dichloromethane
DIAD diisopropyl azodicarboxylate
DIBAL-H diisobutylaluminum hydride
DIEA diisopropylethylamine
DMF dimethylformamide
DMSO dimethyl sulfoxide
Dppf diphenylphosphinoferrocene
EDC N-(3-dimethylaminopropyl)-N'-ethylcarbodiimide
Et₂O diethyl ether
Et₃N triethylamine
EtOAc ethyl acetate
EtOH ethanol
HATU O-(7-azabenzotriazol-1-yl)-N,N,N',N'-tetramethyluronium hexafluorophosphate
HCl hydrochloric acid
(HF)₃-Et₃N triethylamine trihydrofluoride
IPA isopropanol
K₂CO₃ potassium carbonate
KHSO₄ potassium bisulfate
LiOH lithium hydroxide
MeCN acetonitrile
MeOH methanol
MgSO₄ magnesium Sulfate
Na₂SO₄ sodium sulfate
NaHCO₃ sodium bicarbonate
NaOH sodium hydroxide
n-BuLi n-butyl lithium
NIS N-iodosuccinimide
Pd(Ph₃P)₄ tetrakis(triphenylphosphine) palladium (0)
Pd/C palladium on carbon
PdCl₂(dppf)-CH₂Cl₂ adduct dichloro[1,1'-bis(diphenylphosphino)ferrocene]palladium (II) dichloromethane adduct
PE Petroleum ether
POCl₃ phosphorous oxychloride
PPh₃ triphenylphosphine
RT, r.t., rt room temperature
TBTU O-benzotriazol-1-yl-N,N,N',N'-tetramethyluronium tetrafluoroborate
Tf₂O triflic anhydride
TFA trifluoroacetatic acid
TfOH trifluoromethanesulfonic acid
THF tetrahydofuran For the below examples where a single isomer is drawn, enantiomers were separated but absolute configuration was not established.

Example 1-1

2-chloro-N,N-dimethyl-4-(3-((R or S)-3,3,3-trifluoro-2-hydroxy-2-(3-methoxyphenyl)propanoyl)-3-azaspiro[5.5]undecan-9-yloxy)benzamide

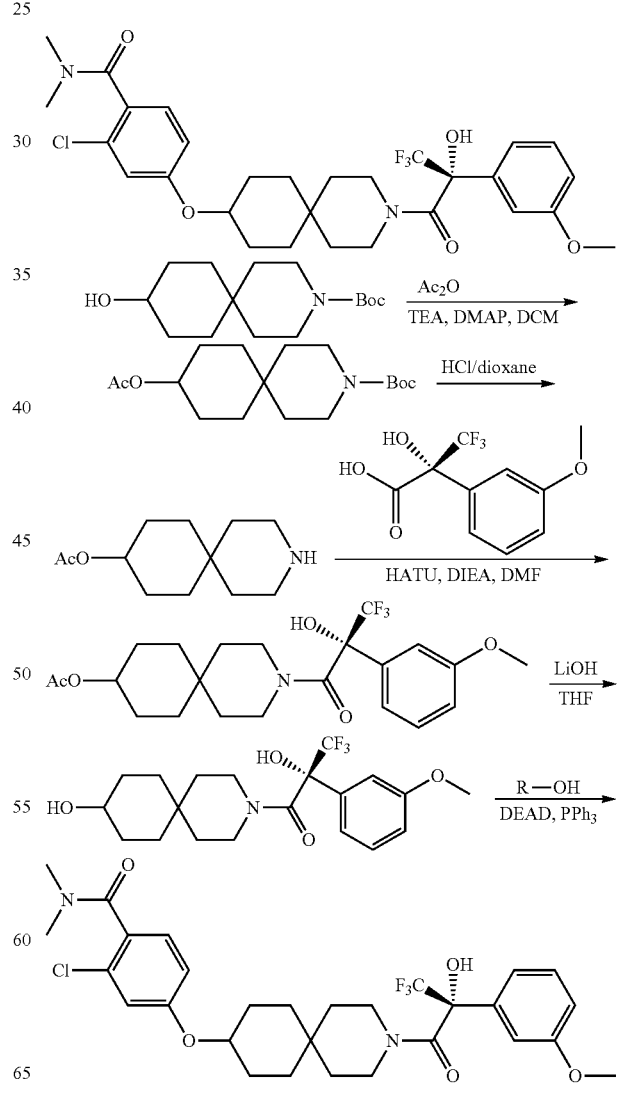

tert-butyl 9-acetoxy-3-azaspiro[5.5]undecane-3-carboxylate

A mixture of tert-butyl 9-hydroxy-3-azaspiro[5.5]undecane-3-carboxylate (2.0 g, 7.43 mmol), Ac₂O (909 mg, 8.92 mmol), TEA (976 mg, 9.66 mmol) and DMAP (91 mg, 0.743 mmol) in CHCl₃ (20 ml) was stirred at 70° C. overnight. Then the mixture was diluted with DCM (300 ml), washed with 10% citric acid (50 ml*2), sat. NaHCO₃ (50 ml), brine (50 ml), dried and concentrated to give tert-butyl 9-acetoxy-3-azaspiro[5.5]undecane-3-carboxylate. LRMS m/z (M+Na) 334.1 found, 334.2 required.

3-azaspiro[5.5]undecan-9-yl acetate

A mixture of tert-butyl 9-acetoxy-3-azaspiro[5.5]undecane-3-carboxylate (2.0 g, 6.43 mmol) and HCl/dioxane (6.43 ml, 25.72 mmol, 4 M) in DCM (10 ml) was stirred at rt for 3 h. The solvent was removed under reduced pressure and the residue was basified to pH=7-8 with sat. NaHCO₃, extracted with DCM (150 ml*3), washed with brine (50 ml), dried over anhydrous Na₂SO₄, evaporated to give 3-azaspiro[5.5]undecan-9-yl acetate. LRMS m/z (M+H) 212.1 found, 212.1 required.

3-((R or S)-3,3,3-trifluoro-2-hydroxy-2-(3-methoxyphenyl)propanoyl)-3-azaspiro[5.5]undecan-9-yl acetate To a solution of (R or S)-3,3,3-trifluoro-2-hydroxy-2-(3-methoxyphenyl)propanoic acid (1.92 g, 7.68 mmol) in DMF (2 ml) was added a solution of HATU (2.92 g, 7.68 mol) in DMF (2.0 ml) at room temperature, followed by addition of 3-azaspiro[5.5]undecan-9-yl acetate (1.35 g, 6.4 mmol) and DIPEA (1.65 g, 12.8 mmol) in DMF (2.0 ml) at room temperature. The resulting mixture was stirred overnight. Then the solvent was removed under reduced pressure and the residue was purified by column chromatography (silica gel: 200-300 mesh, PE/EtOAc=5/1 to 2/1) to give 3-((R or S)-3,3,3-trifluoro-2-hydroxy-2-(3-methoxyphenyl)propanoyl)-3-azaspiro[5.5]undecan-9-yl acetate. LRMS m/z (M+H) 444.1 found, 444.2 required.

(2R)-3,3,3-trifluoro-2-hydroxy-1-(9-hydroxy-3-azaspiro[5.5]undecan-3-yl)-2-(3-methoxyphenyl)propan-1-one A mixture of 3-((R or S)-3,3,3-trifluoro-2-hydroxy-2-(3-methoxyphenyl)propanoyl)-3-azaspiro[5.5]undecan-9-yl acetate (1.9 g, 4.29 mmol) and 1 M LiOH (21 ml) in THF (21 ml) was stirred at rt overnight. Then the mixture was extracted with DCM (150 ml*4), washed with brine (60 ml), dried and concentrated to give crude product. The residue was purified by column chromatography (silica gel: 200-300 mesh, PE/EtOAc=5/1 to 1/1) to give (2R)-3,3,3-trifluoro-2-hydroxy-1-(9-hydroxy-3-azaspiro[5.5]undecan-3-yl)-2-(3-methoxyphenyl)propan-1-one. LRMS m/z (M+H) 402.1 found, 402.2 required.

2-chloro-N,N-dimethyl-4-(3-((R or S)-3,3,3-trifluoro-2-hydroxy-2-(3-methoxyphenyl)propanoyl)-3-azaspiro[5.5]undecan-9-yloxy)benzamide To a solution of (2R)-3,3,3-trifluoro-2-hydroxy-1-(9-hydroxy-3-azaspiro[5.5]undecan-3-yl)-2-(3-methoxyphenyl)propan-1-one (12 mg, 0.03 mmol), 2-chloro-4-hydroxy-N,N-dimethylbenzamide (9 mg, 0.045 mmol) and PPh₃ (39 mg, 0.15 mmol) in THF (0.8 ml) was added a solution of DEAD (26 mg, 0.15 mol) in THF (0.2 ml) at dropwise at 0 C. The mixture was stirred at r.t. under N₂ atmosphere overnight. Then the mixture was directly purified by reverse phase HPLC (mobile phase: methanol/water (10 mM NH₄HCO₃)) to afford 2-chloro-N,N-dimethyl-4-(3-((R or S)-3,3,3-trifluoro-2-hydroxy-2-(3-methoxyphenyl)propanoyl)-3-azaspiro[5.5]undecan-9-yloxy)benzamide. LRMS m/z (M+H) 583.2 found, 583.2 required.

Using the same procedure described for example 1-1, but replacing 2-chloro-4-hydroxy-N,N-dimethylbenzamide with the appropriate substituted phenol in the last step, the following compounds were prepared.

| Example | Structure | IUPAC Name | Exact Mass [M + H]+ |
|---|---|---|---|
| 1-2 | 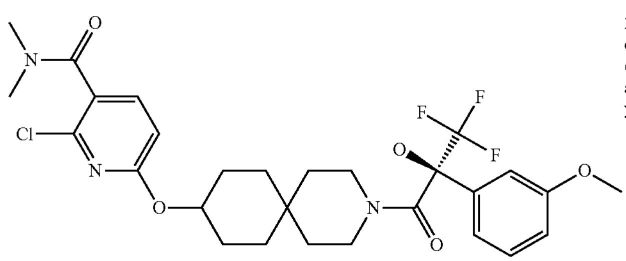 | 2-chloro-N,N-dimethyl-6-(3-((S or R)-3,3,3-trifluoro-2-hydroxy-2-(3-methoxyphenyl)propanoyl)-3-azaspiro[5.5]undecan-9-yloxy)nicotinamide | 584.0 |
| 1-3 | 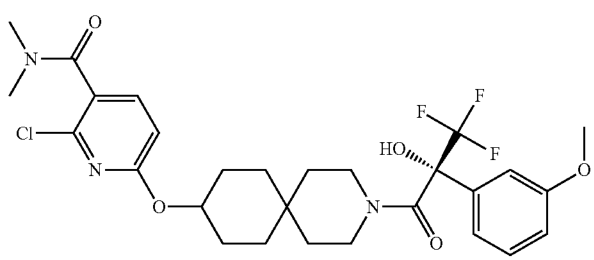 | 2-chloro-N,N-dimethyl-6-(3-((R or S)-3,3,3-trifluoro-2-hydroxy-2-(3-methoxyphenyl)propanoyl)-3-azaspiro[5.5]undecan-9-yloxy)nicotinamide | 584.1 |

Example 2-1

6-(3-((R or S)-2-(3-cyclopropoxyphenyl)-3,3,3-trifluoro-2-hydroxypropanoyl)-3-azaspiro[5.5]undecan-9-yloxy)-N,N,2-trimethylnicotinamide

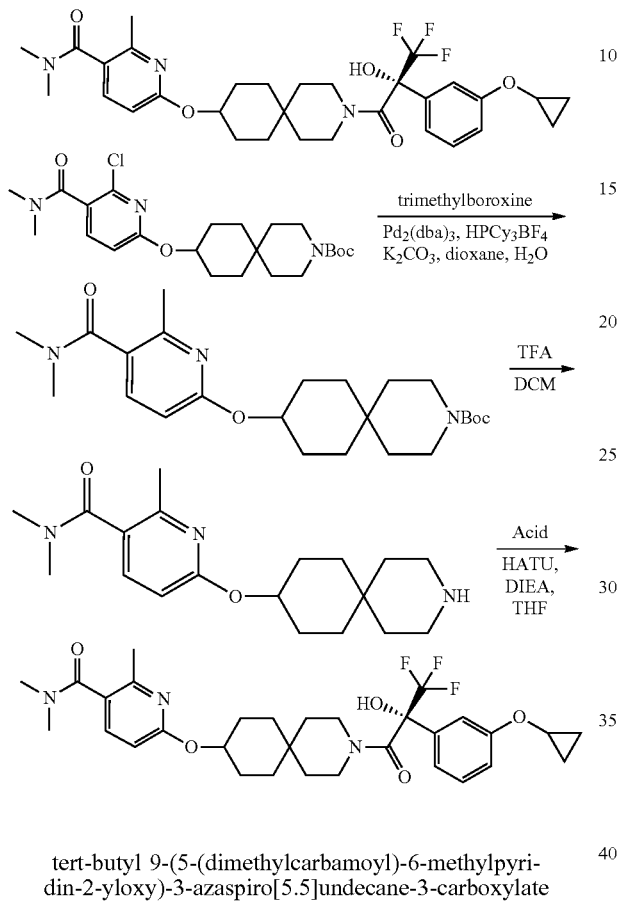

tert-butyl 9-(5-(dimethylcarbamoyl)-6-methylpyridin-2-yloxy)-3-azaspiro[5.5]undecane-3-carboxylate The degassed mixture of tert-butyl 9-((6-chloro-5-(dimethylcarbamoyl)pyridin-2-yl)oxy)-3-azaspiro[5.5]undecane-3-carboxylate (113 mg, 0.230 mmol, 1.0 eq), 2,4,6-trimethyl-1,3,5,2,4,6-trioxatriborinane (61 mg, 0.486 mmol, 2.1 eq), tris(dibenzylideneacetone)dipalladium(0) (42 mg, 0.046 mmol, 0.2 eq), tricyclohexylphosphonium tetrafluoroborate (34 mg, 0.092 mmol, 0.4 eq), and potassium carbonate (48 mg, 0.347 mmol, 1.5 eq) in water (1.0 mL) and 1,4-dioxane (6.0 mL) was heated to 90° C. under nitrogen atmosphere for 18 h. The reaction mixture was cooled, diluted with EtOAc (100 mL), washed with water (5×9 mL) and brine (9 mL), dried over anhydrous sodium sulfate, filtered and the solvent was evaporated under reduced pressure, which was purified by Prep-TLC (silica gel, PE/EtOAc=1/3) to afford the product. The product was further purified by Reverse phase HPLC (mobile phase: acetonitrile/water (10 mM $NH_4HCO_3$)) to afford tert-butyl 9-(5-(dimethylcarbamoyl)-6-methylpyridin-2-yloxy)-3-azaspiro[5.5]undecane-3-carboxylate. LRMS m/z (M+H) 432.3 found, 432.3 required.

6-(3-azaspiro[5.5]undecan-9-yloxy)-N,N,2-trimethylnicotinamide TFA salt

To a solution of tert-butyl 9-(5-(dimethylcarbamoyl)-6-methylpyridin-2-yloxy)-3-azaspiro[5.5]undecane-3-carboxylate (30 mg, 0.070 mmol, 1.0 eq) in DCM (1.5 mL) was added TFA (0.5 mL, 6.49 mmol, 93.3 eq). The mixture was stirred for 2 h and concentrated to afford 6-(3-azaspiro[5.5]undecan-9-yloxy)-N,N,2-trimethylnicotinamide TFA salt (34 mg) which was used in the next step without further purification. LRMS m/z (M+H) 332.3 found, 332.2 required.

(R or S)-6-((3-(2-(3-cyclopropoxyphenyl)-3,3,3-trifluoro-2-hydroxypropanoyl)-3-azaspiro[5.5]undecan-9-yl)oxy)-N,N,2-trimethylnicotinamide To a solution of 6-(3-azaspiro[5.5]undecan-9-yloxy)-N,N,2-trimethylnicotinamide TFA salt (23 mg, 0.05 mmol, 1.0 eq), (R or S)-2-(3-cyclopropoxyphenyl)-3,3,3-trifluoro-2-hydroxypropanoic acid (10 mg, 0.036 mmol, 1.0 eq), and HATU (40 mg, 0.036 mmol, 1.5 eq) in THF (5 mL) was added DIEA (0.06 mL, 0.344 mmol, 9.9 eq) at ambient temperature. The resulting mixture was stirred at 30° C. for 17 h and filtered. The filtrate was purified by reverse phase HPLC (mobile phase: methanol/water (10 mM $NH_4HCO_3$)) to afford (R or S)-6-((3-(2-(3-cyclopropoxyphenyl)-3,3,3-trifluoro-2-hydroxypropanoyl)-3-azaspiro[5.5]undecan-9-yl)oxy)-N,N,2-trimethylnicotinamide. LRMS m/z (M+H) 590.3 found, 590.3 required.

Example 3-1

2-chloro-4-(3-(1-(2,5-difluorobenzoyl)piperidin-4-yl)propoxy)-N,N-dimethylbenzamide

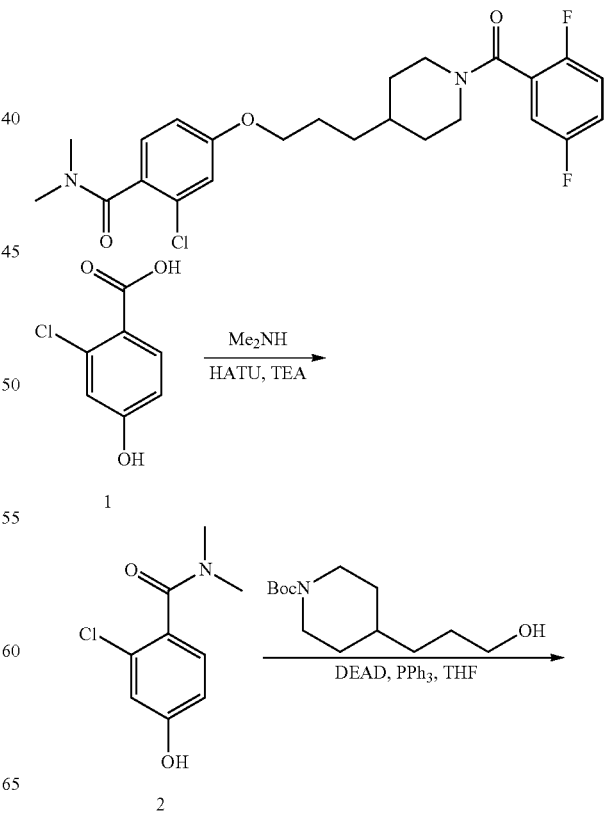

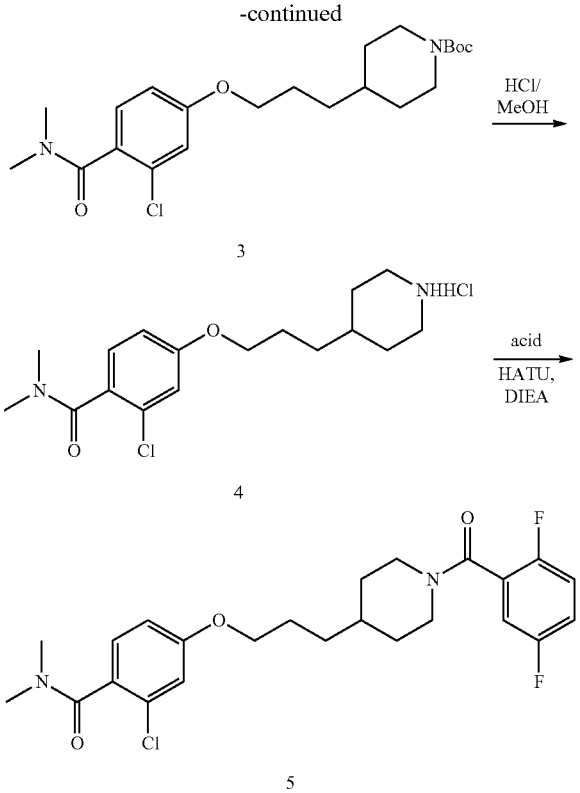

2-chloro-4-hydroxy-N,N-dimethylbenzamide

A mixture of 2-chloro-4-hydroxybenzoic acid (2.0 g, 11.59 mmol, 1.0 eq), dimethylamine (11.59 mL, 23.18 mmol, 2M in THF, 2.0 eq), HATU (6.61 g, 17.38 mmol, 1.5 eq) and triethylamine (2.35 g, 23.18 mmol, 2.0 eq) in anhydrous THF (20 mL) was stirred at rt overnight. The mixture was concentrated in vacuum. The residue was purified by column chromatography (silica gel: 300-400 mesh, PE/EtOAc=5/1 to 2/1) to give pure 2-chloro-4-hydroxy-N,N-dimethylbenzamide. LRMS m/z (M+H) 200.1 found, 200.0 required.

tert-butyl 4-(3-(3-chloro-4-(dimethylcarbamoyl)phenoxy)propyl)piperidine-1-carboxylate To a solution of 2-chloro-4-hydroxy-N,N-dimethylbenzamide (1.3 g, 6.53 mmol, 1.1 eq) in anhydrous THF (100 mL) was added tert-butyl 4-(3-hydroxypropyl)piperidine-1-carboxylate (1.44 g, 5.94 mmol, 1.0 eq) and PPh₃ (1.86 g, 7.1 mmol, 1.2 eq) at rt under N₂ atmosphere. The mixture was cooled to 0° C. and DEAD (1.24 g, 7.11 mmol, 1.2 eq) was added in dropwise. The resulting mixture was stirred at 0° C.~rt overnight. Water (25 mL) was added and the mixture was extracted with EtOAc (30 mL×5). The organic phases were combined, washed with brine (40 mL), dried over anhydrous Na₂SO₄, filtered and concentrated in vacuo to afford the crude product, which was purified by column chromatography (silica gel: 200-300 mesh, PE/EtOAc=20/1 to 10/1) to give pure tert-butyl 4-(3-(3-chloro-4-(dimethylcarbamoyl)phenoxy)propyl)piperidine-1-carboxylate. LRMS m/z (M+H) 425.2 found, 425.2 required.

2-chloro-N,N-dimethyl-4-(3-(piperidin-4-yl)propoxy)benzamide hydrochloride

A mixture of tert-butyl 4-(3-(3-chloro-4-(dimethylcarbamoyl)phenoxy)propyl)piperidine-1-carboxylate (1.3 g, 3.07 mmol, 1.0 eq) and 4M HCl/MeOH (60 mL) was stirred at rt for 1 h. The mixture was concentrated in vacuo to afford 2-chloro-N,N-dimethyl-4-(3-(piperidin-4-yl)propoxy)benzamide hydrochloride. LRMS m/z (M+H) 325.2 found, 325.2 required.

2-chloro-4-(3-(1-(2,5-difluorobenzoyl)piperidin-4-yl)propoxy)-N,N-dimethylbenzamide A mixture of 2-chloro-N,N-dimethyl-4-(3-(piperidin-4-yl)propoxy)benzamide hydrochloride (100 mg, 0.307 mmol, 1.0 eq), 2,5-difluorobenzoic acid (53 mg, 0.338 mmol, 1.1 eq), HATU (175 mg, 0.46 mmol, 1.5 eq) and DIEA (119 mg, 0.92 mmol, 3.0 eq) in anhydrous THF (3.0 mL) was stirred at rt overnight. The mixture was purified directly by reverse phase chromatography (Mobile phase: methanol/water (10 mM NH₄HCO₃)) to give pure 2-chloro-4-(3-(1-(2,5-difluorobenzoyl)piperidin-4-yl)propoxy)-N,N-dimethylbenzamide. LRMS m/z (M+H) 465.1 found, 465.2 required.

Using the same procedure described in example 3-1, but using the appropriate amines, amino-alcohols, and carboxylic acids, the following examples were prepared.

| Example | Structure | IUPAC Name | LRMS, found [M + H]+ |
|---|---|---|---|
| 3-2 | 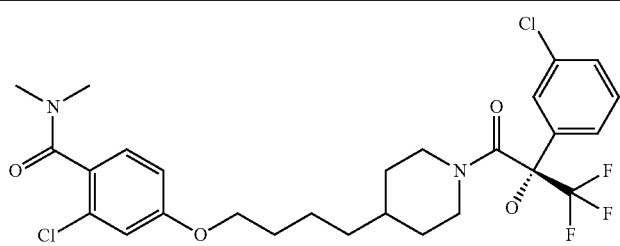 | (S or R)-2-chloro-4-(4-(1-(2-(3-chlorophenyl)-3,3,3-trifluoro-2-hydroxypropanoyl)piperidin-4-yl)butoxy)-N,N-dimethylbenzamide | 575.1 |

-continued

| Example | Structure | IUPAC Name | LRMS, found [M + H]+ |
|---|---|---|---|
| 3-3 | 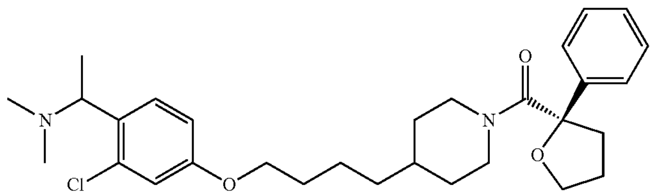 [SMILES: CC(c1ccc(OCCCCC2CCN(C(=O)[C@]3(c4ccccc4)CCCO3)CC2)cc1Cl)N(C)C] | (R or S)-2-chloro-N,N-dimethyl-4-(4-(1-(2-phenyl-tetrahydrofuran-2-carbonyl)piperidin-4-yl)butoxy)benzamide | 513.2 |
| 3-4 | 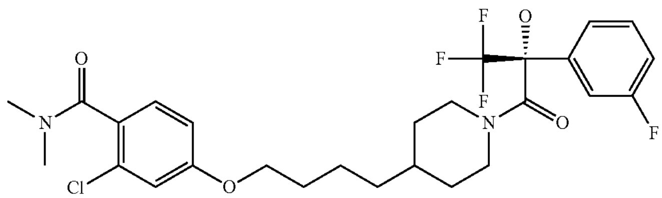 [SMILES: CN(C)C(=O)c1ccc(OCCCCC2CCN(C(=O)[C@](O)(c3cccc(F)c3)C(F)(F)F)CC2)cc1Cl] | (R or S)-2-chloro-N,N-dimethyl-4-(4-(1-(3,3,3-trifluoro-2-(3-fluorophenyl)-2-hydroxypropanoyl)piperidin-4-yl)butoxy)benzamide | 559.2 |
| 3-5 | 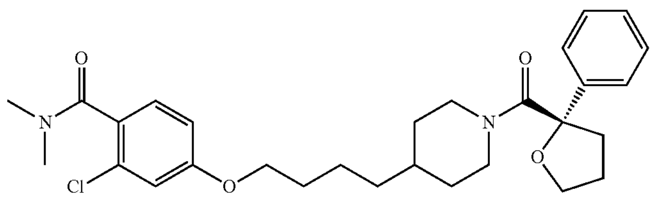 [SMILES: CN(C)C(=O)c1ccc(OCCCCC2CCN(C(=O)[C@@]3(c4ccccc4)CCCO3)CC2)cc1Cl] | (S or R)-2-chloro-N,N-dimethyl-4-(4-(1-(2-phenyl-tetrahydrofuran-2-carbonyl)piperidin-4-yl)butoxy)benzamide | 513.2 |
| 3-6 | 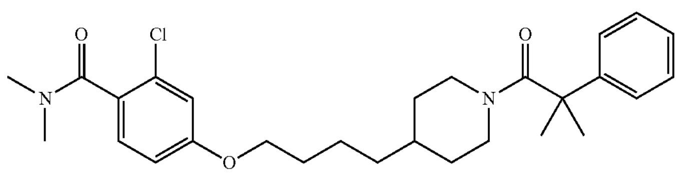 [SMILES: CN(C)C(=O)c1ccc(OCCCCC2CCN(C(=O)C(C)(C)c3ccccc3)CC2)cc1Cl] | 2-chloro-N,N-dimethyl-4-(4-(1-(2-methyl-2-phenylpropanoyl)piperidin-4-yl)butoxy)benzamide | 485.1 |
| 3-7 | 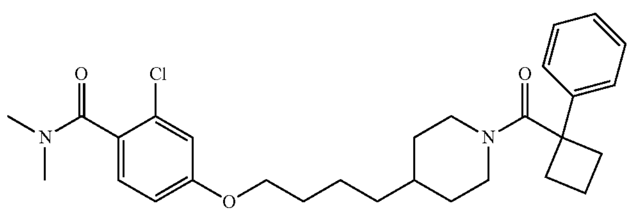 [SMILES: CN(C)C(=O)c1ccc(OCCCCC2CCN(C(=O)C3(c4ccccc4)CCC3)CC2)cc1Cl] | 2-chloro-N,N-dimethyl-4-(4-(1-(1-phenylcyclobutanecarbonyl)piperidin-4-yl)butoxy)benzamide | 497.1 |
| 3-8 | 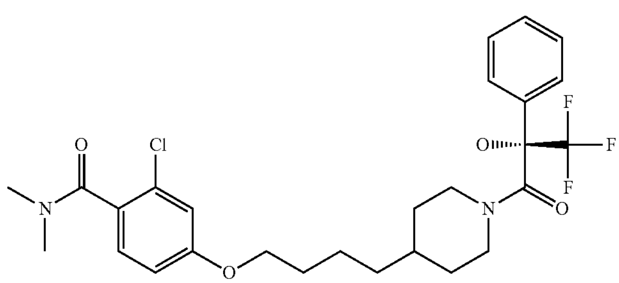 | 2-chloro-N,N-dimethyl-4-(4-(1-(3,3,3-trifluoro-2-hydroxy-2-phenylpropanoyl)piperidin-4-yl)butoxy)benzamide | 541.1 |
| 3-9 | 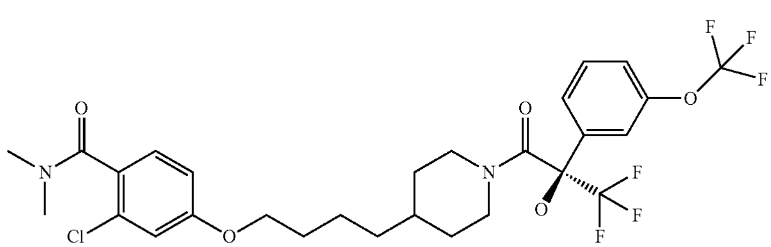 [SMILES: CN(C)C(=O)c1ccc(OCCCCC2CCN(C(=O)[C@](O)(c3cccc(OC(F)(F)F)c3)C(F)(F)F)CC2)cc1Cl] | (R or S)-2-chloro-N,N-dimethyl-4-(4-(1-(3,3,3-trifluoro-2-hydroxy-2-(3-(trifluoromethoxy)phenyl)propanoyl)piperidin-4-yl)butoxy)benzamide | 625.1 |

-continued

| Example | Structure | IUPAC Name | LRMS, found [M + H]+ |
|---|---|---|---|
| 3-10 | 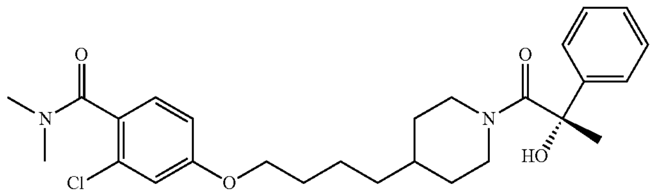 [SMILES: CN(C)C(=O)c1ccc(OCCCCC2CCN(C(=O)[C@@](C)(O)c3ccccc3)CC2)cc1Cl] | (S or R)-2-chloro-4-(4-(1-(2-hydroxy-2-phenylpropanoyl)piperidin-4-yl)butoxy)-N,N-dimethylbenzamide | 487.1 |
| 3-11 | 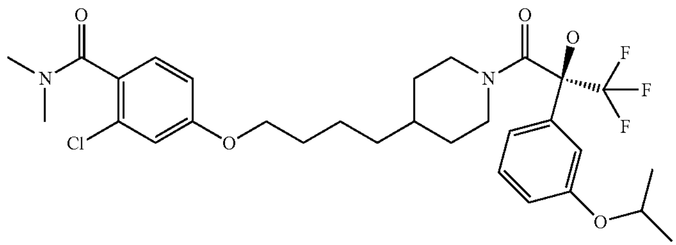 [SMILES: CC(C)Oc1cccc([C@](O)(C(=O)N2CCC(CCCCOc3ccc(C(=O)N(C)C)c(Cl)c3)CC2)C(F)(F)F)c1] | (S or R)-2-chloro-N,N-dimethyl-4-(4-(1-(3,3,3-trifluoro-2-hydroxy-2-(3-isopropoxyphenyl)propanoyl)piperidin-4-yl)butoxy)benzamide | 599.1 |
| 3-12 | 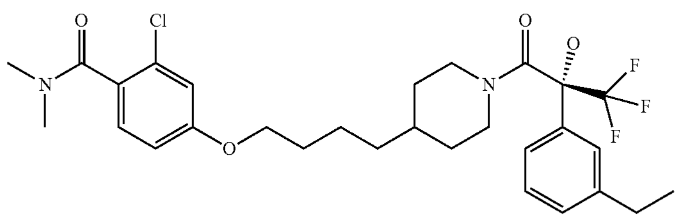 [SMILES: CCc1cccc([C@@](O)(C(=O)N2CCC(CCCCOc3ccc(C(=O)N(C)C)c(Cl)c3)CC2)C(F)(F)F)c1] | (R or S)-2-chloro-4-(4-(1-(2-(3-ethylphenyl)-3,3,3-trifluoro-2-hydroxypropanoyl)piperidin-4-yl)butoxy)-N,N-dimethylbenzamide | 569.1 |
| 3-13 | 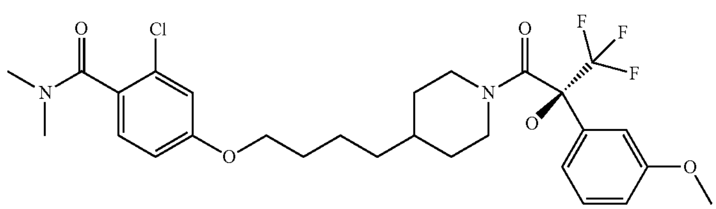 | (S or R)-2-chloro-N,N-dimethyl-4-(4-(1-(3,3,3-trifluoro-2-hydroxy-2-(3-methoxyphenyl)propanoyl)piperidin-4-yl)butoxy)benzamide | 571.1 |
| 3-14 | 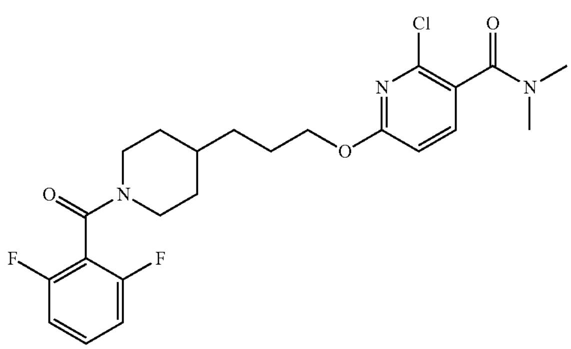 [SMILES: CN(C)C(=O)c1ccc(OCCCC2CCN(C(=O)c3c(F)cccc3F)CC2)nc1Cl] | 2-chloro-6-(3-(1-(2,6-difluorobenzoyl)piperidin-4-yl)propoxy)-N,N-dimethylnicotinamide | 486.1 |
| 3-15 | 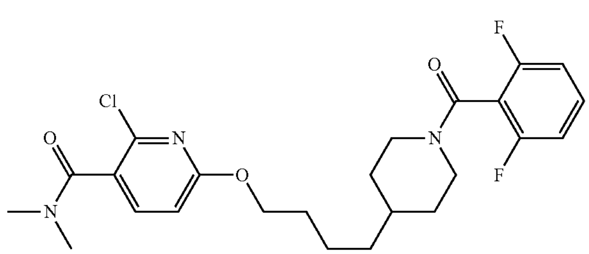 [SMILES: CN(C)C(=O)c1ccc(OCCCCC2CCN(C(=O)c3c(F)cccc3F)CC2)nc1Cl] | 2-chloro-6-(4-(1-(2,6-difluorobenzoyl)piperidin-4-yl)butoxy)-N,N-dimethylnicotinamide | 480.1 |

-continued

| Example | Structure | IUPAC Name | LRMS, found [M + H]+ |
|---|---|---|---|
| 3-16 | 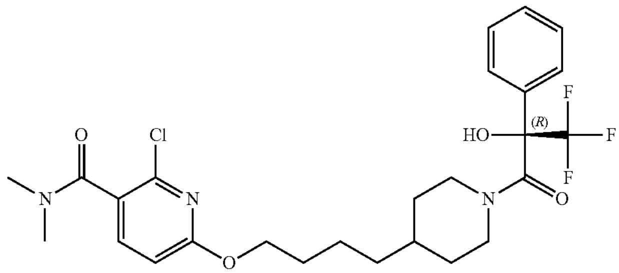 | (R or S)-2-chloro-N,N-dimethyl-6-(4-(1-(3,3,3-trifluoro-2-hydroxy-2-phenylpropanoyl)piperidin-4-yl)butoxy)nicotinamide | 542.2 |
| 3-17 | 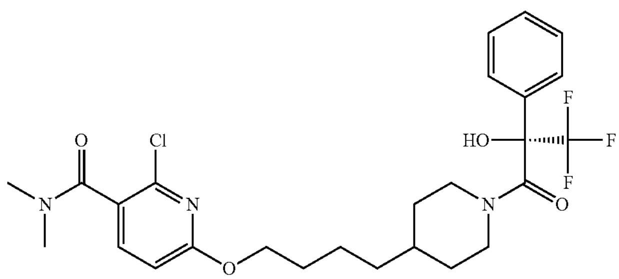 [SMILES: CN(C)C(=O)c1ccc(OCCCCC2CCN(C(=O)[C@@](O)(c3ccccc3)C(F)(F)F)CC2)nc1Cl] | (S or R)-2-chloro-N,N-dimethyl-6-(4-(1-(3,3,3-trifluoro-2-hydroxy-2-phenylpropanoyl)piperidin-4-yl)butoxy)nicotinamide | 542.2 |
| 3-18 | 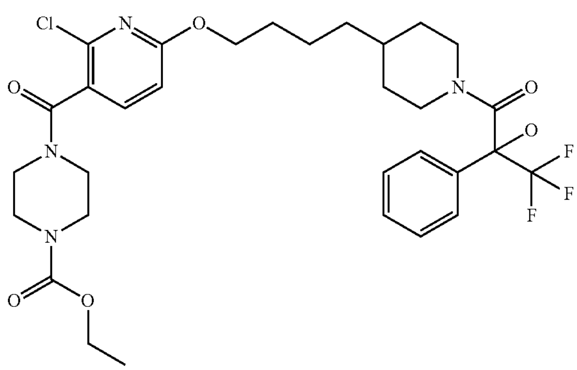 [SMILES: CCOC(=O)N1CCN(C(=O)c2ccc(OCCCCC3CCN(C(=O)C(O)(c4ccccc4)C(F)(F)F)CC3)nc2Cl)CC1] | ethyl 4-(2-chloro-6-(4-(1-(3,3,3-trifluoro-2-hydroxy-2-phenylpropanoyl)piperidin-4-yl)butoxy)nicotinoyl)piperazine-1-carboxylate | 655.1 |
| 3-19 | 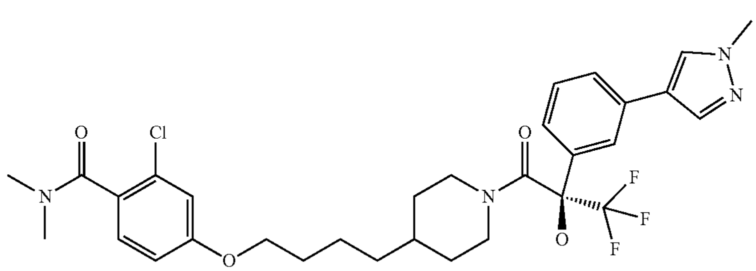 | (R or S)-2-chloro-N,N-dimethyl-4-(4-(1-(3,3,3-trifluoro-2-hydroxy-2-(3-(1-methyl-1H-pyrazol-4-yl)phenyl)propanoyl)piperidin-4-yl)butoxy)benzamide | 621.1 |

Example 3-20

2-Chloro-N,N-dimethyl-6-(3-{1-[(2R)-3,3,3-trifluoro-2-hydroxy-2-phenylpropanoyl]piperidin-4-yl}propoxy)pyridine-3-carboxamide

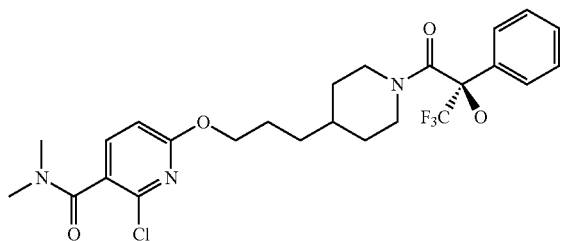 [SMILES: CN(C)C(=O)c1ccc(OCCCC2CCN(C(=O)[C@](O)(c3ccccc3)C(F)(F)F)CC2)nc1Cl]

2-chloro-6-methoxy-N,N-dimethylnicotinamide

To a suspension of 2-chloro-6-methoxynicotinic acid (0.50 Gm, 2.67 mmol), dimethylamine hydrochloride (0.26 Gm, 3.2 mmol), HBTU (1.21 Gm, 3.2 mmol) in dichloromethane (20 mL) was added DIPEA (1.40 mL, 8.0 mmol). The solution was room temperature for 3 hr. The reaction was concentrated under reduced pressure and purified by silica gel chromatography to provide 2-chloro-6-methoxy-N,N'-dimethylnicotinamide. LCMS [M]$^+$=215.0

2-chloro-6-hydroxy-N,N-dimethylnicotinamide

To a 0° solution of 2-chloro-6-methoxy-N,N'-dimethylnicotinamide (0.43 Gm, 0.83 mmol) in dichloromethane (20 mL) was added boron trifluoride methyl sulfide complex (0.38 mL, 3.56 mmol). The reaction was allowed to warm to room temperature and stirred for 16 hr. The reaction was quenched by the addition of water (5 mL) and methanol (15 mL) and nitrogen was bubbled through the solution for 15 minutes to remove excess dimethyl sulfide. The reaction mixture was extracted with EtOAc (3×15 mL) and the organic layers dried over MgSO4. The reaction was purified by silica gel chromatography (40 Gm, 0-100% ethyl acetate/hexanes gradient) to provide 2-chloro-6-hydroxy-N,N'-dimethylnicotinamide. LCMS [M]$^+$=214.99 benzyl 4-(3-((6-chloro-5-(dimethylcarbamoyl)pyridin-2-yl)oxy)propyl)piperidine-1-carboxylate To a solution of 2-chloro-6-hydroxy-N,N'-dimethylnicotinamide (0.029 Gm, 0.145 mmol), benzyl 4-(3-hydroxypropyl)piperidine-1-carboxylate (0.04 Gm, 0.14 mmol) and triphenylphosphine (0.45 Gm, 0.17 mmol) in toluene (15 mL) was added DIAD (0.034 mL, 0.017 mmol). The reaction was stirred at for 72 hours at room temperature. The reaction was concentrated under reduced pressure and purified by reverse phase HPLC (35%-95% gradient) to provide benzyl 4-(-((6-chloro-5-(dimethylcarbamoyl)pyridin-2-yl)oxy)propyl)piperidine-1-carboxylate. LCMS [M+H]$^+$=460.1

2-chloro-N,N-dimethyl-6-(3-(piperidin-4-yl)propoxy)nicotinamide-trifluoroacetate Benzyl 4-(-((6-chloro-5-(dimethylcarbamoyl)pyridin-2-yl)oxy)propyl)piperidine-1-carboxylate (0.59 Gm, 0.13 mmol) was dissolved in TFA (5 mL). The solution was heated to 50° C. for 40 min. The reaction was concentrated under reduced pressure to provide 2-chloro-N,N'-dimethyl-6-(3-(piperidin-4-yl)propoxy)nicotinamide-trifluoroacetate which was used directly without further purification. LCMS [M+H]$^+$=326.2

2-Chloro-N,N-dimethyl-6-(3-{1-[(2R)-3,3,3-trifluoro-2-hydroxy-2-phenylpropanoyl]piperidin-4-yl}propoxy)pyridine-3-carboxamide To a solution of 2-chloro-N,N'-dimethyl-6-(3-(piperidin-4-yl)propoxy)nicotinamide (0.56 g, 0.13 mmol), (R or S)-3,3,3-trifluoro-2-hydroxy-2-phenylpropanoic acid (0.03 Gm, 0.14 mmol), HBTU (0.058 Gm, 0.15 mmol) in dichloromethane (5 mL) was added DIPEA (0.11 mL, 0.64 mmol). The reaction was stirred for 16 h at room temperature. The reaction was concentrated under reduced pressure and purified by reverse phase HPLC (35%-95% gradient) to provide 2-chloro-N,N-dimethyl-6-(3-{1-[(2R)-3,3,3-trifluoro-2-hydroxy-2-phenylpropanoyl]piperidin-4-yl}propoxy)pyridine-3-carboxamide. LCMS [M+H]$^+$=528.1. $^1$H NMR (400 MHz, CDCl$_3$) δ 7.52 (d, J=8.3 Hz, 1H), 7.43-7.27 (m, 5H), 6.66 (d, J=8.2 Hz, 1H), 4.24 (m, 2H), 3.64-3.40 (m, 4H), 3.12 (s, 3H), 2.92 (s, 3H), 2.68 (t, J=13 Hz, 1H), 1.71-1.65 (m, 2H), 1.41 (m, 1H), 1.28-1.26 (m, 2H), 1.13 (m, 2H), 0.88-0.80 (m, 1H).

Using the procedure described in example 3-20, but replacing tert-butyl 4-(3-(3-chloro-4-(dimethylcarbamoyl)phenoxy)propyl)piperidine-1-carboxylate with tert-butyl 4-(4-(6-cyano-5-(dimethylcarbamoyl)pyridin-2-yloxy)butyl)piperidine-1-carboxylate (intermediate A-1) in the third step, and replacing 2,5-difluorobenzoic acid with the appropriate acid, the following compounds were prepared

| Example | Structure | IUPAC Name | LRMS, found [M + H]+ |
|---|---|---|---|
| 4-1 | 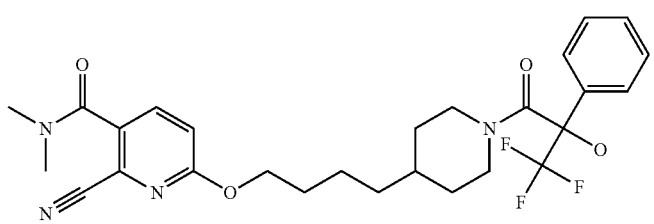 [SMILES: CN(C)C(=O)c1ccc(OCCCCC2CCN(C(=O)C(O)(c3ccccc3)C(F)(F)F)CC2)nc1C#N] | 2-cyano-N,N-dimethyl-6-(4-(1-(3,3,3-trifluoro-2-hydroxy-2-phenylpropanoyl)piperidin-4-yl)butoxy)nicotinamide | 533.1 |

| Example | Structure | IUPAC Name | LRMS, found [M + H]+ |
|---|---|---|---|
| 4-2 | 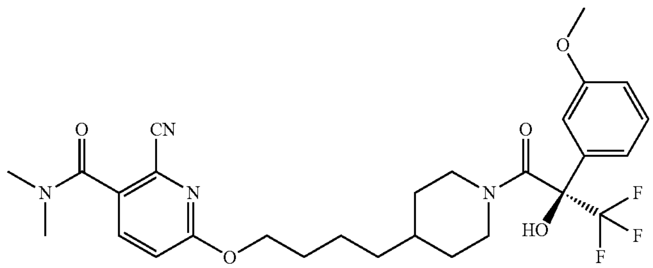 [SMILES: COc1cccc([C@@](O)(C(=O)N2CCC(CCCCOc3ccc(C(=O)N(C)C)c(C#N)n3)CC2)C(F)(F)F)c1] | (R or S)-2-cyano-N,N-dimethyl-6-(4-(1-(3,3,3-trifluoro-2-hydroxy-2-(3-methoxyphenyl)propanoyl)piperidin-4-yl)butoxy)nicotinamide | 563.1 |
Example 5-1
(R or S)-2-methoxy-N,N-dimethyl-4-(4-(1-(3,3,3-trifluoro-2-hydroxy-2-(3-methoxyphenyl)propanoyl)piperidin-4-yl)butoxy)benzamide
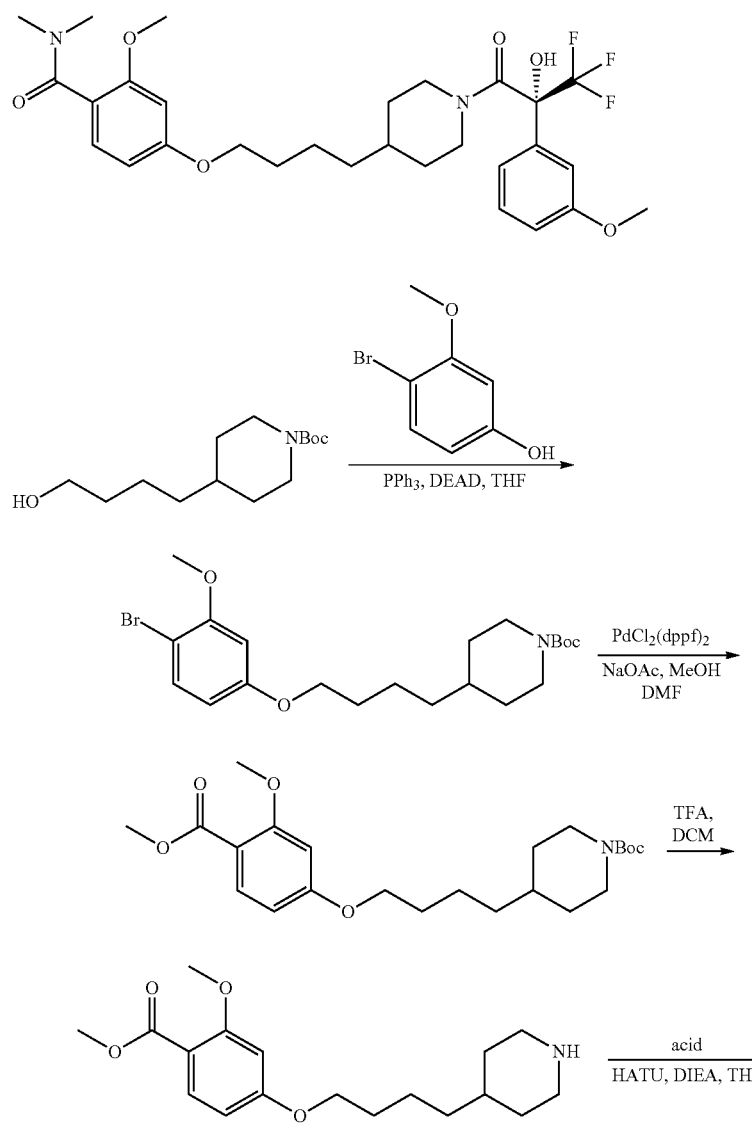

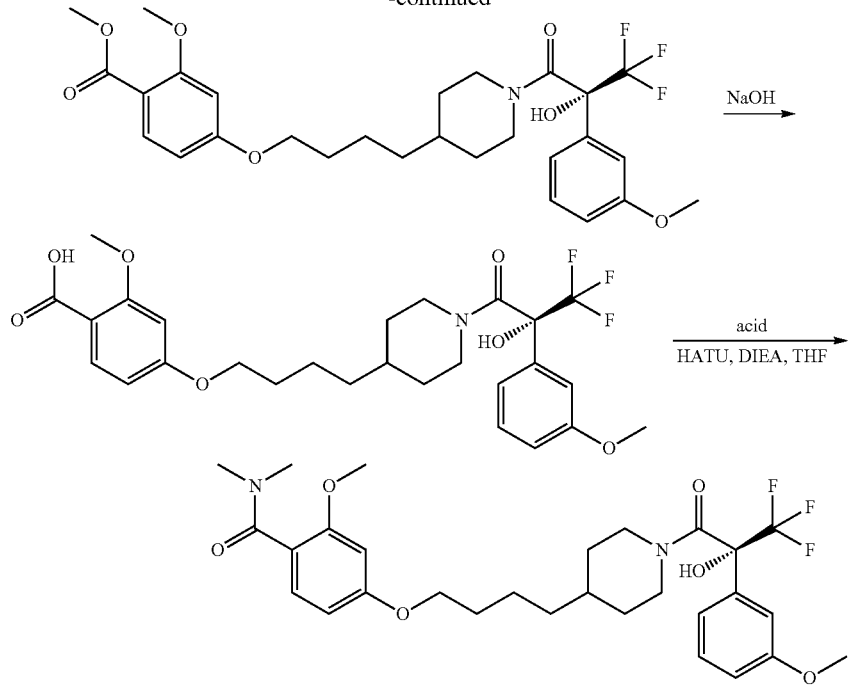

tert-butyl 4-(4-(4-bromo-3-methoxyphenoxy)butyl)piperidine-1-carboxylate

To a solution of tert-butyl 4-(4-hydroxybutyl)piperidine-1-carboxylate (550 mg, 2.1 mmol), 4-bromo-3-methoxyphenol (652 mg, 3.2 mmol) and PPh$_3$ (838 mg, 3.2 mmol) in anhydrous THF (10 mL) at rt under N$_2$ atmosphere was added DEAD (557 mg, 3.2 mmol). The resulting mixture was stirred at rt overnight. Water (25 mL) was added and the mixture was extracted with EtOAc (50 mL×5). The organic phases were combined, washed with brine (40 mL), dried over anhydrous Na$_2$SO$_4$, filtered and concentrated in vacuo to afford the crude product, which was purified by column chromatography (silica gel: 200-300 mesh, PE/EtOAc=20/1 to 10/1) to give tert-butyl 4-(4-(4-bromo-3-methoxyphenoxy)butyl)piperidine-1-carboxylate. LRMS m/z (M+H) 442.2 found, 442.2 required.

tert-butyl 4-(4-(3-methoxy-4-(methoxycarbonyl)phenoxy)butyl)piperidine-1-carboxylate A mixture of tert-butyl 4-(4-(4-bromo-3-methoxyphenoxy)butyl)piperidine-1-carboxylate (600 mg, 1.36 mmol), Pd(dppf)Cl$_2$ (995 mg, 1.36 mmol) and sodium acetate (669 mg, 8.2 mmol) in MeOH (10 mL) and DMF (1.0 mL) was degassed and backfilled with CO balloon (three times). The mixture was heated to 80° C. under CO balloon for 3d and poured into water (30 mL), extracted with EtOAc (100 mL*3). The organic layer was washed with brine (50 mL), dried over anhydrous Na$_2$SO$_4$, filtered and concentrated. The residue was purified by column chromatograph (silica gel, 200-300 meshes) eluting with PE/EtOAc=3/1 to give tert-butyl 4-(4-(3-methoxy-4-(methoxycarbonyl)phenoxy)butyl)piperidine-1-carboxylate. LRMS m/z (M+H) 422.3 found, 422.2 required.

methyl 2-methoxy-4-(4-(piperidin-4-yl)butoxy)benzoate

A mixture of tert-butyl 4-(4-(3-methoxy-4-(methoxycarbonyl)phenoxy)butyl)piperidine-1-carboxylate (86 mg, 0.2 mmol) and TFA (0.5 mL) in DCM (2 mL) was stirred at rt for 2 h. The mixture was basified with 1N NaOH and extracted with EtOAc (50 mL*3). The organic layer was washed with brine (50 mL), dried over anhydrous Na$_2$SO$_4$, filtered and concentrated in vacuo to give crude methyl 2-methoxy-4-(4-(piperidin-4-yl)butoxy)benzoate. LRMS m/z (M+H) 322.1 found, 322.2 required.

(R or S)-methyl 2-methoxy-4-(4-(1-(3,3,3-trifluoro-2-hydroxy-2-(3-methoxyphenyl)propanoyl)piperidin-4-yl)butoxy)benzoate A mixture of crude methyl 2-methoxy-4-(4-(piperidin-4-yl)butoxy)benzoate (60 mg, 0.18 mmol), (R or S)-3,3,3-trifluoro-2-hydroxy-2-(3-methoxyphenyl)propanoic acid (47 mg, 0.19 mmol), HATU (103 mg, 0.27 mmol) and DIEA (70 mg, 0.54 mmol) in anhydrous THF (3.0 mL) was stirred at rt overnight. The mixture was purified directly by reverse phase chromatography (Mobile phase: methanol/water (10 mM NH$_4$HCO$_3$)) to give (R or S)-methyl 2-methoxy-4-(4-(1-(3,3,3-trifluoro-2-hydroxy-2-(3-methoxyphenyl)propanoyl)piperidin-4-yl)butoxy)benzoate. LRMS m/z (M+H) 554.1 found, 554.2 required.

(R or S)-2-methoxy-4-(4-(1-(3,3,3-trifluoro-2-hydroxy-2-(3-methoxyphenyl)propanoyl)piperidin-4-yl)butoxy)benzoic acid A mixture of (R or S)-methyl 2-methoxy-4-(4-(1-(3,3,3-trifluoro-2-hydroxy-2-(3-methoxyphenyl)propanoyl)piperidin-4-yl)butoxy)benzoate (73 mg, 0.13 mmol) and 2N NaOH (2 mL) in MeOH (2 mL) was stirred at rt overnight. The reaction mixture was acidified with 1N HCl to pH=6, extracted with EtOAc (50 mL*3). The organic layer was washed with brine (30 mL), dried over anhydrous Na₂SO₄, filtered and concentrated in vacuo to give crude (R or S)-2-methoxy-4-(4-(1-(3,3,3-trifluoro-2-hydroxy-2-(3-methoxyphenyl)propanoyl)piperidin-4-yl)butoxy)benzoic acid. LRMS m/z (M+H) 540.1 found, 540.2 required.

(R or S)-2-methoxy-N,N-dimethyl-4-(4-(1-(3,3,3-trifluoro-2-hydroxy-2-(3-methoxyphenyl)propanoyl) piperidin-4-yl)butoxy)benzamide A mixture of crude (R or S)-2-methoxy-4-(4-(1-(3,3,3-trifluoro-2-hydroxy-2-(3-methoxyphenyl)propanoyl)piperidin-4-yl)butoxy)benzoic acid (20 mg, 0.037 mmol), dimethylamine hydrochloride (6 mg, 0.074 mmol), HATU (28 mg, 0.074 mmol) and DIEA (14 mg, 0.11 mmol) in anhydrous THF (3.0 mL) was stirred at rt overnight. The mixture was purified directly by reverse phase chromatography (Mobile phase: methanol/water (10 mM NH₄HCO₃)) to give (R or S)-2-methoxy-N,N-dimethyl-4-(4-(1-(3,3,3-trifluoro-2-hydroxy-2-(3-methoxyphenyl)propanoyl)piperidin-4-yl)butoxy)benzamide. LRMS m/z (M+H) 567.2 found, 567.3 required.

Example 5-2

2-ethyl-N,N-dimethyl-6-(4-(1-(3,3,3-trifluoro-2-hydroxy-2-phenylpropanoyl)piperidin-4-yl)butoxyl) nicotinamide N,N-dimethyl-6-(4-(1-(3,3,3-trifluoro-2-hydroxy-2-phenylpropanoyl)piperidin-4-yl)butoxy)-2-vinylnicotinamide The degassed mixture of 2-chloro-N,N-dimethyl-6-(4-(1-(3,3,3-trifluoro-2-hydroxy-2-phenylpropanoyl)piperidin-4-yl)butoxy)nicotinamide (27 mg, 0.05 mmol), tributyl(vinyl)tin (19 mg, 0.06 mmol), and bis(tri-tert-butylphosphine) palladium(0) (4 mg, 0.008 mmol) in DMF (1 mL) was microwaved at 100° C. for 1 h. After being cooled to ambient temperature, the mixture was diluted with EtOAc (20 mL), washed with water (2×10 mL), brine (2×10 mL). The organic layer was dried over anhydrous Na₂SO₄, filtered and concentrated. The crude product was purified by chromatography (PE:EtOAc=1:1) to give N,N-dimethyl-6-(4-(1-(3,3,3-trifluoro-2-hydroxy-2-phenylpropanoyl)piperidin-4-yl)butoxy)-2-vinylnicotinamide. LRMS m/z (M+H) 534.0 found, 534.3 required.

2-ethyl-N,N-dimethyl-6-(4-(1-(3,3,3-trifluoro-2-hydroxy-2-phenylpropanoyl)piperidin-4-yl)butoxyl) nicotinamide A mixture of N,N-dimethyl-6-(4-(1-(3,3,3-trifluoro-2-hydroxy-2-phenylpropanoyl)piperidin-4-yl)butoxy)-2-vinylnicotinamide (25 mg, 0.047 mmol) and platinum(IV) oxide (1 mg, 0.002 mmol) in MeOH (2 mL) was degassed and backfilled with H₂ (three times). The mixture was stirred at rt for 12 h under hydrogen atmosphere by a hydrogen balloon. The catalyst was filtered off and the filtrate was concentrated to afford 2-ethyl-N,N-dimethyl-6-(4-(1-(3,3,3-

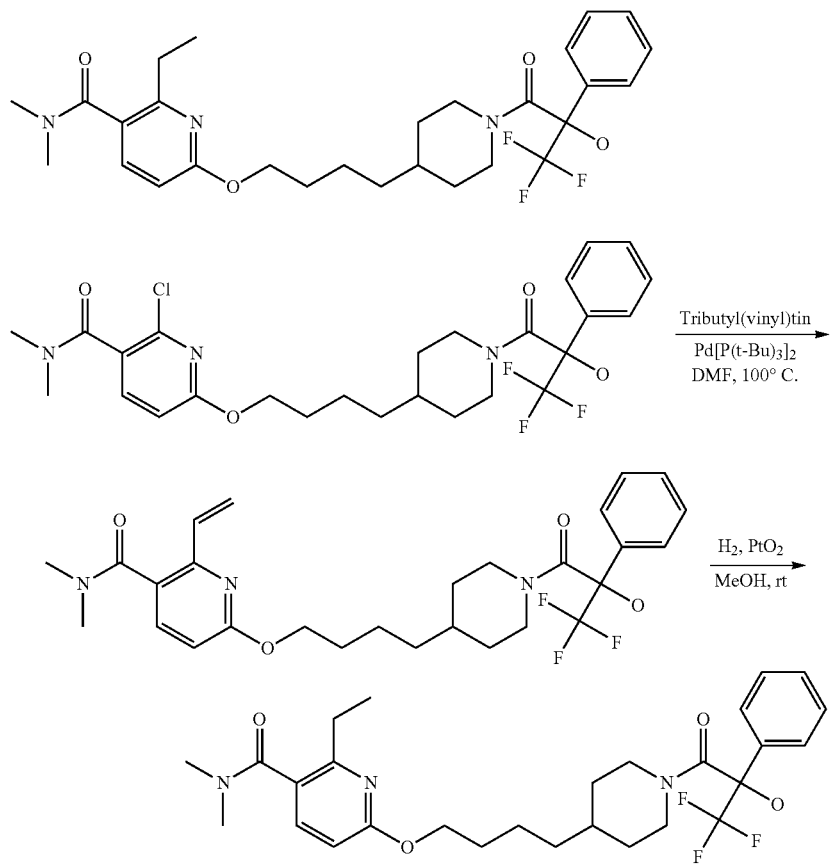

trifluoro-2-hydroxy-2-phenylpropanoyl)piperidin-4-yl)butoxy)nicotinamide. LRMS m/z (M+H) 536.0 found, 536.3 required.

Example 6-1

2-chloro-N,N-dimethyl-6-(4-(1-(3,3,3-trifluoro-2-hydroxy-2-(pyridin-2-yl)propanoyl)piperidin-4-yl)butoxy)nicotinamide

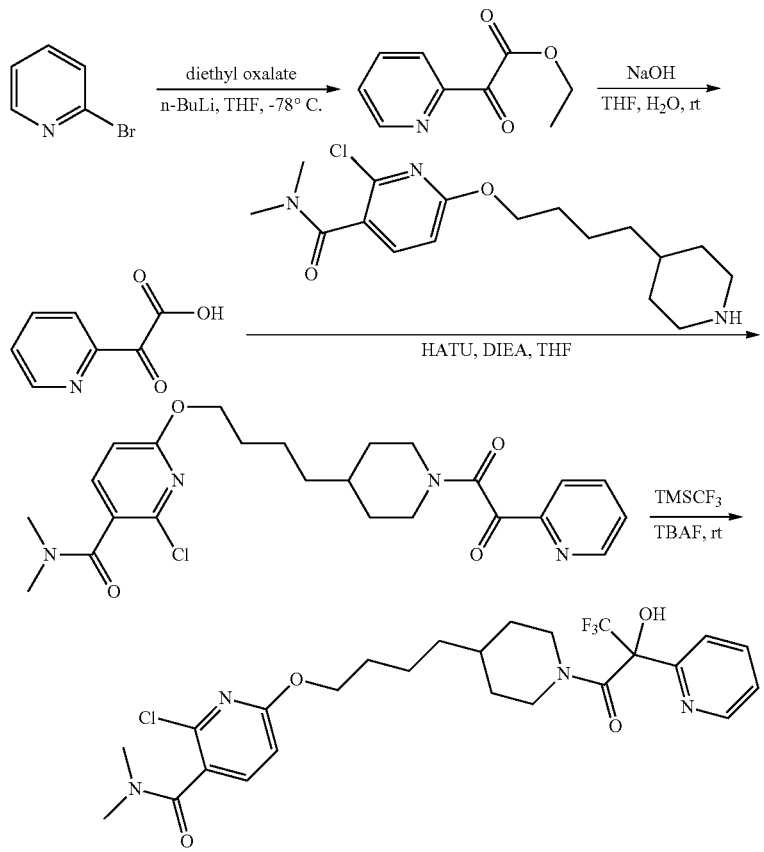

ethyl 2-oxo-2-(pyridin-2-yl)acetate

To a solution of 2-bromopyridine (500 mg, 3.16 mmol) in THF (5 mL) was added n-BuLi (2.4 mL, 3.84 mmol, 1.6M in hexane) at −78° C. under N₂. The mixture was stirred at −78° C. for 1 h. Then diethyl oxalate (560 mg, 3.84 mmol) was added. The resulting mixture was stirred at −78° C. to rt for 2 h and quenched by saturated ammonium chloride (10 mL), then extracted with EtOAc (100 mL), washed with water (20 mL), dried over anhydrous Na₂SO₄ and concentrated. The residue was purified by column chromatography (silica gel: 300-400 mesh, PE/EtOAc=8/1) to afford ethyl 2-oxo-2-(pyridin-2-yl)acetate. LRMS m/z (M+H) 180.1 found, 180.1 required

2-oxo-2-(pyridin-2-yl)acetic acid

To a solution of ethyl 2-oxo-2-(pyridin-2-yl)acetate (300 mg, 1.68 mmol) in THF (2 mL) and water (2 mL) was added NaOH (202 mg, 5.04 mmol). The mixture was stirred at rt overnight. Then the mixture was neutralized by conc. HCl and extracted with EtOAc (60 mL). The organic phase was washed with water (10 mL), dried over anhydrous Na₂SO₄ and concentrated in vacuo to afford 2-oxo-2-(pyridin-2-yl)acetic acid. LRMS m/z (M+H) 152.0 found, 152.0 required

2-chloro-N,N-dimethyl-6-(4-(1-(2-oxo-2-(pyridin-2-yl)acetyl)piperidin-4-yl)butoxy)nicotinamide To a solution of 2-oxo-2-(pyridin-2-yl)acetic acid (10 mg, 0.066 mmol) in THF (1 mL) was added 2-chloro-N,N-dimethyl-6-(4-(piperidin-4-yl)butoxy)nicotinamide (15 mg 0.044 mmol), DIEA (17 mg, 0.132 mmol) and HATU (25 mg, 0.066 mmol). The mixture was stirred at rt overnight. Then the mixture was directly purified by reverse phase chromatography (mobile phase: methanol/water (10 mM NH₄HCO₃) to afford 2-chloro-N,N-dimethyl-6-(4-(1-(2-oxo-2-(pyridin-2-yl)acetyl)piperidin-4-yl)butoxy)nicotinamide. LRMS m/z (M+H) 473.2 found, 473.2 required.

2-chloro-N,N-dimethyl-6-(4-(1-(3,3,3-trifluoro-2-hydroxy-2-(pyridin-2-yl)propanoyl)piperidin-4-yl)butoxy)nicotinamide To a solution of 22-chloro-N,N-dimethyl-6-(4-(1-(2-oxo-2-(pyridin-2-yl)acetyl)piperidin-4-yl)butoxy)nicotinamide (10 mg, 0.021 mmol) in THF (1 mL) was added TMSCF₃ (16 mg, 0.11 mmol). The mixture was stirred at rt for 1 h. Then TBAF (3 mg, 0.011 mmol) was added. The resulting mixture was stirred at rt overnight. Then the mixture was directly purified by reverse phase chromatography (mobile phase: methanol/water (10 mM NH₄HCO₃) to afford 2-chloro-N,N-dimethyl-6-(4-(1-(3,3,3-trifluoro-2-hydroxy-2-(pyridin-2-yl)propanoyl)piperidin-4-yl)butoxy)nicotinamide. LRMS m/z (M+H) 543.1 found, 543.2 required.

Using the same procedure described in example 6-1, but replacing 2-bromopyridine with the appropriate halo-pyridine, the following examples were prepared.

| Example | Structure | IUPAC Name | LRMS, found [M + H]+ |
|---|---|---|---|
| 6-2 | 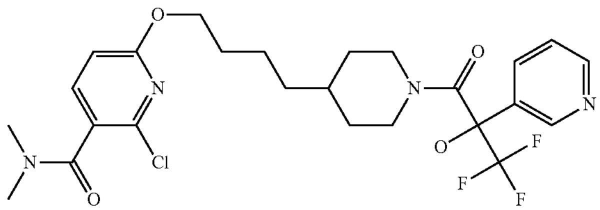 [SMILES: CN(C)C(=O)c1ccc(OCCCCC2CCN(C(=O)C(O)(c3cccnc3)C(F)(F)F)CC2)nc1Cl] | 2-chloro-N,N-dimethyl-6-(4-(1-(3,3,3-trifluoro-2-hydroxy-2-(pyridin-3-yl)propanoyl)piperidin-4-yl)butoxy)nicotinamide | 543.1 |

Example 7-1

2-chloro-N,N-dimethyl-6-(4-(1-(2-(trifluoromethyl)phenylsulfonyl)piperidin-4-yl)butoxy)nicotinamide

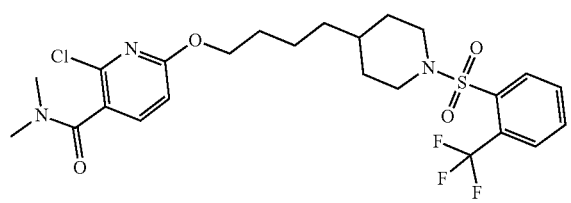 [SMILES: CN(C)C(=O)c1ccc(OCCCCC2CCN(S(=O)(=O)c3ccccc3C(F)(F)F)CC2)nc1Cl]

To a solution of 2-chloro-N,N-dimethyl-6-(4-(piperidin-4-yl)butoxy)nicotinamide (68 mg, 0.2 mmol) and TEA (20 mg, 0.2 mmol) in THF (2 mL) was added 2-(trifluoromethyl)benzene-1-sulfonyl chloride (96 mg, 0.39 mmol) at 0° C. The resulting mixture was stirred at rt overnight and quenched with methanol (0.1 mL). The mixture was concentrated and the residue was purified by reverse phase chromatography (mobile phase: methanol/water (10 mM NH$_4$HCO$_3$)) to afford 2-chloro-N,N-dimethyl-6-(4-(1-(2-(trifluoromethyl)phenylsulfonyl)piperidin-4-yl)butoxy)nicotinamide. LRMS m/z 548.1 found, 548.2 required.

Using the procedure described in example 7-1, but replacing 2-(trifluoromethyl)benzene-1-sulfonyl chloride with the appropriate sulfonyl chloride in the last step, the following examples were prepared.

| Example | Structure | IUPAC Name | Exact Mass [M + H]+ |
|---|---|---|---|
| 7-2 | 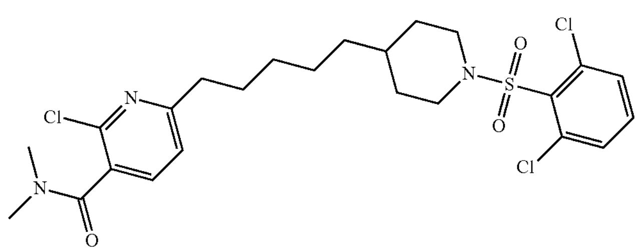 [SMILES: CN(C)C(=O)c1ccc(CCCCCC2CCN(S(=O)(=O)c3c(Cl)cccc3Cl)CC2)nc1Cl] | 2-chloro-6-(4-(1-(2,6-dichlorophenylsulfonyl)piperidin-4-yl)butoxy)-N,N-dimethylnicotinamide | 550.0 |
| 7-3 | 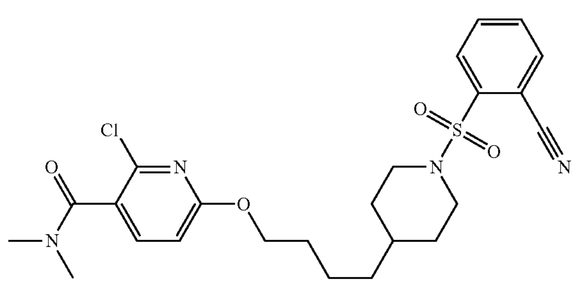 [SMILES: CN(C)C(=O)c1ccc(OCCCCC2CCN(S(=O)(=O)c3ccccc3C#N)CC2)nc1Cl] | 2-chloro-6-(4-(1-(2-cyanophenylsulfonyl)piperidin-4-yl)butoxy)-N,N-dimethylnicotinamide | 505.1 |

Example 8-1

(R or S)-1-(4-(4-(4-(azetidine-1-carbonyl)-3-chlorophenoxy)butyl)piperidin-1-yl)-3,3,3-trifluoro-2-hydroxy-2-phenylpropan-1-one

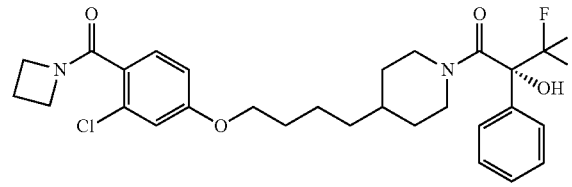

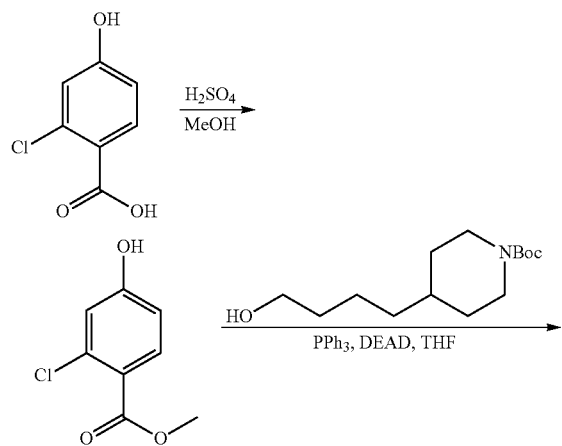

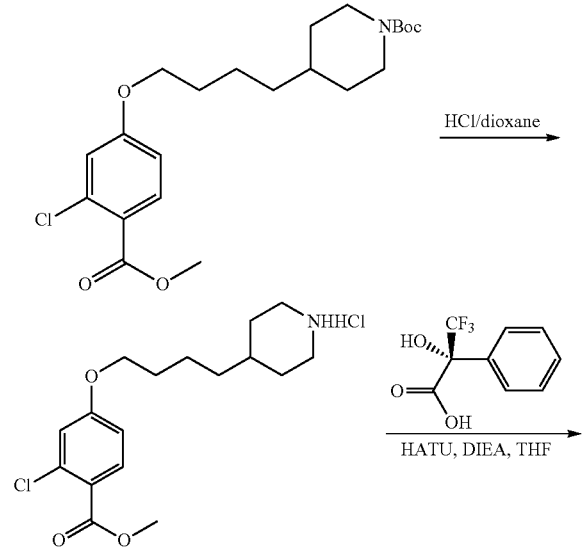

-continued

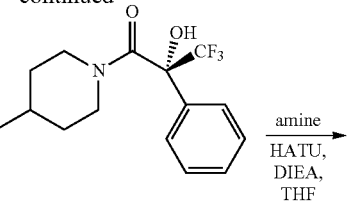

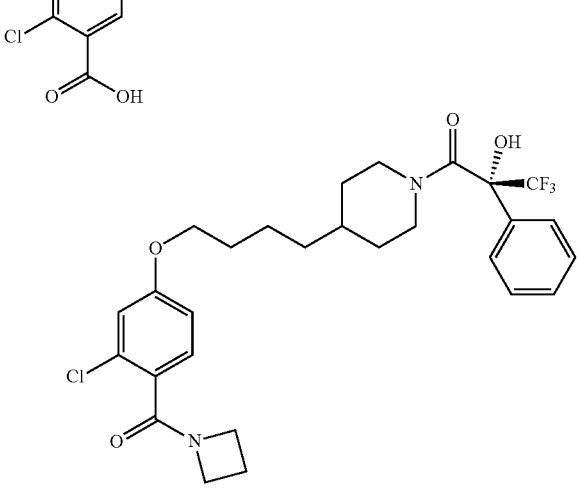

Methyl 2-chloro-4-hydroxybenzoate

To a solution of 2-chloro-4-hydroxybenzoic acid (2.5 g, 14.53 mmol, 1.0 eq) in MeOH (50 mL) was added conc. $H_2SO_4$ (8 mL) dropwise. The mixture was refluxed for 6 h. The solvent was removed under vacuum. Sat. $NaHCO_3$ (100 mL) was added and the reaction mixture was extracted with EtOAc (100 mL×5). The organic phases were combined, washed with brine (200 mL), dried over anhydrous $Na_2SO_4$, filtered and concentrated in vacuo to afford the crude product, which was purified by column chromatography (silica gel: 200-300 mesh, PE/EtOAc=8/1 to 5/1) to give methyl 2-chloro-4-hydroxybenzoate. LRMS m/z (M+H) 186.9 found, 187.0 required.

tert-butyl 4-(4-(3-chloro-4-(methoxycarbonyl)phenoxy)butyl)piperidine-1-carboxylat To a solution of tert-butyl 4-(4-hydroxybutyl)piperidine-1-carboxylate (3.39 g, 13.2 mmol, 1.0 eq) in anhydrous THF (100 mL) was added methyl 2-chloro-4-hydroxybenzoate (2.7 g, 14.52 mmol, 1.1 eq) and $PPh_3$ (5.18 g, 19.79 mmol, 1.5 eq) at rt under $N_2$ atmosphere. The mixture was cooled to 0° C. and DEAD (3.44 g, 19.79 mmol, 1.5 eq) was added dropwise at 0° C. The resulting mixture was stirred at 0° C.~rt overnight. The mixture was concentrated in vacuo and purified by column chromatography (silica gel: 200-300 mesh, PE/EtOAc=10/1) directly to give tert-butyl 4-(4-(3-chloro-4-(methoxycarbonyl)phenoxy)butyl)piperidine-1-carboxylate. LRMS m/z (M+H) 426.1 found, 426.2 required.

Methyl 2-chloro-4-(4-(piperidin-4-yl)butoxy)benzoate hydrochloride

A solution of tert-butyl 4-(4-(3-chloro-4-(methoxycarbonyl)phenoxy)butyl)piperidine-1-carboxylate (1.0 g, 2.35 mmol, 1.0 eq) in 4M HCl/1,4-dioxane (30 mL) was stirred at rt for 1 h. The mixture was concentrated in vacuo to afford methyl 2-chloro-4-(4-(piperidin-4-yl)butoxy)benzoate hydrochloride. LRMS m/z (M+H) 326.1 found, 326.1 required.

(R or S)-methyl 2-chloro-4-(4-(1-(3,3,3-trifluoro-2-hydroxy-2-phenylpropanoyl)piperidin-4-yl)butoxy)benzoate A mixture of methyl 2-chloro-4-(4-(piperidin-4-yl)butoxy)benzoate hydrochloride (550 mg, 1.52 mmol), (R or S)-3,3,3-trifluoro-2-hydroxy-2-phenylpropanoic acid (447 mg, 2.03 mmol), HATU (965 mg, 2.54 mmol) and DIEA (655 mg, 5.08 mmol) in anhydrous THF (20 mL) was stirred at rt overnight. The mixture was concentrated in vacuo and purified by column chromatography (silica gel: 200-300 mesh, PE/EtOAc=10/1) directly to give (R or S)-methyl 2-chloro-4-(4-(1-(3,3,3-trifluoro-2-hydroxy-2-phenylpropanoyl)piperidin-4-yl)butoxy)benzoate. LRMS m/z (M+H) 528.0 found, 528.2 required.

(R or S)-2-chloro-4-(4-(1-(3,3,3-trifluoro-2-hydroxy-2-phenylpropanoyl)piperidin-4-yl)butoxy)benzoic acid 0.3M NaOH (15 mL, 4.5 mmol, 4.0 eq) was added dropwise into a solution of (R or S)-methyl 2-chloro-4-(4-(1-(3,3,3-trifluoro-2-hydroxy-2-phenylpropanoyl)piperidin-4-yl)butoxy)benzoate (600 mg, 1.139 mmol, 1.0 eq) in THF (15 mL). The resulting mixture was stirred at rt overnight. The mixture was concentrated in vacuo, acidified with 1N HCl to pH=3 and extracted with DCM (50 mL×5). The organic phases were combined, washed with brine (100 mL), dried over anhydrous $Na_2SO_4$, filtered and concentrated in vacuo to give (R or S)-2-chloro-4-(4-(1-(3,3,3-trifluoro-2-hydroxy-2-phenylpropanoyl)piperidin-4-yl)butoxy)benzoic acid. LRMS m/z (M+H) 514.0 found, 514.2 required.

(R or S)-1-(4-(4-(4-(azetidine-1-carbonyl)-3-chlorophenoxy)butyl)piperidin-1-yl)-3,3,3-trifluoro-2-hydroxy-2-phenylpropan-1-one A mixture of (R or S)-2-chloro-4-(4-(1-(3,3,3-trifluoro-2-hydroxy-2-phenylpropanoyl)piperidin-4-yl)butoxy)benzoic acid (50 mg, 0.0973 mmol, 1.0 eq), methanamine hydrochloride (8 mg, 0.1167 mmol, 1.2 eq), HATU (55.4 mg, 0.1459 mmol, 1.5 eq) and DIEA (37.7 mg, 0.2919 mmol, 3.0 eq) in anhydrous THF (2.0 mL) was stirred at rt overnight. The mixture was purified directly by reverse phase chromatography (Mobile phase: methanol/water (10 mM $NH_4HCO_3$)) to give (R or S)-1-(4-(4-(4-(azetidine-1-carbonyl)-3-chlorophenoxy)butyl)piperidin-1-yl)-3,3,3-trifluoro-2-hydroxy-2-phenylpropan-1-one. LRMS m/z (M+H) 553.0 found, 553.2 required.

Using the same procedure described in example 8-1, but replacing azetidine with the appropriate amine in the final step, the following compound were prepared.

| Example | Structure | IUPAC Name | LRMS, found [M + H]+ |
|---|---|---|---|
| 8-2 | 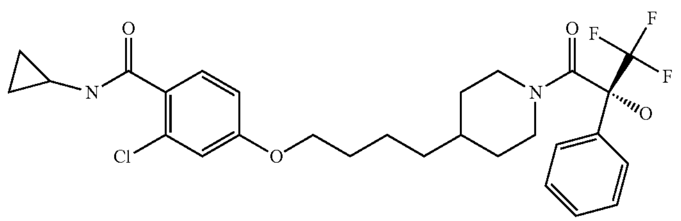 [SMILES: O=C(NC1CC1)c1ccc(OCCCCC2CCN(C(=O)[C@](O)(c3ccccc3)C(F)(F)F)CC2)cc1Cl] | (R or S)-2-chloro-N-cyclopropyl-4-(4-(1-(3,3,3-trifluoro-2-hydroxy-2-phenylpropanoyl)piperidin-4-yl)butoxy)benzamide | 553.3 |
| 8-3 | 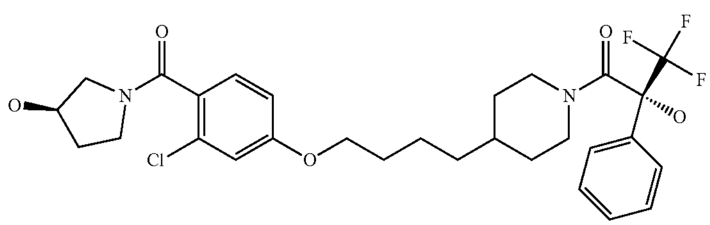 [SMILES: O=C(c1ccc(OCCCCC2CCN(C(=O)[C@](O)(c3ccccc3)C(F)(F)F)CC2)cc1Cl)N1CC[C@@H](O)C1] | (R or S)-1-(4-(4-(3-chloro-4-((R or S)-3-hydroxy-pyrrolidine-1-carbonyl)phenoxy)butyl)piperidin-1-yl)-3,3,3-trifluoro-2-hydroxy-2-phenylpropan-1-one | 583.3 |
| 8-4 | 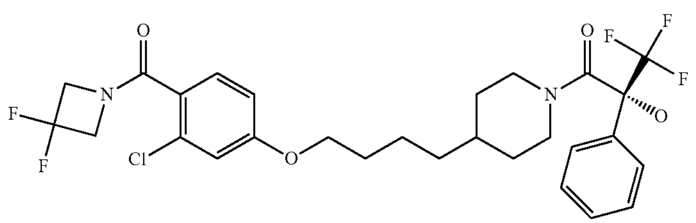 [SMILES: O=C(c1ccc(OCCCCC2CCN(C(=O)[C@](O)(c3ccccc3)C(F)(F)F)CC2)cc1Cl)N1CC(F)(F)C1] | (R or S)-1-(4-(4-(3-chloro-4-(3,3-difluoroazetidine-1-carbonyl)phenoxy)butyl)piperidin-1-yl)-3,3,3-trifluoro-2-hydroxy-2-phenylpropan-1-one | 589.3 |

| Example | Structure | IUPAC Name | LRMS, found [M + H]+ |
|---|---|---|---|
| 8-5 | 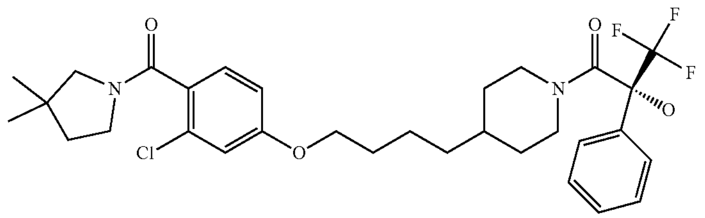 [SMILES: CC1(C)CCN(C(=O)c2ccc(OCCCCC3CCN(C(=O)[C@](O)(c4ccccc4)C(F)(F)F)CC3)cc2Cl)C1] | (R or S)-1-(4-(4-(3-chloro-4-(3,3-dimethyl-pyrrolidine-1-carbonyl)phenoxy)butyl)piperidin-1-yl)-3,3,3-trifluoro-2-hydroxy-2-phenylpropan-1-one | 595.2 |
| 8-6 | 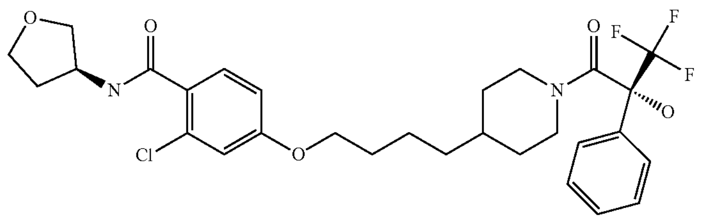 [SMILES: O=C(N[C@H]1CCOC1)c1ccc(OCCCCC2CCN(C(=O)[C@](O)(c3ccccc3)C(F)(F)F)CC2)cc1Cl] | 2-chloro-N-((S or R)-tetrahydrofuran-3-yl)-4-(4-(1-((R or S)-3,3,3-trifluoro-2-hydroxy-2-phenylpropanoyl)piperidin-4-yl)butoxy)benzamide | 583.3 |
| 8-7 | 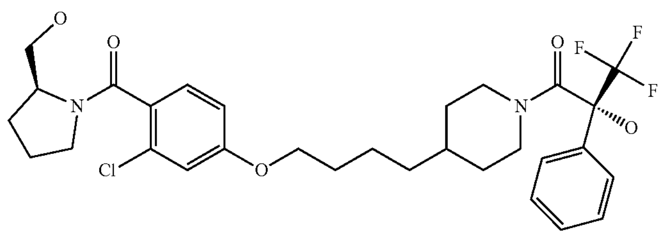 [SMILES: O=C(c1ccc(OCCCCC2CCN(C(=O)[C@](O)(c3ccccc3)C(F)(F)F)CC2)cc1Cl)N1CCC[C@H]1CO] | (R or S)-1-(4-(4-(3-chloro-4-((S or R)-2-(hydroxymethyl)pyrrolidine-1-carbonyl)phenoxy)butyl)piperidin-1-yl)-3,3,3-trifluoro-2-hydroxy-2-phenylpropan-1-one | 597.1 |
| 8-8 | 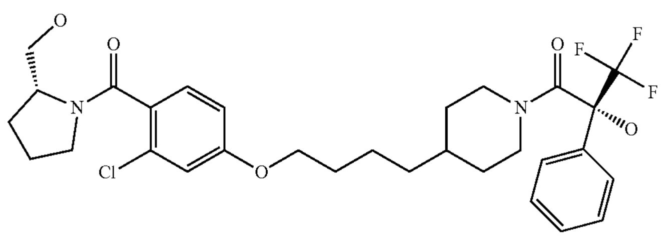 [SMILES: O=C(c1ccc(OCCCCC2CCN(C(=O)[C@](O)(c3ccccc3)C(F)(F)F)CC2)cc1Cl)N1CCC[C@@H]1CO] | (R or S)-1-(4-(4-(3-chloro-4-((R or S)-2-(hydroxymethyl)pyrrolidine-1-carbonyl)phenoxy)butyl)piperidin-1-yl)-3,3,3-trifluoro-2-hydroxy-2-phenylpropan-1-one | 597.3 |
| 8-9 | 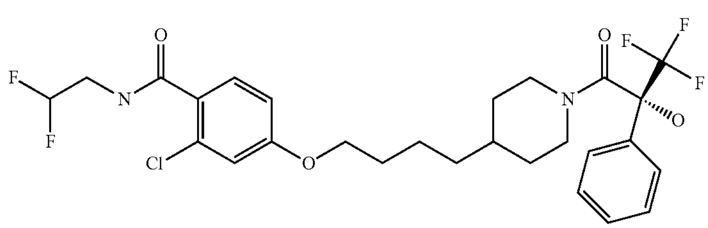 [SMILES: O=C(NCC(F)F)c1ccc(OCCCCC2CCN(C(=O)[C@](O)(c3ccccc3)C(F)(F)F)CC2)cc1Cl] | (R or S)-2-chloro-N-(2,2-difluoroethyl)-4-(4-(1-(3,3,3-trifluoro-2-hydroxy-2-phenylpropanoyl)piperidin-4-yl)butoxy)benzamide | 577.2 |
| 8-10 | 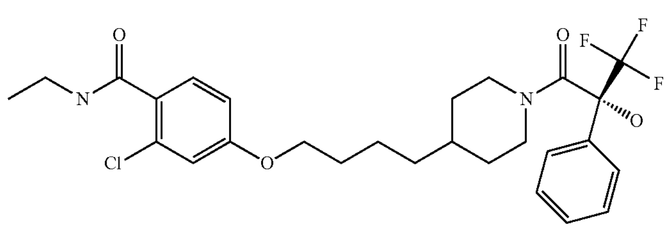 [SMILES: CCNC(=O)c1ccc(OCCCCC2CCN(C(=O)[C@](O)(c3ccccc3)C(F)(F)F)CC2)cc1Cl] | (R or S)-2-chloro-N-ethyl-4-(4-(1-(3,3,3-trifluoro-2-hydroxy-2-phenylpropanoyl)piperidin-4-yl)butoxy)benzamide | 541.2 |

-continued

| Example | Structure | IUPAC Name | LRMS, found [M + H]+ |
|---|---|---|---|
| 8-11 | 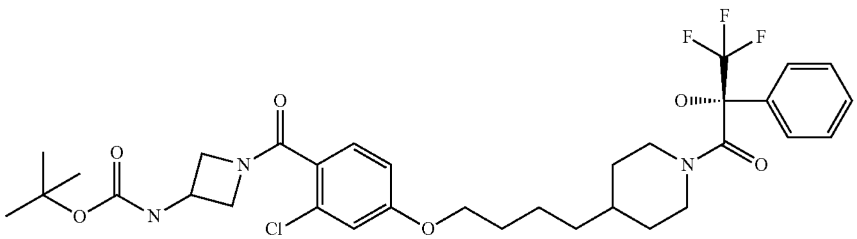 [SMILES: CC(C)(C)OC(=O)NC1CN(C(=O)c2ccc(OCCCCC3CCN(C(=O)[C@](O)(c4ccccc4)C(F)(F)F)CC3)cc2Cl)C1] | (R or S)-tert-butyl 1-(2-chloro-4-(4-(1-(3,3,3-trifluoro-2-hydroxy-2-phenylpropanoyl)piperidin-4-yl)butoxy)benzoyl)azetidin-3-ylcarbamate | 668.3 |
| 8-12 | 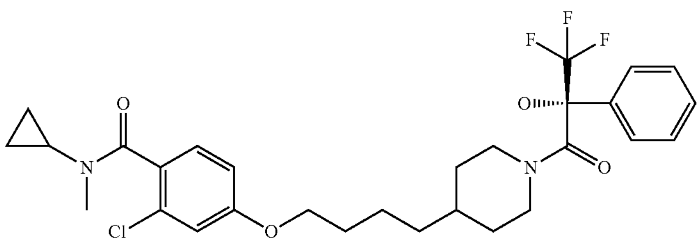 [SMILES: CN(C(=O)c1ccc(OCCCCC2CCN(C(=O)[C@](O)(c3ccccc3)C(F)(F)F)CC2)cc1Cl)C1CC1] | (R or S)-2-chloro-N-cyclopropyl-N-methyl-4-(4-(1-(3,3,3-trifluoro-2-hydroxy-2-phenylpropanoyl)piperidin-4-yl)butoxy)benzamide | 567.3 |
| 8-13 | 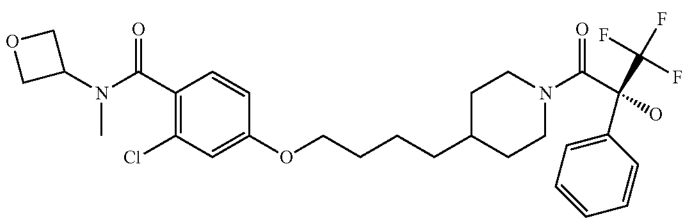 [SMILES: CN(C(=O)c1ccc(OCCCCC2CCN(C(=O)[C@](O)(c3ccccc3)C(F)(F)F)CC2)cc1Cl)C1COC1] | (R or S)-2-chloro-N-methyl-N-(oxetan-3-yl)-4-(4-(1-(3,3,3-trifluoro-2-hydroxy-2-phenylpropanoyl)piperidin-4-yl)butoxy)benzamide | 583.2 |
| 8-14 | 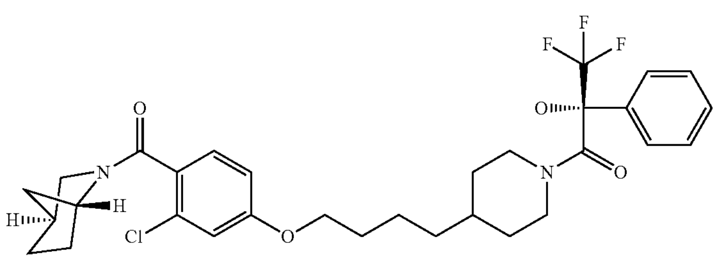 [SMILES: O=C(c1ccc(OCCCCC2CCN(C(=O)[C@](O)(c3ccccc3)C(F)(F)F)CC2)cc1Cl)N1C[C@H]2CC[C@@H]1C2] | (R or S)-1-(4-(4-(4-((1R,4S)-2-azabicyclo[2.2.1]heptane-2-carbonyl)-3-chlorophenoxy)butyl)piperidin-1-yl)-3,3,3-trifluoro-2-hydroxy-2-phenylpropan-1-one | 593.3 |
| 8-15 | 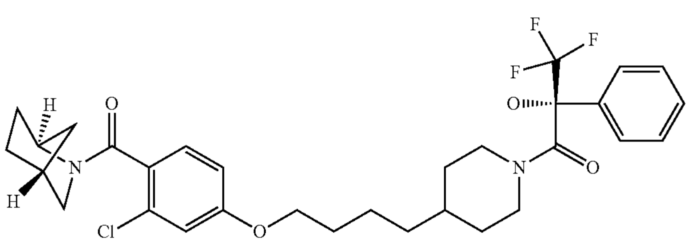 [SMILES: O=C(c1ccc(OCCCCC2CCN(C(=O)[C@](O)(c3ccccc3)C(F)(F)F)CC2)cc1Cl)N1C[C@@H]2CC[C@H]1C2] | (R or S)-1-(4-(4-(4-((1S,4R)-2-azabicyclo[2.2.1]heptane-2-carbonyl)-3-chlorophenoxy)butyl)piperidin-1-yl)-3,3,3-trifluoro-2-hydroxy-2-phenylpropan-1-one | 593.3 |

-continued

| Example | Structure | IUPAC Name | LRMS, found [M + H]+ |
|---|---|---|---|
| 8-16 | 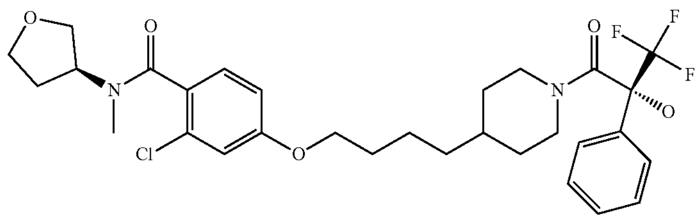 [SMILES: CN(C(=O)c1ccc(OCCCCC2CCN(C(=O)[C@](O)(c3ccccc3)C(F)(F)F)CC2)cc1Cl)[C@H]1CCOC1] | 2-chloro-N-methyl-N-((S or R)-tetrahydrofuran-3-yl)-4-(4-(1-((R or S)-3,3,3-trifluoro-2-hydroxy-2-phenylpropanoyl)piperidin-4-yl)butoxy)benzamide | 597.1 |
| 8-17 | 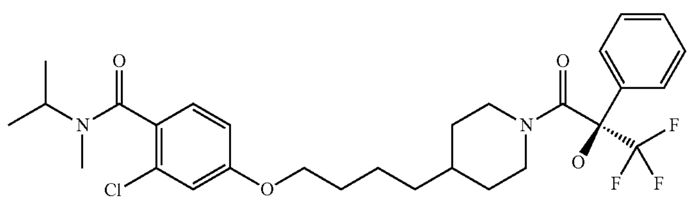 [SMILES: CC(C)N(C)C(=O)c1ccc(OCCCCC2CCN(C(=O)[C@](O)(c3ccccc3)C(F)(F)F)CC2)cc1Cl] | (R or S)-2-chloro-N-isopropyl-N-methyl-4-(4-(1-(3,3,3-trifluoro-2-hydroxy-2-phenylpropanoyl)piperidin-4-yl)butoxy)benzamide | 569.1 |
| 8-18 | 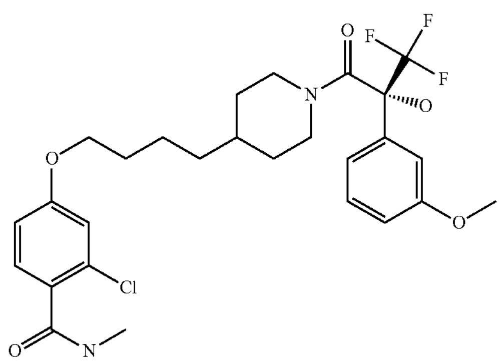 [SMILES: CNC(=O)c1ccc(OCCCCC2CCN(C(=O)[C@](O)(c3cccc(OC)c3)C(F)(F)F)CC2)cc1Cl] | (R or S)-2-chloro-N-methyl-4-(4-(1-(3,3,3-trifluoro-2-hydroxy-2-(3-methoxyphenyl)propanoyl)piperidin-4-yl)butoxy)benzamide | 557.1 |
| 8-19 | 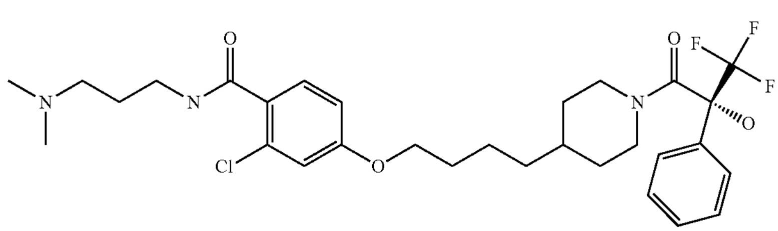 [SMILES: CN(C)CCCNC(=O)c1ccc(OCCCCC2CCN(C(=O)[C@](O)(c3ccccc3)C(F)(F)F)CC2)cc1Cl] | (R or S)-2-chloro-N-(3-(dimethylamino)propyl)-4-(4-(1-(3,3,3-trifluoro-2-hydroxy-2-phenylpropanoyl)piperidin-4-yl)butoxy)benzamide | 598.1 |
| 8-20 | 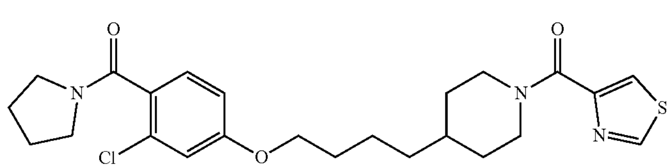 [SMILES: O=C(c1cscn1)N1CCC(CCCCOc2ccc(C(=O)N3CCCC3)c(Cl)c2)CC1] | (2-chloro-4-(4-(1-(thiazole-4-carbonyl)piperidin-4-yl)butoxy)phenyl)(pyrrolidin-1-yl)methanone | 476.1 |

Example 9-1

2-chloro-N,N-dimethyl-4-(4-(4-methyl-1-(1-phenyl-cyclopentanecarbonyl) piperidin-4-yl) butoxy)benzamide

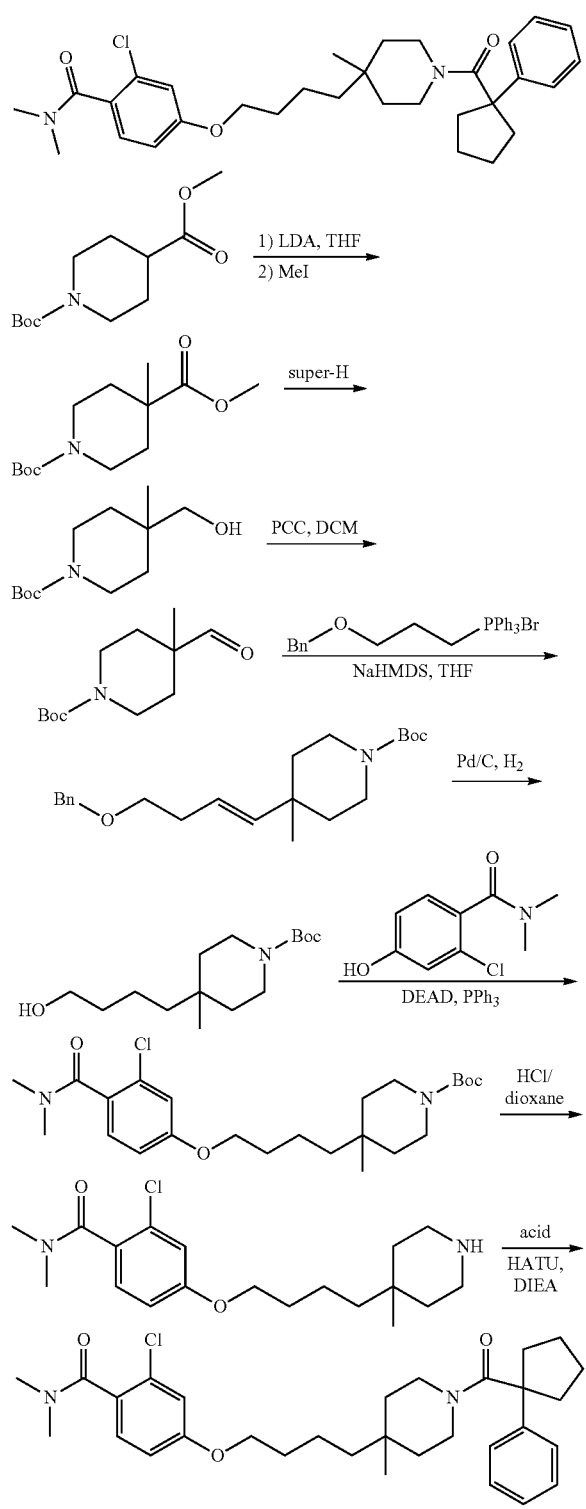

1-tert-butyl 4-methyl 4-methylpiperidine-1,4-dicarboxylate

To a solution of 1-tert-butyl 4-methyl piperidine-1,4-dicarboxylate (1.2 g, 5 mmol) in THF (40 mL) was added LDA (13.8 mL, 27.6 mmol, 2M in THF/heptane/ethylbenzene) at −78° C. After stirring for 2 h at −78° C., MeI (1.06 g, 7.5 mmol) was added dropwise. The resulting solution was stirred at −78° C. for 1 h, quenched with saturated aqueous $NH_4Cl$ (40 mL) and extracted with EtOAc (50 mL). The organic layer was collected, washed with saturated $Na_2CO_3$ (10 mL) and dried over anhydrous $Na_2SO_4$. The solvent was evaporated under reduced pressure and the residue was purified by a silica gel chromatography (silica gel: 300-400 mesh, PE/EtOAc=20/1 to 10/1) to afford 1-tert-butyl 4-methyl 4-methylpiperidine-1,4-dicarboxylate. LRMS m/z (M-99) 158.2 found, 158.2 required.

tert-butyl 4-(hydroxymethyl)-4-methylpiperidine-1-carboxylate

To a solution of 1-tert-butyl 4-methyl 4-methylpiperidine-1,4-dicarboxylate (360 mg, 1.4 mmol) in THF (5 mL) at 0° C. under $N_2$ atmosphere was added super-H (2.8 mL, 2.8 mmol, 1M in THF) dropwise. The mixture was stirred at rt for 2 h, then treated with sat. $NH_4Cl$ (10 mL) at 0° C. and extracted with i-PrOH/$CHCl_3$ (1/3) (20 mL×3). The organic phase was concentrated to give the crude compound which was purified by column chromatography (silica gel: 300-400 mesh, PE/EtOAc=10/1 to 4/1) to give tert-butyl 4-(hydroxymethyl)-4-methylpiperidine-1-carboxylate. LRMS m/z (M-99) 130.1 found, 130.1 required.

tert-butyl 4-formyl-4-methylpiperidine-1-carboxylate

To a solution of tert-butyl 4-(hydroxymethyl)-4-methylpiperidine-1-carboxylate (300 mg, 1.3 mmol) in DCM (10 mL) was added PCC (430 mg, 2 mmol). The reaction mixture was stirred at rt for 4 h. Then the mixture was concentrated under reduced pressure to give crude product which was purified by column chromatography (silica gel: 300-400 mesh, PE/EtOAc=20/1) to give tert-butyl 4-formyl-4-methylpiperidine-1-carboxylate. LRMS m/z (M-99) 128.1 found, 128.1 required.

tert-butyl 4-(4-(benzyloxy)but-1-enyl)-4-methylpiperidine-1-carboxylate

To a solution of (3-(benzyloxy)propyl)triphenylphosphonium bromide (604 mg, 1.23 mmol) in THF (4 mL) was added NaHMDS (1.32 mL, 1.32 mmol, 1M in hexane) at −78° C. After stirring for 60 min −78° C., tert-butyl 4-formyl-4-methylpiperidine-1-carboxylate (200 mg, 0.88 mmol) in THF (2 mL) was added dropwise. The resulting solution was allowed to warm to rt and stirred overnight. The reaction mixture was quenched with saturated $NH_4Cl$ (20 mL), extracted with EtOAc (50 mL×3). The organic layer was collected, washed with saturated $Na_2CO_3$ (20 mL) and dried over anhydrous $Na_2SO_4$. The solvent was evaporated under reduced pressure and the residue was purified by silica gel chromatography (silica gel: 300-400 mesh, PE/EtOAc=20/1) to afford tert-butyl 4-(4-(benzyloxy)but-1-enyl)-4-methylpiperidine-1-carboxylate. LRMS m/z (M-99) 260.1 found, 260.1 required.

tert-butyl 4-(4-hydroxybutyl)-4-methylpiperidine-1-carboxylate

To a solution of tert-butyl 4-(4-(benzyloxy)but-1-enyl)-4-methylpiperidine-1-carboxylate (106 mg, 0.3 mmol) in ethanol (50 mL) was added 10% dry Pd/C (40 mg). The mixture was stirred under H₂ balloon at rt overnight. The catalyst was filtered off and the filtrate was concentrated to afford crude product tert-butyl 4-(4-hydroxybutyl)-4-methylpiperidine-1-carboxylate. LRMS m/z (M-99) 172.1 found, 172.1 required.

tert-butyl 4-(4-(3-chloro-4-(dimethylcarbamoyl)phenoxy)butyl)-4-methylpiperidine-1-carboxylate To a solution of tert-butyl 4-(4-hydroxybutyl)-4-methylpiperidine-1-carboxylate (80 mg, 0.3 mmol), 2-chloro-4-hydroxy-N,N-dimethyl-benzamide (63 mg, 0.32 mmol) and PPh₃ (157 mg, 0.6 mmol) in THF (3 mL) was added DEAD (104 mg, 0.6 mmol) at rt. After stirring for 2 h, the mixture was concentrated under reduced pressure to give crude product which was directly purified by reverse phase chromatography (mobile phase: methanol/water (10 mM NH₄HCO₃)) to afford tert-butyl 4-(4-(3-chloro-4-(dimethylcarbamoyl)phenoxy)butyl)-4-methylpiperidine-1-carboxylate. LRMS m/z (M-99) 353.1 found, 353.2 required.

2-chloro-N,N-dimethyl-4-(4-(4-methylpiperidin-4-yl)butoxy)benzamide

To a solution of tert-butyl 4-(4-(3-chloro-4-(methylcarbamoyl)phenoxy)butyl)-4-methylpiperidine-1-carboxylate (90 mg, 0.2 mmol) in HCl/1,4-dioxane (4 M, 4 mL) was stirred for 2 h at rt. Then the mixture was concentrated under reduced pressure to give crude 2-chloro-N,N-dimethyl-4-(4-(4-methylpiperidin-4-yl)butoxy)benzamide hydrochloric acid. LRMS m/z (M+H) 353.2 found, 353.2 required.

2-chloro-N,N-dimethyl-4-(4-(4-methyl-1-(1-phenylcyclopentanecarbonyl) piperidin-4-yl) butoxy)benzamide A mixture of 2-chloro-N,N-dimethyl-4-(4-(4-methylpiperidin-4-yl)butoxy)benzamide hydrochloric acid (20 mg, 0.05 mmol), HATU (46 mg, 0.12 mmol), DIPEA (46 mg, 0.36 mmol), 1-phenylcyclopentanecarboxylic acid (25 mg, 0.13 mmol) in 1 mL of dry THF was stirred at rt overnight. The mixture was directly purified by reverse phase chromatography (mobile phase: methanol/water (10 mM NH₄HCO₃)) to afford 2-chloro-N,N-dimethyl-4-(4-(4-methyl-1-(1-phenylcyclopentanecarbonyl) piperidin-4-yl) butoxy)benzamide. LRMS m/z (M+H) 525.3 found, 525.3 required.

Example 10-1

2-chloro-N,N-dimethyl-4-(2-((1S,2R or 1R, 2S)-2-(1-((R or S)-3,3,3-trifluoro-2-hydroxy-2-(3-methoxyphenyl)propanoyl)piperidin-4-yl)cyclopropyl)ethoxy)benzamide

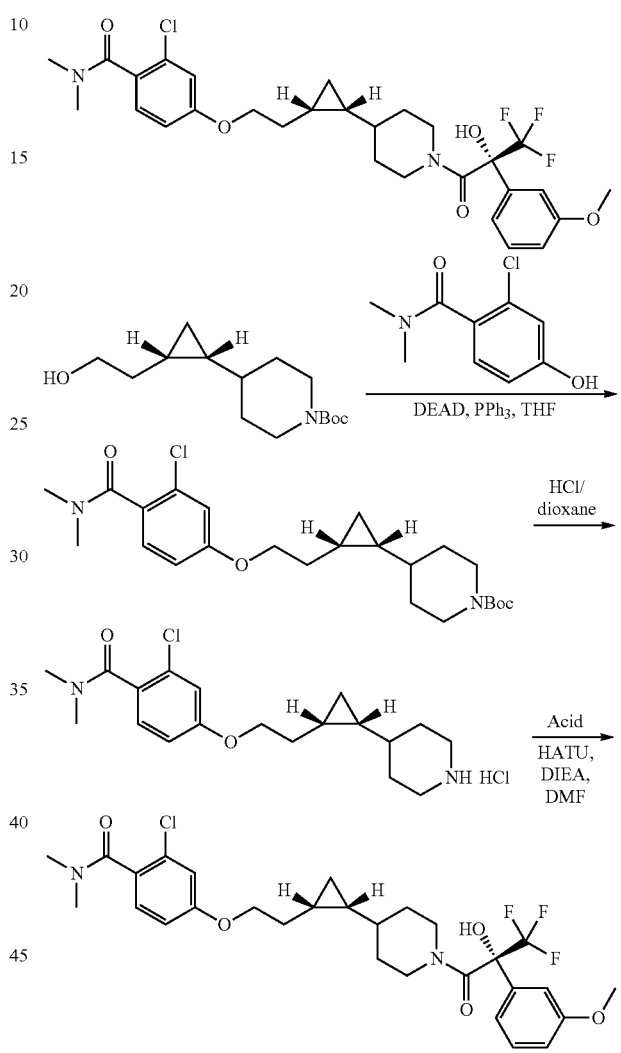

tert-butyl 4-((1R,2S or 1S,2R)-2-(2-(3-chloro-4-(dimethylcarbamoyl)phenoxy)ethyl)cyclopropyl)piperidine-1-carboxylate To a degassed solution of 2-chloro-4-hydroxy-N,N-dimethylbenzamide (200 mg, 1.00 mmol), tert-butyl 4-((1R,2S or 1S,2R)-2-(2-hydroxyethyl)cyclopropyl)piperidine-1-carboxylate (297 mg, 1.10 mmol), and triphenylphosphine (394 mg, 1.50 mmol) in anhydrous THF (5 mL) was added DEAD (262 mg, 1.50 mmol) at 0° C. The reaction mixture was stirred further 30 min, then the ice-water bath was removed, and the reaction mixture was stirred at rt overnight under nitrogen atmosphere. The mixture was concentrated and the residue was purified by Prep-TLC (silica gel, PE/EtOAc=17/10, V/V) to afford tert-butyl 4-((1R,2S or 1S,2R)-2-(2-(3-chloro-4-(dimethylcarbamoyl)phenoxy)

ethyl)cyclopropyl) piperidine-1-carboxylate, which was used in the next step without further purification. LRMS m/z (M+H) 451.2 found, 451.2 required.

2-chloro-N,N-dimethyl-4-(2-((1S,2R or 1R,2S)-2-(piperidin-4-yl)cyclopropyl)ethoxy)benzamide hydrochloride To a solution of tert-butyl 4-((1R,2S or 1S,2R)-2-(2-(3-chloro-4-(dimethylcarbamoyl)phenoxy)ethyl)cyclopropyl) piperidine-1-carboxylate (276 mg, 0.61 mmol) in DCM (3.06 mL) was added 4M HCl/dioxane (3 mL) at rt. After stirring further 1 h, the reaction mixture was concentrated to afford crude 2-chloro-N,N-dimethyl-4-(2-((1S,2R or 1R,2S)-2-(piperidin-4-yl)cyclopropyl)ethoxy)benzamide hydrochloride, which was used in the next step without further purification. LRMS m/z (M+H) 351.1 found, 351.2 required.

2-chloro-N,N-dimethyl-4-(2-((1S,2R or 1R,2S)-2-(1-((R or S)-3,3,3-trifluoro-2-hydroxy-2-(3-methoxyphenyl)propanoyl)piperidin-4-yl)cyclopropyl)ethoxy)benzamide To a solution of crude 2-chloro-N,N-dimethyl-4-(2-((1S,2R or 1R,2S)-2-(piperidin-4-yl)cyclopropyl)ethoxy)benzamide hydrochloride (104 mg, 0.20 mmol, 1.0 eq), (R or S)-3,3,3-trifluoro-2-hydroxy-2-(3-methoxyphenyl)propanoic acid (51 mg, 0.20 mmol, 1.3 eq), and HATU (116 mg, 0.31 mmol, 1.5 eq) in DMF (1 mL) was added DIEA (0.17 mL, 1.02 mmol, 5.0 eq) at rt, and the reaction mixture was stirred at rt for 6 h. The mixture was filtrated, and the filtrate was purified by reverse phase chromatography (mobile phase: methanol/water (10 mM NH$_4$HCO$_3$)) to afford 2-chloro-N,N-dimethyl-4-(2-((1S,2R or 1R,2S)-2-(1-((R or S)-3,3,3-trifluoro-2-hydroxy-2-(3-methoxyphenyl)propanoyl)piperidin-4-yl)cyclopropyl)ethoxy)benzamide. LRMS m/z (M+H) 583.2 found, 583.2 required.

Using the procedure described in Example 10-1, but using the appropriate amine and acid, the following examples were prepared.

| example | Structure | IUPAC Name | LRMS, found [M + H]+ |
|---|---|---|---|
| 10-2 | 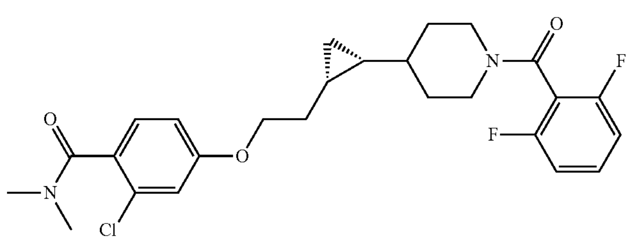 [SMILES: CN(C)C(=O)c1ccc(OCC[C@@H]2C[C@@H]2C2CCN(C(=O)c3c(F)cccc3F)CC2)cc1Cl] | 2-chloro-4-(2-((1S,2R or 1R, 2S)-2-(1-(2,6-difluorobenzoyl)piperidin-4-yl)cyclopropyl)ethoxy)-N,N-dimethylbenzamide | 491.1 |
| 10-3 | 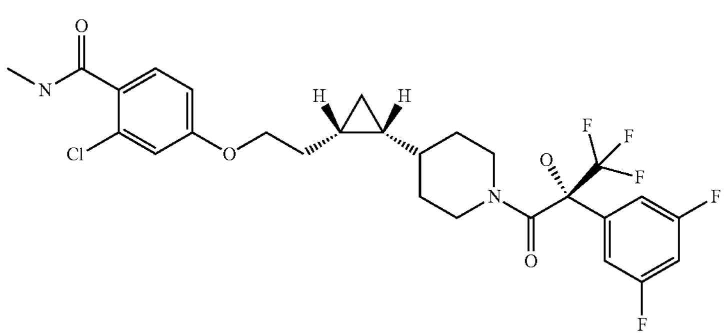 [SMILES: CNC(=O)c1ccc(OCC[C@@H]2C[C@@H]2C2CCN(C(=O)[C@](O)(c3cc(F)cc(F)c3)C(F)(F)F)CC2)cc1Cl] | 2-chloro-4-(2-((1S,2R or 1R, 2S)-2-(1-((R or S)-2-(3,5-difluorophenyl)-3,3,3-trifluoro-2-hydroxypropanoyl)piperidin-4-yl)cyclopropyl)ethoxy)-N-methylbenzamide | 575.1 |
| 10-4 | 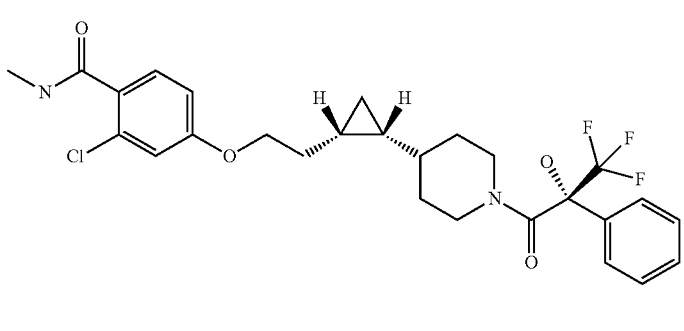 [SMILES: CNC(=O)c1ccc(OCC[C@@H]2C[C@@H]2C2CCN(C(=O)[C@](O)(c3ccccc3)C(F)(F)F)CC2)cc1Cl] | 4-(2-((1S,2R or 1R, 2S)-2-(1-((R or S)-2-amino-3,3,3-trifluoro-2-phenylpropanoyl)piperidin-4-yl)cyclopropyl)ethoxy)-2-chloro-N-methylbenzamide | 538.1 |

| example | Structure | IUPAC Name | LRMS, found [M + H]+ |
|---|---|---|---|
| 10-5 | 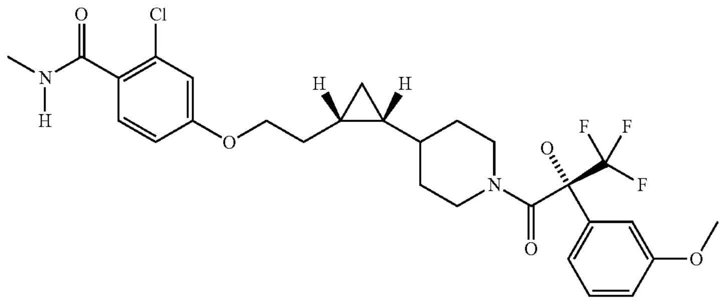 | 2-chloro-N-methyl-4-(2-((1S,2R or 1R, 2S)-2-(1-((R or S)-3,3,3-trifluoro-2-hydroxy-2-(3-methoxyphenyl)propanoyl)piperidin-4-yl)cyclopropyl)ethoxy)benzamide | 569.1 |
| 10-6 | 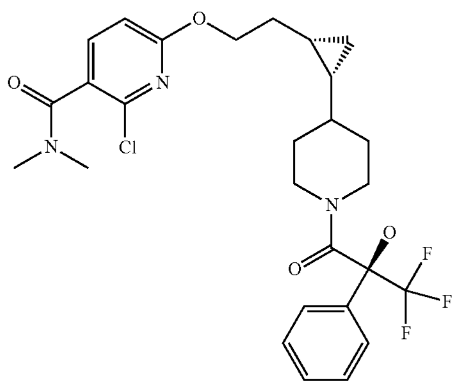 [SMILES: CN(C)C(=O)c1ccc(OCC[C@@H]2C[C@@H]2C2CCN(C(=O)[C@@](O)(c3ccccc3)C(F)(F)F)CC2)nc1Cl] | 2-chloro-N,N-dimethyl-6-(2-((1S,2R or 1R,2S)-2-(1-((S or R)-3,3,3-trifluoro-2-hydroxy-2-phenylpropanoyl)piperidin-4-yl)cyclopropyl)ethoxy)nicotinamide | 554.1 |
| 10-7 | 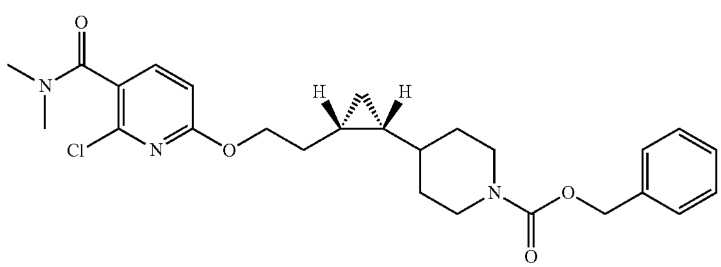 [SMILES: CN(C)C(=O)c1ccc(OCC[C@@H]2C[C@@H]2C2CCN(C(=O)OCc3ccccc3)CC2)nc1Cl] | benzyl 4-((1R,2S or 1S,2R)-2-(2-(6-chloro-5-(dimethylcarbamoyl)pyridin-2-yloxy)ethyl)cyclopropyl)piperidine-1-carboxylate | 486.1 |

Example 11-1

2-cyano-N,N-dimethyl-4-(2-((1R,2S or 1S,2R)-2-(1-((R or S)-3,3,3-trifluoro-2-hydroxy-2-phenylpropanoyl)piperidin-4-yl)cyclopropyl)ethoxy)benzamide

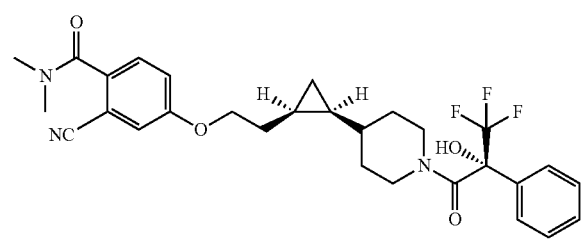

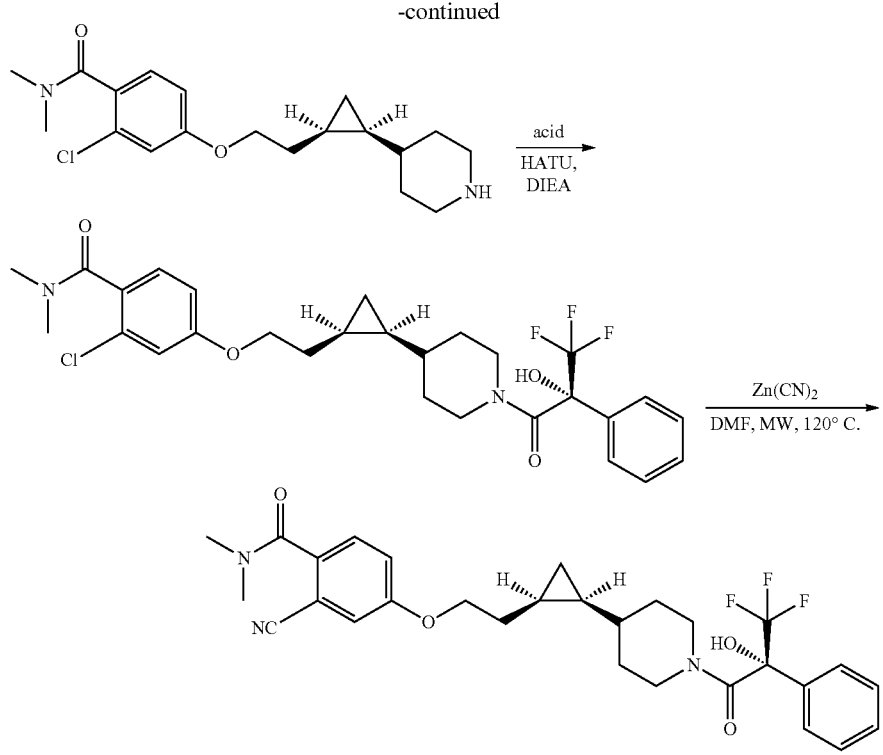

2-chloro-N,N-dimethyl-4-(2-((1R,2S or 1S,2R)-2-(1-((R or S)-3,3,3-trifluoro-2-hydroxy-2-phenylpropanoyl)piperidin-4-yl)cyclopropyl)ethoxy)benzamid To a solution of 2-chloro-N,N-dimethyl-4-(2-((1R,2S or 1S,2R)-2-(piperidin-4-yl)cyclopropyl)ethoxy)benzamide (60 mg, 0.17 mmol) in THF (1 mL) was added (R or S)-3,3,3-trifluoro-2-hydroxy-2-phenylpropanoic acid (57 mg, 0.26 mmol), DIEA (66 mg, 0.51 mmol) and HATU (98 mg, 0.26 mmol). The mixture was stirred at rt overnight. Then the mixture was concentrated and the residue was purified by reverse phase chromatography (mobile phase: methanol/water (10 mM $NH_4HCO_3$)) to afford 2-chloro-N,N-dimethyl-4-(2-((1R,2S or 1S,2R)-2-(1-((R or S)-3,3,3-trifluoro-2-hydroxy-2-phenylpropanoyl)piperidin-4-yl)cyclopropyl)ethoxy)benzamide. LRMS m/z (M+H) 553.3 found, 553.2 required.

2-cyano-N,N-dimethyl-4-(2-((1R,2S or 1S,2R)-2-(1-((R or S)-3,3,3-trifluoro-2-hydroxy-2-phenylpropanoyl)piperidin-4-yl)cyclopropyl)ethoxy)benzamide To a solution of 2-chloro-N,N-dimethyl-4-(2-((1R,2S or 1S,2R)-2-(1-((R or S)-3,3,3-trifluoro-2-hydroxy-2-phenylpropanoyl)piperidin-4-yl)cyclopropyl)ethoxy)benzamide (30 mg, 0.054 mmol) in DMF (1 mL) was added $Zn(CN)_2$ (6 mg, 0.0054 mmol), zinc power (1 mg, 0.015 mmol) and bis(tri-tert-butyphosphine) Pd(0) (3 mg, 0.0054 mmol). The mixture was heated to 120° C. for 30 min under microwave. Then the mixture was filtered and purified by reverse phase chromatography (mobile phase: methanol/water (10 mM $NH_4HCO_3$)) to afford 2-cyano-N,N-dimethyl-4-(2-((1R,2S or 1S,2R)-2-(1-((R or S)-3,3,3-trifluoro-2-hydroxy-2-phenylpropanoyl)piperidin-4-yl)cyclopropyl)ethoxy)benzamide. LRMS m/z (M+H) 544.3 found, 544.2 required.

Example 12-1

(R or S)-2-chloro-N,N-dimethyl-4-(2-(6-(1-phenylcyclopentanecarbonyl)-6-azaspiro[2.5]octan-1-yl)ethoxy)benzamide

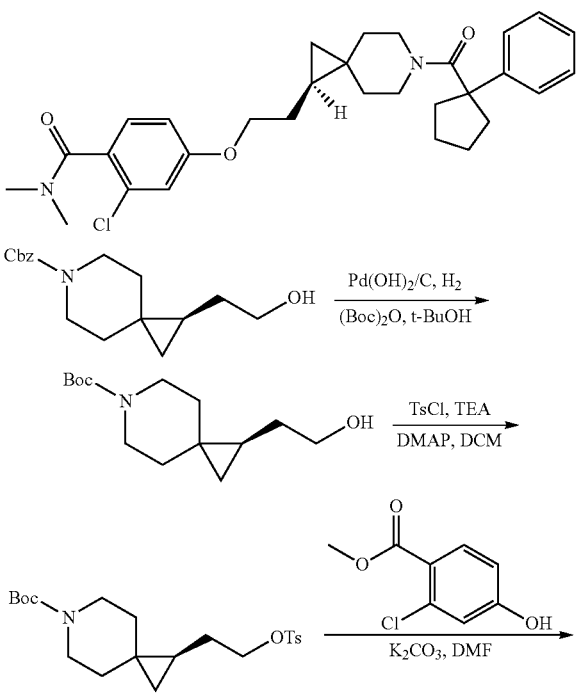

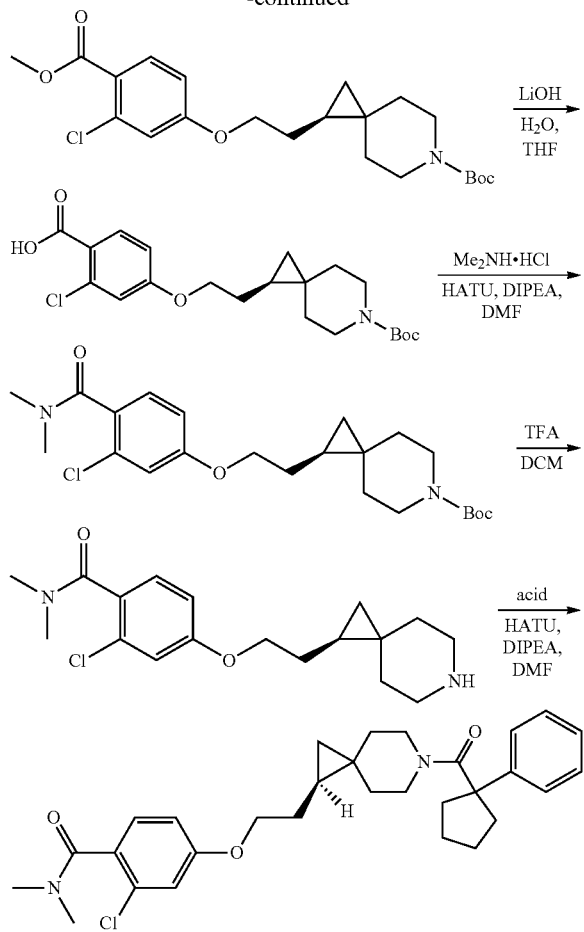

(R or S)-tert-butyl 1-(2-hydroxyethyl)-6-azaspiro[2.5]octane-6-carboxylate

A mixture of (R or S)-benzyl 1-(2-hydroxyethyl)-6-azaspiro[2.5]octane-6-carboxylate (2.0 g, 6.92 mmol), di-tert-butyl dicarbonate (1811 mg, 8.30 mmol), 20% Pd(OH)₂/C (400 mg) in t-BuOH (30 mL) was stirred at rt under H₂ atmosphere for 96 h. The catalyst was filtered off and the filtrate was concentrated. The crude product was purified by column chromatography (silica gel: 300-400 mesh, PE/EtOAc=3/1 to 1/1, v/v) to afford (R or 5)-tert-butyl 1-(2-hydroxyethyl)-6-azaspiro[2.5]octane-6-carboxylate. LRMS m/z (M-55) 200.1 found, 200.2 required.

(R or S)-tert-butyl 1-(2-(tosyloxy)ethyl)-6-azaspiro [2.5]octane-6-carboxylate A solution of (R or S)-tert-butyl 1-(2-hydroxyethyl)-6-azaspiro[2.5]octane-6-carboxylate (2.4 g, 9.41 mmol), TEA (2852 mg, 28.23 mmol), 4-dimethylamiopryidine (1149 mg, 9.41 mmol) and 4-methylbenzene-1-sulfonyl chloride (1968 mg, 10.35 mmol) in DCM (20 mL) was stirred for 3 h under nitrogen atmosphere at rt. The mixture was concentrated. The residue was dissolved in EtOAc (450 mL) and washed with 10% citric acid (20 mL*2), saturated NaHCO₃ (20 mL*2), brine (20 mL). The organic layer was dried over anhydrous Na₂SO₄, filtered and concentrated to afford (R or S)-tert-butyl 1-(2-(tosyloxy)ethyl)-6-azaspiro[2.5]octane-6-carboxylate. LRMS m/z (M-55) 354.0 found, 354.2 required.

(R or S)-tert-butyl 1-(2-(3-chloro-4-(methoxycarbonyl)phenoxy)ethyl)-6-azaspiro[2.5]octane-6-carboxylate A solution of (R or S)-tert-butyl 1-(2-(tosyloxy)ethyl)-6-azaspiro[2.5]octane-6-carboxylate (2.8 g, 6.84 mmol), 2-chloro-4-hydroxy-N,N-dimethylbenzamide (1295 mg, 6.50 mmol) and potassium carbonate (2835 mg, 20.53 mmol) in DMF (12 mL) was stirred overnight at 45° C. under nitrogen atmosphere. The mixture was diluted with EtOAc (400 mL) and washed with saturated Na₂CO₃ (20 mL*2), brine (20 mL). The organic layer was dried over anhydrous Na₂SO₄, filtered and concentrated. The crude product was purified by column chromatography (silica gel: 300-400 mesh, PE/EtOAc=3/1, v/v) to afford (R or S)-tert-butyl 1-(2-(3-chloro-4-(methoxycarbonyl)phenoxy)ethyl)-6-azaspiro[2.5]octane-6-carboxylate. LRMS m/z (M-99) 324.1 found, 324.2 required.

(R or S)-4-(2-(6-(tert-butoxycarbonyl)-6-azaspiro [2.5]octan-1-yl)ethoxy)-2-chlorobenzoic acid A solution of (R or S)-tert-butyl 1-(2-(3-chloro-4-(methoxycarbonyl)phenoxy)ethyl)-6-azaspiro[2.5]octane-6-carboxylate (2.2 g, 5.20 mmol), LiOH (5.2 mL, 52 mmol, 10 M in water) in THF (10 mL) was stirred overnight at 40° C. The mixture was acidified with conc. HCl to pH=3 and the solvent was removed under reduced pressure. The residue was dissolved in EtOAc (500 mL), washed with brine (20 mL), dried over anhydrous Na₂SO₄, filtered and concentrated to afford (R or S)-4-(2-(6-(tert-butoxycarbonyl)-6-azaspiro[2.5]octan-1-yl)ethoxy)-2-chlorobenzoic acid. LRMS m/z (M-55) 355.1 found, 355.2 required.

(R or S)-tert-butyl 1-(2-(3-chloro-4-(dimethylcarbamoyl)phenoxy)ethyl)-6-azaspiro[2.5]octane-6-carboxylate A solution of (R or S)-4-(2-(6-(tert-butoxycarbonyl)-6-azaspiro[2.5]octan-1-yl)ethoxy)-2-chlorobenzoic acid (2.02 g, 4.94 mmol), dimethylamine hydrochloride (520 mg, 6.42 mmol), HATU (2440 mg, 6.42 mmol) and DIPEA (1912 mg, 14.82 mmol) in DMF (5 mL) was stirred overnight at rt. The mixture was diluted with EtOAc (400 mL) and washed with H₂O (20 mL) and brine (20 mL). The organic layer was dried over anhydrous Na₂SO₄, filtered and concentrated. The crude product was purified by column chromatography (silica gel: 300-400 mesh, PE/EtOAc=3/1, v/v) to afford (R or S)-tert-butyl 1-(2-(3-chloro-4-(dimethylcarbamoyl)phenoxy)ethyl)-6-azaspiro[2.5]octane-6-carboxylate. LRMS m/z (M+H) 437.2 found, 437.2 required.

(R or S)-4-(2-(6-azaspiro[2.5]octan-1-yl)ethoxy)-2-chloro-N,N-dimethylbenzamide A solution of (R or S)-tert-butyl 1-(2-(3-chloro-4-(dimethylcarbamoyl)phenoxy)ethyl)-6-azaspiro[2.5]octane-6-carboxylate (1077 mg, 2.47 mmol) and TFA (2 mL) in DCM (10 mL) was stirred for 2 h at rt. The mixture was basified to pH=9.0 with saturated NaHCO₃, diluted with DCM/CH₃OH (10/1, 400 mL) and washed with brine (20 mL), dried over anhydrous Na₂SO₄, filtered and concentrated to afford (R or S)-4-(2-(6-azaspiro[2.5]octan-1-yl)ethoxy)-2-chloro-N,N-dimethylbenzamide. LRMS m/z (M+H) 337.1 found, 337.2 required.

(R or S)-2-chloro-N,N-dimethyl-4-(2-(6-(1-phenyl-cyclopentanecarbonyl)-6-azaspiro[2.5]octan-1-yl)ethoxy)benzamide A solution of (R or S)-4-(2-(6-azaspiro[2.5]octan-1-yl)ethoxy)-2-chloro-N,N-dimethylbenzamide (10 mg, 0.03 mmol), 1-phenylcyclopentanecarboxylic acid (10 mg, 0.05 mmol), HATU (18 mg, 0.05 mmol) and DIPEA (6 mg, 0.05 mmol) in DMF (1 mL) was stirred for 2 h at rt. The mixture was directly purified by reverse phase chromatography (mobile phase: methanol/water (10 mM NH₄HCO₃)) to afford (R or S)-2-chloro-N,N-dimethyl-4-(2-(6-(1-phenylcyclopentanecarbonyl)-6-azaspiro[2.5]octan-1-yl)ethoxy)benzamide. LRMS m/z (M+H) 509.2 found, 509.2 required.

Using the procedure described in Example 12-1, but replacing 1-phenylcyclopentanecarboxylic acid with the appropriate acid various acids in the last step, the following examples were prepared.

| Example | Structure | IUPAC Name | LLRMS, found [M + H]+ |
|---|---|---|---|
| 12-2 | 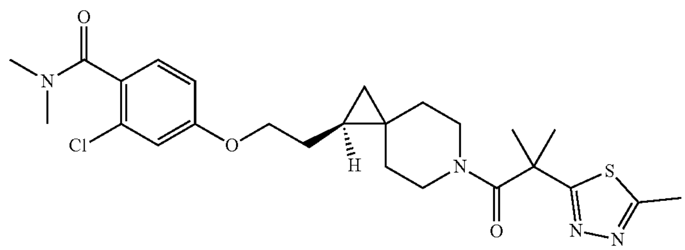 | (R or S)-2-chloro-N,N-dimethyl-4-(2-(6-(2-methyl-2-(5-methyl-1,3,4-thiadiazol-2-yl)propanoyl)-6-azaspiro[2.5]octan-1-yl)ethoxy)benzamide | 505.1 |
| 12-3 | 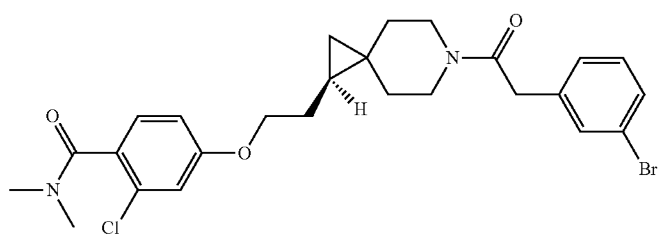 [SMILES: CN(C)C(=O)c1ccc(OCC[C@H]2CC23CCN(C(=O)Cc2cccc(Br)c2)CC3)cc1Cl] | (R or S)-4-(2-(6-(2-(3-bromophenyl)acetyl)-6-azaspiro[2.5]octan-1-yl)ethoxy)-2-chloro-N,N-dimethylbenzamide | 535.0 |
| 12-4 | 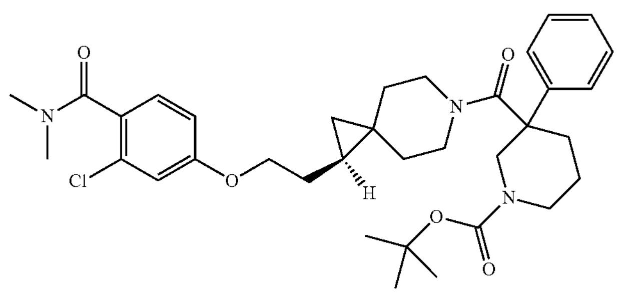 [SMILES: CN(C)C(=O)c1ccc(OCC[C@H]2CC23CCN(C(=O)C2(c4ccccc4)CCCN(C(=O)OC(C)(C)C)C2)CC3)cc1Cl] | tert-butyl 3-((R or S)-1-(2-(3-chloro-4-(dimethylcarbamoyl)phenoxy)ethyl)-6-azaspiro[2.5]octane-6-carbonyl)-3-phenylpiperidine-1-carboxylate | 624.2 |
| 12-5 | 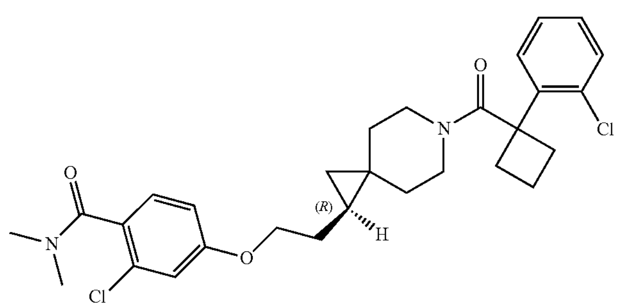 | (R or S)-2-chloro-4-(2-(6-(1-(2-chlorophenyl)cyclobutanecarbonyl)-6-azaspiro[2.5]octan-1-yl)ethoxy)-N,N-dimethylbenzamide | 529.1 |

-continued

| Example | Structure | IUPAC Name | LLRMS, found [M + H]+ |
|---|---|---|---|
| 12-6 | 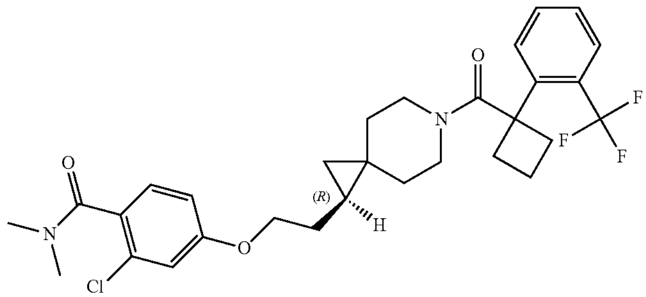 | (R or S)-2-chloro-N,N-dimethyl-4-(2-(6-(1-(2-(trifluoromethyl)phenyl)cyclobutanecarbonyl)-6-azaspiro[2.5]octan-1-yl)ethoxy)benzamide | 563.2 |
| 12-7 | 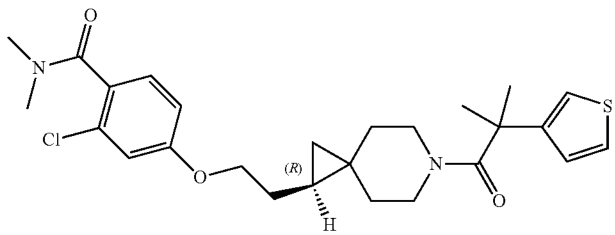 | (R or S)-2-chloro-N,N-dimethyl-4-(2-(6-(2-methyl-2-(thiophen-3-yl)propanoyl)-6-azaspiro[2.5]octan-1-yl)ethoxy)benzamide | 489.2 |
| 12-8 | 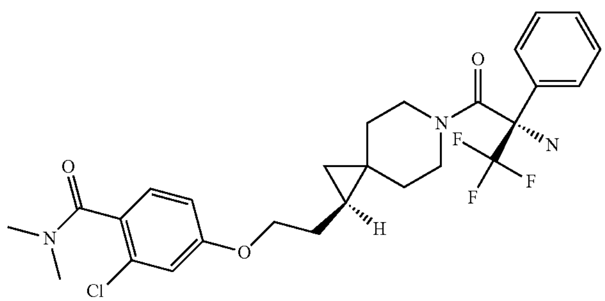 [SMILES: CN(C)C(=O)c1ccc(OCC[C@H]2CC23CCN(C(=O)[C@@](N)(c2ccccc2)C(F)(F)F)CC3)cc1Cl] | 4-(2-((R or S)-6-((S or R)-2-amino-3,3,3-trifluoro-2-phenylpropanoyl)-6-azaspiro[2.5]octan-1-yl)ethoxy)-2-chloro-N,N-dimethylbenzamide | 538.2 |
| 12-9 | 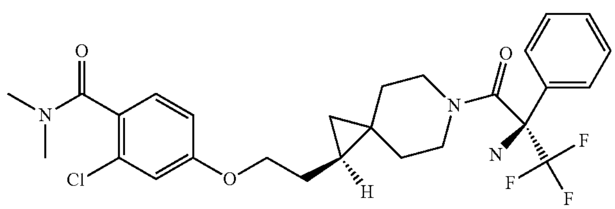 [SMILES: CN(C)C(=O)c1ccc(OCC[C@H]2CC23CCN(C(=O)[C@](N)(c2ccccc2)C(F)(F)F)CC3)cc1Cl] | 4-(2-((R or S)-6-((R or S)-2-amino-3,3,3-trifluoro-2-phenylpropanoyl)-6-azaspiro[2.5]octan-1-yl)ethoxy)-2-chloro-N,N-dimethylbenzamide | 538.2 |
| 12-10 | 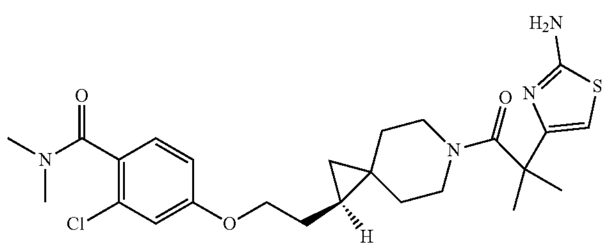 [SMILES: CN(C)C(=O)c1ccc(OCC[C@H]2CC23CCN(C(=O)C(C)(C)c2csc(N)n2)CC3)cc1Cl] | (R or S)-4-(2-(6-(2-(2-aminothiazol-4-yl)-2-methylpropanoyl)-6-azaspiro[2.5]octan-1-yl)ethoxy)-2-chloro-N,N-dimethylbenzamide | 505.2 |
| 12-11 | 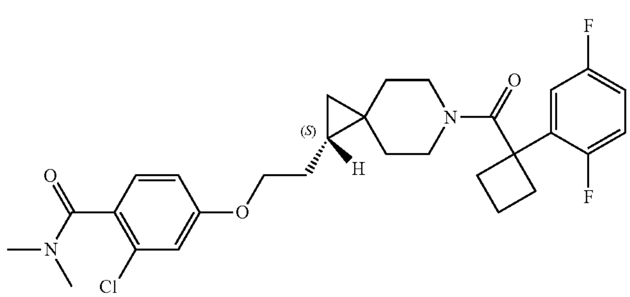 | (S or R)-2-chloro-4-(2-(6-(1-(2,5-difluorophenyl)cyclobutanecarbonyl)-6-azaspiro[2.5]octan-1-yl)ethoxy)-N,N-dimethylbenzamide | 531.0 |

| Example | Structure | IUPAC Name | LLRMS, found [M + H]+ |
|---|---|---|---|
| 12-12 | 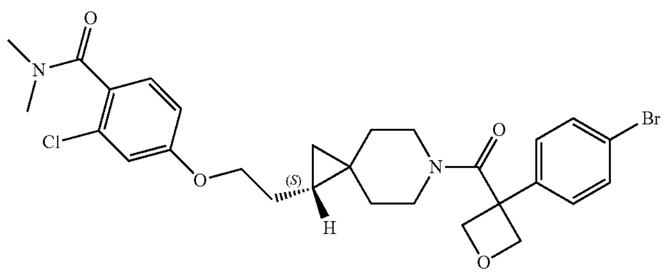 | (S or R)-4-(2-(6-(3-(4-bromophenyl)oxetane-3-carbonyl)-6-azaspiro[2.5]octan-1-yl)ethoxy)-2-chloro-N,N-dimethylbenzamide | 577.1 |
| 12-13 | 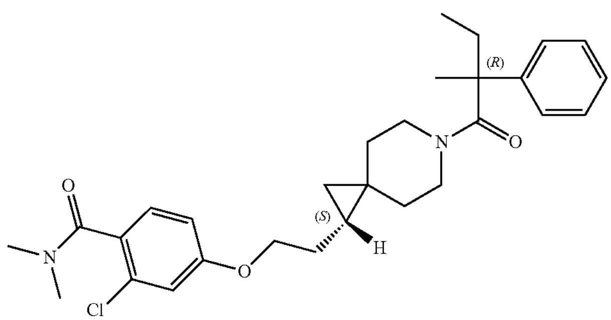 | 2-chloro-N,N-dimethyl-4-(2-((1S or 1R)-6-(2-methyl-2-phenylbutanoyl)-6-azaspiro[2.5]octan-1-yl)ethoxy)benzamide | 497.0 |
| 12-14 | 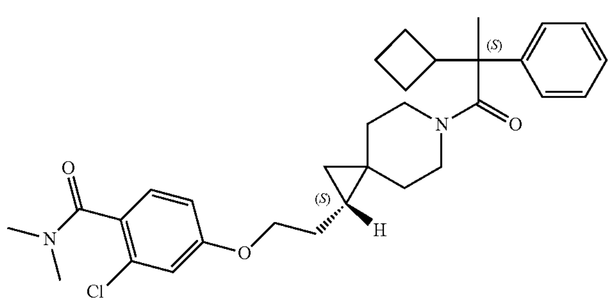 | 2-chloro-4-(2-((S or R)-6-((S or R)-2-cyclobutyl-2-phenylpropanoyl)-6-azaspiro[2.5]octan-1-yl)ethoxy)-N,N-dimethylbenzamide | 523.0 |
| 12-15 | 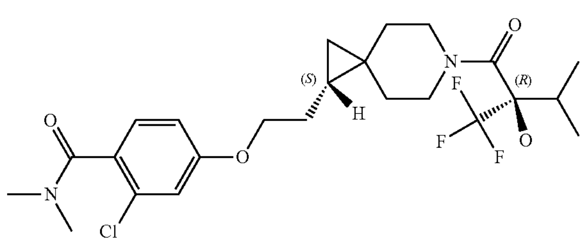 | 2-chloro-4-(2-((S or R)-6-((R or S)-2-hydroxy-3-methyl-2-(trifluoromethyl)butanoyl)-6-azaspiro[2.5]octan-1-yl)ethoxy)-N,N-dimethylbenzamide | 505.1 |
| 12-16 | 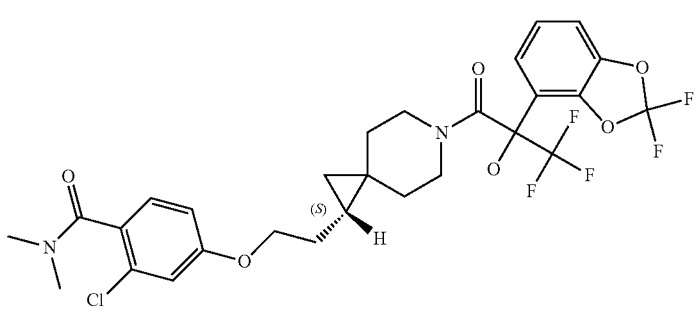 | 2-chloro-4-(2-((1S or 1R)-6-(2-(2,2-difluorobenzo[d][1,3]dioxol-4-yl)-3,3,3-trifluoro-2-hydroxypropanoyl)-6-azaspiro[2.5]octan-1-yl)ethoxy)-N,N-dimethylbenzamide | 619.2 |

-continued

| Example | Structure | IUPAC Name | LLRMS, found [M + H]+ |
|---|---|---|---|
| 12-17 | 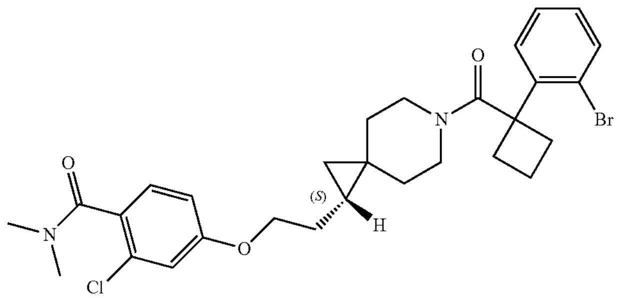 | (S or R)-4-(2-(6-(1-(2-bromophenyl)cyclobutanecarbonyl)-6-azaspiro[2.5]octan-1-yl)ethoxy)-2-chloro-N,N-dimethylbenzamide | 573.2 |
| 12-18 | 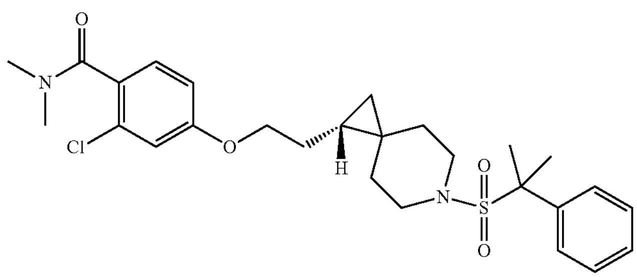 [SMILES: CN(C)C(=O)c1ccc(OCC[C@@H]2CC23CCN(S(=O)(=O)C(C)(C)c2ccccc2)CC3)cc1Cl] | (S or R)-2-chloro-N,N-dimethyl-4-(2-(6-(2-phenylpropan-2-ylsulfonyl)-6-azaspiro[2.5]octan-1-yl)ethoxy)benzamide | 519.2 |
| 12-19 | 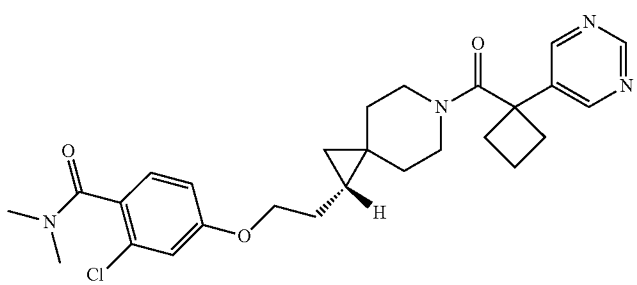 [SMILES: CN(C)C(=O)c1ccc(OCC[C@@H]2CC23CCN(C(=O)C2(c4cncnc4)CCC2)CC3)cc1Cl] | (S or R)-2-chloro-N,N-dimethyl-4-(2-(6-(1-(pyrimidin-5-yl)cyclobutanecarbonyl)-6-azaspiro[2.5]octan-1-yl)ethoxy)benzamide | 497.3 |
| 12-20 | 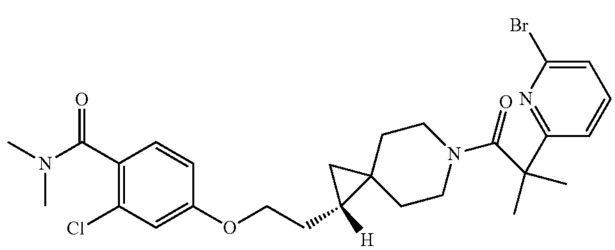 [SMILES: CN(C)C(=O)c1ccc(OCC[C@@H]2CC23CCN(C(=O)C(C)(C)c2cccc(Br)n2)CC3)cc1Cl] | (S or R)-4-(2-(6-(2-(6-bromopyridin-2-yl)-2-methylpropanoyl)-6-azaspiro[2.5]octan-1-yl)ethoxy)-2-chloro-N,N-dimethylbenzamide | 562.1 |
| 12-21 | 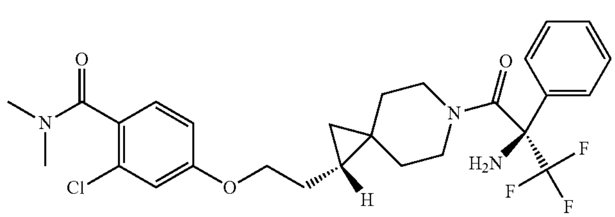 [SMILES: CN(C)C(=O)c1ccc(OCC[C@@H]2CC23CCN(C(=O)[C@](N)(c2ccccc2)C(F)(F)F)CC3)cc1Cl] | 4-(2-((S or R)-6-((R or S)-2-amino-3,3,3-trifluoro-2-phenylpropanoyl)-6-azaspiro[2.5]octan-1-yl)ethoxy)-2-chloro-N,N-dimethylbenzamide | 538.2 |

Example 13-1
2-chloro-N,N-dimethyl-4-((S or R)-1-((R or S)-6-(1-phenylcyclobutanecarbonyl)-6-azaspiro[2.5]octan-1-yl)propan-2-yloxy)benzamide
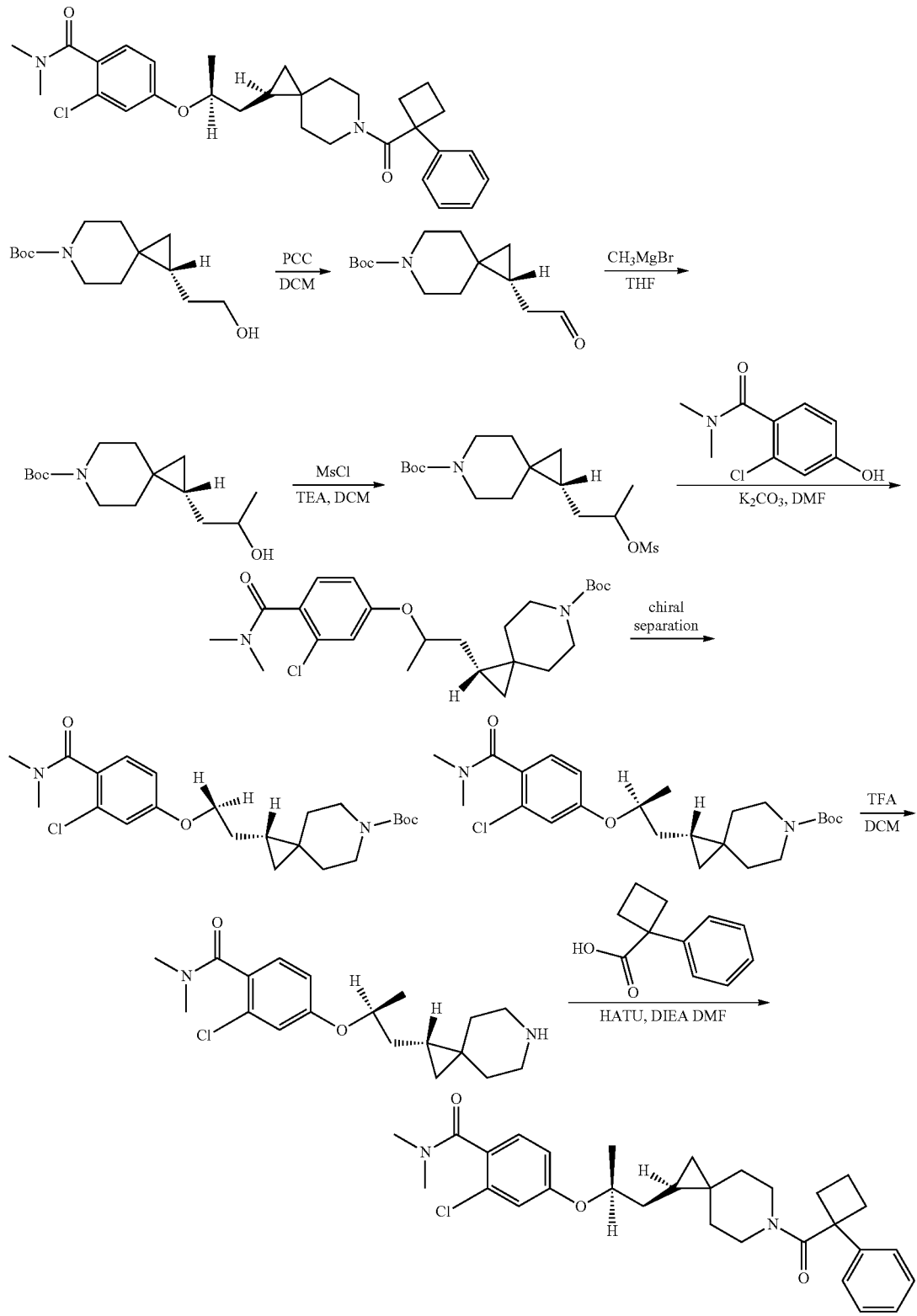

(R or S)-tert-butyl 1-(2-oxoethyl)-6-azaspiro[2.5]octane-6-carboxylate

A mixture of (R or S)-tert-butyl 1-(2-hydroxyethyl)-6-azaspiro[2.5]octane-6-carboxylate ((1.0 g, 3.9 mmol) and PCC (2.5 g, 11.08 mmol) in DCM (35 mL) was stirred at rt for 3 h. Then the mixture was concentrated and the residue was purified by column chromatography (silica gel: 200-300 mesh, PE/EtOAc=5/1) to give (R or S)-tert-butyl 1-(2-oxoethyl)-6-azaspiro[2.5]octane-6-carboxylate. LRMS m/z (M+Na) 276.1 found, 276.2 required.

(1R)-tert-butyl 1-(2-hydroxypropyl)-6-azaspiro[2.5]octane-6-carboxylate

To a solution of (R or S)-tert-butyl 1-(2-oxoethyl)-6-azaspiro[2.5]octane-6-carboxylate ((590 mg, 2.33 mmol) in dry THF (10 mL) was added $CH_3MgBr$ (2.3 mL, 6.99 mmol, 3 M in ether) at 0° C. The mixture was stirred at rt under $N_2$ atmosphere overnight. The reaction mixture was quenched with aqueous ammonium chloride (10 mL), extracted with EtOAc (100 mL×3), washed with brine (40 mL), dried and concentrated to give the crude product, which was purified by column chromatography (silica gel: 200-300 mesh, PE/EtOAc=2/1) to give (1R)-tert-butyl 1-(2-hydroxypropyl)-6-azaspiro[2.5]octane-6-carboxylate. LRMS m/z (M+Na) 292.1 found, 292.2 required.

(1R)-tert-butyl 1-(2-(methylsulfonyloxy)propyl)-6-azaspiro[2.5]octane-6-carboxylate A mixture of (1R)-tert-butyl 1-(2-hydroxypropyl)-6-azaspiro[2.5]octane-6-carboxylate (520 mg, 1.93 mmol), MsCl (264 mg, 2.32 mmol) and TEA (390 mg, 3.87 mmol) in DCM (10 mL) was stirred at rt for 2 h. Water (2 mL) was added and the reaction mixture was diluted with EtOAc (300 mL), washed with sat. $NaHCO_3$ (40 mL×2), brine (40 mL), dried and concentrated to give the crude product, which was purified by column chromatography (silica gel: 200-300 mesh, PE/EtOAc=10/1-5/1) to afford (1R)-tert-butyl 1-(2-(methylsulfonyloxy)propyl)-6-azaspiro[2.5]octane-6-carboxylate. LRMS m/z (M+Na) 370.1 found, 370.2 required.

(1R)-tert-butyl 1-(2-(3-chloro-4-(dimethylcarbamoyl)phenoxy)propyl)-6-azaspiro[2.5]octane-6-carboxylate A mixture of (1R)-tert-butyl 1-(2-(methylsulfonyloxy)propyl)-6-azaspiro[2.5]octane-6-carboxylate (570 mg, 1.64 mmol), 2-chloro-4-hydroxy-N,N-dimethylbenzamide (360 mg, 1.81 mmol) and $K_2CO_3$ (680 mg, 4.92 mmol) in DMF (5 mL) was stirred at 60° C. overnight. Then the mixture was diluted with dichloromethane (300 mL), washed with water (50 mL×2), brine (50 mL), dried and concentrated. The residue was purified by reverse phase chromatography (mobile phase: methanol/water (10 mM $NH_4HCO_3$)) to afford (1R)-tert-butyl 1-(2-(3-chloro-4-(dimethylcarbamoyl)phenoxy)propyl)-6-azaspiro[2.5]octane-6-carboxylate. LRMS m/z (M+H) 451.1 found, 451.2 required. (1R)-tert-butyl 1-(2-(3-chloro-4-(dimethylcarbamoyl)phenoxy)propyl)-6-azaspiro[2.5]octane-6-carboxylate was resolved by Chiral HPLC (column: AD-H (250*4.6 mm 5 um); mobile phase: SCF-CO2:MeOH (0.1% DEA)=70:30; flow: 3.0 mL/min; temperature: 40° C.) to afford (R or S)-tert-butyl 1-((R or S)-2-(3-chloro-4-(dimethylcarbamoyl)phenoxy)propyl)-6-azaspiro[2.5]octane-6-carboxylate (RT=2.86 min) and (R or S)-tert-butyl 1-((S or R)-2-(3-chloro-4-(dimethylcarbamoyl)phenoxy)propyl)-6-azaspiro[2.5]octane-6-carboxylate (RT=3.64 min). Absolute stereochemistry not established.

4-((R or S)-1-((R or S)-6-azaspiro[2.5]octan-1-yl)propan-2-yloxy)-2-chloro-N,N-dimethylbenzamide To a solution of 1-((S or R)-2-(3-chloro-4-(dimethylcarbamoyl)phenoxy)propyl)-6-azaspiro[2.5]octane-6-carboxylate (150.0 mg, 0.33 mmol) in DCM (5 mL) was added 2,2,2-trifluoroacetic acid (2 mL) at rt. The mixture was concentrated in vacuo to afford the crude product 4-((S or R)-1-((R or S)-6-azaspiro[2.5]octan-1-yl)propan-2-yloxy)-2-chloro-N,N-dimethylbenzamide. LRMS m/z (M+H) 351.2 found, 351.2 required.

2-chloro-N,N-dimethyl-4-((S or R)-1-((R or S)-6-(1-phenylcyclobutanecarbonyl)-6-azaspiro[2.5]octan-1-yl)propan-2-yloxy)benzamide A mixture of 4-((S or R)-1-((R or S)-6-azaspiro[2.5]octan-1-yl)propan-2-yloxy)-2-chloro-N,N-dimethylbenzamide (18.0 mg, 0.05 mmol), 1-phenylcyclobutanecarboxylic acid (11 mg, 0.06 mmol), HATU (23.0 mg, 0.06 mmol) and DIEA (13.0 mg, 0.1 mmol) in DMF (1 mL) was stirred at rt overnight. The mixture was directly purified by reverse phase chromatography (mobile phase: methanol/water (10 mM $NH_4HCO_3$)) to afford 2-chloro-N,N-dimethyl-4-((S or R)-1-((R or S)-6-(1-phenylcyclobutanecarbonyl)-6-azaspiro[2.5]octan-1-yl)propan-2-yloxy)benzamide. LRMS m/z (M+H) 509.1 found, 509.2 required.

Example 14-1

2-chloro-N,N-dimethyl-4-(3-((S or R)-6-((S or R)-3,3,3-trifluoro-2-hydroxy-2-phenylpropanoyl)-6-azaspiro[2.5]octan-1-yl)propoxy)benzamide

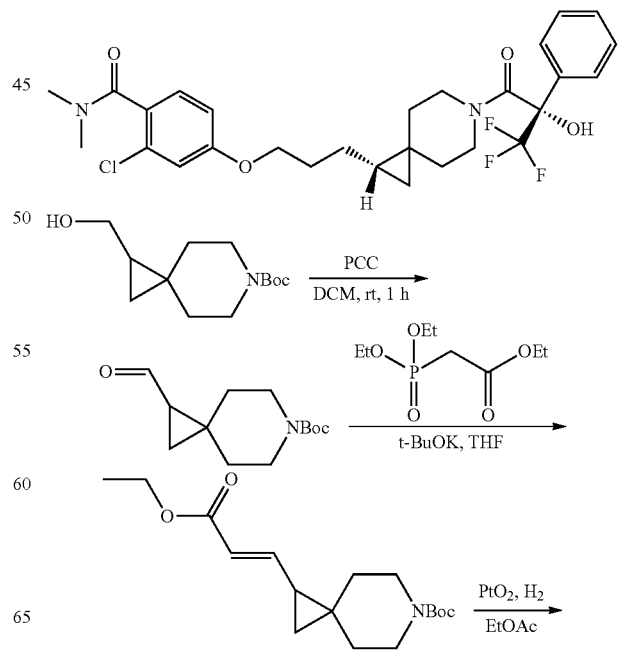

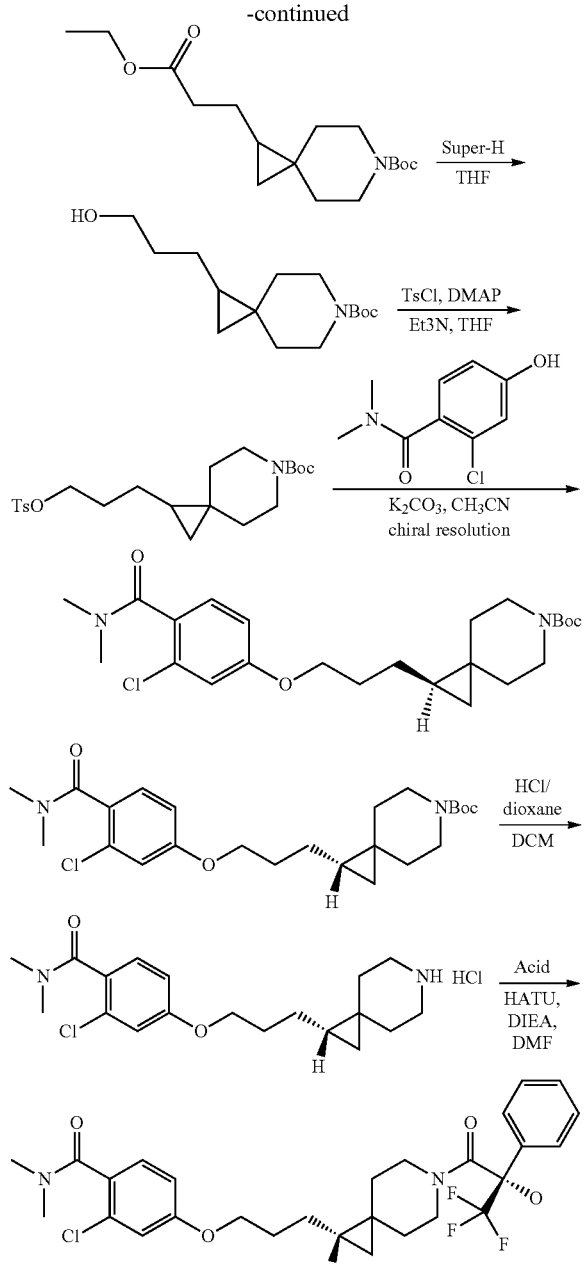

tert-butyl 1-formyl-6-azaspiro[2.5]octane-6-carboxylate

A mixture of tert-butyl 1-(hydroxymethyl)-6-azaspiro[2.5]octane-6-carboxylate (10 g, 41.84 mmol) and PCC (27 g, 125.52 mmol) in DCM (20 mL) was stirred for 1 h at rt. The mixture was concentrated and purified by column chromatography (silica gel: 300-400 mesh, PE/EtOAc=20/1 to 5/1) to give tert-butyl 1-formyl-6-azaspiro[2.5]octane-6-carboxylate. LRMS m/z (M+H) 240.2 found, 240.2 required.

(E)-tert-butyl 1-(3-ethoxy-3-oxoprop-1-enyl)-6-azaspiro[2.5]octane-6-carboxylate A solution of ethyl 2-(diethoxyphosphoryl)acetate (17 g, 53.027 mmol) and t-BuOK (5 g, 53.027 mmol) in dry THF (100 mL) was stirred for 2 h at 0° C. under $N_2$. Then tert-butyl 1-formyl-6-azaspiro[2.5]octane-6-carboxylate (8.5 g, 35.35 mmol) in THF (10 mL) was added to the mixture, which was stirred for 4 h at rt under $N_2$. The mixture was poured into aq. $NH_4Cl$ (100 mL) at 0° C. carefully and stirred for another 30 min. The mixture was extracted with EtOAc (3×500 mL). The combined organic layer was dried over anhydrous $Na_2SO_4$, concentrated and purified by column chromatography (silica gel: 300-400 mesh, PE/EtOAc=20/1 to 5/1, V/V) to give (E)-tert-butyl 1-(3-ethoxy-3-oxoprop-1-enyl)-6-azaspiro[2.5]octane-6-carboxylate. LRMS m/z (M-99) 210.2 found, 210.2 required.

tert-butyl 1-(3-ethoxy-3-oxopropyl)-6-azaspiro[2.5]octane-6-carboxylate

A mixture of (E)-tert-butyl 1-(3-ethoxy-3-oxoprop-1-enyl)-6-azaspiro[2.5]octane-6-carboxylate (6 g, 19.4 mmol), $PtO_2$ (600 mg) in EtOAc (60 mL) was stirred overnight at rt under $H_2$ balloon. The mixture was filtered through a celite pad, and the filtrate was concentrated to give tert-butyl 1-(3-ethoxy-3-oxopropyl)-6-azaspiro[2.5]octane-6-carboxylate. LRMS m/z (M-99) 212.2 found, 212.2 required.

tert-butyl 1-(3-hydroxypropyl)-6-azaspiro[2.5]octane-6-carboxylate

Super-H (51 mL, 51 mmol, 1 M in THF) was added to the mixture of tert-butyl 1-(3-ethoxy-3-oxopropyl)-6-azaspiro[2.5]octane-6-carboxylate (5 g, 16 mmol) in THF (20 mL). And the reaction solution was stirred for 3 h at 0° C. under $N_2$. Then the mixture was quenched with MeOH (50 mL) carefully and stirred for 1 h. Then aq. $NH_4Cl$ (200 mL) was added to the mixture, which was stirred overnight at 50° C. The mixture was extracted with EtOAc (3×300 mL). The organic phase was concentrated, and purified by column chromatography (silica gel: 300-400 mesh, PE/EtOAc=20/1 to 5/1, V/V) to give tert-butyl 1-(3-hydroxypropyl)-6-azaspiro[2.5]octane-6-carboxylate. LRMS m/z (M-99) 170.2 found, 170.2 required.

tert-butyl 1-(3-(tosyloxy)propyl)-6-azaspiro[2.5]octane-6-carboxylate

A solution of tert-butyl 1-(3-hydroxypropyl)-6-azaspiro[2.5]octane-6-carboxylate (2 g, 7.4 mmol), TsCl (19 g, 10.44 mmol), DMAP (0.49 g, 4.01 mmol) and $Et_3N$ (4.8 g, 48.18 mmol) in dry DCM was stirred overnight at rt under $N_2$. Then water (200 mL) was added to the mixture, extracted with EtOAc (3×200 mL), and concentrated. The crude compound was purified by column chromatography (silica gel: 300-400 mesh, PE/EtOAc=20/1 to 5/1, V/V) to give the tert-butyl 1-(3-(tosyloxy)propyl)-6-azaspiro[2.5]octane-6-carboxylate. LRMS m/z (M-55) 368.2 found, 368.2 required.

(S or R)-tert-butyl 1-(3-(3-chloro-4-(dimethylcarbamoyl)phenoxy)propyl)-6-azaspiro[2.5]octane-6-carboxylate A mixture of tert-butyl 1-(3-(tosyloxy)propyl)-6-azaspiro[2.5]octane-6-carboxylate (2.4 g, 5.67 mmol), 2-chloro-4-hydroxy-N,N-dimethylbenzamide (1.36 g, 6.81 mmol), $K_2CO_3$ (3.13 g, 22.70 mmol) in MeCN (20 mL) was stirred overnight at 80° C. under $N_2$. The mixture was diluted with 100 mL of water, extracted with EtOAc (3×200 mL), and concentrated. The residue was purified by column chromatography (silica gel: 300-400 mesh, PE/EtOAc=20/1 to 4/1, V/V). The product was resolved by Chiral HPLC (column: OJ-H (250*4.6 mm 5 um); mobile phase: SCF-CO2/IPA (0.1% DEA)=2.1/0.9; flow: 3 mL/min; temperature: 40° C.) to afford (R or S)-tert-butyl 1-(3-(3-chloro-4-(dimethylcarbamoyl)phenoxy)propyl)-6-azaspiro[2.5]octane-6-carboxylate (RT=5.2 min) (LRMS m/z (M+Na) 473.0 found, 473.2 required) and (S or R)-tert-butyl 1-(3-(3-chloro-4-(dimethylcarbamoyl)phenoxy)propyl)-6-azaspiro[2.5]octane-6-carboxylate (RT=6.2 min) (LRMS m/z (M+Na) 473.0 found, 473.2 required). The absolute stereochemistry not confirmed.

(S or R)-4-(3-(6-azaspiro[2.5]octan-1-yl)propoxy)-2-chloro-N,N-dimethylbenzamide hydrochloride To a solution of (S or R)-tert-butyl 1-(3-(3-chloro-4-(dimethylcarbamoyl)phenoxy)propyl)-6-azaspiro[2.5]octane-6-carboxylate (38 mg, 0.084 mmol, 1.0 eq) in DCM (0.42 mL) was added 4M HCl/1,4-dioxane (0.42 mL, 1.69 mmol, 20.0 eq). After stirring for 3 h, the reaction mixture was concentrated to afford (S or R)-4-(3-(6-azaspiro[2.5]octan-1-yl)propoxy)-2-chloro-N,N-dimethylbenzamide hydrochloride, which was used in the next step without further purification. LRMS m/z (M+H) 351.0 found, 351.2 required.

2-chloro-N,N-dimethyl-4-(3-((S or R)-6-((S or R)-3,3,3-trifluoro-2-hydroxy-2-phenylpropanoyl)-6-azaspiro[2.5]octan-1-yl)propoxy)benzamide To a solution of (S or R)-4-(3-(6-azaspiro[2.5]octan-1-yl)propoxy)-2-chloro-N,N-dimethylbenzamide hydrochloride (39 mg, 0.084 mmol, 1.0 eq), (S or R)-3,3,3-trifluoro-2-hydroxy-2-phenylpropanoic acid (19 mg, 0.084 mmol, 1.0 eq), and HATU (48 mg, 0.13 mmol, 1.5 eq) in DMF (0.76 mL) was added DIEA (0.07 mL, 0.42 mmol, 5.0 eq). The reaction mixture was stirred at rt for 118 h. The mixture was directly purified by reverse phase chromatography (mobile phase: methanol/water (10 mM NH₄HCO₃)) to afford 2-chloro-N,N-dimethyl-4-(3-((S or R)-6-((S or R)-3,3,3-trifluoro-2-hydroxy-2-phenylpropanoyl)-6-azaspiro[2.5]octan-1-yl)propoxy)benzamide. LRMS m/z (M+H) 553.0 found, 553.2 required.

Using the same procedure described in Example 14-1, but replacing (S or R)-3,3,3-trifluoro-2-hydroxy-2-phenylpropanoic acid with the appropriate acid in last step, the following examples were prepared. Absolute stereochemistry not confirmed

| Example | Structure | IUPAC Name | LRMS, found [M + H]+ |
| --- | --- | --- | --- |
| 14-2 | 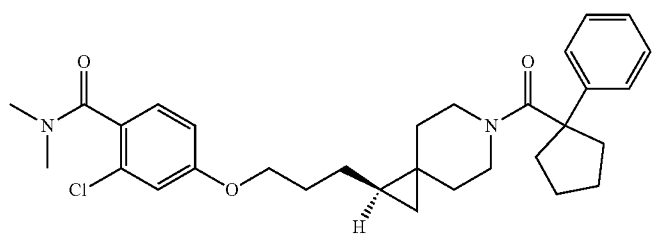 [SMILES: CN(C)C(=O)c1ccc(OCCC[C@@H]2CC23CCN(C(=O)C2(c4ccccc4)CCCC2)CC3)cc1Cl] | (R or S)-2-chloro-N,N-dimethyl-4-(3-(6-(1-phenylcyclopentanecarbonyl)-6-azaspiro[2.5]octan-1-yl)propoxy)benzamide | 523.2 |
| 14-3 | 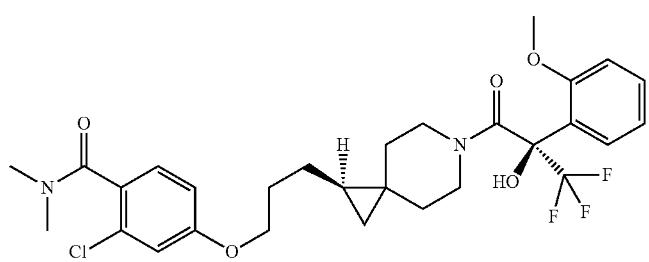 [SMILES: COc1ccccc1[C@@](O)(C(=O)N1CCC2(CC1)C[C@H]2CCCOc1ccc(C(=O)N(C)C)c(Cl)c1)C(F)(F)F] | 2-chloro-N,N-dimethyl-4-(3-((R or S)-6-((R or S)-3,3,3-trifluoro-2-hydroxy-2-(2-methoxyphenyl)propanoyl)-6-azaspiro[2.5]octan-1-yl)propoxy)benzamide | 583.2 |
| 14-4 | 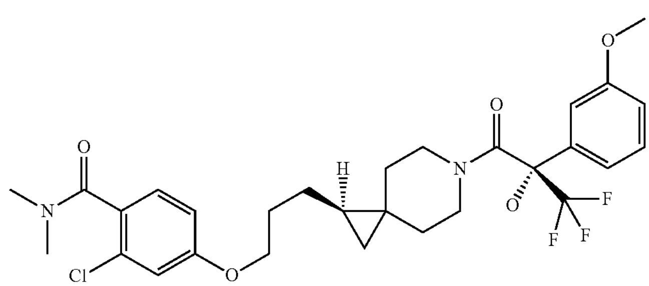 | 2-chloro-N,N-dimethyl-4-(3-((R or S)-6-((S or R)-3,3,3-trifluoro-2-hydroxy-2-(3-methoxyphenyl)propanoyl)-6-azaspiro[2.5]octan-1-yl)propoxy)benzamide | 583.2 |

-continued

| Example | Structure | IUPAC Name | LRMS, found [M + H]+ |
|---|---|---|---|
| 14-5 | 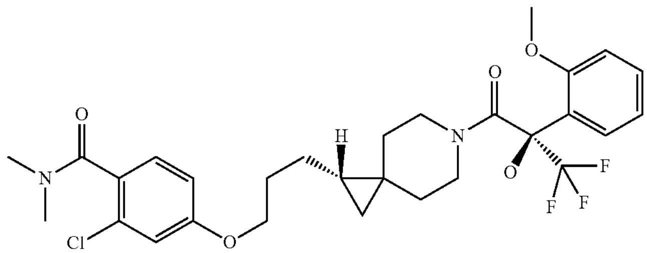 [SMILES: COc1ccccc1[C@@](O)(C(=O)N1CCC2(CC1)C[C@@H]2CCCOc1ccc(C(=O)N(C)C)c(Cl)c1)C(F)(F)F] | 2-chloro-N,N-dimethyl-4-(3-((S or R)-6-((R or S)-3,3,3-trifluoro-2-hydroxy-2-(2-methoxyphenyl)propanoyl)-6-azaspiro[2.5]octan-1-yl)propoxy)benzamide | 583.2 |
| 14-6 | 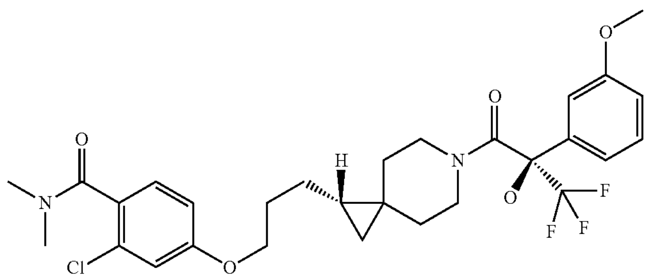 | 2-chloro-N,N-dimethyl-4-(3-((S or R)-6-((R or S)-3,3,3-trifluoro-2-hydroxy-2-(3-methoxyphenyl)propanoyl)-6-azaspiro[2.5]octan-1-yl)propoxy)benzamide | 583.2 |
| 14-7 | 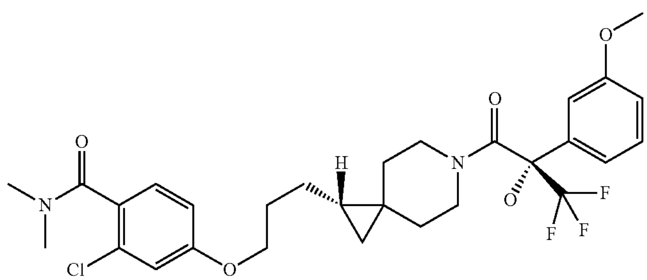 | 2-chloro-N,N-dimethyl-4-(3-((S or R)-6-((S or R)-3,3,3-trifluoro-2-hydroxy-2-(3-methoxyphenyl)propanoyl)-6-azaspiro[2.5]octan-1-yl)propoxyl)benzamide | 583.2 |

Example 15-1

2-chloro-N,N-dimethyl-6-(3-((S or R)-6-((R or S)-3,3,3-trifluoro-2-hydroxy-2-phenylpropanoyl)-6-azaspiro[2.5]octan-1-yl)propoxy)nicotinamide

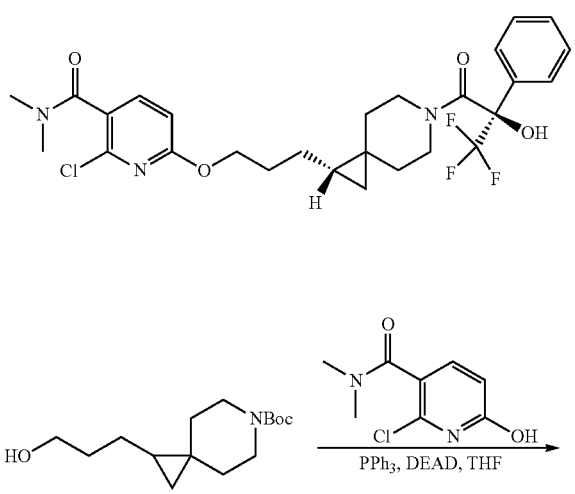

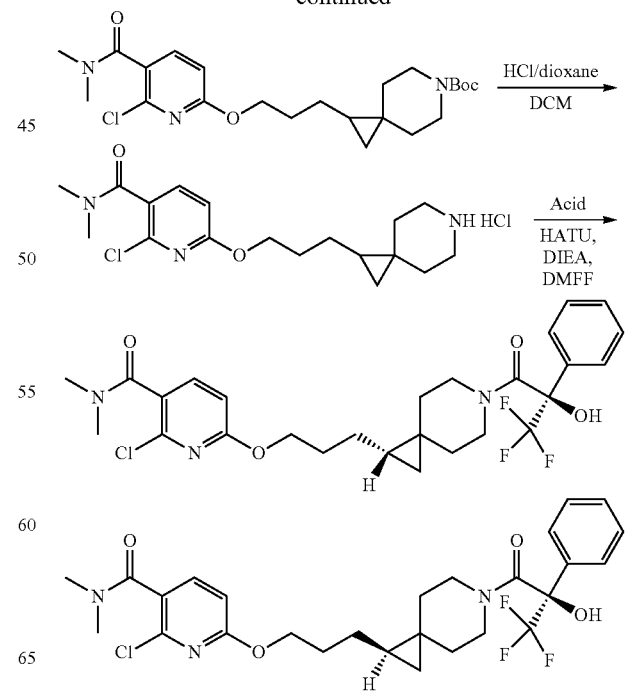

tert-butyl 1-(3-(6-chloro-5-(dimethylcarbamoyl) pyridin-2-yloxy)propyl)-6-azaspiro[2.5]octane-6-carboxylate To a solution of tert-butyl 1-(3-hydroxypropyl)-6-azaspiro[2.5]octane-6-carboxylate (170 mg, 0.62 mmol, 1.0 eq), 2-chloro-6-hydroxy-N,N-dimethylnicotinamide (126 mg, 0.62 mmol, 1.0 eq) and tripheylphosphine (296 mg, 1.14 mmol, 1.8 eq) in anhydrous THF (9 mL) was added DEAD (132 mg, 0.76 mmol, 1.2 eq) at 0° C. After stirring for 15 min at 0° C., the reaction mixture was warmed to rt and stirred overnight. The mixture was concentrated in vacuo to afford the crude product, which was purified by column chromatography (silica gel: 300-400 mesh, PE/EtOAc=2/1) to give tert-butyl 1-(3-(6-chloro-5-(dimethylcarbamoyl) pyridin-2-yloxy)propyl)-6-azaspiro[2.5]octane-6-carboxylate. LRMS m/z (M+Na) 473.9 found, 474.2 required.

6-(3-(6-azaspiro[2.5]octan-1-yl)propoxy)-2-chloro-N,N-dimethylnicotinamide hydrochloride To a solution of tert-butyl 1-(3-(6-chloro-5-(dimethylcarbamoyl)pyridin-2-yloxy)propyl)-6-azaspiro[2.5]octane-6-carboxylate (224 mg, 0.5 mmol) in DCM (3.6 mL) was added 4M HCl/1,4-dioxane (3.6 mL, 14.4 mmol) at rt. After stirring for 3 h, the reaction mixture was concentrated to afford 6-(3-(6-azaspiro[2.5]octan-1-yl)propoxy)-2-chloro-N,N-dimethylnicotinamide hydrochloride, which was used in the next step without further purification. LRMS m/z (M+H) 352.1 found, 352.2 required.

2-chloro-N,N-dimethyl-6-(3-((S or R)-6-((R or S)-3,3,3-trifluoro-2-hydroxy-2-phenylpropanoyl)-6-azaspiro[2.5]octan-1-yl)propoxy)nicotinamide To a solution of 6-(3-(6-azaspiro[2.5]octan-1-yl)propoxy)-2-chloro-N,N-dimethylnicotinamide hydrochloride (89 mg, 0.23 mmol, 1.0 eq), (R or S)-3,3,3-trifluoro-2-hydroxy-2-phenylpropanoic acid (51 mg, 0.23 mmol, 1.0 eq), and HATU (132 mg, 0.35 mmol, 1.5 eq) in DMF (1 mL) was added DIEA (150 mg, 1.16 mmol, 5.0 eq) at rt. The reaction mixture was stirred at rt for 3 h. The mixture was filtered and the filtrate was purified by reverse phase chromatography (mobile phase: methanol/water (10 mM $NH_4HCO_3$)) to afford racemic product. The racemic product was resolved by Chiral HPLC (column: OZ (250*4.6 mm 5 um); mobile phase: SCF-$CO_2$/EtOH (0.1% DEA)=1.8/1.2; flow: 3 mL/min; temperature: 39.5° C.) to afford 2-chloro-N,N-dimethyl-6-(3-((S or R)-6-((R or S)-3,3,3-trifluoro-2-hydroxy-2-phenylpropanoyl)-6-azaspiro[2.5]octan-1-yl) propoxy)nicotinamide (RT=5.5 min) (LRMS m/z (M+H) 554.2 found, 554.2 required) and 2-chloro-N,N-dimethyl-6-(3-((R or S)-6-((R or S)-3,3,3-trifluoro-2-hydroxy-2-phenylpropanoyl)-6-azaspiro[2.5]octan-1-yl)propoxy)nicotinamide (RT=6.14 min) (LRMS m/z (M+H) 554.2 found, 554.2 required). Absolute stereochemistry not confirmed.

Using the same procedure described for Example 15-1, but replacing (S or R)-3,3,3-trifluoro-2-hydroxy-2-phenylpropanoic acid with the appropriate acid, the following examples were prepared. Absolute stereochemistry not confirmed

| Example | Structure | IUPAC Name | LRMS, found [M + H]+ |
|---|---|---|---|
| 15-2 | 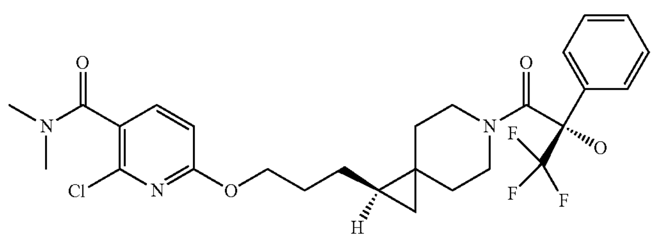 [SMILES: CN(C)C(=O)c1ccc(OCCC[C@@H]2CC23CCN(C(=O)[C@@](O)(c2ccccc2)C(F)(F)F)CC3)nc1Cl] | 2-chloro-N,N-dimethyl-6-(3-((R or S)-6-((S or R)-3,3,3-trifluoro-2-hydroxy-2-phenylpropanoyl)-6-azaspiro[2.5]octan-1-yl)propoxy)nicotinamide | 554.2 |
| 15-3 | 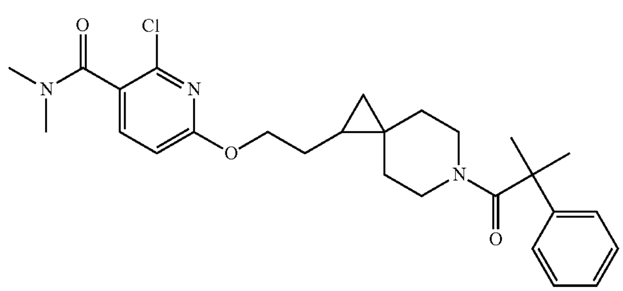 [SMILES: CN(C)C(=O)c1ccc(OCCC2CC23CCN(C(=O)C(C)(C)c2ccccc2)CC3)nc1Cl] | 2-chloro-N,N-dimethyl-6-(2-(6-(2-methyl-2-phenylpropanoyl)-6-azaspiro[2.5]octan-1-yl)ethoxy)nicotinamide | 484.1 |

Example 16-1

2-chloro-N,N-dimethyl-4-((1-methyl-2-(1-((R or S)-3,3,3-trifluoro-2-hydroxy-2-(3-methoxyphenyl)propanoyl)piperidin-4-yl)cyclopropyl)methoxy)benzamide

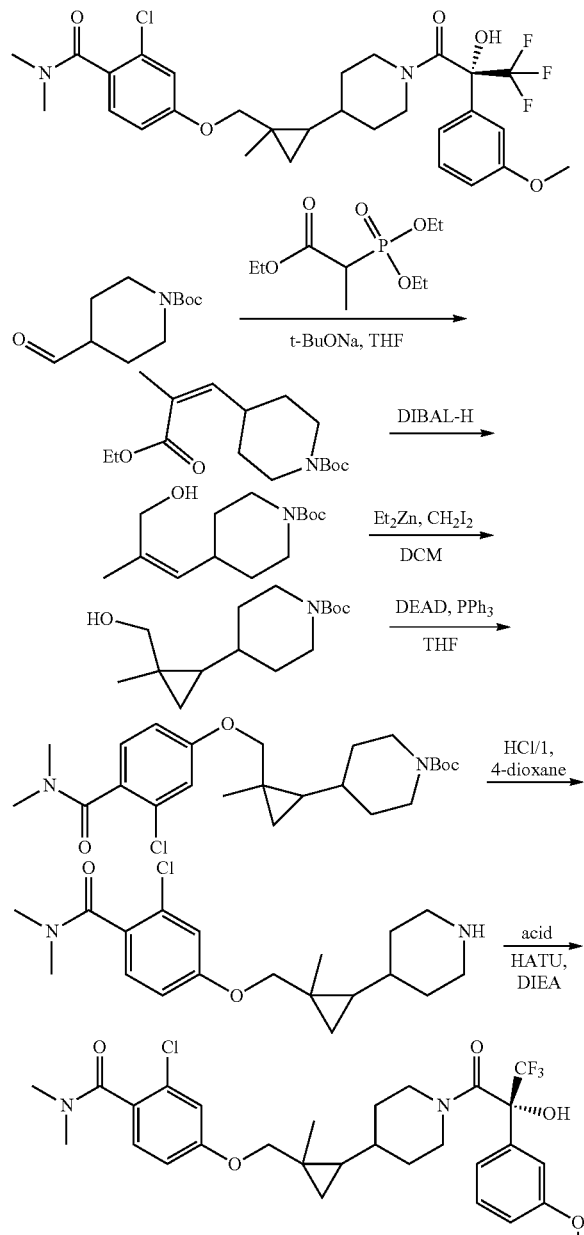

(Z)-tert-butyl 4-(3-ethoxy-2-methyl-3-oxoprop-1-enyl)piperidine-1-carboxylate To a solution of t-BuONa (379 mg, 3.94 mmol) in anhydrous THF (20 mL) at 0° C. under $N_2$ balloon was added ethyl 2-(diethoxyphosphoryl)propanoate (871 mg, 3.66 mmol). And the mixture was stirred at room temperature for 1 h. After cooling to 0° C., tert-butyl 4-formylpiperidine-1-carboxylate (600 mg, 2.81 mmol) was added. The resulting mixture was stirred at room temperature for 1 h. LRMS showed the reaction was completed. The mixture was quenched with sat. $NH_4Cl$ (20 mL), diluted with EtOAc (200 mL), washed with brine (30 mL×3), dried ($Na_2SO_4$) and concentrated. The residue was purified by column chromatography (silica gel, PE/EtOAc=10/1 to 5/1) to give (Z)-tert-butyl 4-(3-ethoxy-2-methyl-3-oxoprop-1-enyl)piperidine-1-carboxylate. LRMS m/z (M+Na), 320.2 found, 320.2 required.

(Z)-tert-butyl 4-(3-hydroxy-2-methylprop-1-enyl)piperidine-1-carboxylate

To a solution of (Z)-tert-butyl 4-(3-ethoxy-2-methyl-3-oxoprop-1-enyl)piperidine-1-(220 mg, 0.74 mmol) in anhydrous DCM (8 mL) at 0° C. under $N_2$ was added DIBAL-H (2.2 mL, 2.2 mmol, 1 M in cyclohexane). Then the mixture was stirred at 0° C. for 2 h. LC-MS showed the reaction was completed. The mixture was quenched with aq potassium sodium tartrate (10%, 20 mL), diluted with DCM (200 mL), washed with brine (30 mL×3), dried over anhydrous $Na_2SO_4$ and concentrated. The residue was purified by column chromatography (silica gel, PE/EtOAc=2/1 to 1/1) to give (Z)-tert-butyl 4-(3-hydroxy-2-methylprop-1-enyl)piperidine-1-carboxylate. LRMS m/z (M+Na), 278.2 found, 278.2 required.

tert-butyl 4-(2-(hydroxymethyl)-2-methylcyclopropyl)piperidine-1-carboxylate At −15° C., to a solution of $ZnEt_2$ (1.1 mL, 1.2 mmol, 1.1 M in toluene) in anhydrous DCM (8 mL) under $N_2$ was added dropwise $CH_2I_2$ (315 mg, 1.2 mmol). Then the mixture was stirred at −15° C. for 20 min. Then (Z)-tert-butyl 4-(3-hydroxy-2-methylprop-1-enyl)piperidine-1-carboxylate (100 mg, 0.41 mmol) was added. The mixture was warmed to room temperature overnight, quenched with sat. $NH_4Cl$ (20 mL), diluted with EtOAc (80 mL) and washed with water (30 mL×3), brine (30 mL), dried over anhydrous $Na_2SO_4$) and concentrated. The residue was purified by column chromatography (Silica gel, PE:EtOAc=2:1 to 1:1) to give tert-butyl 4-(2-(hydroxymethyl)-2-methylcyclopropyl)piperidine-1-carboxylate. LRMS m/z (M+Na) 292.2 found, 292.2 required.

tert-butyl 4-(2-((3-chloro-4-(dimethylcarbamoyl)phenoxy)methyl)-2-methylcyclopropyl)piperidine-1-carboxylate To a solution of tert-butyl 4-(2-(hydroxymethyl)-2-methylcyclopropyl)piperidine-1-carboxylate (53 mg, 0.20 mmol), 2-chloro-4-hydroxy-N,N-dimethylbenzamide (43 mg, 0.22 mmol) and $PPh_3$ (88 mg, 0.33 mmol) in toluene (1.5 mL) was added a solution of DEAD (69 mg, 0.39 mmol) in toluene (0.5 mL) at room temperature. The resulting mixture was stirred at 50° C. under $N_2$ atmosphere for 1 h, concentrated and the residue was purified by reverse phase chromatography (mobile phase: methanol/water (10 mM $NH_4HCO_3$)) to afford tert-butyl 4-(2-((3-chloro-4-(dimethylcarbamoyl)phenoxy)methyl)-2-methylcyclopropyl)piperidine-1-carboxylate. LRMS m/z (M+H) 451.2 found, 451.2 required.

2-chloro-N,N-dimethyl-4-((1-methyl-2-(piperidin-4-yl)cyclopropyl)methoxy)benzamide A mixture of tert-butyl 4-(2-((3-chloro-4-(dimethylcarbamoyl)phenoxy)methyl)-2-methylcyclopropyl)piperidine- 1-carboxylate (85 mg, 0.19 mmol) in 4M HCl/dioxane (5 mL) was stirred at room temperature for 2 h. After evaporation of solvent, 10 mL of sat. NaHCO$_3$ was added to the residue and extracted with DCM (20 mL×3). The combined organic phase was washed with brine (20 mL) and dried over anhydrous Na$_2$SO$_4$ and concentrated. The residue was purified by reverse phase chromatography (mobile phase: methanol/water (10 mM NH$_4$HCO$_3$)) to give 2-chloro-N,N-dimethyl-4-((1-methyl-2-(piperidin-4-yl)cyclopropyl)methoxy)benzamide. LRMS m/z (M+H) 351.2 found, 351.2 required.

2-chloro-N,N-dimethyl-4-((1-methyl-2-(1-((R or S)-3,3,3-trifluoro-2-hydroxy-2-(3-methoxyphenyl)propanoyl)piperidin-4-yl)cyclopropyl)methoxy)benzamide A mixture of 2-chloro-N,N-dimethyl-4-((1-methyl-2-(piperidin-4-yl)cyclopropyl)methoxy)benzamide (30 mg, 0.09 mmol), HATU (56 mg, 0.15 mmol), DIPEA (33 mg, 0.26 mmol) and (R or S)-3,3,3-trifluoro-2-hydroxy-2-(3-methoxyphenyl)propanoic acid (33 mg, 0.13 mmol) in THF (3 mL) was stirred at room temperature under N$_2$ overnight. The mixture was diluted with EtOAc (50 mL), washed with water (10 mL×3), brine (10 mL) and dried over anhydrous Na$_2$SO$_4$. The solvent was removed under reduced pressure and the residue was purified by reverse phase chromatography (mobile phase: methanol/water (10 mM NH$_4$HCO$_3$)) to give 2-chloro-N,N-dimethyl-4-((1-methyl-2-(1-((R or S)-3,3,3-trifluoro-2-hydroxy-2-(3-methoxyphenyl)propanoyl)piperidin-4-yl)cyclopropyl)methoxy)benzamide. LRMS m/z (M+H) 583.2 found, 583.2 required.

Example 17-1

(R or S)-2-chloro-N,N-dimethyl-4-((1-((1-(3,3,3-trifluoro-2-hydroxy-2-phenylpropanoyl)piperidin-4-yl)methyl)cyclopropyl)methoxy)benzamide

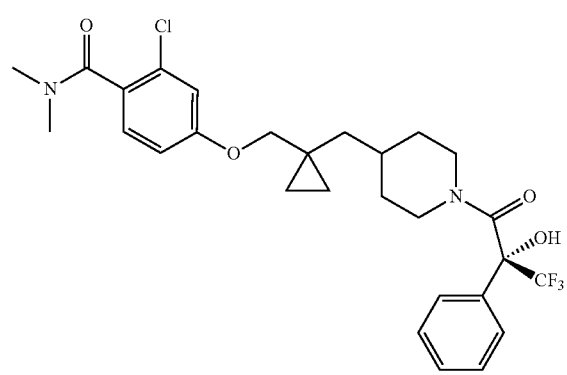

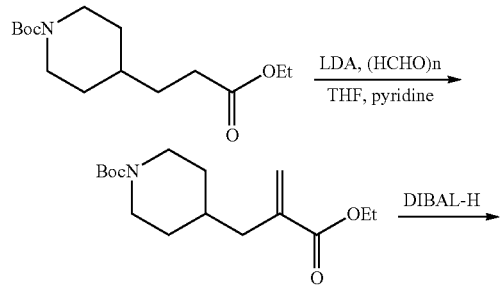

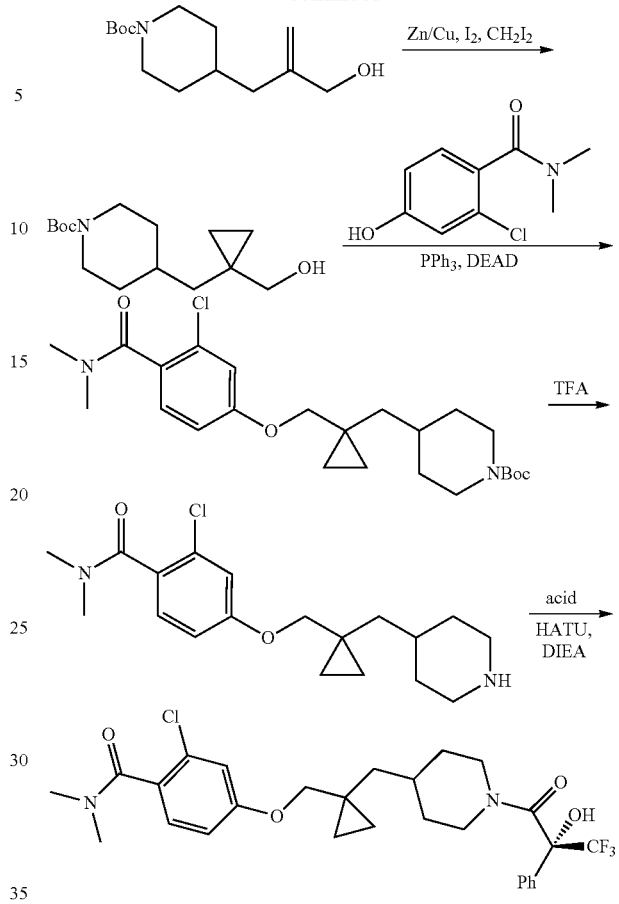

tert-butyl 4-(2-(ethoxycarbonyl)allyl)piperidine-1-carboxylate

To a solution of tert-butyl 4-(3-ethoxy-3-oxopropyl)piperidine-1-carboxylate (1.5 g, 5.3 mmol) in THF (10 mL) was added LDA (8 mL, 8 mmol, 1M in THF) at −78° C. After stirring for 1 h, (HCHO)n (240 mg, 8 mmol) was added to the mixture. The resulting mixture was stirred for 4 h at rt before MsCl (912 mg, 8 mmol) and pyridine (1 mL) was added. The reaction mixture was heated to 50° C. overnight, quenched with aq NH$_4$Cl (50 mL) and extracted with EtOAc (50 mL*3). The organic layers were washed with brine (10 mL), dried over anhydrous Na$_2$SO$_4$, filtered and concentrated. The residue was purified by chromatography (silica gel: 300-400 mesh, PE/EtOAc=10/1 to 5/1) to give tert-butyl 4-(2-(ethoxycarbonyl)allyl)piperidine-1-carboxylate. LRMS m/z (M+H) 298.2 found, 298.2 required.

tert-butyl 4-(2-(hydroxymethyl)allyl)piperidine-1-carboxylate

To a solution of tert-butyl 4-(2-(ethoxycarbonyl)allyl)piperidine-1-carboxylate (300 mg, 1 mmol) in DCM (3 mL) was added DIBAL-H (3 mL, 3 mmol, 1M in hexane) at 0° C. The mixture was stirred at rt overnight, quenched with 1N NaOH (10 mL) and extracted with EtOAc (30 mL*3). The organic layers were washed with brine (10 mL), dried over anhydrous Na$_2$SO$_4$, filtered and concentrated. The residue was purified by chromatography (silica gel: 300-400 mesh, PE/EtOAc=10/1 to 3/1) to give tert-butyl 4-(2-(hydroxymethyl)allyl)piperidine-1-carboxylate. LRMS m/z (M+H) 256.2 found, 256.2 required.

tert-butyl 4-((1-(hydroxymethyl)cyclopropyl)methyl)piperidine-1-carboxylate

A mixture of Zn—Cu couple (104 mg, 1.6 mmol), $CH_2I_2$ (214 mg, 0.8 mmol) and $I_2$ (13 mg, 0.05 mmol) in ether (3 mL) was stirred at rt for 1 h. tert-butyl 4-(2-(hydroxymethyl)allyl)piperidine-1-carboxylate (137 mg, 0.54 mmol) was added to the mixture and the resulting mixture was stirred at rt overnight. The mixture was filtered and the filtrate was concentrated. The residue was purified by chromatography (silica gel: 300-400 mesh, PE/EtOAc=10/1 to 3/1) to give tert-butyl 4-((1-(hydroxymethyl)cyclopropyl)methyl)piperidine-1-carboxylate. LRMS m/z (M+H) 270.2 found, 270.2 required.

tert-butyl 4-((1-((3-chloro-4-(dimethylcarbamoyl)phenoxy)methyl)cyclopropyl)methyl)piperidine-1-carboxylate A mixture of tert-butyl 4-((1-(hydroxymethyl)cyclopropyl)methyl)piperidine-1-carboxylate (50 mg, 0.18 mmol), 2-chloro-4-hydroxy-N,N-dimethylbenzamide (40 mg, 0.2 mmol), $PPh_3$ (71 mg, 0.27 mmol) and DEAD (47 mg, 0.27 mmol) in THF (2 mL) was stirred at rt overnight. The mixture was directly purified by reverse phase chromatography (mobile phase: methanol/water (10 mM $NH_4HCO_3$)) to give tert-butyl 4-((1-((3-chloro-4-(dimethylcarbamoyl)phenoxy)methyl)cyclopropyl)methyl)piperidine-1-carboxylate. LRMS m/z (M+H) 451.3 found, 451.2 required.

2-chloro-N,N-dimethyl-4-((1-(piperidin-4-ylmethyl)cyclopropyl)methoxy)benzamide

A mixture of tert-butyl 4-((1-((3-chloro-4-(dimethylcarbamoyl)phenoxy)methyl)cyclopropyl)methyl)piperidine-1-carboxylate (65 mg, 0.14 mmol) and TFA (1 mL) in DCM (2 mL) was stirred at rt for 2 h. The mixture was concentrated in vacuo to give 2-chloro-N,N-dimethyl-4-((1-(piperidin-4-ylmethyl)cyclopropyl)methoxy)benzamide TFA salt. LRMS m/z (M+H) 351.3 found, 351.2 required.

(R or S)-2-chloro-N,N-dimethyl-4-((1-((1-(3,3,3-trifluoro-2-hydroxy-2-phenylpropanoyl)piperidin-4-yl)methyl)cyclopropyl)methoxy)benzamide A mixture of 2-chloro-N,N-dimethyl-4-((1-(piperidin-4-ylmethyl)cyclopropyl)methoxy)benzamide (20 mg, 0.04 mmol), (R or S)-3,3,3-trifluoro-2-hydroxy-2-phenylpropanoic acid (11 mg, 0.05 mmol), HATU (23 mg, 0.06 mmol) and DIEA (15 mg, 0.12 mmol) in DMF (1 mL) was stirred at rt overnight. The mixture was directly purified by reverse phase chromatography (mobile phase: methanol/water (10 mM $NH_4HCO_3$)) to give (R or S)-2-chloro-N,N-dimethyl-4-((1-((1-(3,3,3-trifluoro-2-hydroxy-2-phenylpropanoyl)piperidin-4-yl)methyl)cyclopropyl)methoxy)benzamide. LRMS m/z (M+H) 553.3 found, 553.2 required.

Example 18-1

2-chloro-N,N-dimethyl-4-((1S,2S or 1R,2R)-2-(2-(1-((R or S)-3,3,3-trifluoro-2-hydroxy-2-phenylpropanoyl)piperidin-4-yl)ethyl)cyclopropoxy)benzamide

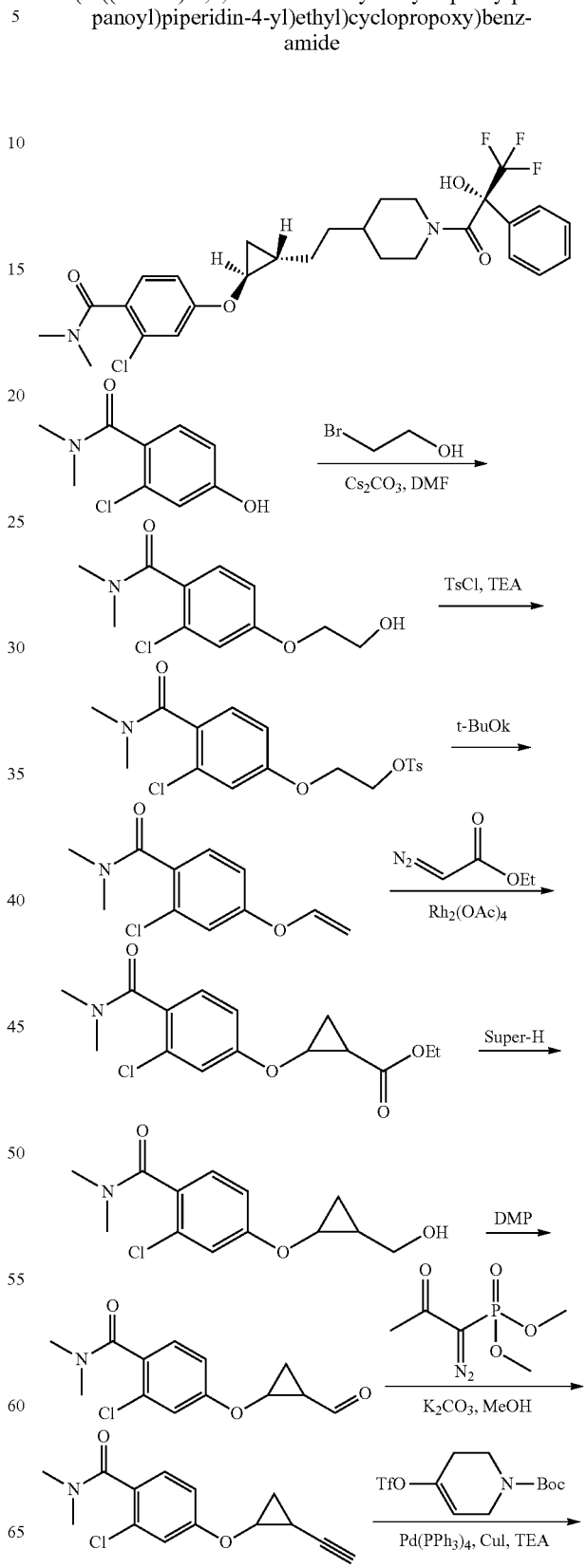

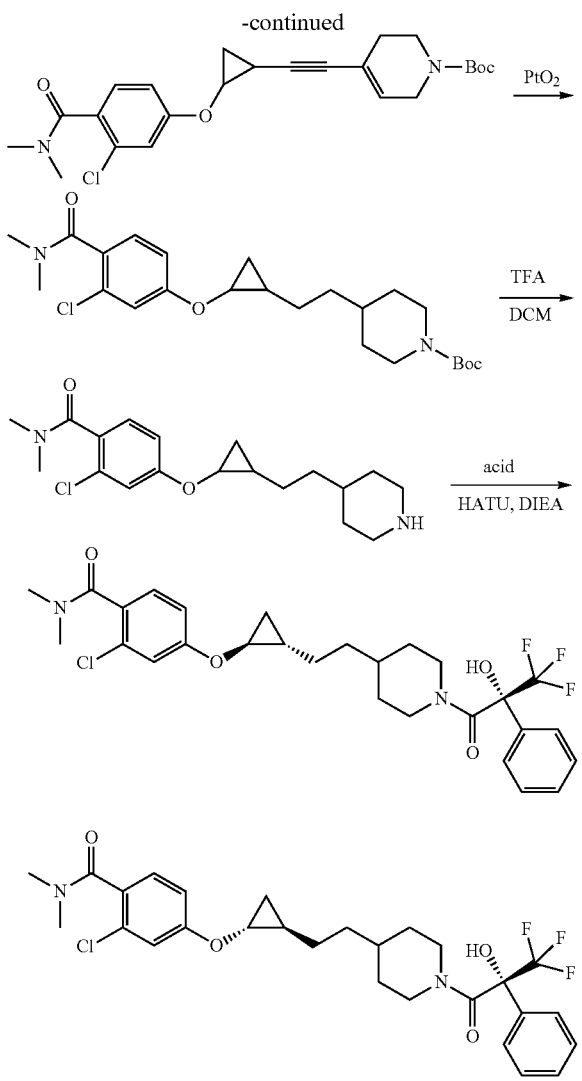

2-chloro-4-(2-hydroxyethoxy)-N,N-dimethylbenzamide

A mixture of 2-chloro-4-hydroxy-N,N-dimethylbenzamide (10 g, 50.0 mmol), Cs$_2$CO$_3$ (24.5 g, 75 mmol) and 2-bromoethanol (7.5 g, 60.0 mmol) in DMF (100 mL) was stirred overnight at 120° C. Then the mixture was concentrated, diluted with EtOAc (200 mL) and washed with water (3×50 mL). The organic layer was dried over anhydrous Na$_2$SO$_4$, concentrated and the residue was purified by column chromatography (PE:EtOAc=1:1) to give 2-chloro-4-(2-hydroxyethoxy)-N,N-dimethylbenzamide. LRMS m/z (M+H) 244.2 found, 244.1 required.

2-(3-chloro-4-(dimethylcarbamoyl)phenoxy)ethyl 4-methylbenzenesulfonate

To a solution of 2-chloro-4-(2-hydroxyethoxy)-N,N-dimethylbenzamide (10 g, 40.9 mmol) in DCM (100 mL) at 0° C. was added 4-toluene sulfonyl chloride (9.4 g, 49 mmol), DMAP (300 mg, 2.45 mmol) and TEA (10 mL). The reaction mixture was stirred overnight at RT, then concentrated, diluted with EtOAc (200 mL) and washed with water (3×20 mL). The organic layer was dried over anhydrous Na$_2$SO$_4$ and concentrated to give 2-(3-chloro-4-(dimethylcarbamoyl)phenoxy)ethyl 4-methylbenzenesulfonate. LRMS m/z (M+H) 398.2 found, 398.1 required.

2-chloro-N,N-dimethyl-4-(vinyloxy)benzamide

A mixture of 2-(3-chloro-4-(dimethylcarbamoyl)phenoxy)ethyl 4-methylbenzenesulfonate (12 g, 30 mmol) and potassium tert-butylate (6.77 g, 60 mmol) in DMSO (50 mL) was stirred for 3 h at RT. Then the mixture was diluted with EtOAc (200 mL) and washed with water (5×20 mL). The organic layer was dried over anhydrous Na$_2$SO$_4$, concentrated, and purified by column chromatography (silica gel: 300-400 mesh, PE/EtOAc=4/1) to give 2-chloro-N,N-dimethyl-4-(vinyloxy)benzamide. LRMS m/z (M+H) 226.2 found, 226.1 required.

ethyl 2-(3-chloro-4-(dimethylcarbamoyl)phenoxy)cyclopropanecarboxylate

To a solution of 2-chloro-N,N-dimethyl-4-(vinyloxy)benzamide (5 g, 22.2 mmol) and Rh$_2$(OAc)$_4$ (980 mg, 2.2 mmol) in DCM (30 mL) was added dropwise ethyl diazoacetate (7.6 g, 66.6 mmol) in DCM (10 mL) over 2 h at RT. After stirring at RT overnight, the mixture was concentrated. The residue was purified by column chromatography (silica gel: 300-400 mesh, PE/EtOAc=3/1 to 1/1) to afford trans-ethyl 2-(3-chloro-4-(dimethylcarbamoyl)phenoxy)cyclopropanecarboxylate (1.5 g, LCMS: RT=1.52 min) and cis-ethyl 2-(3-chloro-4-(dimethylcarbamoyl)phenoxy)cyclopropanecarboxylate (LCMS: RT=1.61 min). LRMS m/z (M+H) 312.2 found, 312.1 required.

Trans-2-chloro-4-(2-(hydroxymethyl)cyclopropoxy)-N,N-dimethylbenzamide

To a solution of trans-ethyl 2-(3-chloro-4-(dimethylcarbamoyl)phenoxy)cyclopropanecarboxylate (1.5 g, 4.5 mmol) in DCM (10 mL) was added Super-hydride (13 mL, 13 mmol, 1M in THF) at 0° C. The mixture was stirred for 3 h at RT, then quenched with aq NH$_4$Cl (20 mL) and extracted with EtOAc (3×30 mL). The organic layer was dried over anhydrous Na$_2$SO$_4$, filtered and concentrated. The crude product was purified by chromatography (PE:EtOAc=1:1) to give trans-2-chloro-4-(2-(hydroxymethyl)cyclopropoxy)-N,N-dimethylbenzamide. LRMS m/z (M+H) 270.1 found, 270.1 required.

Trans-2-chloro-4-(2-formylcyclopropoxy)-N,N-dimethylbenzamide

A mixture of trans-2-chloro-4-(2-(hydroxymethyl)cyclopropoxy)-N,N-dimethylbenzamide (1 g, 3.7 mmol) and pyridinium dichromate (3 g, 7.9 mmol) in DCM (20 mL) was stirred for 3 h at RT. Then the mixture was diluted with Et$_2$O (50 mL) and filtered. The filtrate was washed with water (3×20 mL) and brine (2×10 mL). The organic layer was dried over anhydrous Na$_2$SO$_4$ and concentrated and the residue was purified by column chromatography (silica gel: 300-400 mesh, PE/EtOAc=5/1) to afford trans-2-chloro-4-(2-formylcyclopropoxy)-N,N-dimethylbenzamide. LRMS m/z (M+H) 268.1 found, 268.1 required.

Trans-2-chloro-4-(2-ethynylcyclopropoxy)-N,N-dimethylbenzamide

A mixture of trans-2-chloro-4-(2-formylcyclopropoxy)-N,N-dimethylbenzamide (800 mg, 2.99 mmol), K$_2$CO$_3$ (1.2 g, 8.7 mmol) and dimethyl 1-diazo-2-oxopropylphosphonate (864 mg, 4.5 mmol) in MeOH (10 mL) was stirred for 3 h at RT. Then the mixture was concentrated. The residue was purified by column chromatography (silica gel: 300-400 mesh, PE/EtOAc=20/1) to afford trans-2-chloro-4-(2-ethynylcyclopropoxy)-N,N-dimethylbenzamide. LRMS m/z (M+H) 264.1 found, 264.1 required.

Trans-tert-butyl 4-((2-(3-chloro-4-(dimethylcarbamoyl)phenoxy)cyclopropyl)ethynyl)-5,6-dihydropyridine-1(2H)-carboxylate A mixture of trans-2-chloro-4-(2-ethynylcyclopropoxy)-N,N-dimethylbenzamide (700 mg, 2.66 mmol), tert-butyl 4-(trifluoromethylsulfonyloxy)-5,6-dihydropyridine-1(2H)-carboxylate (968 mg, 2.92 mmol), tetrakis(triphenylphosphine)palladium (462 mg, 0.4 mmol) and CuI (76 mg, 0.4 mmol) in TEA (2 mL) and THF (20 mL) was stirred for 2 h at RT. Then the mixture was filtered, concentrated and purified by column chromatography (silica gel: 300-400 mesh, PE/EtOAc=3/1) to afford trans-tert-butyl 4-((2-(3-chloro-4-(dimethylcarbamoyl)phenoxy)cyclopropyl)ethynyl)-5,6-dihydropyridine-1(2H)-carboxylate. LRMS m/z (M+H) 445.2 found, 445.2 required.

Trans-tert-butyl 4-(2-(2-(3-chloro-4-(dimethylcarbamoyl)phenoxy)cyclopropyl)ethyl)piperidine-1-carboxylate A mixture of trans-tert-butyl 4-((2-(3-chloro-4-(dimethylcarbamoyl)phenoxy)cyclopropyl)ethynyl)-5,6-dihydropyridine-1(2H)-carboxylate (860 mg, 1.94 mmol) and PtO₂ (200 mg) in EtOAc (20 mL) was evacuated and then refilled with hydrogen balloon (three times). The mixture was stirred overnight at RT under hydrogen balloon, then filtered and concentrated to afford trans-tert-butyl 4-(2-(2-(3-chloro-4-(dimethylcarbamoyl)phenoxy)cyclopropyl)ethyl)piperidine-1-carboxylate. LRMS m/z (M+H) 451.2 found, 451.2 required.

Trans-2-chloro-N,N-dimethyl-4-(2-(2-(piperidin-4-yl)ethyl)cyclopropoxy)benzamide A mixture of trans-tert-butyl 4-(2-(2-(3-chloro-4-(dimethylcarbamoyl)phenoxy)cyclopropyl)ethyl)piperidine-1-carboxylate (860 mg, 1.91 mmol) and TFA (5 mL) in DCM (10 mL) was stirred for 2 h at RT. Then the mixture was concentrated to give trans-2-chloro-N-methyl-4-(((1S,2S or 1R,2R)-2-(piperidin-4-yl)cyclopropyl)methylthio)benzamide. LRMS m/z (M+H) 351.2 found, 351.2 required.

2-chloro-N,N-dimethyl-4-((1S,2S or 1R,2R)-2-(2-(1-((R or S)-3,3,3-trifluoro-2-hydroxy-2-phenylpropanoyl)piperidin-4-yl)ethyl)cyclopropoxy)benzamide and 2-chloro-N,N-dimethyl-4-((1S,2S or 1R,2R)-2-(2-(1-((R or S)-3,3,3-trifluoro-2-hydroxy-2-phenylpropanoyl)piperidin-4-yl)ethyl)cyclopropoxy)benzamide A mixture of trans-2-chloro-N,N-dimethyl-4-(2-(2-(piperidin-4-yl)ethyl)cyclopropoxy)benzamide (668 mg, 1.91 mmol), (R or S)-3,3,3-trifluoro-2-hydroxy-2-phenylpropanoic acid (500 mg, 2.27 mmol), HATU (950 mg, 2.5 mmol) and DIEA (740 mg, 5.73 mmol) in DMF (6 mL) was stirred at RT overnight. The mixture was directly purified by reverse phase chromatography (mobile phase: methanol/water (10 mM NH₄HCO₃)) to afford racemic product. LRMS m/z (M+H) 553.2 found, 553.2 required, which was resolved by Chiral HPLC (column: IC (150*4.6 mm 5 um); mobile phase: n-hexane (0.1% DEA):EtOH (0.1% DEA) =85:15; flow: 1.0 mL/min; temperature: 40° C.) to afford 2-chloro-N,N-dimethyl-4-((1S,2S, or 1R,2R)-2-(2-(1-((R or S)-3,3,3-trifluoro-2-hydroxy-2-phenylpropanoyl)piperidin-4-yl)ethyl)cyclopropoxy)benzamide (RT=14.83 min) and 2-chloro-N,N-dimethyl-4-((1S,2S or 1R,2R)-2-(2-(1-((R or S)-3,3,3-trifluoro-2-hydroxy-2-phenylpropanoyl)piperidin-4-yl)ethyl)cyclopropoxy)benzamide (RT=16.73 min). LRMS m/z (M+H) 553.2 found, 553.2 required. Absolute stereochemistry not confirmed.

Example 19-1

(R or S)-2-chloro-4-(1,1-difluoro-4-(1-(3,3,3-trifluoro-2-hydroxy-2-phenylpropanoyl)piperidin-4-yl)butoxy)-N,N-dimethylbenzamide

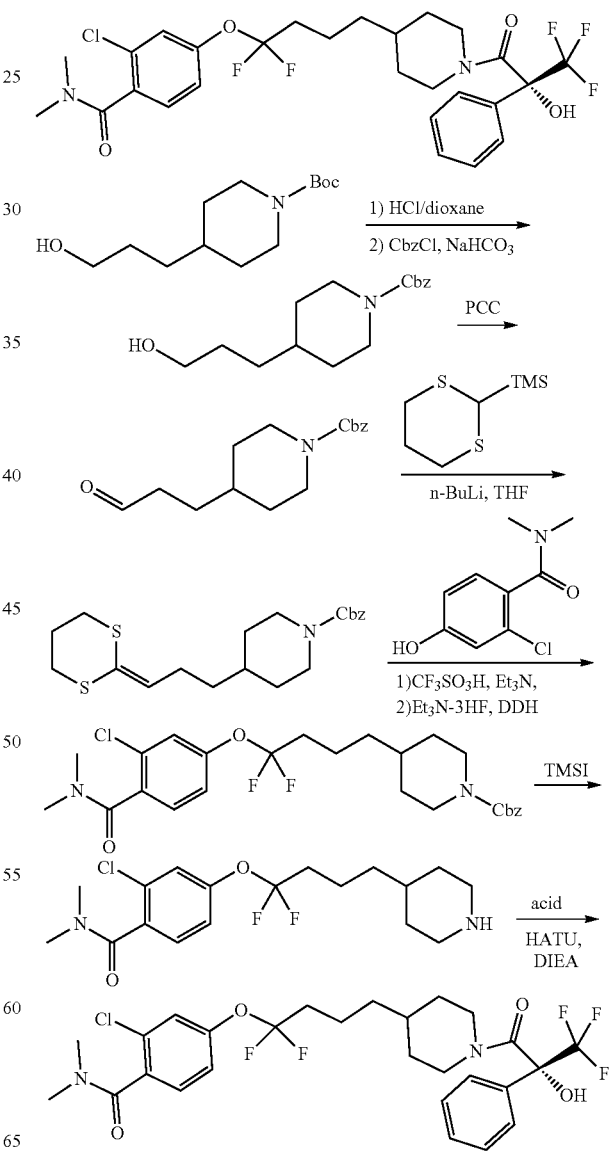

benzyl 4-(3-hydroxypropyl)piperidine-1-carboxylate

To a solution of tert-butyl 4-(3-hydroxypropyl)piperidine-1-carboxylate (1.22 g, 5 mmol) in DCM (2 mL) was added 4M HCl/MeOH (15 mL) at rt. After stirring for 2 h at rt, the mixture was concentrated under reduced pressure to give a crude oil. The crude oil was dissolved in 3 mL of THF and 10 mL of saturated NaHCO$_3$, followed by addition of benzyl carbonochloridate (0.94 g, 5.5 mmol) at 0° C. After stirring for 1 h, the mixture was extracted with EtOAc (50 mL×3). The organic layer was collected and dried over anhydrous Na$_2$SO$_4$. The solvent was evaporated under reduced pressure to afford the crude benzyl 4-(3-hydroxypropyl)piperidine-1-carboxylate. LRMS m/z (M+H) 278.2 found, 278.2 required.

benzyl 4-(3-oxopropyl)piperidine-1-carboxylate

To a solution of benzyl 4-(3-hydroxypropyl)piperidine-1-carboxylate (1.3 g, 5 mmol) in DCM (50 mL) was added PCC (1.62 g, 7.5 mmol) and 3 g of silica gel. The mixture was stirred at rt for 1 h. Then the mixture was filtered and concentrated under reduced pressure to give crude product which was purified by column chromatography (silica gel: 300-400 mesh, PE/EtOAc=10:1) to give benzyl 4-(3-oxopropyl)piperidine-1-carboxylate. LRMS m/z (M+H) 276.2 found, 276.2 required.

benzyl 4-(3-(1,3-dithian-2-ylidene)propyl)piperidine-1-carboxylate

To a solution of (1,3-dithian-2-yl)trimethylsilane (250 mg, 1.3 mmol) in anhydrous THF (5 mL) was added n-BuLi (0.57 mL, 1.4 mmol, 2.5 M in hexane) at −78° C. After stirring for 2 h, the benzyl 4-(3-oxopropyl)piperidine-1-carboxylate (340 mg, 1.2 mmol) was added. After stirring for 1 h, the mixture was quenched by 20 mL of aqueous NH$_4$Cl and extracted with EtOAc (20 mL×3). The organic layer was collected and dried over anhydrous Na$_2$SO$_4$. The solvent was evaporated under reduced pressure and residue was purified by a silica gel chromatography (silica gel: 300-400 mesh, PE/EtOAc=30:1) to afford benzyl 4-(3-(1,3-dithian-2-ylidene)propyl)piperidine-1-carboxylate. LRMS m/z (M+H) 378.1 found, 378.1 required.

benzyl 4-(4-(3-chloro-4-(dimethylcarbamoyl)phenoxy)-4,4-difluorobutyl)piperidine-1-carboxylate Trifluoromethanesulfonic acid (60 mg, 0.4 mmol) was added dropwise to a solution of benzyl 4-(3-(1,3-dithian-2-ylidene)propyl)piperidine-1-carboxylate (156 mg, 0.4 mmol) in DCM (2 mL) at 0° C. The mixture was stirred for 30 min at rt. Then it was cooled to −70° C. and a solution of 2-chloro-4-hydroxy-N,N-dimethylbenzamide (120 mg, 0.6 mmol) and Et$_3$N (73 mg, 0.72 mmol) in DCM (1 mL) was added. After stirring for 1 h at −70° C., 1,3-dibromo-5,5-dimethyl imidazolidine-2,4-dione (570 mg, 2 mmol) and Et$_3$N·3HF complex (322 mg, 2 mmol) was added. After stirring for additional 1 h, the mixture was allowed to warm up to 0° C., and then poured into ice-cold 1N NaOH (7 mL), extracted with DCM (20 mL×3). The solvent was evaporated under reduced pressure and the residue was purified by reverse phase chromatography (mobile phase: methanol/water (10 mM NH$_4$HCO$_3$)) to afford benzyl 4-(4-(3-chloro-4-(dimethylcarbamoyl)phenoxy)-4,4-difluorobutyl)piperidine-1-carboxylate. LRMS m/z (M+H) 509.2 found, 509.2 required.

2-chloro-4-(1,1-difluoro-4-(piperidin-4-yl)butoxy)-N,N-dimethylbenzamid

To a solution of benzyl 4-(4-(3-chloro-4-(dimethylcarbamoyl)phenoxy)-4,4-difluorobutyl)piperidine-1-carboxylate (90 mg, 0.17 mmol) in DCM (4 mL) was added TMSI (1 mL). After stirring for 1 h at rt, the mixture was quenched by 10 mL of methanol, and concentrated under reduced pressure to give crude product which was purified by reverse phase chromatography (mobile phase: methanol/water (10 mM NH$_4$HCO$_3$)) to afford 2-chloro-4-(1,1-difluoro-4-(piperidin-4-yl)butoxy)-N,N-dimethylbenzamide. LRMS m/z (M+H) 374.2 found, 374.2 required.

(R or S)-2-chloro-4-(1,1-difluoro-4-(1-(3,3,3-trifluoro-2-hydroxy-2-phenylpropanoyl)piperidin-4-yl)butoxy)-N,N-dimethylbenzamide A mixture of 2-chloro-4-(1,1-difluoro-4-(piperidin-4-yl)butoxy)-N,N-dimethylbenzamide (16 mg, 0.04 mmol), (R or S)-3,3,3-trifluoro-2-hydroxy-2-phenylpropanoic acid (20 mg, 0.08 mmol), DIPEA (21 mg, 0.16 mmol) and HATU (30 mg, 0.08 mmol) in 1 mL of dry THF was stirred at rt for 4 h. The mixture was concentrated at reduced pressure to give the crude compound which was directly purified by reverse phase chromatography (mobile phase: methanol/water (10 mM NH$_4$HCO$_3$)) to afford (R or S)-2-chloro-4-(1,1-difluoro-4-(1-(3,3,3-trifluoro-2-hydroxy-2-phenylpropanoyl)piperidin-4-yl)butoxy)-N,N-dimethylbenzamide. LRMS m/z (M+H) 577.2 found, 577.2 required. $^1$H NMR (400 MHz, CDCl$_3$): δ 7.44-7.40 (m, 5H), 7.28 (d, J=8.4 Hz, 1H), 7.23 (d, J=2.0 Hz, 1H), 7.13 (d, J=8.4 Hz, 1H), 3.15 (s, 3H), 2.89 (s, 3H), 2.72 (t, J=12.0 Hz, 2H), 2.08 (m, 2H), 1.62-1.20 (m, 11H).

Example 20-1

2-chloro-4-(2-fluoro-4-(1-((R or S)-3,3,3-trifluoro-2-hydroxy-2-phenylpropanoyl)piperidin-4-yl)butoxy)-N,N-dimethylbenzamide

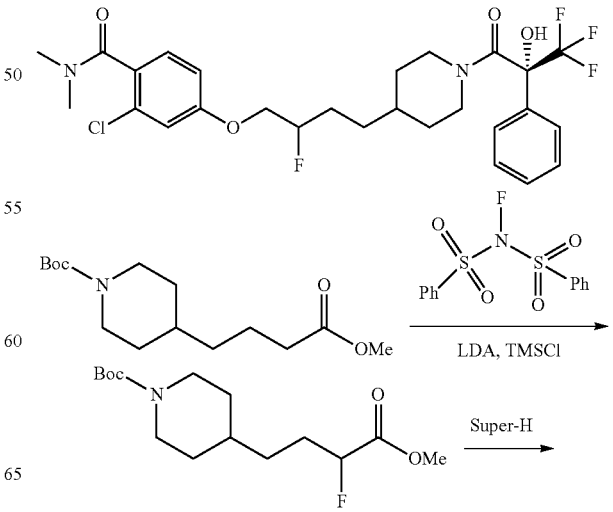

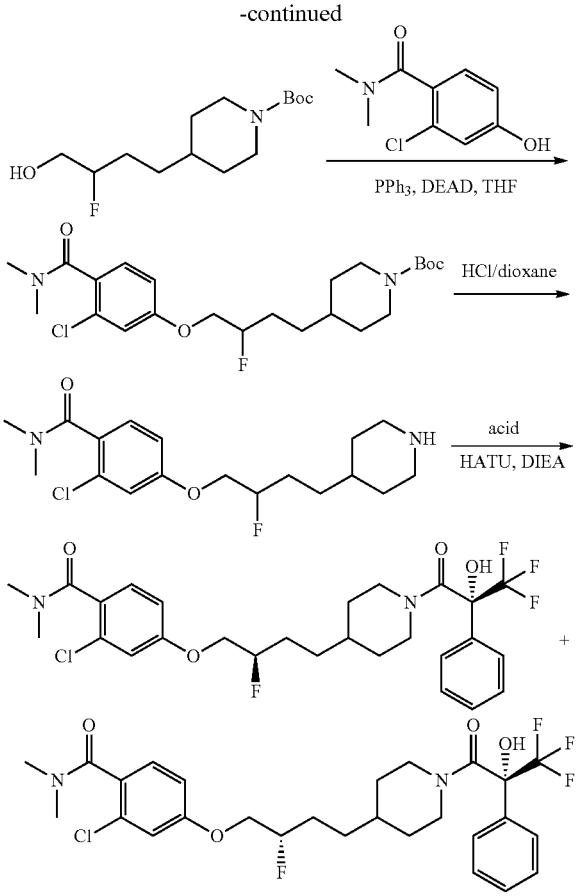

tert-butyl 4-(3-fluoro-4-methoxy-4-oxobutyl)piperidine-1-carboxylate

To a solution of tert-butyl 4-(4-methoxy-4-oxobutyl)piperidine-1-carboxylate (500 mg, 1.75 mmol) in THF (20 mL) was added dropwise LDA (2.0 mL, 2.0 mmol, 1 M in THF) at −78° C. under nitrogen atmosphere. The mixture was stirred at −78° C. for 30 min. TMSCl (379 mg, 3.5 mmol) was added and the reaction mixture was allowed to warm up to room temperature. After 30 min, the mixture was concentrated in vacuo and the residue was taken up in DCM (15 mL). The resulting mixture was filtered and the filtrate was cooled to 10° C., and treated with a solution of N-fluoro-N-(phenylsulfonyl)benzenesulfonamide (553 mg, 1.75 mmol) in DCM (5 mL). The resulting mixture was stirred at rt for 3 h. The mixture was concentrated in vacuo and the residue was directly purified by reverse phase chromatography (mobile phase: methanol/water (10 mM $NH_4HCO_3$) to afford tert-butyl 4-(3-fluoro-4-methoxy-4-oxobutyl)piperidine-1-carboxylate. LRMS m/z (M-99) 204.1 found, 204.2 required.

tert-butyl 4-(3-fluoro-4-hydroxybutyl)piperidine-1-carboxylate

To a solution of tert-butyl 4-(3-fluoro-4-methoxy-4-oxobutyl)piperidine-1-carboxylate (200 mg, 0.66 mmol) in THF (1 mL) was added dropwise Super-H (1.3 mL, 1.3 mmol, 1 M in THF) at 0° C. under nitrogen atmosphere. The mixture was stirred at 0° C. to rt overnight. Then the mixture was quenched by the addition of MeOH (2 mL) and saturated ammonium chloride (2 mL). The mixture was concentrated in vacuo and then dissolved with EtOAc (60 mL). The organic phase was washed with water (10 mL×2), dried over anhydrous $Na_2SO_4$ and concentrated. The residue was purified by column chromatography (silica gel: 300-400 mesh, PE/EtOAc=4/1) to give tert-butyl 4-(3-fluoro-4-hydroxybutyl)piperidine-1-carboxylate. LRMS m/z (M+H) 276.1 found, 276.2 required.

tert-butyl 4-(4-(3-chloro-4-(dimethylcarbamoyl)phenoxy)-3-fluorobutyl)piperidine-1-carboxylate To a solution of tert-butyl 4-(3-fluoro-4-hydroxybutyl)piperidine-1-carboxylate (100 mg, 0.36 mmol) in THF (1.5 mL) was added 2-chloro-4-hydroxy-N,N-dimethylbenzamide (72 mg, 0.36 mmol), $PPh_3$ (105 mg, 0.40 mmol) and DEAD (70 mg, 0.4 mmol) at 0° C. under nitrogen atmosphere. The mixture was stirred at rt for 2 h and was directly purified by reverse phase chromatography (mobile phase: methanol/water (10 mM $NH_4HCO_3$)) to afford tert-butyl 4-(4-(3-chloro-4-(dimethylcarbamoyl)phenoxy)-3-fluorobutyl)piperidine-1-carboxylate. LRMS m/z (M-99) 357.1 found, 357.2 required.

2-chloro-4-(2-fluoro-4-(piperidin-4-yl)butoxy)-N,N-dimethylbenzamide

To a solution of tert-butyl 4-(4-(3-chloro-4-(dimethylcarbamoyl)phenoxy)-3-fluorobutyl)piperidine-1-carboxylate (60 mg, 0.13 mmol) in THF (1 mL) was added 4M HCl/1,4-dioxane (3 mL) at 0° C. The mixture was stirred at rt for 2 h and concentrated in vacuo to afford the crude product 2-chloro-4-(2-fluoro-4-(piperidin-4-yl)butoxy)-N,N-dimethylbenzamide. LRMS m/z (M+H) 357.1 found, 357.2 required.

2-chloro-4-(2-fluoro-4-(1-((R or S)-3,3,3-trifluoro-2-hydroxy-2-phenylpropanoyl)piperidin-4-yl)butoxy)-N,N-dimethylbenzamide To a solution of 2-chloro-4-(2-fluoro-4-(piperidin-4-yl)butoxy)-N,N-dimethylbenzamide (25 mg, 0.064 mmol) in THF (1 mL) was added (R or S)-3,3,3-trifluoro-2-hydroxy-2-phenylpropanoic acid (28 mg, 0.13 mmol), DIEA (25 mg, 0.19 mmol) and HATU (36 mg, 0.096 mmol). The mixture was stirred at rt overnight. Then the mixture was directly purified by reverse phase chromatography (mobile phase: methanol/water (10 mM $NH_4HCO_3$) to afford 2-chloro-4-((R or S)-2-fluoro-4-(1-((R or S)-3,3,3-trifluoro-2-hydroxy-2-phenylpropanoyl)piperidin-4-yl)butoxy)-N,N-dimethylbenzamide (reverse phase chromatography: RT=7.5 min, LCMS: RT=1.974 min) (LRMS m/z (M+H) 559.2 found, 559.2 required) and 2-chloro-4-((S or R)-2-fluoro-4-(1-((R or S)-3,3,3-trifluoro-2-hydroxy-2-phenylpropanoyl)piperidin-4-yl)butoxy)-N,N-dimethylbenzamide, (reverse phase chromatography: RT=8.2 min, LCMS: RT=1.976 min) (LRMS m/z (M+H) 559.2 found, 559.2 required). Absolute stereochemistry not confirmed.

| Example | Structure | IUPAC Name | LRMS, found [M + H]+ |
|---|---|---|---|
| 20-2 | 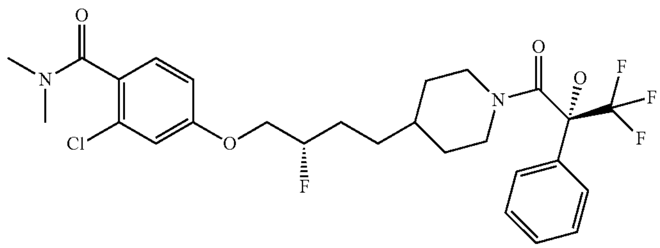 [SMILES: CN(C)C(=O)c1ccc(OC[C@@H](F)CCC2CCN(C(=O)[C@](O)(c3ccccc3)C(F)(F)F)CC2)cc1Cl] | 2-chloro-4-((S or R)-2-fluoro-4-(1-((R or S)-3,3,3-trifluoro-2-hydroxy-2-phenylpropanoyl)piperidin-4-yl)butoxy)-N,N-dimethylbenzamide | 559.2 |

Example 21-1

2-chloro-4-(4-fluoro-4-(1-((R or S)-3,3,3-trifluoro-2-hydroxy-2-(3-methoxyphenyl)propanoyl)piperidin-4-yl)butoxy)-N,N-dimethylbenzamide

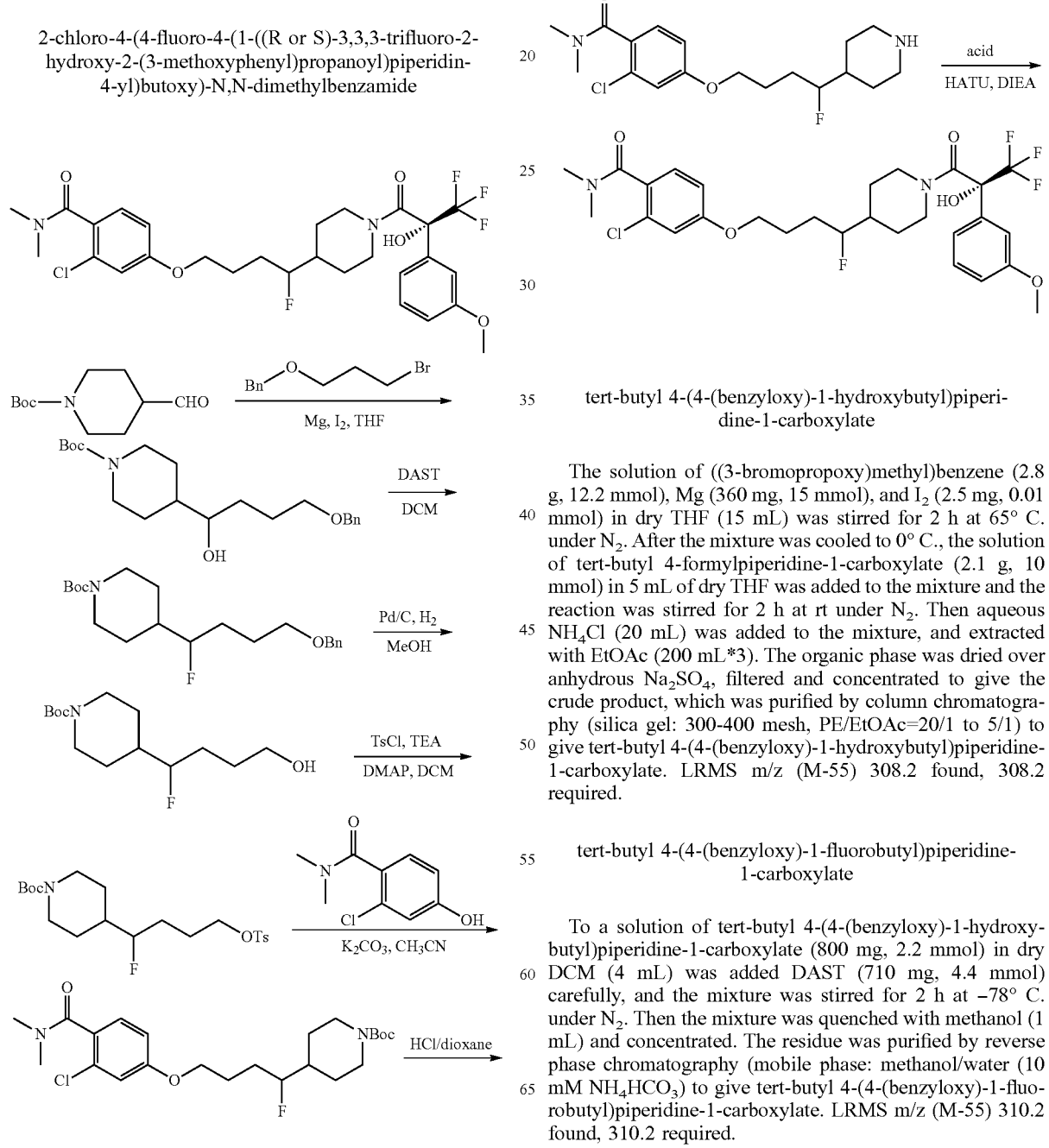

tert-butyl 4-(4-(benzyloxy)-1-hydroxybutyl)piperidine-1-carboxylate

The solution of ((3-bromopropoxy)methyl)benzene (2.8 g, 12.2 mmol), Mg (360 mg, 15 mmol), and $I_2$ (2.5 mg, 0.01 mmol) in dry THF (15 mL) was stirred for 2 h at 65° C. under $N_2$. After the mixture was cooled to 0° C., the solution of tert-butyl 4-formylpiperidine-1-carboxylate (2.1 g, 10 mmol) in 5 mL of dry THF was added to the mixture and the reaction was stirred for 2 h at rt under $N_2$. Then aqueous $NH_4Cl$ (20 mL) was added to the mixture, and extracted with EtOAc (200 mL*3). The organic phase was dried over anhydrous $Na_2SO_4$, filtered and concentrated to give the crude product, which was purified by column chromatography (silica gel: 300-400 mesh, PE/EtOAc=20/1 to 5/1) to give tert-butyl 4-(4-(benzyloxy)-1-hydroxybutyl)piperidine-1-carboxylate. LRMS m/z (M-55) 308.2 found, 308.2 required.

tert-butyl 4-(4-(benzyloxy)-1-fluorobutyl)piperidine-1-carboxylate

To a solution of tert-butyl 4-(4-(benzyloxy)-1-hydroxybutyl)piperidine-1-carboxylate (800 mg, 2.2 mmol) in dry DCM (4 mL) was added DAST (710 mg, 4.4 mmol) carefully, and the mixture was stirred for 2 h at −78° C. under $N_2$. Then the mixture was quenched with methanol (1 mL) and concentrated. The residue was purified by reverse phase chromatography (mobile phase: methanol/water (10 mM $NH_4HCO_3$) to give tert-butyl 4-(4-(benzyloxy)-1-fluorobutyl)piperidine-1-carboxylate. LRMS m/z (M-55) 310.2 found, 310.2 required.

tert-butyl 4-(1-fluoro-4-hydroxybutyl)piperidine-1-carboxylate

The solution of tert-butyl 4-(4-(benzyloxy)-1-fluorobutyl) piperidine-1-carboxylate (160 mg, 0.42 mmol) and 10% Pd/C (50 mg) in MeOH (5 mL) was stirred at rt under H₂ balloon overnight. Then the mixture was filtered, and concentrated to give the crude tert-butyl 4-(1-fluoro-4-hydroxybutyl)piperidine-1-carboxylate. LRMS m/z (M-55) 220.2 found, 220.2 required.

tert-butyl 4-(1-fluoro-4-(tosyloxy)butyl)piperidine-1-carboxylate

The solution of tert-butyl 4-(1-fluoro-4-hydroxybutyl) piperidine-1-carboxylate (160 mg, 0.58 mmol), DMAP (14 mg, 0.11 mmol), Et₃N (351 mg, 3.48 mmol) and TsCl (220 mg, 1.16 mmol) in dry DCM (10 mL) was stirred at rt overnight. H₂O (100 mL) was added to the mixture, and the mixture was extracted with EtOAc (100 mL*3). The organic phase was dried over anhydrous Na₂SO₄, filtered and concentrated to give the crude compound, which was purified by column chromatography (silica gel: 300-400 mesh, PE/EtOAc=20/1 to 5/1) to give tert-butyl 4-(1-fluoro-4-(tosyloxy)butyl)piperidine-1-carboxylate. LRMS m/z (M-55) 374.2 found, 374.2 required.

tert-butyl 4-(4-(3-chloro-4-(dimethylcarbamoyl)phenoxy)-1-fluorobutyl)piperidine-1-carboxylate The solution of tert-butyl 4-(1-fluoro-4-(tosyloxy)butyl) piperidine-1-carboxylate (120 mg, 0.28 mmol), 3-chloro-4-hydroxy-N,N-dimethylbenzamide (85 mg, 0.42 mmol), and Cs₂CO₃ (182 mg, 0.56 mmol) in acetonitrile (10 mL) was stirred at 80° C. under N₂ overnight. Then the mixture was filtered and concentrated to give the crude compound, which was purified by column chromatography (silica gel: 300-400 mesh, PE/EtOAc=20/1 to 5/1) to give tert-butyl 4-(4-(3-chloro-4-(dimethylcarbamoyl)phenoxy)-1-fluorobutyl)piperidine-1-carboxylate. LRMS m/z (M-55) 401.2 found, 401.2 required.

2-chloro-4-(4-fluoro-4-(piperidin-4-yl)butoxy)-N,N-dimethylbenzamide

The solution of tert-butyl 4-(4-(3-chloro-4-(dimethylcarbamoyl)phenoxy)-1-fluorobutyl)piperidine-1-carboxylate (83 mg, 0.18 mmol) in 4M HCl/dioxane (5 mL) was stirred for 1 h at rt. Then the mixture was concentrated to give the crude 3-chloro-N,N-dimethyl-4-(4-(piperidin-4-yl)pentyloxy)benzamide. LRMS m/z (M+H) 357.2 found, 357.2 required.

2-chloro-4-(4-fluoro-4-(1-((R or S)-3,3,3-trifluoro-2-hydroxy-2-(3-methoxyphenyl)propanoyl)piperidin-4-yl)butoxy)-N,N-dimethylbenzamide A solution of 2-chloro-4-(4-fluoro-4-(piperidin-4-yl)butoxy)-N,N-dimethylbenzamide (10 mg, 0.02 mmol), (R or S)-3,3,3-trifluoro-2-hydroxy-2-phenylpropanoic acid (7.5 mmol, 0.03 mmol), HATU (11 mg, 0.03 mmol), and DIEA (8 mmol, 0.06 mmol) in THF (2 mL) was stirred at rt overnight. Then the mixture was concentrated to give the crude compound, which was purified by reverse phase chromatography (mobile phase: methanol/water (10 mM NH₄HCO₃) to give 2-chloro-N,N-dimethyl-4-((R or S)-4-(1-((R or S)-3,3,3-trifluoro-2-hydroxy-2-(3-methoxyphenyl) propanoyl)piperidin-4-yl)pentyloxy)benzamide. LRMS m/z (M+H) 589.2 found, 589.2 required.

Example 22-1

(R or S)-2-chloro-4-(4,4-difluoro-4-(1-(3,3,3-trifluoro-2-hydroxy-2-(3-methoxyphenyl)propanoyl)piperidin-4-yl)butoxy)-N,N-dimethylbenzamide

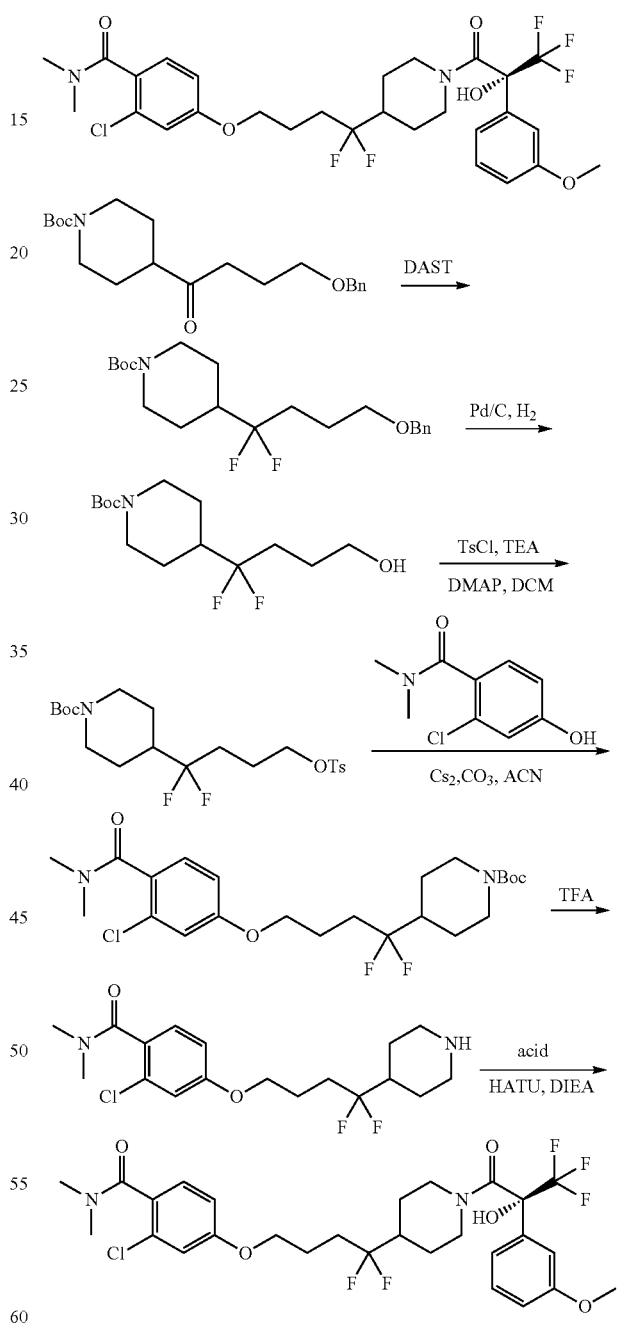

tert-butyl 4-(4-(benzyloxy)-1,1-difluorobutyl)piperidine-1-carboxylate

To a solution of tert-butyl 4-(4-(benzyloxy)butanoyl)piperidine-1-carboxylate (361 mg, 1.0 mmol, 1.0 eq) in DCM (5 mL) at 0° C. under N₂ was added DAST (1.61 g, 10.0 mmol, 10.0 eq). After stirring at RT for 7 day, the mixture was poured into 20 mL of ice-water carefully and diluted with dichloromethane (200 mL). The organic phase was separated and washed with water (100 mL×3), brine (10 mL×3) and dried over anhydrous Na₂SO₄. The organic phase was concentrated and the residue was purified by reverse phase chromatography directly (mobile phase: methanol/water (10 mM NH₄HCO₃)) to give tert-butyl 4-(4-(benzyloxy)-1,1-difluorobutyl)piperidine-1-carboxylate. LRMS m/z (M-99) 284.1 found, 284.2 required.

tert-butyl 4-(1,1-difluoro-4-hydroxybutyl)piperidine-1-carboxylate

The solution of tert-butyl 4-(4-(benzyloxy)-1,1-difluorobutyl)piperidine-1-carboxylate ((383 mg, 10 mmol, 1.0 eq) and 5% Pd/C (38 mg) in EtOH (3 mL) was heated to 50° C. overnight under H₂ balloon. After the reaction was cooled down to room temperature, Pd/C was filtered off and the filtrate was concentrated under vacuum to afford tert-butyl 4-(1,1-difluoro-4-hydroxybutyl)piperidine-1-carboxylate which was used in the next step without purification. LRMS m/z (M-55) 238.1 found, 238.2 required.

tert-butyl 4-(1,1-difluoro-4-(tosyloxy)butyl)piperidine-1-carboxylate

To a solution of tert-butyl 4-(1,1-difluoro-4-hydroxybutyl)piperidine-1-carboxylate (689 mg, 2.35 mmol) in DCM (6.0 mL) was added TEA (660 ul, 4.10 mmol) and DMAP (100 mg, 0.81 mmol) and TsCl (492 mg, 2.58 mmol). The mixture was stirred at rt for 5 h and directly purified by silica gel column chromatography (EtOAc/PE=5/95 to 10/90) to give tert-butyl 4-(1,1-difluoro-4-(tosyloxy)butyl)piperidine-1-carboxylate. LRMS m/z (M-99) 348.1 found, 348.2 required.

tert-butyl 4-(4-(3-chloro-4-(dimethylcarbamoyl)phenoxy)-1,1-difluorobutyl)piperidine-1-carboxylate A mixture of tert-butyl 4-(1,1-difluoro-4-(tosyloxy)butyl) piperidine-1-carboxylate (448 mg, 1.0 mmol, 1.0 eq), 2-chloro-4-hydroxy-N,N-dimethylbenzamide (200 mg, 1.0 mmol, 1.0 eq) and Cs₂CO₃ (978 mg, 3.0 mmol, 3.0 eq) in CH₃CN (10 mL) was stirred at 80° C. for 1 h. The mixture was filtered and concentrated. The residue was directly purified by reverse phase chromatography (mobile phase: methanol/water (10 mM NH₄HCO₃)) to afford tert-butyl 4-(4-(3-chloro-4-(dimethylcarbamoyl)phenoxy)-1,1-difluorobutyl)piperidine-1-carboxylate. LRMS m/z (M-99) 375.1 found, 375.2 required.

2-chloro-4-(4,4-difluoro-4-(piperidin-4-yl)butoxy)-N,N-dimethylbenzamide

To a solution of tert-butyl 4-(4-(3-chloro-4-(dimethylcarbamoyl)phenoxy)-1,1-difluorobutyl) piperidine-1-carboxylate (475 mg, 1.0 mmol, 1.0 eq) in dry DCM (2 mL) was added TFA (1.0 mL) at 0° C. The mixture was stirred at 0° C. for 40 min. The mixture was concentrated in vacuo to afford the crude product 2-chloro-4-(4,4-difluoro-4-(piperidin-4-yl)butoxy)-N,N-dimethylbenzamide which was used directly in the next step without purification. LRMS m/z (M+H) 375.1 found, 375.2 required.

(R or S)-2-chloro-4-(4,4-difluoro-4-(1-(3,3,3-trifluoro-2-hydroxy-2-(3-methoxyphenyl)propanoyl) piperidin-4-yl)butoxy)-N,N-dimethylbenzamide A mixture of 2-chloro-4-(4,4-difluoro-4-(piperidin-4-yl) butoxy)-N,N-dimethylbenzamide (38 mg, 0.1 mmol, 1.0 eq), (R or S)-3,3,3-trifluoro-2-hydroxy-2-(3-methoxyphenyl)propanoic acid (30 mg, 0.12 mmol, 1.2 eq), HATU (46 mg, 0.12 mmol, 1.2 eq), and DIEA (39 mg, 0.3 mmol, 3.0 eq) in THF (2 mL) was stirred at rt overnight. The mixture was directly purified by reverse phase chromatography (mobile phase: methanol/water (10 mM NH₄HCO₃)) to afford (R or S)-2-chloro-4-(4,4-difluoro-4-(1-(3,3,3-trifluoro-2-hydroxy-2-(3-methoxyphenyl)propanoyl)piperidin-4-yl)butoxy)-N,N-dimethylbenzamide. LRMS m/z (M+H) 607.2 found, 607.2 required.

Example 23-1

2-chloro-N,N-dimethyl-4-((R or S)-2-methyl-4-(1-((R or S)-3,3,3-trifluoro-2-hydroxy-2-phenylpropanoyl)piperidin-4-yl)butoxy)benzamide

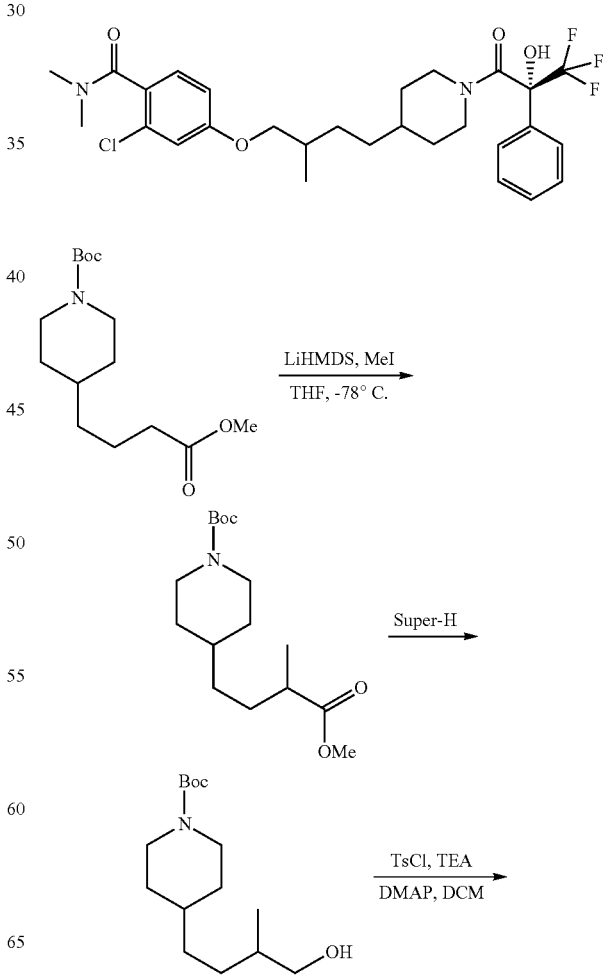

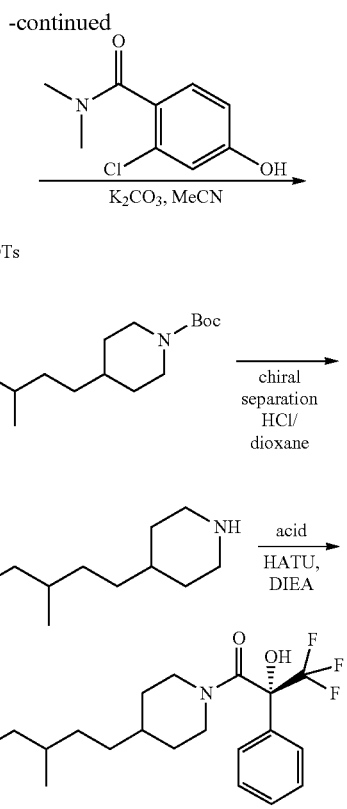

tert-butyl 4-(4-methoxy-3-methyl-4-oxobutyl)piperidine-1-carboxylate

To a solution of tert-butyl 4-(4-methoxy-4-oxobutyl)piperidine-1-carboxylate (4.0 g, 14 mmol) in THF (15 mL) was added dropwise LiHMDS (28 mL, 28 mmol, 1 M in THF) at −78° C. under nitrogen atmosphere. After stirring at −78° C. for 1 h, MeI (7.97 g, 56.14 mmol) was added. The resulting mixture was stirred at −78° C. to rt overnight. Then the mixture was quenched by the addition of saturated ammonium chloride (30 mL) and extracted with EtOAc (200 mL). The organic phase was washed with water (20 mL×2) and dried over anhydrous $Na_2SO_4$. The organic phase was concentrated and the residue was purified by column chromatography (silica gel: 300-400 mesh, PE/EtOAc=10/1) to give tert-butyl 4-(4-methoxy-3-methyl-4-oxobutyl)piperidine-1-carboxylate. LRMS m/z (M-99) 200.2 found, 200.2 required.

tert-butyl 4-(4-hydroxy-3-methylbutyl)piperidine-1-carboxylate

To a solution of tert-butyl 4-(4-methoxy-3-methyl-4-oxobutyl)piperidine-1-carboxylate (2.14 g, 10.75 mmol) in THF (20 mL) was added dropwise Super-H (22 mL, 22 mmol, 1 M in THF) at 0° C. under nitrogen atmosphere. The mixture was stirred at 0° C. to rt overnight. Then the mixture was quenched by the addition of MeOH (20 mL) and saturated ammonium chloride (20 mL). The mixture was concentrated in vacuo, extracted with EtOAc (200 mL). The organic phase was washed with water (20 mL×2), dried over anhydrous $Na_2SO_4$ and concentrated. The residue was purified by column chromatography (silica gel: 300-400 mesh, PE/EtOAc=4/1) to give tert-butyl 4-(4-hydroxy-3-methylbutyl)piperidine-1-carboxylate. LRMS m/z (M-99) 172.3 found, 172.2 required.

tert-butyl 4-(3-methyl-4-(tosyloxy)butyl)piperidine-1-carboxylate

To a solution of tert-butyl 4-(4-hydroxy-3-methylbutyl)piperidine-1-carboxylate (1.3 g, 4.8 mmol) in DCM (40 mL) was added TEA (0.97 g, 9.6 mmol), DMAP (59 mg, 0.48 mmol) and 4-methylbenzene-1-sulfonyl chloride (1.1 g, 5.77 mmol) at 0° C. The mixture was stirred at 0° C. to rt overnight. The mixture was concentrated and the residue was directly purified by column chromatography (silica gel: 300-400 mesh, PE/EtOAc=8/1) to give tert-butyl 4-(3-methyl-4-(tosyloxy)butyl)piperidine-1-carboxylate. LRMS m/z (M+H) 425.1 found, 425.2 required.

tert-butyl 4-(4-(3-chloro-4-(dimethylcarbamoyl)phenoxy)-3-methylbutyl)piperidine-1-carboxylate To a solution of tert-butyl 4-(3-methyl-4-(tosyloxy)butyl)piperidine-1-carboxylate (1.88 g, 4.42 mmol) in MeCN (40 mL) was added $K_2CO_3$ (1.22 g, 8.84 mmol) and 2-chloro-4-hydroxy-N,N-dimethylbenzamide (1.06 g, 5.31 mmol). The mixture was stirred at 70° C. overnight. The mixture was concentrated in vacuo and then extracted with EtOAc (200 mL). The organic phase was washed with water (20 mL×2), dried over anhydrous $Na_2SO_4$ and concentrated. The residue was purified by column chromatography (silica gel: 300-400 mesh, PE/EtOAc=3/1) to give tert-butyl 4-(4-(3-chloro-4-(dimethylcarbamoyl)phenoxy)-3-methylbutyl)piperidine-1-carboxylate. The product was resolved by Chiral HPLC (column: AS-H (250*4.6 mm 5 um); mobile phase: SFC-$CO_2$:MeOH=85:15; flow: 3 mL/min; temperature: 37.4° C.) to afford the isomer 1 (RT=2.76 min) and isomer2 (RT=3.5 min). LRMS m/z (M+H) 453.3 found, 453.2 required. Absolute stereochemistry not confirmed 2-chloro-N,N-dimethyl-4-(2-methyl-4-(piperidin-4-yl)butoxy)benzamide To a solution of (S or R)-tert-butyl 4-(4-(3-chloro-4-(dimethylcarbamoyl)phenoxy)-3-methylbutyl)piperidine-1-carboxylate (RT=2.76 min) (680 mg, 1.5 mmol) in THF (4 mL) was added 4M HCl/1,4-dioxane (20 mL) at 0° C. The mixture was stirred at rt for 2 h and concentrated in vacuo to afford the crude product (S or R)-2-chloro-N,N-dimethyl-4-(2-methyl-4-(piperidin-4-yl)butoxy)benzamide. LRMS m/z (M+H) 353.2 found, 353.2 required.

2-chloro-N,N-dimethyl-4-((S or R)-2-methyl-4-(1-((R or S)-3,3,3-trifluoro-2-hydroxy-2-phenylpropanoyl)piperidin-4-yl)butoxy)benzamide To a solution of 2-chloro-N,N-dimethyl-4-(2-methyl-4-(piperidin-4-yl)butoxy)benzamide enantiomer 1 (20 mg, 0.052 mmol) in THF (1 mL) was added (R or S)-3,3,3-trifluoro-2-hydroxy-2-phenylpropanoic acid (23 mg, 0.104 mmol), DIEA (20 mg, 0.155 mmol) and HATU (30 mg, 0.077 mmol). The mixture was stirred at rt overnight. Then the mixture was directly purified by reverse phase chromatography (mobile phase: methanol/water (10 mM $NH_4HCO_3$) to afford the title compound. LRMS m/z (M+H) 555.2 found, 555.2 required. $^1$H NMR (400 MHz, $CDCl_3$):

δ 7.48-7.38 (m, 5H), 7.21 (d, J=8.4 Hz, 1H), 6.90 (d, J=2.4 Hz, 1H), 6.83-6.80 (m, 1H), 3.78-3.71 (m, 2H), 3.16 (s, 3H), 2.90 (s, 3H), 2.72-2.66 (t, 1H), 1.91-1.84 (m, 1H), 1.47-1.43 (m, 1H), 1.36-1.34 (m, 1H), 1.28-1.17 (m, 4H), 0.99-0.96 (m, 3H).

Using the procedure described for example 23-1 using the appropriate amines and acids, the following examples were prepared. The following examples were isolated as single enantiomers, but absolute stereochemistry was not determined

| Example | Structure | IUPAC Name | LRMS, found [M + H]+ |
|---|---|---|---|
| 23-2 | 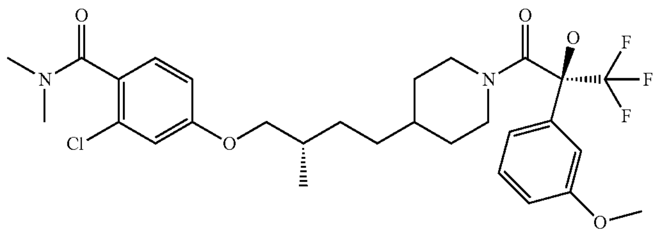 [SMILES: COc1cccc([C@](O)(C(=O)N2CCC(CC[C@H](C)COc3ccc(C(=O)N(C)C)c(Cl)c3)CC2)C(F)(F)F)c1] | 2-chloro-N,N-dimethyl-4-((S or R)-2-methyl-4-(1-((S or R)-3,3,3-trifluoro-2-hydroxy-2-(3-methoxyphenyl)propanoyl)piperidin-4-yl)butoxy)benzamide | 585.1 |
| 23-3 | 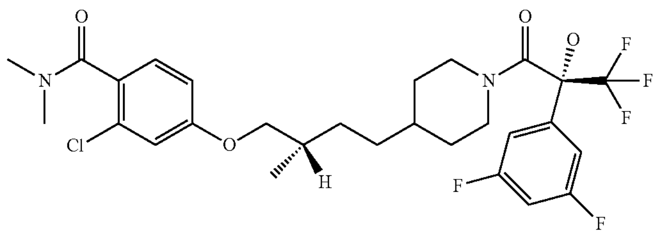 [SMILES: C[C@@H](CCC1CCN(C(=O)[C@](O)(c2cc(F)cc(F)c2)C(F)(F)F)CC1)COc1ccc(C(=O)N(C)C)c(Cl)c1] | 2-chloro-4-((S or R)-4-(1-((R or S)-2-(3,5-difluorophenyl)-3,3,3-trifluoro-2-hydroxypropanoyl)piperidin-4-yl)-2-methylbutoxy)-N,N-dimethylbenzamide | 591.1 |
| 23-4 | 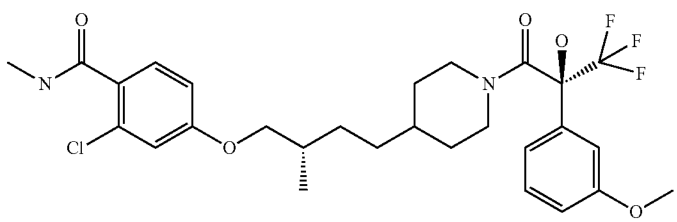 | 2-chloro-N-methyl-4-((S or R)-2-methyl-4-(1-((S or trifluoro-2-hydroxy-2-(3-methoxyphenyl)propanoyl)piperidin-4-yl)butoxy)benzamide | 571.1 |

Example 24-1

2-chloro-4-((R or S)-2-methyl-4-(1-((S or R)-3,3,3-trifluoro-2-hydroxy-2-(3-methoxyphenyl)propanoyl)piperidin-4-yl)butoxy)benzamide

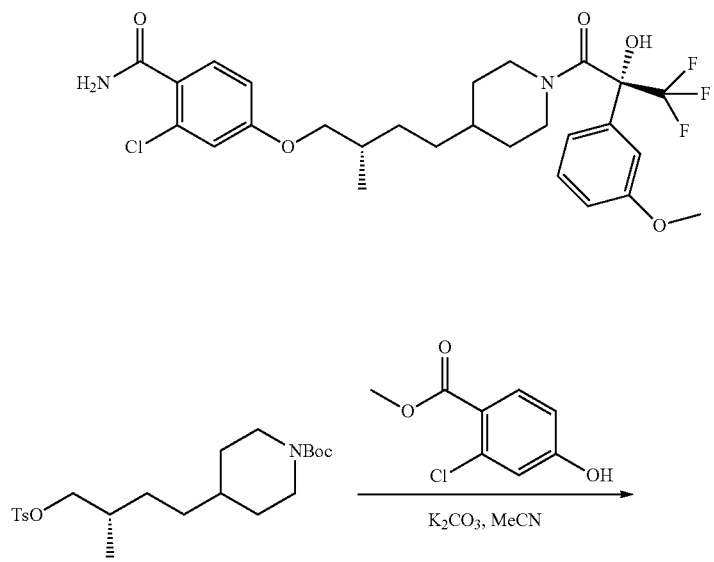

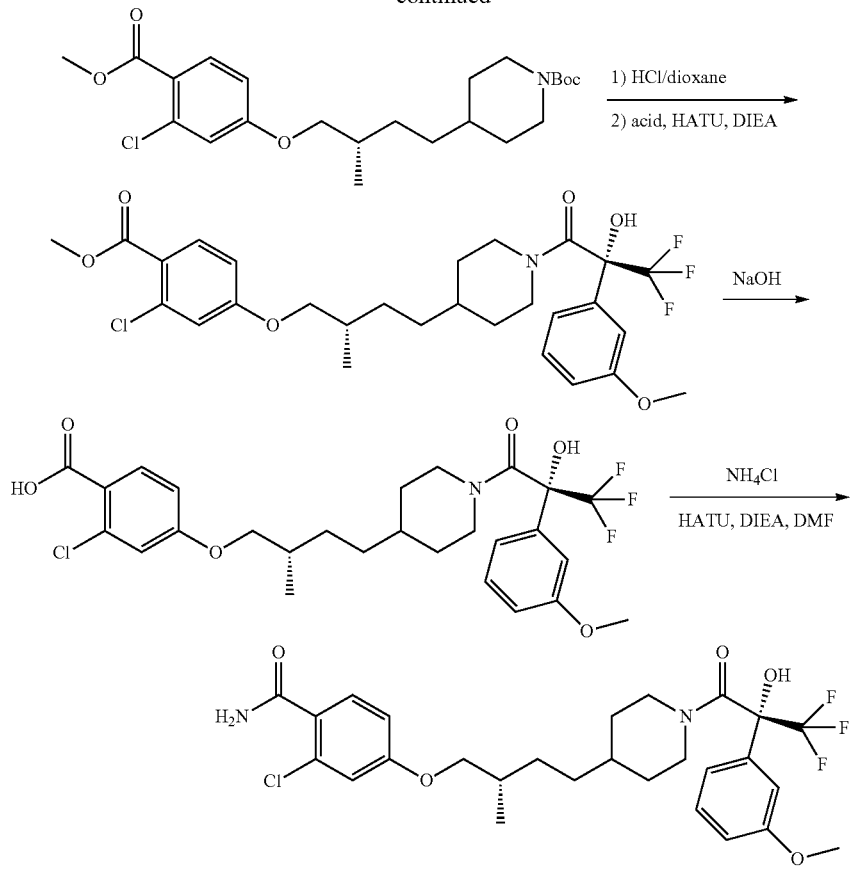

(S or R)-tert-butyl 4-(4-(3-chloro-4-(methoxycarbonyl)phenoxy)-3-methylbutyl)piperidine-1-carboxylate A mixture of (S or R)-tert-butyl 4-(3-methyl-4-(tosyloxy)butyl)piperidine-1-carboxylate (200 mg, 0.47 mmol), methyl 2-chloro-4-hydroxybenzoate (93 mg, 0.5 mmol) and $K_2CO_3$ (138 mg, 1 mmol) in acetonitrile (4 mL) was stirred at 50° C. overnight. The mixture was filtered and the filtrate was concentrated. The residue was purified by Prep-TLC (silica gel, PE/EtOAc=2/1) to give (S or R)-tert-butyl 4-(4-(3-chloro-4-(methoxycarbonyl)phenoxy)-3-methylbutyl)piperidine-1-carboxylate. LRMS m/z (M+H) 440.1 found, 440.2 required.

methyl 2-chloro-4-((S or R)-2-methyl-4-(1-((R or S)-3,3,3-trifluoro-2-hydroxy-2-(3-methoxyphenyl)propanoyl)piperidin-4-yl)butoxy)benzoate A mixture of (S or R)-tert-butyl 4-(4-(3-chloro-4-(methoxycarbonyl)phenoxy)-3-methylbutyl)piperidine-1-carboxylate (150 mg, 0.34 mmol) in 4M HCl/dioxane (2 mL) was stirred at rt for 2 h. The mixture was concentrated to give crude product which was dissolved in THF (2 mL). A solution of (R or S)-3,3,3-trifluoro-2-hydroxy-2-(3-methoxyphenyl)propanoic acid (85 mg, 0.34 mmol), HATU (190 mg, 0.5 mmol) and DIEA (129 mg, 1 mmol) in THF (2 mL) was added to above solution at rt. The resulting mixture was stirred at rt overnight and purified by reverse phase chromatography (mobile phase: methanol/water (10 mM $NH_4HCO_3$) to afford 2-chloro-4-((S or R)-2-methyl-4-(1-((R or S)-3,3,3-trifluoro-2-hydroxy-2-(3-methoxyphenyl)propanoyl)piperidin-4-yl)butoxy)benzoate. LRMS m/z (M+H) 572.1 found, 572.2 required.

2-chloro-4-((S or R)-2-methyl-4-(1-((R or S)-3,3,3-trifluoro-2-hydroxy-2-(3-methoxyphenyl)propanoyl)piperidin-4-yl)butoxy)benzoic acid A mixture of 2-chloro-4-((S or R)-2-methyl-4-(1-((R or S)-3,3,3-trifluoro-2-hydroxy-2-(3-methoxyphenyl)propanoyl)piperidin-4-yl)butoxy)benzoate (150 mg, 0.26 mmol) and 2N NaOH (1 mL) in methanol (2 mL) was stirred at rt overnight. The reaction mixture was acidified with 1N HCl to pH=5 and extracted with EtOAc (20 mL*3). The combined organic phases were washed with brine (20 mL), dried over anhydrous $Na_2SO_4$, filtered and concentrated in vacuo to afford crude 2-chloro-4-((S or R)-2-methyl-4-(1-((R or S)-3,3,3-trifluoro-2-hydroxy-2-(3-methoxyphenyl)propanoyl)piperidin-4-yl)butoxy)benzoic acid. LRMS m/z (M+H) 558.1 found, 558.2 required.

2-chloro-4-((S or R)-2-methyl-4-(1-((R or S)-3,3,3-trifluoro-2-hydroxy-2-(3-methoxyphenyl)propanoyl)piperidin-4-yl)butoxy)benzamide A mixture of 2-chloro-4-((S or R)-2-methyl-4-(1-((R or S)-3,3,3-trifluoro-2-hydroxy-2-(3-methoxyphenyl)propanoyl)piperidin-4-yl)butoxy)benzoic acid (30 mg, 0.054 mmol), $NH_4Cl$ (29 mg, 0.54 mmol), HATU (31 mg, 0.081 mmol) and DIEA (20 mg, 0.16 mmol) in DMF (2 mL) was stirred at rt overnight. The mixture was filtered and purified by reverse phase chromatography (mobile phase: methanol/water (10 mM NH$_4$HCO$_3$)) to afford 2-chloro-4-((S or R)-2-methyl-4-(1-((R or S)-3,3,3-trifluoro-2-hydroxy-2-(3-methoxyphenyl)propanoyl)piperidin-4-yl)butoxy)benzamide. LRMS m/z (M+H) 557.1 found, 557.2 required.

Absolute stereochemistry not confirmed

Example 25-1

2-chloro-N,N-dimethyl-4-((R or S)-5-(1-((R or S)-3,3,3-trifluoro-2-hydroxy-2-phenylpropanoyl)piperidin-4-yl)pentan-2-yloxy)benzamide

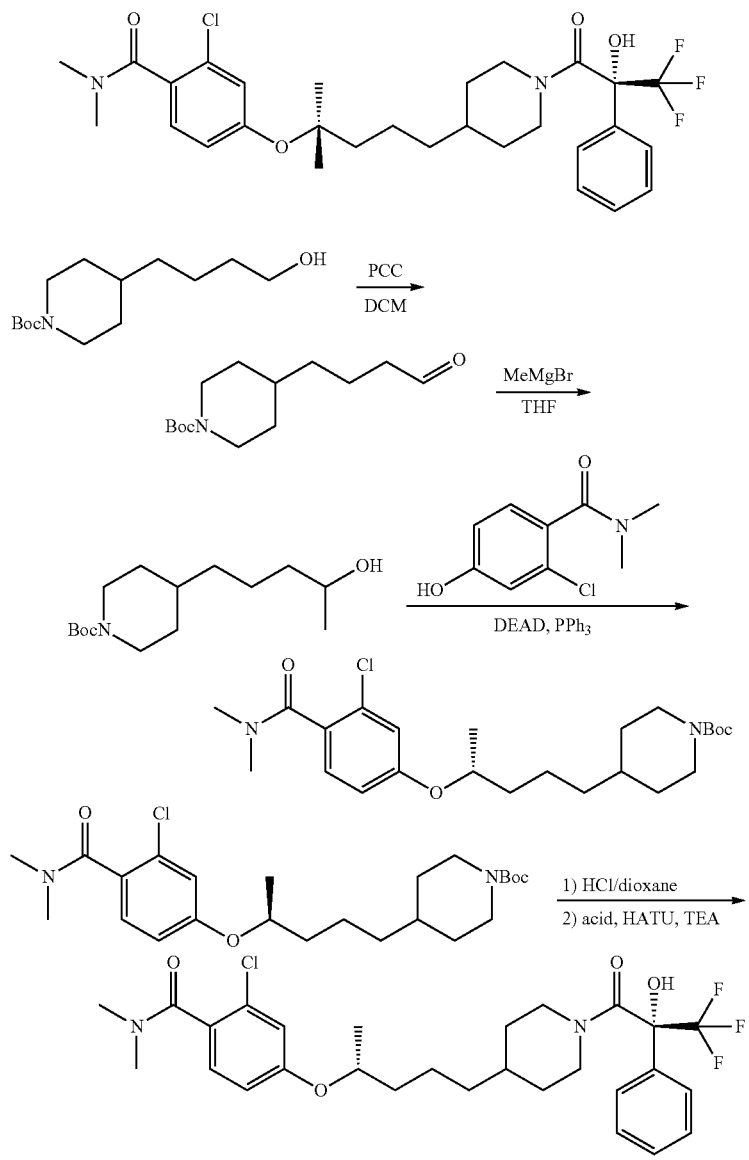

tert-butyl 4-(4-oxobutyl)piperidine-1-carboxylate

To a mixture of tert-butyl 4-(4-hydroxybutyl)piperidine-1-carboxylate (2 g, 7.8 mmol) in DCM (40 mL) cooled to 0° C. was added pyridinium chlorochromate (2.5 g, 11.7 mmol). The mixture was stirred at room temperature for 3 h. Then the mixture was poured into ether (500 mL) and filtered. The filtrate was washed with water until the aqueous phase was colorless. The organic phase was dried and concentrated to give tert-butyl 4-(4-oxobutyl)piperidine-1-carboxylate. LRMS m/z (M+Na) 278.1 found, 278.2 required.

tert-butyl 4-(4-hydroxypentyl)piperidine-1-carboxylate

To a mixture of tert-butyl 4-(4-oxobutyl)piperidine-1-carboxylate (1.8 g, 7.0 mmol) in THF (15 mL) at −78° C. was added methylmagnesium bromide (5.0 mL, 15 mmol, 3.0 M in ether). The mixture was stirred at −78° C. for 20 min, quenched with sat. ammonium chloride (50 mL), extracted with EtOAc (50 mL*2). The organic phases were combined, dried over sodium sulfate and concentrated. The residue was purified by silica gel column chromatography (PE/EtOAc=10/1) to give tert-butyl 4-(4-hydroxypentyl)piperidine-1-carboxylate. LRMS m/z (M+Na) 294.1 found, 294.2 required.

(R or S)-tert-butyl 4-(4-(3-chloro-4-(dimethylcar-bamoyl)phenoxy)pentyl)piperidine-1-carboxylate and (S or R)-tert-butyl 4-(4-(3-chloro-4-(dimethylcarbamoyl)phenoxy)pentyl)piperidine-1-carboxylate A mixture of 2-chloro-4-hydroxy-N,N-dimethylbenzamide (1.05 g, 5.2 mmol), triphenylphosphine (1.96 g, 7.5 mmol), tert-butyl 4-(4-hydroxypentyl)piperidine-1-carboxylate (1.35 g, 5.0 mmol) and diethyl diazene-1,2-dicarboxylate (1.39 g, 8.0 mmol) in THF (25 mL) was stirred at room temperature overnight. The mixture was concentrated and purified by silica gel column (PE/EtOAc=4/1) to give racemic tert-butyl 4-(4-(3-chloro-4-(dimethylcarbamoyl)phenoxy)pentyl)piperidine-1-carboxylate, which was resolved by Chiral HPLC (column: AD-H (250*4.6 mm 5 um); mobile phase: SFC-$CO_2$:MeOH=2.4:0.6; flow: 3 mL/min; temperature: 39.9° C.) to afford (R or S)-tert-butyl 4-(4-(3-chloro-4-(dimethylcarbamoyl)phenoxy)pentyl)piperidine-1-carboxylate (RT=3.04 min) and (S or R)-tert-butyl 4-(4-(3-chloro-4-(dimethylcarbamoyl)phenoxy)pentyl)piperidine-1-carboxylate (RT=3.92 min). LRMS m/z (M+H) 453.1 found, 453.2 required. Absolute stereochemistry not confirmed 2-chloro-N,N-dimethyl-4-((R or S)-5-(1-((R or S)-3,3,3-trifluoro-2-hydroxy-2-phenylpropanoyl)piperidin-4-yl)pentan-2-yloxy)benzamide A mixture of (R or S)-tert-butyl 4-(4-(3-chloro-4-(dimethylcarbamoyl)phenoxy)pentyl)piperidine-1-carboxylate (570 mg, 0.34 mmol) and 4M HCl/dioxane (6 mL) was stirred at room temperature for 2 h. The mixture was concentrated give the crude de-Boc product (440 mg). Then a mixture of the crude de-Boc product (30 mg, 0.085 mmol), HATU (55 mg, 0.14 mmol), (R or S)-3,3,3-trifluoro-2-hydroxy-2-phenylpropanoic acid (28 mg, 0.13 mmol) and triethylamine (26 mg, 0.26 mmol) in THF (2 mL) was stirred at room temperature overnight. The mixture was directly purified by prep-HPLC (mobile phase: methanol/water (10 mM $NH_4HCO_3$)) to give 2-chloro-N,N-dimethyl-4-((R or S)-5-(1-((R or S)-3,3,3-trifluoro-2-hydroxy-2-phenylpropanoyl)piperidin-4-yl)pentan-2-yloxy)benzamide. LRMS m/z (M+H) 555.1 found, 555.2 required.

Example 26-1

2-chloro-N,N-dimethyl-4-((R or S)-4-(1-((R or S)-3,3,3-trifluoro-2-hydroxy-2-(3-methoxyphenyl)propanoyl)piperidin-4-yl)pentyloxy)benzamide

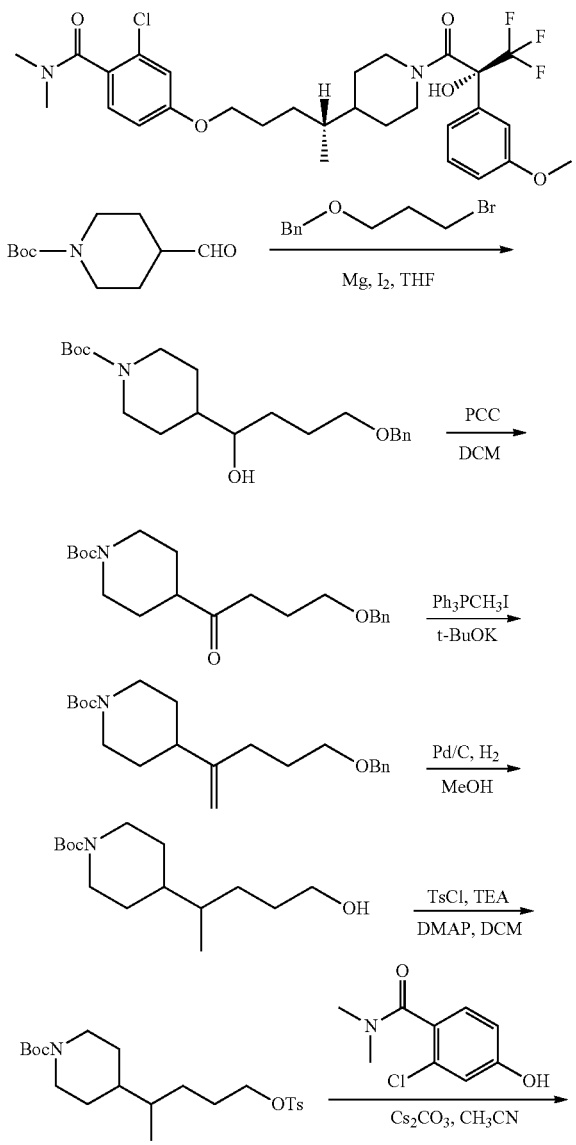

| Example | Structure | IUPAC Name | LRMS, found [M + H]+ |
|---|---|---|---|
| 25-2 | 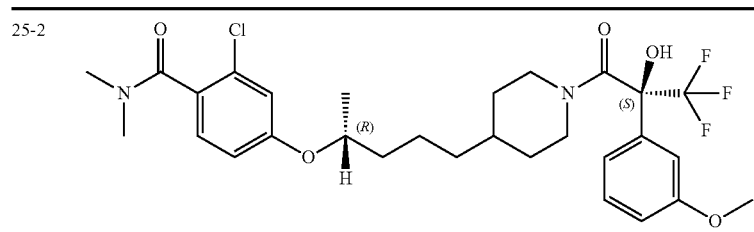 | 2-chloro-N,N-dimethyl-4-((R or S)-5-(1-((S or R)-3,3,3-trifluoro-2-hydroxy-2-(3-methoxyphenyl)propanoyl)piperidin-4-yl)pentan-2-yloxy)benzamide | 585.1 |

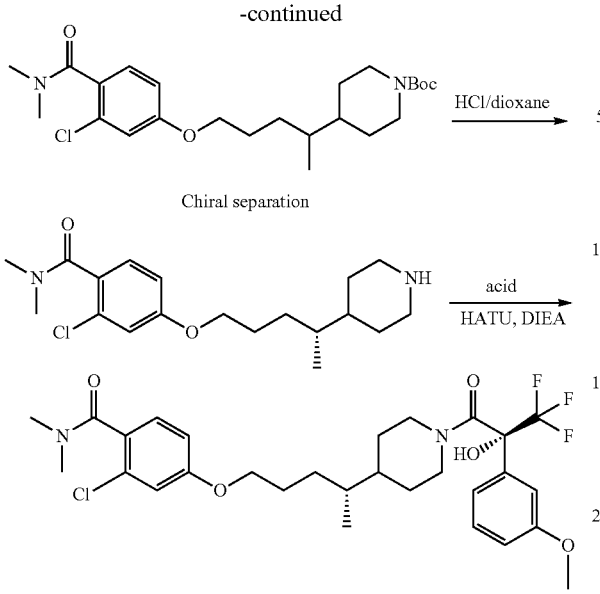

tert-butyl 4-(4-(benzyloxy)-1-hydroxybutyl)piperidine-1-carboxylate

The solution of ((3-bromopropoxy)methyl)benzene (2.8 g, 12.2 mmol), Mg (360 mg, 15 mmol), and $I_2$ (2.5 mg, 0.01 mmol) in dry THF (15 mL) was stirred for 2 h at 65° C. under $N_2$. After the mixture was cooled to 0° C., the solution of tert-butyl 4-formylpiperidine-1-carboxylate (1) (2.1 g, 10 mmol) in 5 mL of dry THF was added to the mixture and the reaction was stirred for 2 h at rt under $N_2$. Then aqueous $NH_4Cl$ (20 mL) was added to the mixture, and extracted with EtOAc (200 mL*3). The organic phase was dried over anhydrous $Na_2SO_4$, filtered and concentrated to give the crude product, which was purified by column chromatography (silica gel: 300-400 mesh, PE/EtOAc=20/1 to 5/1) to give tert-butyl 4-(4-(benzyloxy)-1-hydroxybutyl)piperidine-1-carboxylate. LRMS m/z (M-55) 308.2 found, 308.2 required.

tert-butyl 4-(4-(benzyloxy)butanoyl)piperidine-1-carboxylate

To the solution of tert-butyl 4-(4-(benzyloxy)-1-hydroxybutyl)piperidine-1-carboxylate (1.41 g, 3.9 mmol) in DCM (40 mL) was added PCC (1.68 g, 7.78 mmol). After stirring at rt for 3 h, the mixture was concentrated to give the crude product, which was purified by column chromatography (silica gel: 300-400 mesh, PE/EtOAc=20/1 to 5/1) to give tert-butyl 4-(4-(benzyloxy)butanoyl)piperidine-1-carboxylate. LRMS m/z (M-55) 306.2 found, 306.2 required.

tert-butyl 4-(5-(benzyloxy)pent-1-en-2-yl)piperidine-1-carboxylate

The mixture of methyltriphenylphosphonium iodide (4 g, 10 mmol) and t-BuOK (1.12 g, 10 mmol) in dry toluene (20 mL) was stirred for 1 h at 50° C. under $N_2$ balloon. Then tert-butyl 4-(4-(benzyloxy)butanoyl)piperidine-1-carboxylate (900 mg, 2.5 mmol) was added to the mixture, which was stirred for 1 h at rt. The mixture was quenched with aq $NH_4Cl$ (20 mL), extracted with EtOAc (200 mL*3). The organic phase was concentrated, and purified by column chromatography (silica gel: 300-400 mesh, PE/EtOAc=40/1) to give tert-butyl 4-(5-(benzyloxy)pent-1-en-2-yl)piperidine-1-carboxylate. LRMS m/z (M-55) 304.2 found, 304.2 required.

tert-butyl 4-(5-hydroxypentan-2-yl)piperidine-1-carboxylate

A mixture of tert-butyl 4-(5-(benzyloxy)pent-1-en-2-yl)piperidine-1-carboxylate (720 mg, 2 mmol) and 5% Pd/C (220 mg) in MeOH (15 mL) was stirred at rt under $H_2$ balloon overnight. Then the mixture was filtered, and concentrated to give the crude tert-butyl 4-(5-hydroxypentan-2-yl)piperidine-1-carboxylate. LRMS m/z (M-55) 216.2 found, 216.2 required tert-butyl 4-(5-(tosyloxy)pentan-2-yl)piperidine-1-carboxylate

A mixture of tert-butyl 4-(5-hydroxypentan-2-yl)piperidine-1-carboxylate (490 mg, 1.8 mmol), DMAP (24 mg, 0.2 mmol), $Et_3N$ (1.1 g, 11 mmol) and TsCl (684 mg, 3.6 mmol) in dry DCM (30 mL) was stirred at rt overnight. The reaction was quenched with $H_2O$ (100 mL), extracted with EtOAc (200 mL*3). The organic phase was dried over anhydrous $Na_2SO_4$, filtered and concentrated to give the crude compound, which was purified by column chromatography (silica gel: 300-400 mesh, PE/EtOAc=20/1 to 5/1) to give tert-butyl 4-(5-(tosyloxy)pentan-2-yl)piperidine-1-carboxylate. LRMS m/z (M-55) 370.2 found, 370.2 required.

tert-butyl 4-(5-(2-chloro-4-(dimethylcarbamoyl)phenoxy)pentan-2-yl)piperidine-1-carboxylate (7)

A mixture of tert-butyl 4-(5-(tosyloxy)pentan-2-yl)piperidine-1-carboxylate (570 mg, 1.3 mmol), 3-chloro-4-hydroxy-N,N-dimethylbenzamide (400 mg, 2.0 mmol), and $Cs_2CO_3$ (825 mg, 2.6 mmol) in acetonitrile (10 mL) was stirred at 80° C. under $N_2$ overnight. Then the mixture was filtered, and concentrated to give the crude compound, which was purified by column chromatography (silica gel: 300-400 mesh, PE/EtOAc=20/1 to 5/1) to give tert-butyl 4-(5-(2-chloro-4-(dimethylcarbamoyl)phenoxy)pentan-2-yl)piperidine-1-carboxylate. LRMS m/z (M-55) 397.2 found, 397.2 required. The racemic product was resolved by Chiral HPLC (column: AS-H (250*4.6 mm 5 um); mobile phase: SCF $CO_2$:MeOH=90:10; flow: 3.0 mL/min; temperature: 38° C.) to afford the (S or R)-tert-butyl 4-(5-(2-chloro-4-(dimethylcarbamoyl)phenoxy)pentan-2-yl)piperidine-1-carboxylate (RT=4.39 min) and (R or S)-tert-butyl 4-(5-(2-chloro-4-(dimethylcarbamoyl)phenoxy)pentan-2-yl)piperidine-1-carboxylate (RT=5.09 min). Absolute stereochemistry not confirmed

(R or S)-tert-butyl 4-(5-(2-chloro-4-(dimethylcarbamoyl)phenoxy)pentan-2-yl)piperidine-1-carboxylate A solution of (R or S)-tert-butyl 4-(5-(2-chloro-4-(dimethylcarbamoyl)phenoxy)pentan-2-yl)piperidine-1-carboxylate (RT=5.09 min) (190 mg, 0.5 mmol) in 4M HCl/dioxane (5 mL) was stirred for 30 min at rt. Then the mixture was concentrated to give the crude (R or S)-2-chloro-N,N-dimethyl-4-(4-(piperidin-4-yl)pentyloxy)benzamide. LRMS m/z (M+H) 353.2 found, 353.2 required.

131

2-chloro-N,N-dimethyl-4-((R or S)-4-(1-((R or S)-3,3,3-trifluoro-2-hydroxy-2-(3-methoxyphenyl)propanoyl)piperidin-4-yl)pentyloxy)benzamide A solution (R or S)-2-chloro-N,N-dimethyl-4-(4-(piperidin-4-yl)pentyloxy)benzamide (10 mg, 0.028 mmol), (R or S)-3,3,3-trifluoro-2-hydroxy-2-(3-methoxyphenyl)propanoic acid (7.5 mmol, 0.03 mmol), HATU (11 mg, 0.03 mmol) and DIEA (8 mmol, 0.06 mmol) in THF (2 mL) was stirred at rt overnight. Then the mixture was concentrated and purified by reverse phase chromatography (mobile phase: methanol/water (10 mM $NH_4HCO_3$)) to give 2-chloro-N,N-dimethyl-4-((R or S)-4-(1-((R or S)-3,3,3-trifluoro-2-hydroxy-2-(3-methoxyphenyl)propanoyl)piperidin-4-yl)pentyloxy)benzamide. LRMS m/z (M+H) 585.2 found, 585.2 required.

Using the same procedure described in example 26-1, but replacing (R or S)-3,3,3-trifluoro-2-hydroxy-2-(3-methoxyphenyl)propanoic acid with the appropriate acid in the last step, the following examples were prepared.

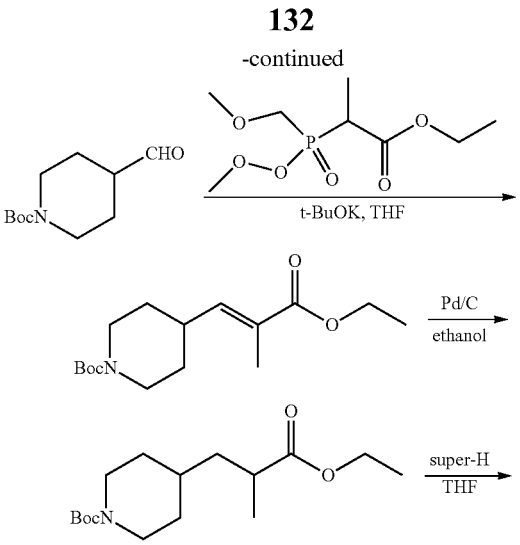

| Example | Structure | IUPAC Name | LRMS, found M + H]+ |
|---|---|---|---|
| 26-2 | 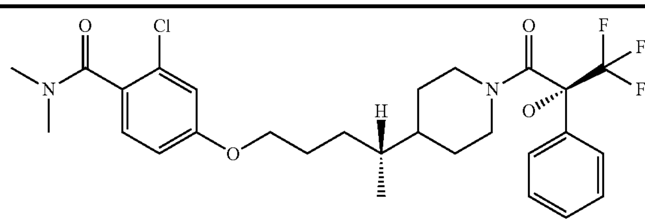 | 2-chloro-N,N-dimethyl-4-((R or S)-4-(1-((R or S)-3,3,3-trifluoro-2-hydroxy-2-phenylpropanoyl)piperidin-4-yl)pentyloxy)benzamide | 555.2 |
| 26-3 | 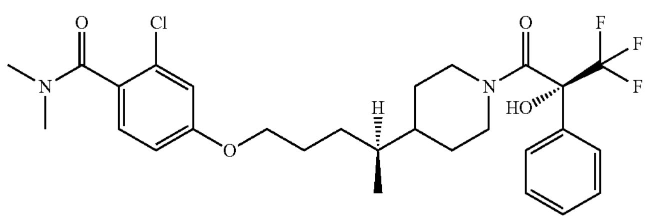 | 2-chloro-N,N-dimethyl-4-((S or R)-4-(1-((R or S)-3,3,3-trifluoro-2-hydroxy-2-phenylpropanoyl)piperidin-4-yl)pentyloxy)benzamide | 555.2 |
| 26-4 | 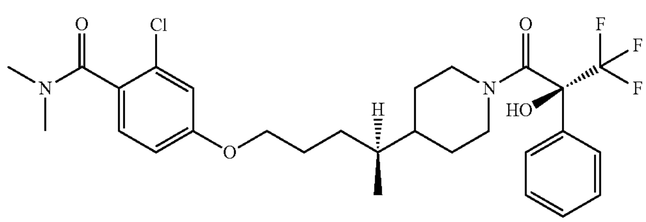 | 2-chloro-N,N-dimethyl-4-((S or R)-4-(1-((S or R)-3,3,3-trifluoro-2-hydroxy-2-phenylpropanoyl)piperidin-4-yl)pentyloxy)benzamide | 555.2 |

Example 27-1

2-chloro-N,N-dimethyl-4-((R or S)-3-methyl-4-(1-((R or S)-3,3,3-trifluoro-2-hydroxy-2-(3-methoxyphenyl)propanoyl)piperidin-4-yl)butoxy)benzamide

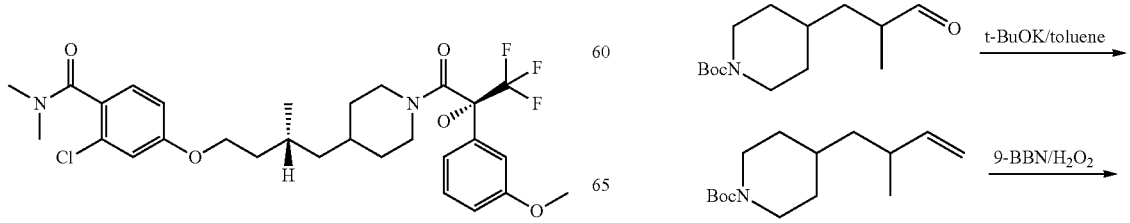

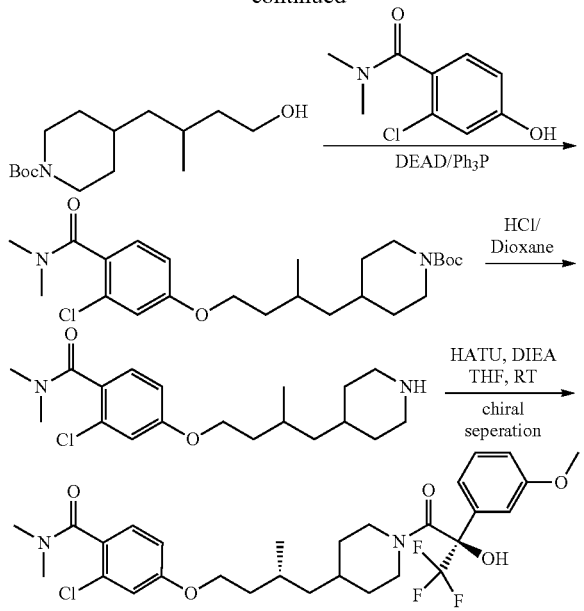

(E)-tert-butyl 4-(3-ethoxy-2-methyl-3-oxoprop-1-enyl)piperidine-1-carboxylat

The solution of ethyl 2-(diethoxyphosphoryl)propanoate (1.4 g, 5.63 mmol), t-BuOK (631 mg, 5.63 mmol) in THF (20 mL) was stirred for 1 h at 0° C. under $N_2$. Then tert-butyl 4-formylpiperidine-1-carboxylate (1 g, 4.69 mmol) in 10 mL of THF was added to the mixture, which was stirred for 4 h at rt under $N_2$. Then the reaction was quenched by adding aq $NH_4Cl$ (100 mL) carefully and stirred for another 30 min. The mixture was extracted with EtOAc (150 mL*3), and dried over anhydrous $Na_2SO_4$, filtered and concentrated to give the crude compound, which was purified by column chromatography (silica gel: 300-400 mesh, PE/EtOAc=20/1 to 5/1) to give the (E)-tert-butyl 4-(3-ethoxy-2-methyl-3-oxoprop-1-enyl)piperidine-1-carboxylate. LRMS m/z (M-99) 198.2 found, 198.2 required tert-butyl 4-(3-ethoxy-2-methyl-3-oxopropyl)piperidine-1-carboxylate The solution of (E)-tert-butyl 4-(3-ethoxy-2-methyl-3-oxoprop-1-enyl)piperidine-1-carboxylate (1.2 g, 4 mmol) and 5% Pd/C (500 mg) in MeOH (20 mL) was stirred for 4 h at rt under $H_2$ balloon. Then the mixture was filtered, and the filtrate was concentrated to give the crude tert-butyl 4-(3-ethoxy-2-methyl-3-oxopropyl)piperidine-1-carboxylate. LRMS m/z (M-99) 200.2 found, 200.2 required.

tert-butyl 4-(3-hydroxy-2-methylpropyl)piperidine-1-carboxylate

Super-H (11 mL, 11 mmol, 1M in THF) was added to the mixture of tert-butyl 4-(3-ethoxy-2-methyl-3-oxopropyl)piperidine-1-carboxylate (1 g, 3.3 mmol) in 10 mL of THF. Then the mixture was stirred for 3 h at 0° C. To the mixture was added MeOH (20 mL), and it's stirred for 1 h. And then aq $NH_4Cl$ (50 mL) was added to the mixture, which was stirred for 2 h. Then the reaction mixture was extracted with EtOAc (200 mL*3), and the organic phase was concentrated to give the crude compound, which was purified by column chromatography (silica gel: 300-400 mesh, PE/EtOAc=20/1 to 5/1) to give tert-butyl 4-(3-hydroxy-2-methylpropyl)piperidine-1-carboxylate. LRMS m/z (M-55) 202.2 found, 202.2 required.

tert-butyl 4-(2-methyl-3-oxopropyl)piperidine-1-carboxylate

A mixture of tert-butyl 4-(3-hydroxy-2-methylpropyl)piperidine-1-carboxylate (773 mg, 3 mmol) and PCC (2 g, 7.8 mmol) in DCM (40 mL) was stirred for 2 h at rt. Then the mixture was concentrated to give the crude compound, which was purified by column chromatography (silica gel: 300-400 mesh, PE/EtOAc=5/1 to 15/1) to give tert-butyl 4-(2-methyl-3-oxopropyl)piperidine-1-carboxylate. LRMS m/z (M-99) 156.2 found, 156.2 required.

tert-butyl 4-(2-methylbut-3-enyl)piperidine-1-carboxylate

A mixture of methyltriphenylphosphonium iodide (2.5 g, 6.3 mmol) and t-BuOK (705 mg, 6.3 mmol) in dry toluene (15 mL) was stirred for 1 h at rt under $N_2$. Then tert-butyl 4-(2-methyl-3-oxopropyl)piperidine-1-carboxylate (450 mg, 1.76 mmol) was added to the mixture, which was stirred for 1 h at rt under $N_2$. Then aq $NH_4Cl$ (10 mL) was added to the mixture, and the mixture was extracted with EtOAc (100 mL*3). The organic phase was concentrated, and purified by column chromatography (silica gel: 300-400 mesh, PE/EtOAc=40/1) to give tert-butyl 4-(2-methylbut-3-enyl)piperidine-1-carboxylate. LRMS m/z (M-55) 198.2 found, 198.2 required.

tert-butyl 4-(4-hydroxy-2-methylbutyl)piperidine-1-carboxylate

To a solution of tert-butyl 4-(2-methylbut-3-enyl)piperidine-1-carboxylate (400 mg, 1.6 mmol) in dry THF (10 mL) was added 9-BBN (16 mL, 8 mmol, 0.5 M in THF). Then the mixture was stirred overnight at rt under $N_2$. 5N NaOH (5 mL) was added to the solution, and then 30% $H_2O_2$ (5 mL) was added to the mixture carefully. After stirring for 1 h at rt, the mixture was extracted with EtOAc (100 mL*3). The organic phase was concentrated, and purified by column chromatography (silica gel: 300-400 mesh, PE/EtOAc=20/1 to 5/1) to give the tert-butyl 4-(4-hydroxy-2-methylbutyl)piperidine-1-carboxylate. LRMS m/z (M+H) 216.2 found, 216.2 required.

tert-butyl 4-(4-(3-chloro-4-(dimethylcarbamoyl)phenoxy)-2-methylbutyl)piperidine-1-carboxylate The solution of tert-butyl 4-(4-hydroxy-2-methylbutyl)piperidine-1-carboxylate (300 mg, 1.1 mmol), 2-chloro-4-hydroxy-N,N-dimethylbenzamide (330 mg, 1.73 mmol) and $Ph_3P$ (870 mg, 3.36 mmol) in 2 mL of THF was stirred for 5 min at rt under $N_2$. Then a solution of DEAD (580 mg, 3.36 mmol) in 1 mL of THF was added to the mixture. After stirring for 2 h at rt under $N_2$, the mixture was purified by reverse phase chromatography (mobile phase: methanol/water (10 mM $NH_4HCO_3$)) to give tert-butyl 4-(4-(3-chloro-4-(dimethylcarbamoyl)phenoxy)-2-methylbutyl)piperidine-1-carboxylate. LRMS m/z (M-99) 353.2 found, 353.2 required.

2-chloro-N,N-dimethyl-4-(3-methyl-4-(piperidin-4-yl)butoxy)benzamide

The solution of tert-butyl 4-(4-(3-chloro-4-(dimethylcarbamoyl)phenoxy)-2-methylbutyl)piperidine-1-carboxylate (490 mg, 1.1 mmol) in 4M HCl/dioxane (10 mL) was stirred for 1 h at rt. Then the mixture was concentrated to give the crude 2-chloro-N,N-dimethyl-4-(3-methyl-4-(piperidin-4-yl)butoxy)benzamide. LRMS m/z (M+H) 353.2 found, 353.2 required.

2-chloro-N,N-dimethyl-4-((R or S)-3-methyl-4-(1-((R or S)-3,3,3-trifluoro-2-hydroxy-2-(3-methoxyphenyl)propanoyl)piperidin-4-yl)butoxy)benzamide The solution of 2-chloro-N,N-dimethyl-4-(3-methyl-4-(piperidin-4-yl)butoxy)benzamide (100 mg, 0.28 mmol), (R or S)-3,3,3-trifluoro-2-hydroxy-2-(3-methoxyphenyl)propanoic acid (104 mg, 0.42 mmol), HATU (162 mg, 0.42 mmol), and DIEA (110 mg, 0.85 mmol) in THF (5 mL) was stirred overnight at rt. Then the mixture was purified by reverse phase chromatography (mobile phase: methanol/water (10 mM NH$_4$HCO$_3$)) to give 2-chloro-N,N-dimethyl-4-(3-methyl-4-(1-((R or S)-3,3,3-trifluoro-2-hydroxy-2-(3-methoxyphenyl)propanoyl)piperidin-4-yl)butoxy) benzamide. The racemic product was resolved by Chiral HPLC (column: AD-H (250*4.6 mm 5 um); mobile phase: SCF-CO$_2$:MeOH=70:30; flow: 3.0 mL/min; temperature: 40° C.) to afford the 2-chloro-N,N-dimethyl-4-((S or R)-3-methyl-4-(1-((R or S)-3,3,3-trifluoro-2-hydroxy-2-(3-methoxyphenyl)propanoyl)piperidin-4-yl)butoxy)benzamide (RT=2.75 min) and 2-chloro-N,N-dimethyl-4-((R or S)-3-methyl-4-(1-((R or S)-3,3,3-trifluoro-2-hydroxy-2-(3-methoxyphenyl)propanoyl)piperidin-4-yl)butoxy)benzamide (RT=4.09 min). LRMS m/z (M+H) 585.2 found, 585.2 required. Absolute stereochemistry not confirmed.

Example 28-1

2-chloro-4-((R or S)-1,1-difluoro-3-methyl-4-(1-((R or S)-3,3,3-trifluoro-2-hydroxy-2-(3-methoxyphenyl)propanoyl)piperidin-4-yl)butoxy)-N,N-dimethylbenzamide

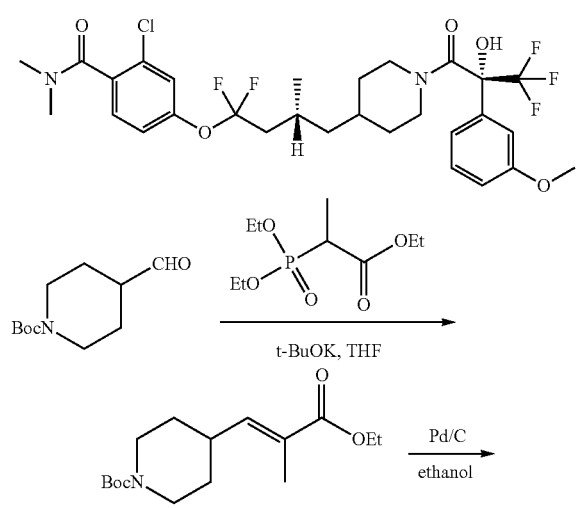

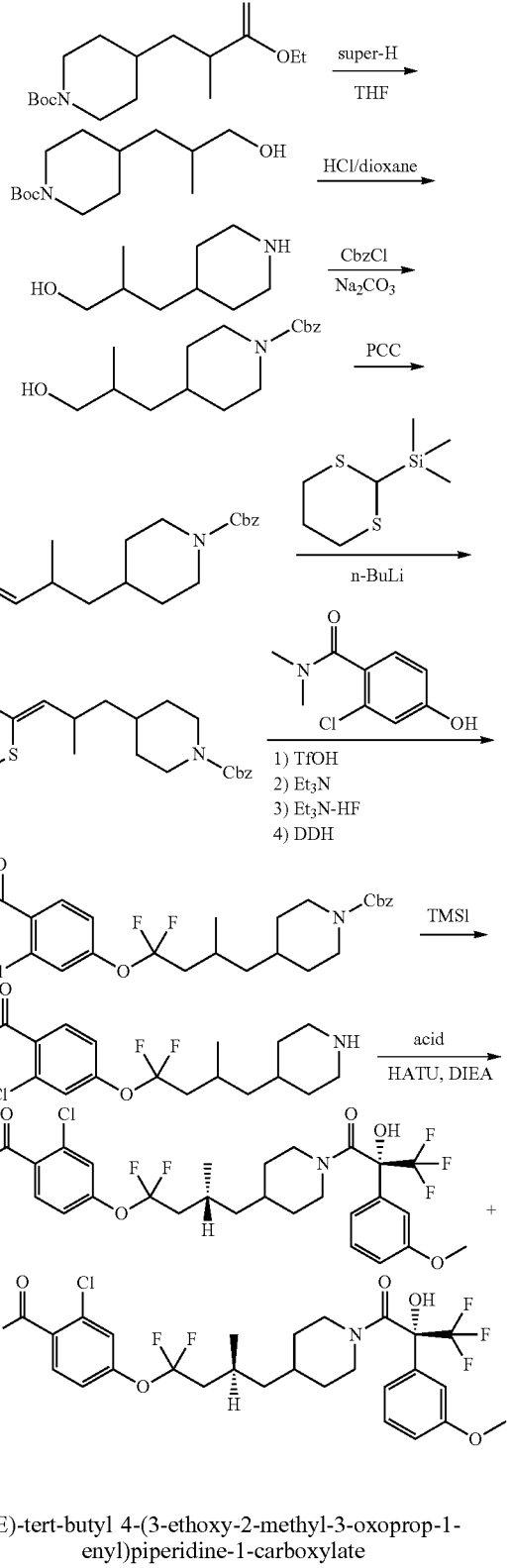

(E)-tert-butyl 4-(3-ethoxy-2-methyl-3-oxoprop-1-enyl)piperidine-1-carboxylate The solution of ethyl 2-(diethoxyphosphoryl)propanoate (1.4 g, 5.63 mmol), t-BuOK (631 mg, 5.63 mmol) in THF (20 mL) was stirred for 1 h at 0° C. under N$_2$. Then tert-butyl 4-formylpiperidine-1-carboxylate (1 g, 4.69 mmol) in 10 mL of THF was added to the mixture, which was stirred for 4 h at rt under N$_2$. Then the reaction was quenched by adding aq NH$_4$Cl (100 mL) carefully and stirred for another 30 min. The mixture was extracted with EtOAc (150 mL*3), and dried over anhydrous Na$_2$SO$_4$, filtered and concentrated to give the crude compound, which was purified by column chromatography (silica gel: 300-400 mesh, PE/EtOAc=20/1 to 5/1) to give the (E)-tert-butyl 4-(3-ethoxy-2-methyl-3-oxoprop-1-enyl)piperidine-1-carboxylate. LRMS m/z (M-99) 198.2 found, 198.2 required.

tert-butyl 4-(3-ethoxy-2-methyl-3-oxopropyl)piperidine-1-carboxylate

The solution of (E)-tert-butyl 4-(3-ethoxy-2-methyl-3-oxoprop-1-enyl)piperidine-1-carboxylate (1.2 g, 4 mmol) and 5% Pd/C (500 mg) in MeOH (20 mL) was stirred for 4 h at rt under H$_2$ balloon. Then the mixture was filtered, and the filtrate was concentrated to give the crude tert-butyl 4-(3-ethoxy-2-methyl-3-oxopropyl)piperidine-1-carboxylate. LRMS m/z (M-99) 200.2 found, 200.2 required.

tert-butyl 4-(3-hydroxy-2-methylpropyl)piperidine-1-carboxylate

Super-H (11 mL, 11 mmol, 1M in THF) was added to the mixture of tert-butyl 4-(3-ethoxy-2-methyl-3-oxopropyl)piperidine-1-carboxylate (1 g, 3.3 mmol) in 10 mL of THF. Then the mixture was stirred for 3 h at 0° C. To the mixture was added MeOH (20 mL), and it's stirred for 1 h. And then aq NH$_4$Cl (50 mL) was added to the mixture, which was stirred for 2 h. Then the reaction mixture was extracted with EtOAc (200 mL*3), and the organic phase was concentrated to give the crude compound, which was purified by column chromatography (silica gel: 300-400 mesh, PE/EtOAc=20/1 to 5/1) to give tert-butyl 4-(3-hydroxy-2-methylpropyl)piperidine-1-carboxylate. LRMS m/z (M-55) 202.2 found, 202.2 required.

2-methyl-3-(piperidin-4-yl)propan-1-ol

A solution of tert-butyl 4-(3-hydroxy-2-methylpropyl)piperidine-1-carboxylate (3.2 g, 13 mmol) in 4M HCl/dioxane (20 mL) was stirred for 2 h at rt. Then the mixture was concentrated to give the crude 2-methyl-3-(piperidin-4-yl)propan-1-ol. LRMS m/z (M+H) 158.1 found, 158.1 required.

benzyl 4-(3-hydroxy-2-methylpropyl)piperidine-1-carboxylate

A solution of 2-methyl-3-(piperidin-4-yl)propan-1-ol (2.1 g, 13 mmol), benzyl carbonochloridate (2.3 g, 15 mmol), Na$_2$CO$_3$ (4 g, 38 mmol) in H$_2$O/dioxane (50 mL) was stirred for 2 h at rt. Then the mixture was extracted with EtOAc (200 mL*3), and the organic phase was concentrated to give the crude compound, which was purified by column chromatography (silica gel: 300-400 mesh, PE/EtOAc=20/1 to 5/1) to give the benzyl 4-(3-hydroxy-2-methylpropyl)piperidine-1-carboxylate. LRMS m/z (M+H) 292.2 found, 292.2 required.

benzyl 4-(2-methyl-3-oxopropyl)piperidine-1-carboxylate

The solution of benzyl 4-(3-hydroxy-2-methylpropyl)piperidine-1-carboxylate (3.8 g, 13 mmol) and PCC (9 g, 41 mmol) in DCM (100 mL) was stirred for 2 h at rt. Then the mixture was concentrated to give the crude compound, which was purified by column chromatography (silica gel: 300-400 mesh, PE/EtOAc=50/1 to 15/1) to give benzyl 4-(2-methyl-3-oxopropyl)piperidine-1-carboxylate. LRMS m/z (M+H) 290.2 found, 290.2 required.

benzyl 4-(3-(1,3-dithian-2-ylidene)-2-methylpropyl)piperidine-1-carboxylate

To a solution of (1,3-dithian-2-yl)trimethylsilane (560 mg, 2.9 mmol) in dry THF (3 mL) mL was added n-BuLi (1.2 mL, 3 mmol, 2.5 M in hexane) at −78° C. under N$_2$ atmosphere. After stirring for 2 h, a solution of benzyl 4-(2-methyl-3-oxopropyl)piperidine-1-carboxylate (740 mg, 2.6 mmol) in dry THF (2 mL) was added to the mixture carefully and stirred for 1 h at −78° C. The mixture was quenched by 20 mL of saturated NH$_4$Cl and extracted with EtOAc (20 mL×3). The organic layer was dried over anhydrous Na$_2$SO$_4$, concentrated, and purified by a silica gel chromatography (silica gel: 300-400 mesh, PE/EtOAc=30:1) to give benzyl 4-(3-(1,3-dithian-2-ylidene)-2-methylpropyl)piperidine-1-carboxylate. LRMS m/z (M+H) 392.2 found, 392.2 required.

benzyl 4-(4-(3-chloro-4-(dimethylcarbamoyl)phenoxy)-4,4-difluoro-2-methylbutyl)piperidine-1-carboxylate Trifluoromethanesulfonic acid (150 mg, 1.0 mmol) was added dropwise at 0° C. to a solution of benzyl 4-(3-(1,3-dithian-2-ylidene)-2-methylpropyl)piperidine-1-carboxylate (400 mg, 1.0 mmol) in DCM (4 mL). The mixture was stirred for 30 min at rt. Then it was cooled to −70° C. and a solution of 2-chloro-4-hydroxy-N,N-dimethylbenzamide (308 mg, 1.5 mmol) and Et$_3$N (182 mg, 1.8 mmol) in DCM (1 mL) was added. After stirring for 1 h at −70° C., 1,3-dibromo-5,5-dimethyl imidazolidine-2,4-dione (1.4 mg, 5 mmol), Et$_3$N·3HF complex (805 mg, 5 mmol) was added. After stirring for additional 1 h, the mixture was allowed to warm up to 0° C., and then poured into ice-cold 1N NaOH (15 mL), diluted with 50 mL of water, and extracted with DCM (100 mL*3). The solvent was evaporated under reduced pressure and the residue was purified by reverse phase chromatography (mobile phase: methanol/water (10 mM NH$_4$HCO$_3$)) to afford benzyl 4-(4-(3-chloro-4-(dimethylcarbamoyl)phenoxy)-4,4-difluoro-2-methylbutyl)piperidine-1-carboxylate. LRMS m/z (M+H) 523.2 found, 523.2 required.

2-chloro-4-(1,1-difluoro-3-methyl-4-(piperidin-4-yl)butoxy)-N,N-dimethylbenzamide To a solution of benzyl 4-(4-(3-chloro-4-(dimethylcarbamoyl)phenoxy)-4,4-difluoro-2-methylbutyl)piperidine-1-carboxylate (440 mg, 0.85 mmol) in DCM (4 mL) was added TMSI (510 mg, 2.5 mmol). The mixture was stirred for 30 min, quenched with methanol (1 mL) and concentrated. The residue was purified by reverse phase chromatography (mobile phase: methanol/water (10 mM NH$_4$HCO$_3$) to give 2-chloro-4-(1,1-difluoro-3-methyl-4-(piperidin-4-yl)butoxy)-N,N-dimethylbenzamide. LRMS m/z (M+H) 389.2 found, 389.2 required.

2-chloro-4-((R or S)-1,1-difluoro-3-methyl-4-(1-((R or S)-3,3,3-trifluoro-2-hydroxy-2-(3-methoxyphenyl)propanoyl)piperidin-4-yl)butoxy)-N,N-dimethylbenzamide A solution of 2-chloro-4-(1,1-difluoro-3-methyl-4-(piperidin-4-yl)butoxy)-N,N-dimethylbenzamide (40 mg, 0.10 mmol), (R or S)-3,3,3-trifluoro-2-hydroxy-2-(3-methoxyphenyl)propanoic acid (31 mg, 0.12 mmol), HATU (60 mg, 0.15 mmol) and DIEA (106 mg, 0.82 mmol) in THF (2 mL) was stirred at rt overnight. Then the mixture was purified by reverse phase chromatography (mobile phase: methanol/water (10 mM NH$_4$HCO$_3$) to give a mixture of two isomers. LRMS m/z (M+H) 621.2 found, 621.2 required. The product was resolved by Chiral HPLC (column: AY-H (250*4.6 mm 5 um); mobile phase: n-Hexane (0.1% DEA):MeOH (0.1% DEA)=80:20; flow: 1.0 mL/min; temperature: 40° C.) to afford 2-chloro-4-((S or R)-1,1-difluoro-3-methyl-4-(1-((R or S)-3,3,3-trifluoro-2-hydroxy-2-(3-methoxyphenyl)propanoyl)piperidin-4-yl)butoxy)-N,N-dimethylbenzamide (RT=7.85 min) and 2-chloro-4-((R or S)-1,1-difluoro-3-methyl-4-(1-((R or S)-3,3,3-trifluoro-2-hydroxy-2-(3-methoxyphenyl)propanoyl)piperidin-4-yl)butoxy)-N,N-dimethylbenzamide (RT=11.07 min). Absolute stereochemistry not confirmed.

Example 29-1

(R or S)-2-chloro-4-(2,2-dimethyl-4-(1-(3,3,3-trifluoro-2-hydroxy-2-phenylpropanoyl)piperidin-4-yl)butoxy)-N,N-dimethylbenzamide

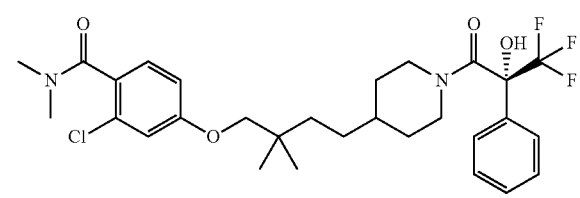

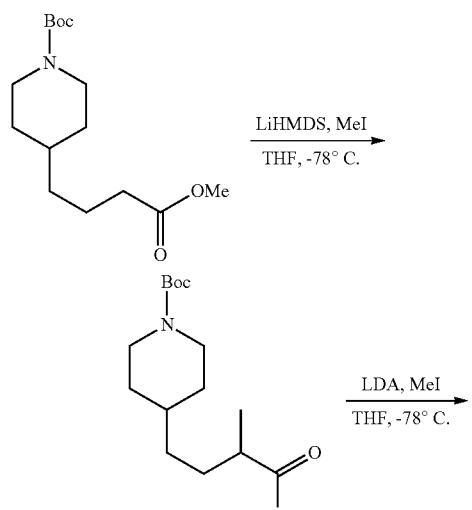

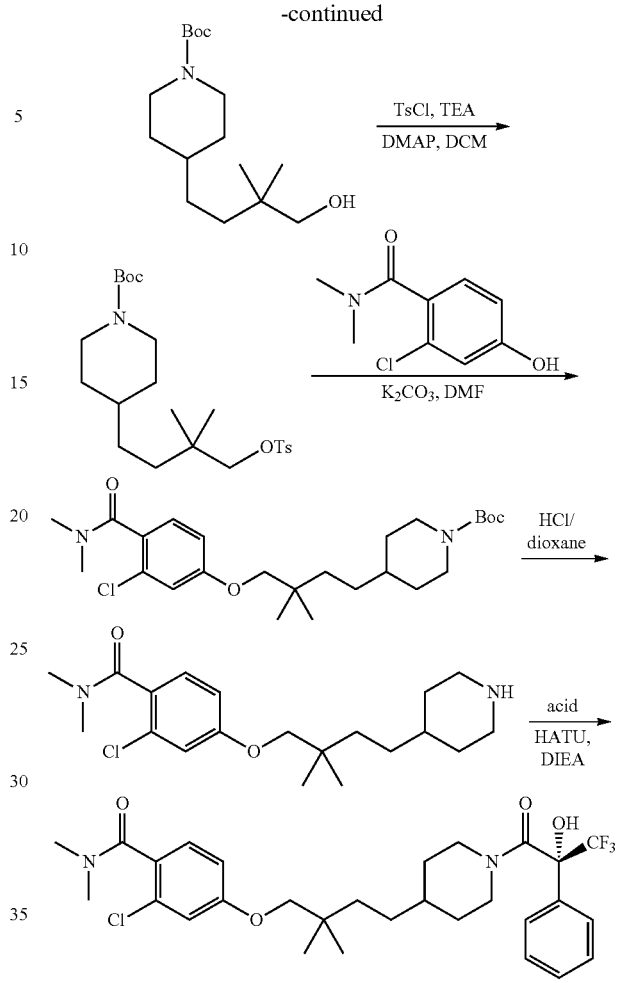

tert-butyl 4-(4-methoxy-3-methyl-4-oxobutyl)piperidine-1-carboxylate

To a solution of tert-butyl 4-(4-methoxy-4-oxobutyl)piperidine-1-carboxylate (300 mg, 1.05 mmol) in THF (5 mL) was added dropwise LiHMDS (2.2 mL, 2.2 mmol, 1 M in THF) at −78° C. under nitrogen atmosphere. The mixture was stirred at −78° C. for 1 h. MeI (581 mg, 4.09 mmol) was added. The resulting mixture was stirred at −78° C. to rt overnight. Then the mixture was quenched with methanol (1 mL) and directly purified by reverse phase chromatography (mobile phase: methanol/water (10 mM NH$_4$HCO$_3$) to afford tert-butyl 4-(4-methoxy-3-methyl-4-oxobutyl)piperidine-1-carboxylate. LRMS m/z (M+H) 300.3 found, 300.2 required.

tert-butyl 4-(4-methoxy-3,3-dimethyl-4-oxobutyl)piperidine-1-carboxylate

To a solution of tert-butyl 4-(4-methoxy-3-methyl-4-oxobutyl)piperidine-1-carboxylate (140 mg, 0.47 mmol) in THF (3 mL) was added dropwise LDA (0.94 mL, 0.94 mmol, 1 M in THF) at −78° C. under nitrogen atmosphere. The mixture was stirred at −78° C. for 1 h. MeI (266 mg, 1.87 mmol) was added. The resulting mixture was stirred at −78° C. to rt overnight. Then the mixture was quenched with methanol (1 mL) and directly purified by reverse phase chromatography (mobile phase: methanol/water (10 mM NH₄HCO₃) to afford tert-butyl 4-(4-methoxy-3,3-dimethyl-4-oxobutyl)piperidine-1-carboxylate. LRMS m/z (M+H) 314.3 found, 314.2 required.

tert-butyl 4-(4-hydroxy-3,3-dimethylbutyl)piperidine-1-carboxylate

To a solution of tert-butyl 4-(4-methoxy-3,3-dimethyl-4-oxobutyl)piperidine-1-carboxylate (85 mg, 0.27 mmol) in THF (1 mL) was added dropwise Super-H (0.82 mL, 0.82 mmol, 1 M in THF) at 0° C. under nitrogen atmosphere. The mixture was stirred at 0° C. to rt overnight. Then the mixture was quenched by the addition of MeOH (1 mL) and saturated ammonium chloride (1 mL). The mixture was filtered and directly purified by reverse phase chromatography (mobile phase: methanol/water (10 mM NH₄HCO₃)) to afford tert-butyl 4-(4-hydroxy-3,3-dimethylbutyl)piperidine-1-carboxylate. LRMS m/z (M+H) 286.2 found, 286.2 required.

tert-butyl 4-(3,3-dimethyl-4-(tosyloxy)butyl)piperidine-1-carboxylate

To a solution of tert-butyl 4-(4-hydroxy-3,3-dimethylbutyl)piperidine-1-carboxylate (30 mg, 0.11 mmol) in DCM (1 mL) was added TEA (32 mg, 0.32 mmol), DMAP (2 mg, 0.02 mmol) and 4-methylbenzene-1-sulfonyl chloride (24 mg, 0.13 mmol) at 0° C. The mixture was stirred at 0° C.~rt overnight. The mixture was concentrated and the residue was directly purified by reverse phase chromatography (mobile phase: methanol/water (10 mM NH₄HCO₃)) to afford tert-butyl 4-(3,3-dimethyl-4-(tosyloxy)butyl)piperidine-1-carboxylate. LRMS m/z (M+H) 440.2 found, 440.2 required.

tert-butyl 4-(4-(3-chloro-4-(dimethylcarbamoyl)phenoxy)-3,3-dimethylbutyl)piperidine-1-carboxylate To a solution of tert-butyl 4-(3,3-dimethyl-4-(tosyloxy)butyl)piperidine-1-carboxylate (20 mg, 0.046 mmol) in DMF (1 mL) was added K₂CO₃ (13 mg, 0.09 mmol) and 2-chloro-4-hydroxy-N,N-dimethylbenzamide (11 mg, 0.055 mmol). The mixture was stirred at 120° C. for 2 h under microwave. The mixture was purified by reverse phase chromatography (mobile phase: methanol/water (10 mM NH₄HCO₃)) to afford the tert-butyl 4-(4-(3-chloro-4-(dimethylcarbamoyl)phenoxy)-3,3-dimethylbutyl)piperidine-1-carboxylate. LRMS m/z (M+H) 467.3 found, 467.3 required.

2-chloro-4-(2,2-dimethyl-4-(piperidin-4-yl)butoxy)-N,N-dimethylbenzamide

To a solution of tert-butyl 4-(4-(3-chloro-4-(dimethylcarbamoyl)phenoxy)-3,3-dimethylbutyl)piperidine-1-carboxylate (10 mg, 0.022 mmol) in THF (0.5 mL) was added 4M HCl/dioxane (3 mL) at 0° C. The mixture was stirred at rt for 2 h and concentrated in vacuo to afford the crude product 2-chloro-4-(2,2-dimethyl-4-(piperidin-4-yl)butoxy)-N,N-dimethylbenzamide. LRMS m/z (M+H) 367.3 found, 367.2 required.

(R or S)-2-chloro-4-(2,2-dimethyl-4-(1-(3,3,3-trifluoro-2-hydroxy-2-phenylpropanoyl)piperidin-4-yl)butoxy)-N,N-dimethylbenzamide To a solution of 2-chloro-4-(2,2-dimethyl-4-(piperidin-4-yl)butoxy)-N,N-dimethylbenzamide (8 mg, 0.022 mmol) in THF (1 mL) was added (R or S)-3,3,3-trifluoro-2-hydroxy-2-phenylpropanoic acid (7 mg, 0.033 mmol), DIEA (9 mg, 0.066 mmol) and HATU (13 mg, 0.0.33 mmol). The mixture was stirred at rt overnight. Then the mixture was directly purified by reverse phase chromatography (mobile phase: methanol/water (10 mM NH₄HCO₃) to afford (R or S)-2-chloro-4-(2,2-dimethyl-4-(1-(3,3,3-trifluoro-2-hydroxy-2-phenylpropanoyl)piperidin-4-yl)butoxy)-N,N-dimethylbenzamide. LRMS m/z (M+H) 569.3 found, 569.2 required.

Example 30-1

2-chloro-N,N-dimethyl-4-(4-methyl-5-(1-((R or S)-3,3,3-trifluoro-2-hydroxy-2-(3-methoxyphenyl)propanoyl)piperidin-4-yl)pentan-2-yloxy)benzamide

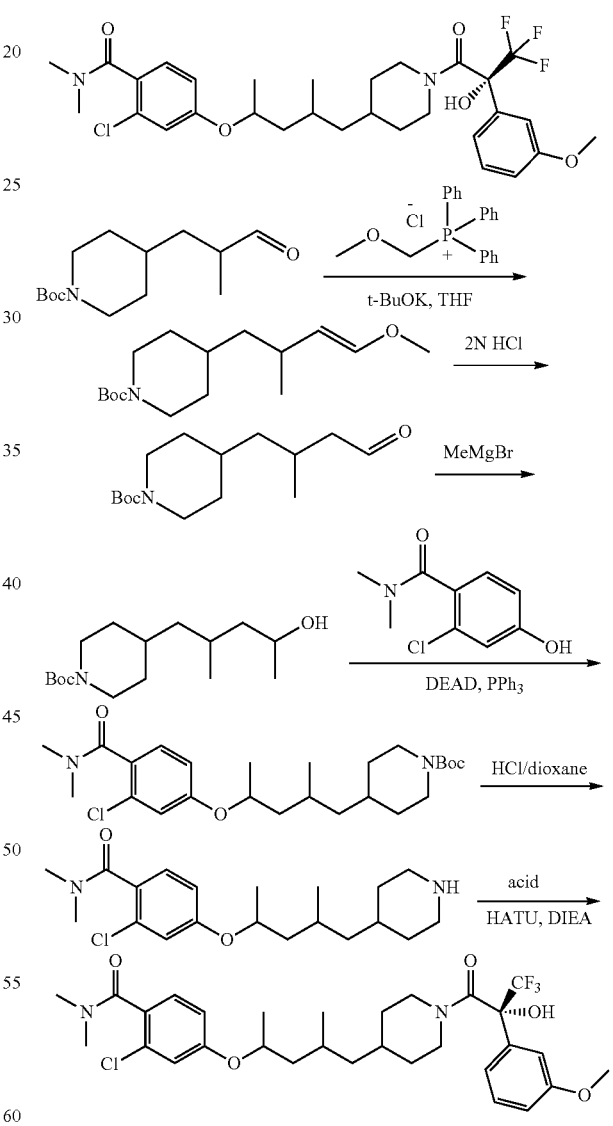

(E)-tert-butyl 4-(4-methoxy-2-methylbut-3-enyl)piperidine-1-carboxylate

A mixture of (methoxymethyl)triphenylphosphonium chloride (861 mg, 2.5 mmol) and t-BuOK (280 mg, 2.5 mmol) in THF (10 mL) was stirred at rt under N₂ atmosphere. After 0.5 h, a yellow precipitate was formed. Then tert-butyl 4-(2-methyl-3-oxopropyl)piperidine-1-carboxylate (400 mg, 1.57 mmol) was added, and stirred for 2 h at rt. The reaction was quenched by 20 mL of saturated NH₄Cl and extracted with EtOAc (30 mL×3). The combined organic layers were washed with brine (10 mL), dried over anhydrous Na₂SO₄ and concentrated under reduced pressure to give a crude product, which was purified by column chromatography (silica gel: 300-400 mesh, PE/EtOAc=50/1) to give (E)-tert-butyl 4-(4-methoxy-2-methylbut-3-enyl)piperidine-1-carboxylate. LRMS m/z (M+Na) 306.2 found, 306.2 required.

tert-butyl 4-(2-methyl-4-oxobutyl)piperidine-1-carboxylate

A solution of (E)-tert-butyl 4-(4-methoxy-2-methylbut-3-enyl)piperidine-1-carboxylate (347 mg, 1.2 mmol) and 2 M HCl (1.5 mL) in 3 mL of THF was stirred at rt for 4 h. The mixture was concentrated under reduced pressure to give the crude compound which was purified by column chromatography (silica gel: 300-400 mesh, PE/EtOAc=20/1) to give tert-butyl 4-(2-methyl-4-oxobutyl)piperidine-1-carboxylate. LRMS m/z (M+Na) 292.2 found, 292.2 required.

tert-butyl 4-(4-hydroxy-2-methylpentyl)piperidine-1-carboxylate

To a solution of tert-butyl 4-(2-methyl-4-oxobutyl)piperidine-1-carboxylate (321 mg, 1.19 mmol) in THF (6 mL) was added methylmagnesium bromide (0.52 mL, 1.56 mmol, 3M in Et₂O) at 0° C. The mixture was allowed to warm to rt and stirred for 2 h. The reaction was quenched by 20 mL of saturated NH₄Cl and extracted with EtOAc (30 mL×3). The combined organic layers were washed with brine (10 mL), dried over anhydrous Na₂SO₄ and concentrated under reduced pressure to give a crude product, which was purified by column chromatography (silica gel: 300-400 mesh, PE/EtOAc=20/1 to 5/1) to afford tert-butyl 4-(4-hydroxy-2-methylpentyl)piperidine-1-carboxylate. LRMS m/z (M+Na) 308.2 found, 308.2 required.

tert-butyl 4-(4-(3-chloro-4-(dimethylcarbamoyl)phenoxy)-2-methylpentyl)piperidine-1-carboxylate To a solution of tert-butyl 4-(4-hydroxy-2-methylpentyl)piperidine-1-carboxylate (240 mg, 0.84 mmol), 2-chloro-4-hydroxy-N,N-dimethyl-benzamide (167 mg, 0.84 mmol) and triphenylphosphine (441 mg, 1.68 mmol) in THF (6 mL) was added DEAD (292 mg, 1.68 mmol) at rt. After stirring for 2 h, the mixture was concentrated under reduced pressure to give crude product which was purified by reverse phase chromatography (mobile phase: methanol/water (10 mM NH₄HCO₃)) to afford tert-butyl 4-(4-(3-chloro-4-(dimethylcarbamoyl)phenoxy)-2-methylpentyl)piperidine-1-carboxylate. LRMS m/z (M+Na) 489.3 found, 489.3 required.

2-chloro-N,N-dimethyl-4-(4-methyl-5-(piperidin-4-yl)pentan-2-yloxy)benzamide hydrochloride A solution of tert-butyl 4-(4-(3-chloro-4-(dimethylcarbamoyl)phenoxy)-2-methylpentyl)piperidine-1-carboxylate (233 mg, 0.5 mmol) in 4M HCl/1,4-dioxane (5 mL) was stirred for 1 h at rt. Then the mixture was concentrated under reduced pressure to give crude 2-chloro-N,N-dimethyl-4-(4-methyl-5-(piperidin-4-yl)pentan-2-yloxy)benzamide hydrochloride. LRMS m/z (M+H) 367.2 found, 367.2 required.

2-chloro-N,N-dimethyl-4-(4-methyl-5-(1-((R or S)-3,3,3-trifluoro-2-hydroxy-2-(3-methoxyphenyl)propanoyl)piperidin-4-yl)pentan-2-yloxy)benzamide A mixture of 2-chloro-N,N-dimethyl-4-(4-methyl-5-(piperidin-4-yl)pentan-2-yloxy)benzamide hydrochloride (15 mg, 0.04 mmol), HATU (23 mg, 0.06 mmol), (R or S)-3,3,3-trifluoro-2-hydroxy-2-(3-methoxyphenyl)propanoic acid (13 mg, 0.049 mmol) and DIEA (10 mg, 0.08 mmol) in THF (1 mL) was stirred at rt overnight. The mixture was directly purified by reverse phase chromatography (mobile phase: methanol/water (10 mM NH₄HCO₃)) to afford 2-chloro-N,N-dimethyl-4-(4-methyl-5-(1-((R or S)-3,3,3-trifluoro-2-hydroxy-2-(3-methoxyphenyl)propanoyl)piperidin-4-yl)pentan-2-yloxy)benzamide. LRMS m/z (M+H) 599.2 found, 599.2 required.

Example 31-1

2-chloro-N,N-dimethyl-4-(2-methyl-4-(1-((R or S)-3,3,3-trifluoro-2-hydroxy-2-phenylpropanoyl)piperidin-4-yl)pentyloxy)benzamide

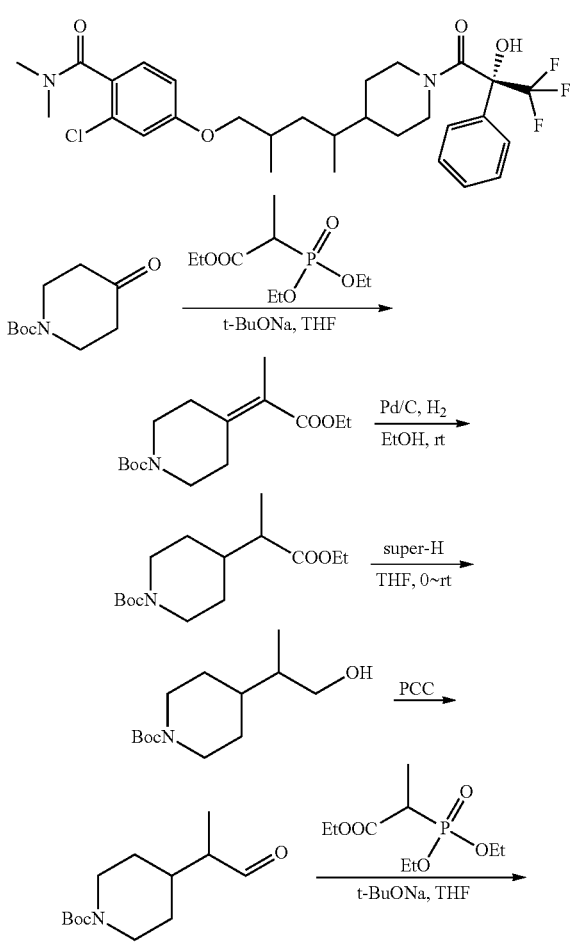

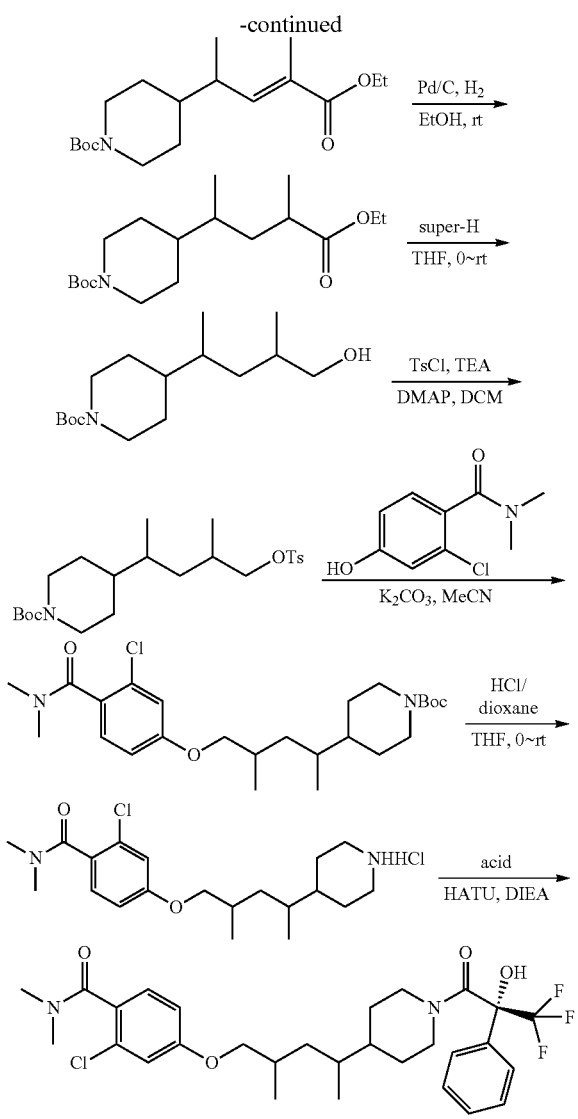

tert-butyl 4-(1-ethoxy-1-oxopropan-2-ylidene)piperidine-1-carboxylate

To a solution of ethyl 2-(diethoxyphosphoryl)propanoate (15.55 g, 65.33 mmol) in THF (60 mL) was added t-BuONa (6.76 g, 70.35 mmol) at 0° C. under nitrogen atmosphere. After stirring at 0° C. for 1 h, tert-butyl 4-oxopiperidine-1-carboxylate (10.0 g, 50.25 mmol) in THF (40 mL) was added at 0° C. The resulting mixture was stirred at 0° C. to rt for 2 h. The mixture was quenched by the addition of saturated ammonium chloride (50 mL) and then extracted with EtOAc (300 mL). The organic phase was washed with water (40 mL×2) and dried over anhydrous $Na_2SO_4$. The organic phase was concentrated and the residue was purified by column chromatography (silica gel: 300-400 mesh, PE/EtOAc=10/1) to afford tert-butyl 4-(1-ethoxy-1-oxopropan-2-ylidene)piperidine-1-carboxylate. LRMS m/z (M-99) 184.3 found, 184.2 required.

tert-butyl 4-(1-ethoxy-1-oxopropan-2-yl)piperidine-1-carboxylate

To a solution of tert-butyl 4-(1-ethoxy-1-oxopropan-2-ylidene)piperidine-1-carboxylate (13.5 g, 45.94 mmol) in ethanol (150 mL) was added palladium on carbon (1.5 g, 10% on carbon). The mixture was stirred at rt under $H_2$ balloon for 2 h. The mixture was filtered and the filtrate was concentrated in vacuo to give tert-butyl 4-(1-ethoxy-1-oxopropan-2-yl)piperidine-1-carboxylate. LRMS m/z (M+H) 286.1 found, 286.2 required.

tert-butyl 4-(1-hydroxypropan-2-yl)piperidine-1-carboxylate

To a solution of tert-butyl 4-(1-ethoxy-1-oxopropan-2-yl)piperidine-1-carboxylate (13.0 g, 45.61 mmol) in THF (40 mL) was added dropwise Super-H (91 mL, 91 mmol, 1 M in THF) at 0° C. under nitrogen atmosphere. The mixture was stirred at 0° C.~rt overnight. Then the mixture was quenched by the addition of MeOH (50 mL) and saturated ammonium chloride (50 mL). The mixture was concentrated in vacuo and then extracted with EtOAc (400 mL). The organic phase was washed with water (40 mL×2), dried over anhydrous $Na_2SO_4$ and concentrated. The residue was purified by column chromatography (silica gel: 300-400 mesh, PE/EtOAc=3/1) to give tert-butyl 4-(1-hydroxypropan-2-yl)piperidine-1-carboxylate. LRMS m/z (M+H) 244.2 found, 244.2 required.

tert-butyl 4-(1-oxopropan-2-yl)piperidine-1-carboxylate

To a solution of tert-butyl 4-(1-hydroxypropan-2-yl)piperidine-1-carboxylate (6.0 g, 24.69 mmol) in DCM (60 mL) was added PCC (7.98 g, 37.04 mmol) at 0° C. The mixture was stirred at 0° C.~rt for 4 h. Celite (6 g) and ether (300 mL) were added. The resulting mixture was stirred at rt for 20 min and filtered. The filtrate was washed with water (50 mL×6) and dried over anhydrous $Na_2SO_4$. The organic phase was concentrated in vacuo to afford the crude product tert-butyl 4-(1-oxopropan-2-yl)piperidine-1-carboxylate. LRMS m/z (M+K) 280.1 found, 280.1 required

(E)-tert-butyl 4-(5-ethoxy-4-methyl-5-oxopent-3-en-2-yl)piperidine-1-carboxylate To a solution of ethyl 2-(diethoxyphosphoryl)propanoate (7.06 g, 29.67 mmol) in THF (30 mL) was added t-BuONa (3.07 g, 31.95 mmol) at 0° C. under nitrogen atmosphere. After stirring at 0° C. for 1 h, tert-butyl 4-(1-oxopropan-2-yl)piperidine-1-carboxylate (5.5 g, 22.82 mmol) in THF (30 mL) was added at 0° C. The resulting mixture was stirred at 0° C.~rt for 2 h. The mixture was quenched by the addition of saturated ammonium chloride (30 mL) and then extracted with EtOAc (300 mL). The organic phase was washed with water (30 mL×2), dried over anhydrous $Na_2SO_4$ and concentrated. The residue was purified by column chromatography (silica gel: 300-400 mesh, PE/EtOAc=10/1) to give (E)-tert-butyl 4-(5-ethoxy-4-methyl-5-oxopent-3-en-2-yl)piperidine-1-carboxylate. LRMS m/z (M+Na) 348.2 found, 348.2 required.

tert-butyl 4-(5-ethoxy-4-methyl-5-oxopentan-2-yl)piperidine-1-carboxylate

To a solution of (E)-tert-butyl 4-(5-ethoxy-4-methyl-5-oxopent-3-en-2-yl)piperidine-1-carboxylate (5.5 g, 45.94 mmol) in ethanol (50 mL) was added palladium on carbon (600 mg, 10% on carbon). The mixture was stirred at rt under $H_2$ balloon for 2 h. The mixture was filtered and the filtrate was concentrated in vacuo to give tert-butyl 4-(5- ethoxy-4-methyl-5-oxopentan-2-yl)piperidine-1-carboxylate. LRMS m/z (M-99) 228.2 found, 228.2 required.

tert-butyl 4-(5-hydroxy-4-methylpentan-2-yl)piperidine-1-carboxylate

To a solution of tert-butyl 4-(5-ethoxy-4-methyl-5-oxopentan-2-yl)piperidine-1-carboxylate (5.5 g, 16.82 mmol) in THF (30 mL) was added dropwise Super-H (34 mL, 34 mmol, 1 M in THF) at 0° C. under nitrogen atmosphere. The mixture was stirred at 0° C.~rt overnight. Then the mixture was quenched by the addition of MeOH (30 mL) and saturated ammonium chloride (30 mL). The mixture was concentrated in vacuo, and then extracted with EtOAc (300 mL). The organic phase was washed with water (30 mL×2), dried over anhydrous $Na_2SO_4$ and concentrated. The residue was purified by column chromatography (silica gel: 300-400 mesh, PE/EtOAc=3/1) to give tert-butyl 4-(5-hydroxy-4-methylpentan-2-yl)piperidine-1-carboxylate. LRMS m/z (M-99) 186.4 found, 186.2 required.

tert-butyl 4-(4-methyl-5-(tosyloxy)pentan-2-yl)piperidine-1-carboxylate

To a solution of tert-butyl 4-(5-hydroxy-4-methylpentan-2-yl)piperidine-1-carboxylate (2.4 g, 8.4 mmol) in DCM (40 mL) was added TEA (1.7 g, 16.8 mmol), DMAP (102 mg, 0.84 mmol) and 4-methylbenzene-1-sulfonyl chloride (1.92 g, 10.07 mmol) at 0° C. The mixture was stirred at 0° C.~rt overnight. The mixture was concentrated and the residue was directly purified by column chromatography (silica gel: 300-400 mesh, PE/EtOAc=8/1) to afford tert-butyl 4-(4-methyl-5-(tosyloxy)pentan-2-yl)piperidine-1-carboxylate. LRMS m/z (M+H) 440.2 found, 440.2 required.

tert-butyl 4-(5-(3-chloro-4-(dimethylcarbamoyl)phenoxy)-4-methylpentan-2-yl)piperidine-1-carboxylate To a solution of tert-butyl 4-(4-methyl-5-(tosyloxy)pentan-2-yl)piperidine-1-carboxylate (2.0 g, 4.56 mmol) in MeCN (30 mL) was added $K_2CO_3$ (1.26 g, 9.12 mmol) and 2-chloro-4-hydroxy-N,N-dimethylbenzamide (1.0 g, 5.01 mmol). The mixture was stirred at 70° C. overnight. The mixture was concentrated in vacuo and then extracted with EtOAc (200 mL). The organic phase was washed with water (30 mL×2), dried over anhydrous $Na_2SO_4$ and concentrated. The residue was purified by column chromatography (silica gel: 300-400 mesh, PE/EtOAc=4/1) to give tert-butyl 4-(5-(3-chloro-4-(dimethylcarbamoyl)phenoxy)-4-methylpentan-2-yl)piperidine-1-carboxylate. LRMS m/z (M-99) 367.3 found, 367.2 required.

2-chloro-N,N-dimethyl-4-(2-methyl-4-(piperidin-4-yl)pentyloxy)benzamide hydrochloride To a solution of tert-butyl 4-(5-(3-chloro-4-(dimethylcarbamoyl)phenoxy)-4-methylpentan-2-yl)piperidine-1-carboxylate (600 mg, 1.29 mmol) in THF (6 mL) was added 4M HCl/1,4-dioxane (30 mL) at 0° C. The mixture was stirred at rt for 2 h and concentrated in vacuo to afford the crude 2-chloro-N,N-dimethyl-4-(2-methyl-4-(piperidin-4-yl)pentyloxy)benzamide hydrochloride. LRMS m/z (M+H) 367.3 found, 367.2 required.

2-chloro-N,N-dimethyl-4-(2-methyl-4-(1-((R or S)-3,3,3-trifluoro-2-hydroxy-2-phenylpropanoyl)piperidin-4-yl)pentyloxy)benzamide To a solution of 2-chloro-N,N-dimethyl-4-(2-methyl-4-(piperidin-4-yl)pentyloxy)benzamide hydrochloride (40 mg, 0.099 mmol) in THF (1 mL) was added (R or S)-3,3,3-trifluoro-2-hydroxy-2-phenylpropanoic acid (33 mg, 0.15 mmol), DIEA (38 mg, 0.3 mmol) and HATU (57 mg, 0.15 mmol). The mixture was stirred at rt overnight. Then the mixture was directly purified by reverse phase chromatography (mobile phase: methanol/water (10 mM $NH_4HCO_3$) to afford 2-chloro-N,N-dimethyl-4-(2-methyl-4-(1-((R or S)-3,3,3-trifluoro-2-hydroxy-2-phenylpropanoyl)piperidin-4-yl)pentyloxy)benzamide. LRMS m/z (M+H) 569.3 found, 569.2 required. $^1$H NMR (400 MHz, $CDCl_3$): δ 7.45-7.41 (m, 5H), 7.21 (d, J=8.4 Hz, 1H), 6.91-6.89 (t, 1H), 6.84-6.80 (m, 1H), 3.76-3.70 (m, 2H), 3.15 (s, 3H), 2.90 (s, 3H), 2.66-2.64 (m, 1H), 1.96-1.94 (m, 1H), 1.46-1.38 (m, 4H), 1.32-1.28 (m, 2H), 1.03-1.01 (d, J=8 Hz, 2H), 0.96-0.94 (d, J=8 Hz, 2H), 0.80-0.78 (t, 3H).

Using the procedure described for example 31-1, but replacing (R or S)-3,3,3-trifluoro-2-hydroxy-2-phenylpropanoic acid with the appropriate acid, the following examples were prepared.

| Example | Structure | IUPAC Name | LRMS, found [M + H]+ |
|---|---|---|---|
| 31-2 | (structure) | 2-chloro-N,N-dimethyl-4-(2-methyl-4-(1-((R or S)-3,3,3-trifluoro-2-hydroxy-2-(3-methoxyphenyl)propanoyl)piperidin-4-yl)pentyloxy)benzamide | 599.3 |

Example 32-1- and 32-2

2-chloro-4-(((1R,2S or 1S,2R)-2-(1-((S or R)-2-hydroxy-3-methyl-2-(trifluoromethyl)butanoyl)piperidin-4-yl)cyclopropyl)methoxy)-N,N-dimethylbenzamide and 2-chloro-4-(((1R,2S or 1S,2R)-2-(1-((R or S)-2-hydroxy-3-methyl-2-(trifluoromethyl)butanoyl)piperidin-4-yl)cyclopropyl)methoxy)-N,N-dimethylbenzamide

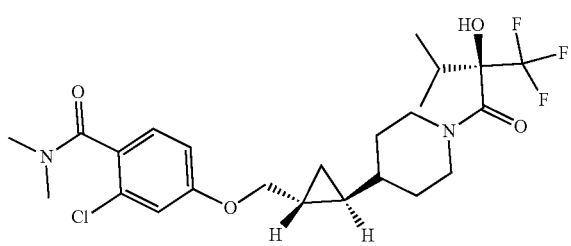

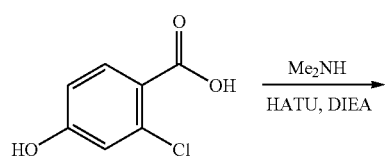

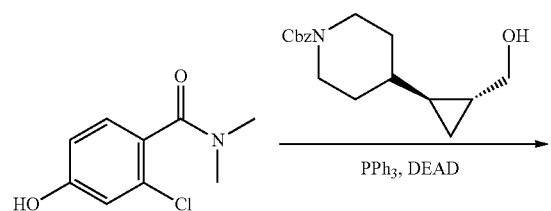

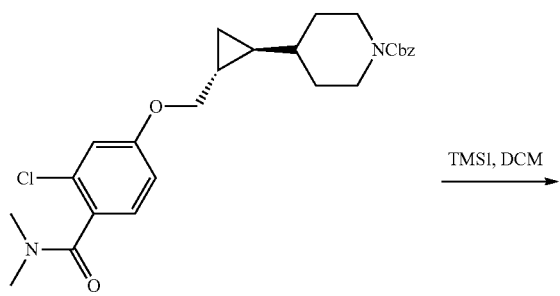

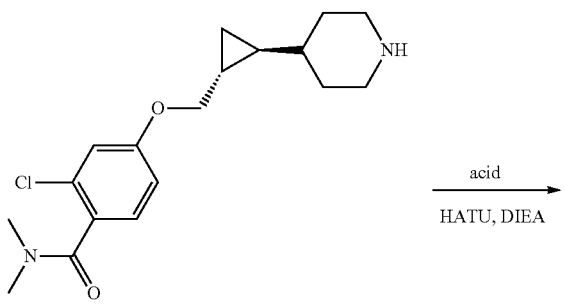

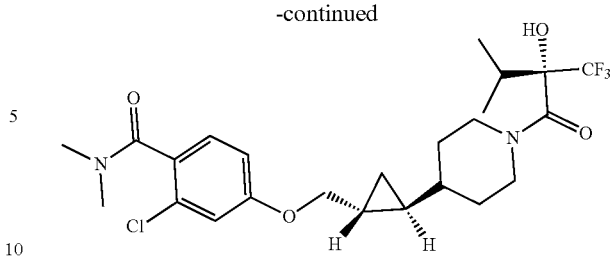

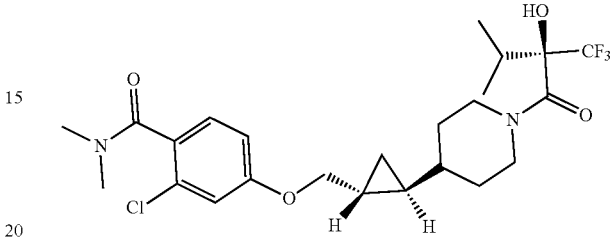

2-chloro-4-hydroxy-N,N-dimethylbenzamide

To a solution of 2-chloro-4-hydroxybenzoic acid (2.0 g, 11.59 mmol, 1.0 eq) in THF (40 mL) was added dimethylamine (11.6 mL, 23.2 mmol, 2 M in THF, 2.0 eq), DIEA (4.49 g, 34.77 mmol) and HATU (6.61 g, 17.39 mmol). The mixture was stirred at rt overnight. Then the mixture was directly purified by column chromatography (silica gel: 300-400 mesh, PE/EtOAc=1:1) to give 2-chloro-4-hydroxy-N,N-dimethylbenzamide. LRMS m/z (M+H) 200.0 found, 200.0 required.

benzyl 4-((1S,2R or 1R,2S)-2-((3-chloro-4-(dimethylcarbamoyl)phenoxy)methyl)cyclopropyl)piperidine-1-carboxylate To a solution of 2-chloro-4-hydroxy-N,N-dimethylbenzamide (150 mg, 0.52 mmol, 1.0 eq) in THF (2 mL) was added benzyl 4-((1S,2R or 1R,2S)-2-(hydroxymethyl)cyclopropyl)piperidine-1-carboxylate (124 mg, 0.62 mmol, 1.2 eq), PPh₃ (163 mg, 0.62 mmol, 1.2 eq) and DEAD (108 mg, 0.62 mmol, 1.2 eq) at 0° C. under nitrogen atmosphere. The mixture was stirred at rt for 2 h and was directly purified by reverse phase chromatography (mobile phase: methanol/water (10 mM NH₄HCO₃)) to afford benzyl 4-((1S,2R or 1R,2S)-2-((3-chloro-4-(dimethylcarbamoyl)phenoxy)methyl)cyclopropyl)piperidine-1-carboxylate. LRMS m/z (M+H) 471.2 found, 471.2 required.

2-chloro-N,N-dimethyl-4-(((1R,2S or 1S,2R)-2-(piperidin-4-yl)cyclopropyl)methoxy)benzamide To a solution of benzyl 4-((1S,2R or 1R,2S)-2-((3-chloro-4-(dimethylcarbamoyl)phenoxy)methyl)cyclopropyl)piperidine-1-carboxylate (160 mg, 0.34 mmol, 1.0 eq) in DCM (5 mL) was added TMSI (170 mg, 0.85 mmol, 2.5 eq) at 0° C. The mixture was stirred at 0° C. for 30 min, quenched with MeOH (0.5 mL) and directly purified by Prep-TLC (EtOAc: MeOH=6:1) to afford 2-chloro-N,N-dimethyl-4-(((1R,2S or 1S,2R)-2-(piperidin-4-yl)cyclopropyl)methoxy)benzamide. LRMS m/z (M+H) 337.0 found, 337.2 required.

2-chloro-4-(((1R,2S or 1S,2R)-2-(1-((R or S)-2-hydroxy-3-methyl-2-(trifluoromethyl)butanoyl)piperidin-4-yl)cyclopropyl)methoxy)-N,N-dimethylbenzamide To a solution of 2-chloro-4-(((1R,2S or 1S,2R)-2-(1-(2-hydroxy-3-methyl-2-(trifluoromethyl)butanoyl)piperidin-4- yl)cyclopropyl)methoxy)-N,N-dimethylbenzamide (40 mg, 0.12 mmol, 1.0 eq) in THF (1.5 mL) was added 2-hydroxy-3-methyl-2-(trifluoromethyl)butanoic acid (33 mg, 0.18 mmol, 1.5 eq), DIEA (46 mg, 0.36 mmol, 3.0 eq) and HATU (68 mg, 0.18 mmol, 1.5 eq). The mixture was stirred at rt overnight. Then the mixture was directly purified by reverse phase chromatography (mobile phase: methanol/water (10 mM NH₄HCO₃) to afford 2-chloro-4-(((1R,2S or 1S,2R)-2-(1-(2-hydroxy-3-methyl-2-(trifluoromethyl)butanoyl)piperidin-4-yl)cyclopropyl)methoxy)-N,N-dimethylbenzamide. The product was resolved by Chiral HPLC (column: AD-H (250*4.6 mm 5 um); mobile phase: SCF-CO₂: MeOH=60:40; flow: 3 mL/min; temperature: 39.6° C.) to afford 2-chloro-4-(((1R,2S or 1S,2R)-2-(1-((S or R)-2-hydroxy-3-methyl-2-(trifluoromethyl)butanoyl)piperidin-4-yl)cyclopropyl)methoxy)-N,N-dimethylbenzamide (RT=1.99 min) and 2-chloro-4-(((1R,2S or 1S,2R)-2-(1-((R or S)-2-hydroxy-3-methyl-2-(trifluoromethyl)butanoyl)piperidin-4-yl)cyclopropyl)methoxy)-N,N-dimethylbenzamide (RT=2.82 min). LRMS m/z (M+H) 505.1 found, 505.2 required. Absolute stereochemistry not determined.

Using the procedure described in example 32-1/32-2, but replacing 2-hydroxy-3-methyl-2-(trifluoromethyl)butanoic acid with the appropriate acid and amine, the following examples were prepared.

| Example | Structure | IUPAC Name | LRMS, found [M + H]+ |
|---|---|---|---|
| 32-3 | 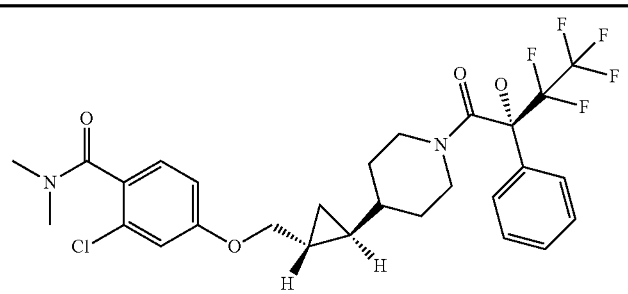 | 2-chloro-N,N-dimethyl-4-(((1R,2S or 1S,2R)-2-(1-((R or S)-3,3,4,4,4-pentafluoro-2-hydroxy-2-phenylbutanoyl)piperidin-4-yl)cyclopropyl)methoxy)benzamide | 589.0 |
| 32-4 | 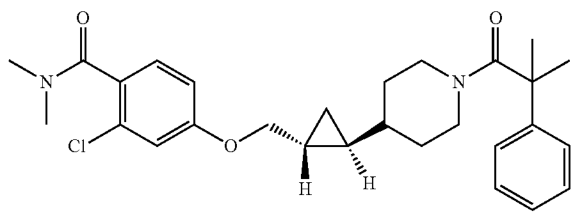 [SMILES: CN(C)C(=O)c1ccc(OC[C@@H]2C[C@H]2C2CCN(C(=O)C(C)(C)c3ccccc3)CC2)cc1Cl] | 2-chloro-N,N-dimethyl-4-(((1R,2S or 1S,2R)-2-(1-(2-methyl-2-phenylpropanoyl)piperidin-4-yl)cyclopropyl)methoxy)benzamide | 483.3 |
| 32-5 | 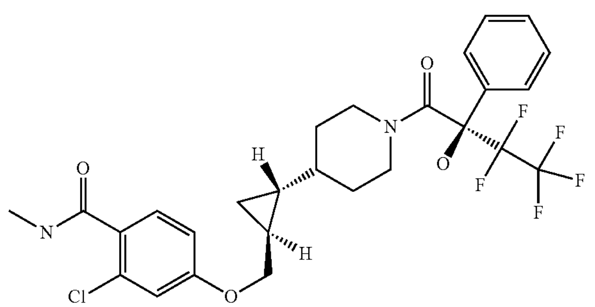 [SMILES: CNC(=O)c1ccc(OC[C@H]2C[C@@H]2C2CCN(C(=O)[C@](O)(c3ccccc3)C(F)(F)C(F)(F)F)CC2)cc1Cl] | 2-chloro-N-methyl-4-(((1S,2R or 1R,2S)-2-(1-((R or S)-3,3,4,4,4-pentafluoro-2-hydroxy-2-phenylbutanoyl)piperidin-4-yl)cyclopropyl)methoxy)benzamide | 575.1 |
| 32-6 | 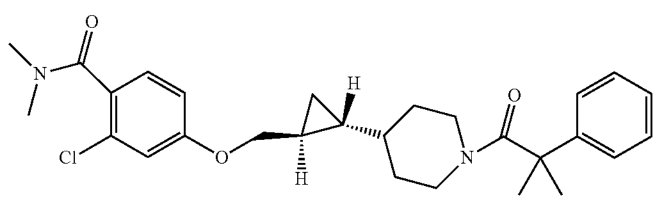 [SMILES: CN(C)C(=O)c1ccc(OC[C@H]2C[C@@H]2C2CCN(C(=O)C(C)(C)c3ccccc3)CC2)cc1Cl] | 2-chloro-N,N-dimethyl-4-(((1S,2R or 1R,2S)-2-(1-(2-methyl-2-phenylpropanoyl)piperidin-4-yl)cyclopropyl)methoxy)benzamide | 483.1 |

Example 33-1

2-chloro-N,N-dimethyl-4-((7-((R or S)-3,3,3-trifluoro-2-hydroxy-2-phenylpropanoyl)-7-azaspiro[3.5]nonan-2-yl)methoxy)benzamide

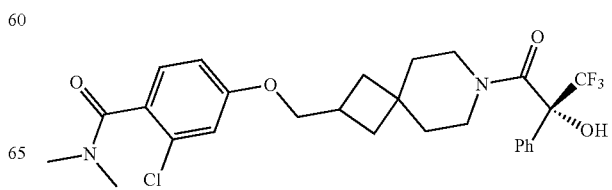

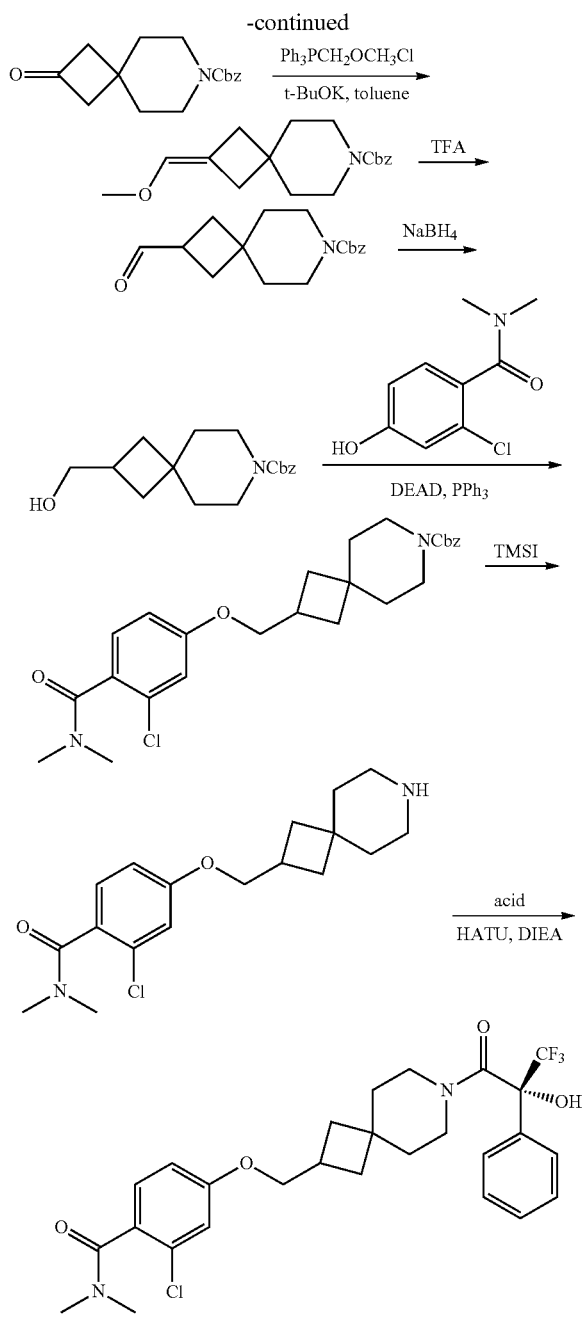

benzyl 2-(methoxymethylene)-7-azaspiro[3.5]nonane-7-carboxylate

To a solution of (methoxymethyl)triphenylphosphonium chloride (800 mg, 2.34 mmol) in toluene (7 mL) was added t-BuOK (262 mg, 2.34 mmol) at rt. The resulting mixture was stirred at rt for 1 h and a solution of benzyl 2-oxo-7-azaspiro[3.5]nonane-7-carboxylate (1) (426 mg, 1.56 mmol) in toluene (3 mL) was added to the mixture. The reaction solution was stirred at rt overnight, diluted with EtOAc (20 mL), washed with water (10 mL×2), brine (5 mL×1) and dried over anhydrous Na$_2$SO$_4$, filtered and concentrated. The crude product was purified by column chromatography (silica gel: 300-400 mesh, PE/EtOAc=50/1 to 10/1) to afford pure benzyl 2-(methoxymethylene)-7-azaspiro[3.5]nonane-7-carboxylate. LRMS m/z (M+H) 302.2 found, 302.1 required.

benzyl 2-formyl-7-azaspiro[3.5]nonane-7-carboxylate

To a solution of benzyl 2-(methoxymethylene)-7-azaspiro[3.5]nonane-7-carboxylate (340 mg, 1.12 mmol) in DCM (3 mL) was added TFA (3 mL) at 0° C. The resulting mixture was stirred at 0° C. for 1 h and concentrated in vacuo to afford the crude product. The crude product was dissolved in EtOAc (20 mL), washed with sat. NaHCO$_3$ (4 mL), dried over anhydrous Na$_2$SO$_4$, filtered and concentrated in vacuo to afford benzyl 2-formyl-7-azaspiro[3.5]nonane-7-carboxylate. LRMS m/z (M+H) 288.2 found, 288.2 required.

benzyl 2-(hydroxymethyl)-7-azaspiro[3.5]nonane-7-carboxylate

To a solution of benzyl 2-formyl-7-azaspiro[3.5]nonane-7-carboxylate (260 mg, 0.9 mmol) in THF (5 mL) was added NaBH$_4$ (68 mg, 1.8 mmol) at rt. The resulting mixture was stirred at rt for 1 h and poured into EtOAc (20 mL). The organic phase was washed with water (10 mL×2), brine (5 mL×1) and dried over anhydrous Na$_2$SO$_4$, filtered and concentrated. The crude product was purified by column chromatography (silica gel: 300-400 mesh, PE/EtOAc=50/1 to 5/1) to give pure benzyl 2-(hydroxymethyl)-7-azaspiro[3.5]nonane-7-carboxylate. LRMS m/z (M+H) 290.1 found, 290.2 required.

benzyl 2-((3-chloro-4-(dimethylcarbamoyl)phenoxy)methyl)-7-azaspiro[3.5]nonane-7-carboxylate A solution of benzyl 2-(hydroxymethyl)-7-azaspiro[3.5]nonane-7-carboxylate (200 mg, 0.69 mmol), 2-chloro-4-hydroxy-N,N-dimethylbenzamide (137 mg, 0.69 mmol), PPh$_3$ (262 mg, 1 mmol) in THF (4 mL) was stirred for 5 min at rt under N$_2$ balloon. Then a solution of DEAD (174 mg, 1 mmol) in THF (1 mL) was added to the mixture. The resulting mixture was stirred for 2 h at rt. Then the mixture was purified by reverse phase chromatography (mobile phase: methanol/water (10 mM NH$_4$HCO$_3$) to give the benzyl 2-((3-chloro-4-(dimethylcarbamoyl)phenoxy)methyl)-7-azaspiro[3.5]nonane-7-carboxylate. LRMS m/z (M+H) 471.2 found, 471.2 required.

4-(7-azaspiro[3.5]nonan-2-ylmethoxy)-2-chloro-N,N-dimethylbenzamide

To a solution of benzyl 2-((3-chloro-4-(dimethylcarbamoyl)phenoxy)methyl)-7-azaspiro[3.5]nonane-7-carboxylate (180 mg, 0.38 mmol) in DCM (2.5 mL) was added iodotrimethylsilane (222 mg, 1.11 mmol) at 0° C. After addition, the ice-water bath was removed, and the reaction mixture was stirred at rt for 2 h and the solvent was removed under reduced pressure. The residue was purified by reverse phase chromatography (mobile phase: methanol/water (10 mM NH$_4$HCO$_3$)) to afford the 4-(7-azaspiro[3.5]nonan-2-ylmethoxy)-2-chloro-N,N-dimethylbenzamide. LRMS m/z (M+H) 337.0 found, 337.1 required.

2-chloro-N,N-dimethyl-4-((7-((R or S)-3,3,3-trifluoro-2-hydroxy-2-phenylpropanoyl)-7-azaspiro[3.5]nonan-2-yl)methoxy)benzamide A mixture of 4-(7-azaspiro[3.5]nonan-2-ylmethoxy)-2-chloro-N,N-dimethylbenzamide (30 mg, 0.089 mmol), (R or S)-3,3,3-trifluoro-2-hydroxy-2-phenylpropanoic acid (28 mg, 0.127 mmol), HATU (48 mg, 0.127 mmol) and TEA (35 mg, 0.34 mmol) in THF (2 mL) was stirred at rt overnight. The mixture was directly purified by reversereverse phase chromatography (mobile phase: methanol/water (10 mM NH₄HCO₃)) to afford 2-chloro-N,N-dimethyl-4-((7-((R or S)-3,3,3-trifluoro-2-hydroxy-2-phenylpropanoyl)-7-azaspiro[3.5]nonan-2-yl)methoxy)benzamide. LRMS m/z (M+H) 539.2 found, 539.2 required.

Using the procedure described in Example 33-1, but replacing (R or S)-3,3,3-trifluoro-2-hydroxy-2-phenylpropanoic acid with the appropriate acid, the following examples were prepared.

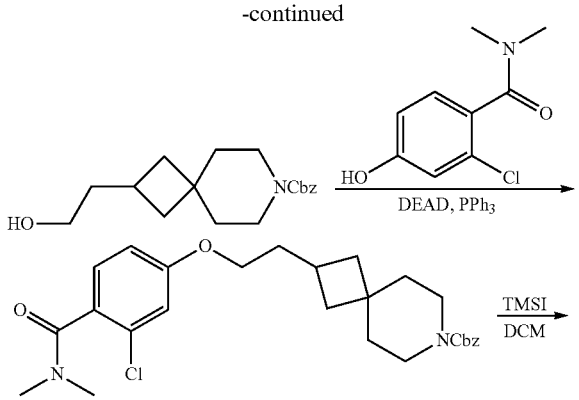

| Example | Structure | IUPAC Name | LRMS, found [M + H]+ |
|---|---|---|---|
| 33-2 | 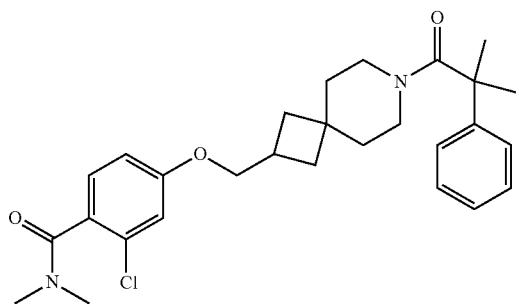 [SMILES: CN(C)C(=O)c1ccc(OCC2CC3(CCN(C(=O)C(C)(C)c4ccccc4)CC3)C2)cc1Cl] | 2-chloro-N,N-dimethyl-4-((7-(2-methyl-2-phenylpropanoyl)-7-azaspiro[3.5]nonan-2-yl)methoxy)benzamide | 483.1 |

Example 34-1

2-chloro-N,N-dimethyl-4-(2-(7-((R or S)-3,3,3-trifluoro-2-hydroxy-2-phenylpropanoyl)-7-azaspiro[3.5]nonan-2-yl)ethoxy)benzamide

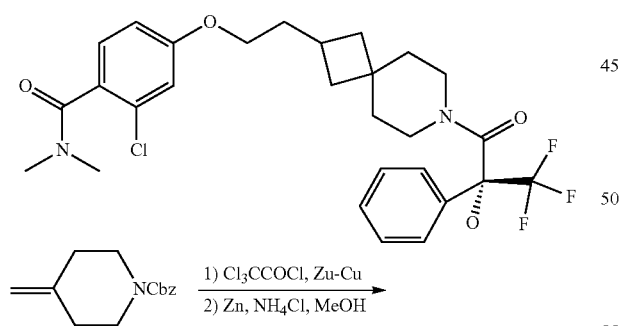

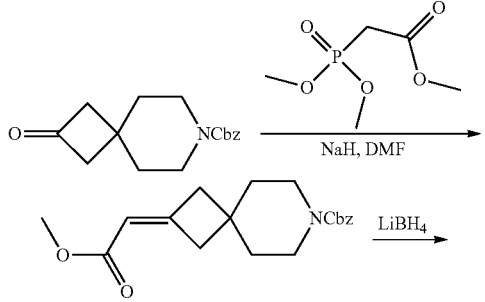

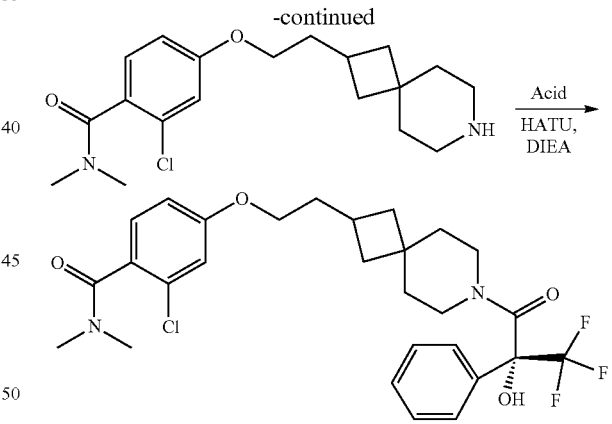

benzyl 2-oxo-7-azaspiro[3.5]nonane-7-carboxylate

To a suspension of zinc-copper couple (3.9 g, 60 mmol) and benzyl 4-methylenepiperidine-1-carboxylate (1.4 g, 6 mmol) in Et₂O (50 mL) was added trichloroacetyl chloride (5.4 g, 30 mmol) dropwise at rt under nitrogen atmosphere. After stirring at rt for 12 h, the reaction mixture was poured into aqueous NaHCO₃ (50 mL) at 0° C., and the precipitate was filtrated off and the filtrate was extracted with EtOAc (40 mL*2). The organic phase was washed with brine (20 mL*2), dried over anhydrous Na₂SO₄, filtered and concentrated. The residue was passed through short silica gel column (20% EtOAc/hexane) to afford the crude dichloroketone. To a solution of the crude dichloroketone in saturated NH₄Cl/MeOH (50 mL) was added zinc powder (1.98 g, 30.5 mmol) at rt. The reaction mixture was stirred at rt for 8 h, and then zinc was filtered off. The filtrate was concentrated. The residue was purified by chromatography on silica gel (20% EtOAc/hexane) to give benzyl 2-oxo-7-azaspiro[3.5]nonane-7-carboxylate. LRMS m/z (M+H) 274.3 found, 274.1 required.

benzyl 2-(2-methoxy-2-oxoethylidene)-7-azaspiro [3.5]nonane-7-carboxylate

A mixture of methyl 2-(dimethoxyphosphoryl)acetate (2.28 g, 12 mmol) and NaH (480 mg, 12 mmol, 60% in oil) in dry THF (15 mL) was stirred for 2 h at 0° C. under N₂ balloon. Then benzyl 2-oxo-7-azaspiro[3.5]nonane-7-carboxylate (2.7 g, 10 mmol) was added to the mixture at 0° C. And the resulting mixture was stirred overnight at rt, quenched with aq NH₄Cl (100 mL) carefully and stirred for another 30 min, and then extracted with EtOAc (80 mL*3). The organic phase was dried over anhydrous Na₂SO₄, filtered and concentrated. The crude compound was purified by column chromatography (silica gel: 300-400 mesh, PE/EtOAc=40/1 to 5/1) to give benzyl 2-(2-methoxy-2-oxoethylidene)-7-azaspiro[3.5]nonane-7-carboxylate. LRMS m/z (M+H) 330.2 found, 330.2 required.

benzyl 2-(2-hydroxyethyl)-7-azaspiro[3.5]nonane-7-carboxylate

To A solution of benzyl 2-(2-methoxy-2-oxoethylidene)-7-azaspiro[3.5]nonane-7-carboxylate (2 g, 6.07 mmol) in THF (20 mL) was added LiBH₄ (666 mg, 30.3 mmol). The resulting mixture was stirred overnight at 0° C. and quenched with MeOH (200 mL) and aq NH₄Cl (200 mL). Then methanol was removed and the aqueous was extracted with EtOAc (100 mL*3). The organic phase was dried over anhydrous Na₂SO₄, filtered and concentrated. The crude compound was purified by column chromatography (silica gel: 300-400 mesh, PE/EtOAc=40/1 to 5/1) to give benzyl 2-(2-hydroxyethyl)-7-azaspiro[3.5]nonane-7-carboxylate. LRMS m/z (M+H) 304.1 found, 304.2 required.

benzyl 2-(2-(3-chloro-4-(dimethylcarbamoyl)phenoxy)ethyl)-7-azaspiro[3.5]nonane-7-carboxylate The solution of benzyl 2-(2-hydroxyethyl)-7-azaspiro [3.5]nonane-7-carboxylate (200 mg, 0.66 mmol), 2-chloro-4-hydroxy-N,N-dimethylbenzamide (131 mg, 0.66 mmol) and PPh₃ (262 mg, 1 mmol) in THF (4 mL) was stirred for 5 min at rt under N₂. Then a solution of DEAD (174 mg, 1 mmol) in THF (1 mL) was added to the mixture. The resulting mixture was stirred for 2 h at rt under N₂ and the mixture was directly purified by reverse phase chromatography (mobile phase: methanol/water (10 mM NH₄HCO₃)) to give benzyl 2-(2-(3-chloro-4-(dimethylcarbamoyl)phenoxy) ethyl)-7-azaspiro[3.5]nonane-7-carboxylate. LRMS m/z (M+H) 485.2 found, 485.2 required.

4-(2-(7-azaspiro[3.5]nonan-2-yl)ethoxy)-2-chloro-N,N-dimethylbenzamide

To a solution of benzyl 2-(2-(3-chloro-4-(dimethylcarbamoyl)phenoxy)ethyl)-7-azaspiro[3.5]nonane-7-carboxylate (180 mg, 0.37 mmol) in DCM (2.5 mL) was added iodotrimethylsilane (222 mg, 1.11 mmol) at 0° C. After addition, the ice-water bath was removed, and the reaction mixture was stirred at rt for 2 h, quenched with MeOH (1 mL) and the solvent was removed under reduced pressure. The residue was purified by reverse phase chromatography (mobile phase: methanol/water (10 mM NH₄HCO₃)) to afford 4-(2-(7-azaspiro[3.5]nonan-2-yl)ethoxy)-2-chloro-N,N-dimethylbenzamide. LRMS m/z (M+H) 351.0 found, 351.2 required.

2-chloro-N,N-dimethyl-4-(2-(7-((R or S)-3,3,3-trifluoro-2-hydroxy-2-phenylpropanoyl)-7-azaspiro[3.5] nonan-2-yl)ethoxy)benzamide A mixture of 4-(2-(7-azaspiro[3.5]nonan-2-yl)ethoxy)-2-chloro-N,N-dimethylbenzamide (30 mg, 0.085 mmol), (R or S)-3,3,3-trifluoro-2-hydroxy-2-phenylpropanoic acid (28 mg, 0.127 mmol), HATU (48 mg, 0.127 mmol) and TEA (35 mg, 0.34 mmol) in THF (2 mL) was stirred at rt overnight. The mixture was directly purified by reverse phase chromatography (mobile phase: methanol/water (10 mM NH₄HCO₃)) to afford 2-chloro-N,N-dimethyl-4-(2-(7-((R or S)-3,3,3-trifluoro-2-hydroxy-2-phenylpropanoyl)-7-azaspiro[3.5]nonan-2-yl)ethoxy)benzamide. LRMS m/z (M+H) 553.2 found, 553.2 required.

Using the same procedure described in Example 34-1, but using the appropriate acid and amine, the following examples were prepared.

| Example | Structure | IUPAC Name | LRMS, found [M + H]+ |
|---|---|---|---|
| 34-2 | 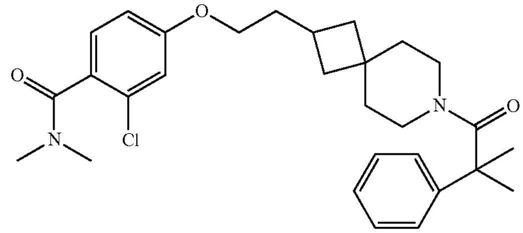 [SMILES: CN(C)C(=O)c1ccc(OCCC2CC3(CCN(C(=O)C(C)(C)c4ccccc4)CC3)C2)cc1Cl] | 2-chloro-N,N-dimethyl-4-(2-(7-(2-methyl-2-phenylpropanoyl)-7-azaspiro[3.5]nonan-2-yl)ethoxy)benzamide | 497.1 |

| Example | Structure | IUPAC Name | LRMS, found [M + H]+ |
|---|---|---|---|
| 34-3 | 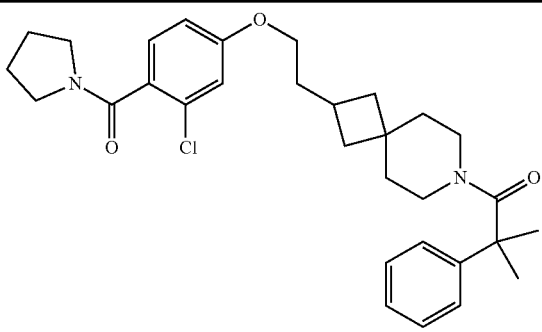 | 1-(2-(2-(3-chloro-4-(pyrrolidine-1-carbonyl)phenoxy)ethyl)-7-azaspiro[3.5]nonan-7-yl)-2-methyl-2-phenylpropan-1-one | 523.2 |

Example 35-1

2-chloro-N,N-dimethyl-4-(3-(7-((R or S)-3,3,3-trifluoro-2-hydroxy-2-phenylpropanoyl)-7-azaspiro[3.5]nonan-2-yl)propoxy)benzamide

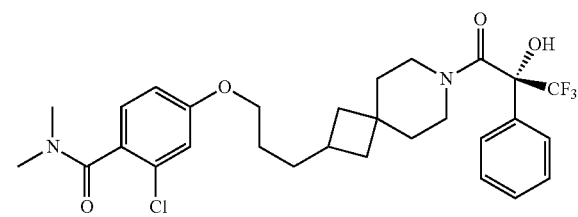

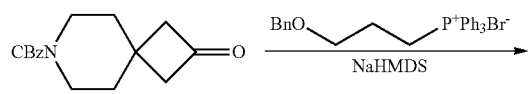

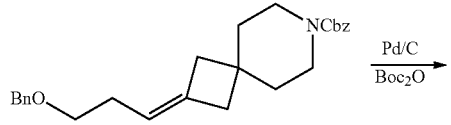

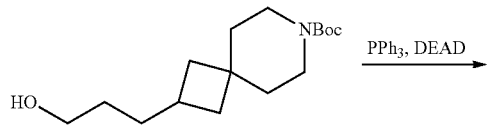

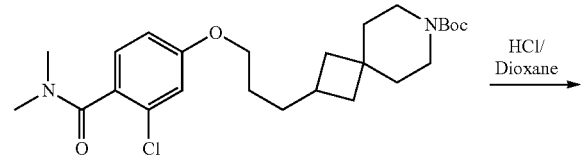

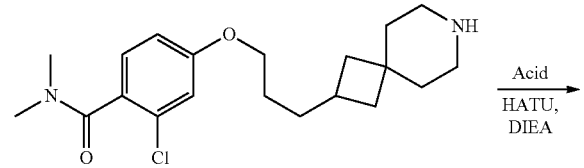

benzyl 2-(3-(benzyloxy)propylidene)-7-azaspiro[3.5]nonane-7-carboxylate

To a solution of (3-(benzyloxy)propyl)triphenylphosphonium bromide (810 mg, 1.6 mmol) in THF (1 mL) at −78° C. was added NaHMDS (1.8 mL, 1.8 mmol, 1.0 M in THF). After stirring at −78° C. for 30 min, a solution of benzyl 2-oxo-7-azaspiro[3.5]nonane-7-carboxylate (300 mg, 1.1 mmol) in THF (1 mL) was added. The resulting mixture was stirred at room temperature overnight and then quenched with aq ammonium chloride (10 mL). The mixture was extracted with EtOAc (15 mL*2). The organic layer was dried over anhydrous Na$_2$SO$_4$, filtered and concentrated and the residue was purified by Prep-TLC (PE/EtOAc=20/1) to afford the benzyl 2-(3-(benzyloxy)propylidene)-7-azaspiro[3.5]nonane-7-carboxylate. LRMS m/z (M+H) 406.2 found, 406.2 required.

tert-butyl 2-(3-hydroxypropyl)-7-azaspiro[3.5]nonane-7-carboxylate

To a mixture of benzyl 2-(3-(benzyloxy)propylidene)-7-azaspiro[3.5]nonane-7-carboxylate (264 mg, 0.65 mmol) in methanol (5 mL) was added 10% dry Pd/C (50 mg) and Boc$_2$O (130 mg, 0.72 mmol). The resulting mixture was degassed and backfilled with H$_2$ (three times). The mixture was stirred under H$_2$ balloon at room temperature overnight. The catalyst was filtered off and the filtrate was concentrated. The residue was purified by Prep-TLC (PE/EtOAc=2/1) to afford tert-butyl 2-(3-hydroxypropyl)-7-azaspiro[3.5]nonane-7-carboxylate. LRMS m/z (M+Na) 306.2 found, 306.2 required.

tert-butyl 2-(3-(3-chloro-4-(dimethylcarbamoyl)phenoxy)propyl)-7-azaspiro[3.5]nonane-7-carboxylate A mixture of 2-chloro-4-hydroxy-N,N-dimethylbenzamide (78 mg, 0.39 mmol), triphenylphosphine (185 mg, 0.70 mmol), tert-butyl 2-(3-hydroxypropyl)-7-azaspiro[3.5]nonane-7-carboxylate (100 mg, 0.35 mmol) and DEAD (123 mg, 0.70 mmol) in THF (4 mL) was stirred at room temperature overnight. The mixture was purified by Prep-TLC (PE/EtOAc, 2:1) to afford tert-butyl 2-(3-(3-chloro-4-(dimethylcarbamoyl)phenoxy)propyl)-7-azaspiro[3.5]nonane-7-carboxylate. LRMS m/z (M+H) 465.2 found, 465.2 required.

4-(3-(7-azaspiro[3.5]nonan-2-yl)propoxy)-2-chloro-N,N-dimethylbenzamide

A mixture of tert-butyl 2-(3-(3-chloro-4-(dimethylcarbamoyl)phenoxy)propyl)-7-azaspiro[3.5]nonane-7-carboxylate (150 mg, 0.32 mmol) in 4M HCl/dioxane (5 mL) was stirred at room temperature for 1 h. The mixture was concentrated to afford crude 4-(3-(7-azaspiro[3.5]nonan-2-yl)propoxy)-2-chloro-N,N-dimethylbenzamide. LRMS m/z (M+H) 365.2 found, 365.2 required.

2-chloro-N,N-dimethyl-4-(3-(7-((R or S)-3,3,3-trifluoro-2-hydroxy-2-phenylpropanoyl)-7-azaspiro[3.5]nonan-2-yl)propoxy)benzamide A mixture of 4-(3-(7-azaspiro[3.5]nonan-2-yl)propoxy)-2-chloro-N,N-dimethylbenzamide (40 mg, 0.11 mmol), HATU (71 mg, 0.19 mmol), (R or S)-3,3,3-trifluoro-2-hydroxy-2-phenylpropanoic acid (35 mg, 0.16 mmol) and triethylamine (34 mg, 0.33 mmol) in THF (2 mL) was stirred at room temperature overnight. The mixture was directly purified by Prep-HPLC (mobile phase: methanol/water (10 mM NH$_4$HCO$_3$)) to afford 2-chloro-N,N-dimethyl-4-(3-(7-((R or S)-3,3,3-trifluoro-2-hydroxy-2-phenylpropanoyl)-7-azaspiro[3.5]nonan-2-yl)propoxy)benzamide. LRMS m/z (M+H) 567.2 found, 567.2 required.

Example 36-1

2-chloro-N,N-dimethyl-4-(3-(7-((R or S)-3,3,3-trifluoro-2-hydroxy-2-(3-methoxyphenyl)propanoyl)-7-azaspiro[3.5]nonan-1-yl)propoxy)benzamide

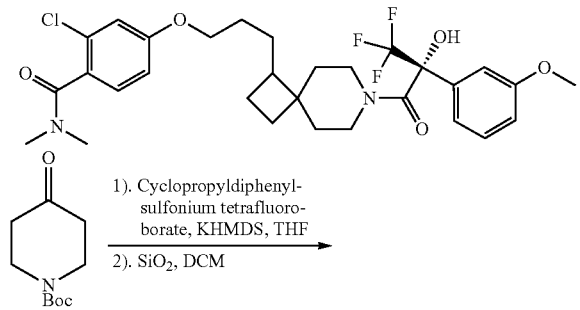

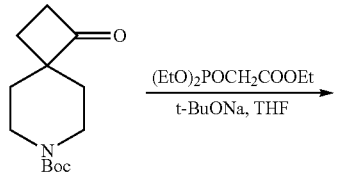

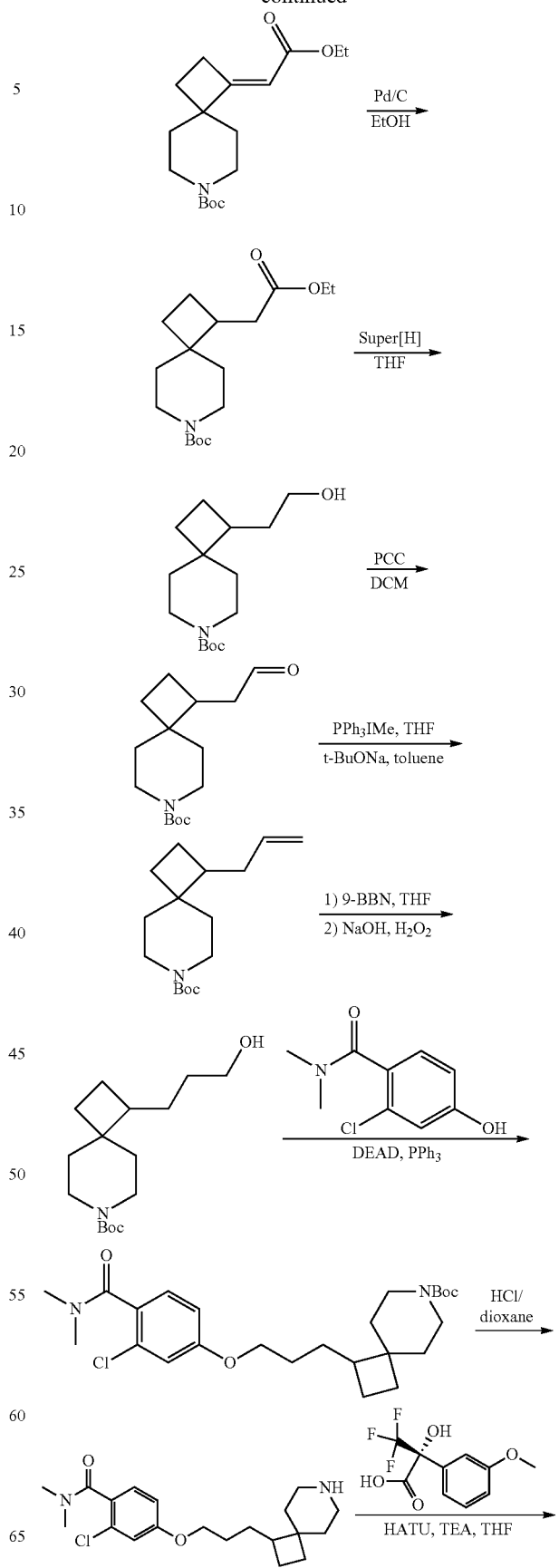

-continued

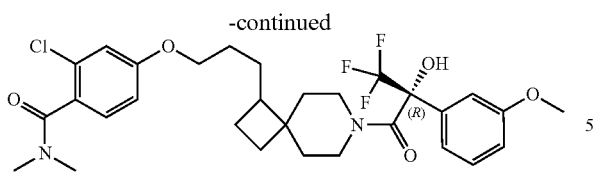

tert-butyl 1-oxo-7-azaspiro[3.5]nonane-7-carboxylate

KHMDS (5.5 mL, 11 mmol, 2M in THF, 1.1 eq) was added to a solution of cyclopropyldiphenylsulfonium tetrafluoroborate (3.4 g, 11 mmol, 1.1 eq) in THF (20 mL) at −78° C. After stirring for 0.5 h, tert-butyl 4-oxopiperidine-1-carboxylate (2 g, 10 mmol, 1 eq) was added to the mixture. The reaction mixture was warmed to room temperature and stirred for another 1 h. The mixture was quenched with sat. NH$_4$Cl (30 mL) and extracted with EtOAc (20 mL×2), dried over anhydrous Na$_2$SO$_4$, filtered and concentrated to afford a crude compound. The crude product and SiO$_2$ (6 g) in DCM (50 mL) was stirred at 40° C. for 3 h, concentrated and purified by column chromatography (silica gel: 300-400 mesh, PE/EtOAc=5/1) to afford pure tert-butyl 1-oxo-7-azaspiro[3.5]nonane-7-carboxylate. LRMS m/z (M+H) 240.2 found, 240.1 required.

(E)-tert-butyl 1-(2-ethoxy-2-oxoethylidene)-7-azaspiro[3.5]nonane-7-carboxylate

A mixture of ethyl 2-(diethoxyphosphoryl)acetate (1.4 g, 6.27 mmol, 1.5 eq) and t-BuONa (602 mg, 6.27 mmol, 1.5 eq) in THF (15 mL) was stirred at 0° C. for 0.5 h. Tert-butyl 1-oxo-7-azaspiro[3.5]nonane-7-carboxylate (1 g, 4.18 mmol, 1 eq) was added and the resulting mixture was stirred at room temperature overnight. The mixture was concentrated and the crude was purified by column chromatography (silica gel: 300-400 mesh, PE/EtOAc=3/1) to give pure (E)-tert-butyl 1-(2-ethoxy-2-oxoethylidene)-7-azaspiro[3.5]nonane-7-carboxylate. LRMS m/z (M+Na) 332.1 found, 332.2 required.

tert-butyl 1-(2-ethoxy-2-oxoethyl)-7-azaspiro[3.5]nonane-7-carboxylate

The mixture of (E)-tert-butyl 1-(2-ethoxy-2-oxoethylidene)-7-azaspiro[3.5]nonane-7-carboxylate (950 mg, 3.07 mmol), 10% Pd/C (100 mg) in MeOH (10 mL) was stirred overnight at rt under H$_2$ balloon. The mixture was filtered though a celite pad, and the filtrate was concentrated to give tert-butyl 1-(2-ethoxy-2-oxoethyl)-7-azaspiro[3.5]nonane-7-carboxylate. LRMS m/z (M+Na) 334.2 found, 334.2 required.

tert-butyl 1-(2-hydroxyethyl)-7-azaspiro[3.5]nonane-7-carboxylate

Super-H (8.7 mL, 8.7 mmol, 1M in THF) was added to a mixture of tert-butyl 1-(2-ethoxy-2-oxoethyl)-7-azaspiro[3.5]nonane-7-carboxylate (907 mg, 2.9 mmol) in THF (10 mL). The mixture was stirred for 3 h at 0° C. and quenched with MeOH (20 mL) and aq NH$_4$Cl (50 mL). The methanol was removed and the aqueous was extracted with EtOAc (200 mL*3). The organic phase was concentrated to give the crude compound which was purified by column chromatography (silica gel: 300-400 mesh, PE/EtOAc=20/1 to 5/1) to afford tert-butyl 1-(2-hydroxyethyl)-7-azaspiro[3.5]nonane-7-carboxylate. LRMS m/z (M+Na) 292.2 found, 292.2 required.

tert-butyl 1-(2-oxoethyl)-7-azaspiro[3.5]nonane-7-carboxylate

A mixture of tert-butyl 1-(2-hydroxyethyl)-7-azaspiro[3.5]nonane-7-carboxylate (680 mg, 2.5 mmol) and PCC (1.28 g, 5 mmol) in DCM (10 mL) was stirred for 2 h at rt. Then the mixture was concentrated to give the crude compound which was purified by column chromatography (silica gel: 300-400 mesh, PE/EtOAc=50/1 to 10/1) to afford tert-butyl 1-(2-oxoethyl)-7-azaspiro[3.5]nonane-7-carboxylate. LRMS m/z (M+H) 268.3 found, 268.2 required.

tert-butyl 1-allyl-7-azaspiro[3.5]nonane-7-carboxylate

To a solution of methyltriphenylphosphonium iodide (896 mg, 2.22 mmol) in THF (10 mL) was added sodium tert-butoxide (213 mg, 2.22 mmol). The resulting mixture was stirred at rt for 1 h and a solution of tert-butyl 1-(2-oxoethyl)-7-azaspiro[3.5]nonane-7-carboxylate (410 mg, 1.48 mmol) in THF (3 mL) was added. The reaction solution was stirred at rt overnight and diluted with EtOAc (100 mL). The organic phase was washed with water (20 mL×3), brine (10 mL×3) and dried over anhydrous Na$_2$SO$_4$, filtered and concentrated. The crude product was purified by column chromatography (silica gel: 300-400 mesh, PE/EtOAc=50/1 to 10/1) to afford pure tert-butyl 1-allyl-7-azaspiro[3.5]nonane-7-carboxylate. LRMS m/z (M+H) 266.3 found, 266.2 required.

tert-butyl 1-(3-hydroxypropyl)-7-azaspiro[3.5]nonane-7-carboxylate (1-8)

To a solution of tert-butyl 1-allyl-7-azaspiro[3.5]nonane-7-carboxylate (303 mg, 1.14 mmol) in dry THF (5 mL) was added 9-BBN (11 mL, 5.6 mmol, 0.5 M in THF). Then the mixture was stirred overnight at rt under N$_2$. Aqueous NaOH (5M, 15 mL) was added to the solution, and then treated with 30% H$_2$O$_2$ (19 mL) and the resulting mixture was stirred for 1 h at rt. The mixture was diluted with EtOAc (100 mL), washed with brine (30 mL×2), dried over anhydrous Na$_2$SO$_4$, filtered and concentrated. The residue was purified by column chromatography (silica gel: 300-400 mesh, PE/EtOAc=20/1 to 3/1) to give tert-butyl 1-(3-hydroxypropyl)-7-azaspiro[3.5]nonane-7-carboxylate. LRMS m/z (M+Na) 306.2 found, 306.2 required.

tert-butyl 1-(3-(3-chloro-4-(dimethylcarbamoyl)phenoxy)propyl)-7-azaspiro[3.5]nonane-7-carboxylate The solution of tert-butyl 1-(3-hydroxypropyl)-7-azaspiro[3.5]nonane-7-carboxylate (210 mg, 0.74 mmol), 2-chloro-4-hydroxy-N,N-dimethylbenzamide (147 mg, 0.74 mmol), PPh$_3$ (290 mg, 1.11 mmol) in THF (4 mL) was stirred for 5 min at rt under N$_2$ balloon. Then a solution of DEAD (191 mg, 1.11 mmol) in THF (1 mL) was added to the mixture. The resulting mixture was stirred for 2 h at rt and purified by reverse phase chromatography (mobile phase: methanol/water (10 mM NH$_4$HCO$_3$)) to give tert-butyl 1-(3-(3-chloro-4-(dimethylcarbamoyl)phenoxy)propyl)-7-azaspiro[3.5]nonane-7-carboxylate. LRMS m/z (M+H) 465.2 found, 465.2 required.

4-(3-(7-azaspiro[3.5]nonan-1-yl)propoxy)-2-chloro-N,N-dimethylbenzamide

A solution of tert-butyl 1-(3-(3-chloro-4-(dimethylcarbamoyl)phenoxy)propyl)-7-azaspiro[3.5]nonane-7-carboxylate (270 mg, 0.58 mmol) in 4M HCl/dioxane (7 mL) was stirred for 1 h at rt. Then the mixture was concentrated to give the crude 4-(3-(7-azaspiro[3.5]nonan-1-yl)propoxy)-2-chloro-N,N-dimethylbenzamide. LRMS m/z (M+H) 365.2 found, 365.2 required.

2-chloro-N,N-dimethyl-4-(3-(7-((R or S)-3,3,3-trifluoro-2-hydroxy-2-(3-methoxyphenyl)propanoyl)-7-azaspiro[3.5]nonan-1-yl)propoxy)benzamide A solution of 4-(3-(7-azaspiro[3.5]nonan-1-yl)propoxy)-2-chloro-N,N-dimethylbenzamide (40 mg, 0.11 mmol), (R or S)-3,3,3-trifluoro-2-hydroxy-2-(3-methoxyphenyl)propanoic acid (41.2 mg, 0.165 mmol), HATU (62.7 mg, 0.165 mmol), and TEA (44 mg, 0.44 mmol) in THF (2 mL) was stirred overnight at rt. Then the mixture was purified by reverse phase chromatography (mobile phase: methanol/water (10 mM NH$_4$HCO$_3$)) to give the 2-chloro-N,N-dimethyl-4-(3-(7-((R or S)-3,3,3-trifluoro-2-hydroxy-2-(3-methoxyphenyl)propanoyl)-7-azaspiro[3.5]nonan-1-yl)propoxy)benzamide. LRMS m/z (M+Na) 619.0 found, 619.2 required.

Example 37-1

2-chloro-N,N-dimethyl-4-((1R,3s)-3-((1-((R or S)-3,3,3-trifluoro-2-hydroxy-2-phenylpropanoyl)piperidin-4-yl)methyl)cyclobutoxy)benzamide

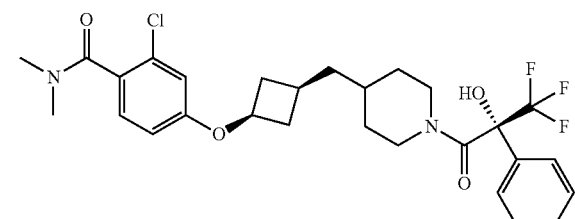

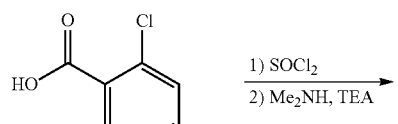

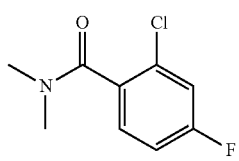

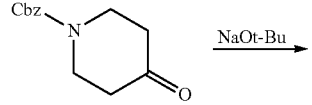

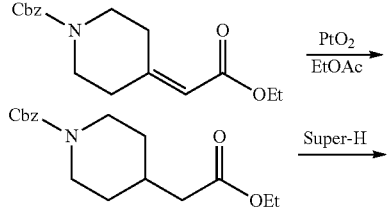

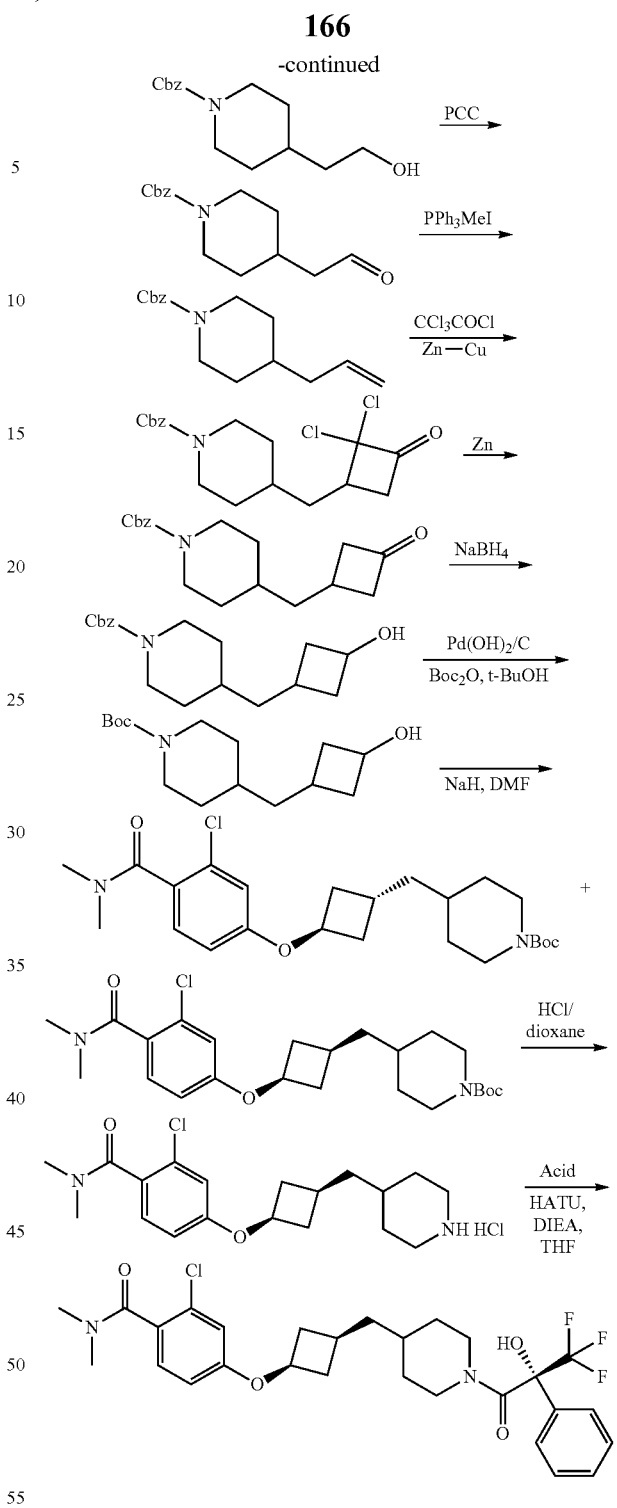

2-chloro-4-fluoro-N,N-dimethylbenzamide

The reaction mixture of 2-chloro-4-fluorobenzoic acid (5 g, 28.6 mmol, 1.0 eq) in thionyl chloride (10 mL, 137 mmol, 4.7 eq) was refluxed for 3 h. Then the mixture was cooled to rt and the solvent was evaporated under reduced pressure to give 2-chloro-4-fluorobenzoyl chloride. The crude chloride was dissolved in THF (5 mL), then treated with triethylamine (16 mL, 115 mmol, 4.0 eq) and dimethylamine (42 mL, 84 mmol, 2M in THF, 2.9 eq) at ambient temperature. The reaction mixture was stirred at ambient temperature for 17 h. The mixture was diluted with ethyl acetate (90 mL), washed with water (10 mL×3), dried over anhydrous Na$_2$SO$_4$, filtered and concentrated. The crude product was purified by column chromatography (silica gel: 300-400 mesh, PE/EtOAc=3/1, V/V) to afford 2-chloro-4-fluoro-N,N-dimethylbenzamide. LRMS m/z (M+H) 202.0 found, 202.0 required.

benzyl 4-(2-ethoxy-2-oxoethylidene)piperidine-1-carboxylate

To a solution of ethyl 2-(dimethoxyphosphoryl)acetate (40.4 g, 206 mmol) in THF (200 mL) was added sodium 2-methylpropan-2-olate (24.72 g, 257 mmol) at 0° C. After stirring for 1 h, benzyl 4-oxopiperidine-1-carboxylate (40 g, 171 mmol) was added to the mixture, then the mixture was stirred for 2 h at RT, quenched with aq NH$_4$Cl (50 mL) and extracted with EtOAc (3×200 mL). The organic layers was dried over anhydrous Na$_2$SO$_4$, filtered and concentrated. The crude product was purified by column chromatography (silica gel: 300-400 mesh, PE/EtOAc=10/1) to give the benzyl 4-(2-ethoxy-2-oxoethylidene)piperidine-1-carboxylate. LRMS m/z (M+H) 304.2 found, 304.1 required.

benzyl 4-(2-ethoxy-2-oxoethyl)piperidine-1-carboxylate

A mixture of benzyl 4-(2-ethoxy-2-oxoethylidene)piperidine-1-carboxylate (44 g, 145 mmol) and platinum(IV) oxide (1.647 g) was evacuated and then refilled with hydrogen (three times). The mixture was stirred overnight at rt under H$_2$ balloon, then filtered and concentrated to afford benzyl 4-(2-ethoxy-2-oxoethyl)piperidine-1-carboxylate. LRMS m/z (M+H) 306.2 found, 306.1 required.

benzyl 4-(2-hydroxyethyl)piperidine-1-carboxylate

To a solution of benzyl 4-(2-ethoxy-2-oxoethyl)piperidine-1-carboxylate (44 g, 144 mmol) in DCM (50 mL) was added Super-hydride (288 mL, 288 mmol, 1M in THF) at 0° C. The mixture was stirred for 3 h at rt, quenched with aq NH$_4$Cl (200 mL) and extracted with EtOAc (3×200 mL). The organic layer was dried over anhydrous Na$_2$SO$_4$, filtered and concentrated. The crude product was purified by column chromatography (silica gel: 300-400 mesh, PE/EtOAc=1/1) to give benzyl 4-(2-hydroxyethyl)piperidine-1-carboxylate. LRMS m/z (M+H) 264.2 found, 264.2 required.

benzyl 4-(2-oxoethyl)piperidine-1-carboxylate

A mixture of benzyl 4-(2-hydroxyethyl)piperidine-1-carboxylate (27 g, 103 mmol), PCC (44.2 g, 205 mmol) and silica gel (50 g) in DCM (300 mL) was stirred for 3 h at rt and then filtered. The filtrate was concentrated, dissolved with Et$_2$O (500 mL) and washed with water (3×100 mL) and brine (3×50 mL). The organic layer was dried over anhydrous Na$_2$SO$_4$, filtered and concentrated to give benzyl 4-(2-oxoethyl)piperidine-1-carboxylate. LRMS m/z (M+H) 262.2 found, 262.1 required.

benzyl 4-allylpiperidine-1-carboxylate

To a solution of iodo(methyl)triphenylphosphorane (16.24 g, 40.2 mmol) in THF (100 mL) was added potassium 2-methylpropan-2-olate (6.01 g, 53.6 mmol) at 0° C. After stirring for 1 h at 0° C., benzyl 4-(2-oxoethyl)piperidine-1-carboxylate (7 g, 26.8 mmol) was added to the mixture, then the mixture was stirred for 2 h at rt, quenched with aq NH$_4$Cl (50 mL) and extracted with EtOAc (3×200 mL). The organic layer was dried over anhydrous Na$_2$SO$_4$, filtered and concentrated. The crude product was purified by column chromatography (silica gel: 300-400 mesh, PE/EtOAc=40/1) to give benzyl 4-allylpiperidine-1-carboxylate. LRMS m/z (M+H) 260.2 found, 260.2 required.

benzyl 4-((2,2-dichloro-3-oxocyclobutyl)methyl)piperidine-1-carboxylate

A mixture of benzyl 4-allylpiperidine-1-carboxylate (3 g, 11.57 mmol) and zinc-copper couple (7.5 g, 58.2 mmol) in Et$_2$O (100 mL) was added 2,2,2-trichloroacetyl chloride (11 g, 60.5 mmol). The resulting mixture was stirred at rt for 2 h. Then the reaction mixture was poured into saturated NaHCO$_3$ (100 mL) and filtered. The filtrate was extracted with EtOAc (100 mL×3), dried, concentrated to give benzyl 4-((2,2-dichloro-3-oxocyclobutyl)methyl)piperidine-1-carboxylate which was used next step directly. LRMS m/z (M+H) 370.2 found, 370.1 required.

benzyl 4-((3-oxocyclobutyl)methyl)piperidine-1-carboxylate

To a mixture of benzyl 4-((2,2-dichloro-3-oxocyclobutyl)methyl)piperidine-1-carboxylate (3.8 g, 10.26 mmol) in saturated ammonium chloride in MeOH (200 mL) was added Zn (3.3 g, 51.3 mmol). The mixture was stirred at rt overnight. The reaction mixture was filtered and the filtrate was concentrated and EtOAc (300 mL) was added. Then this mixture was filtered again. This filtrate was concentrated and purified by column chromatography (silica gel: 300-400 mesh, PE/EtOAc=20/1) to give benzyl 4-((3-oxocyclobutyl)methyl)piperidine-1-carboxylate. LRMS m/z (M+H) 302.2 found, 302.2 required.

benzyl 4-((3-hydroxycyclobutyl)methyl)piperidine-1-carboxylate

A mixture of benzyl 4-((3-oxocyclobutyl)methyl)piperidine-1-carboxylate (2.1 g, 7 mmol) and NaBH$_4$ (798 mg, 21 mmol) in methanol (10 mL) was stirred at rt for 5 h. The reaction mixture was quenched with aq NH$_4$Cl (10 mL) and methanol was removed under reduced pressure. The aqueous was extracted with EtOAc (50 mL×2) and the combined organic layers were washed with brine (20 mL), dried over anhydrous Na$_2$SO$_4$, filtered and concentrated. The crude product was purified by chromatography (silica gel: 300-400 mesh, PE/EtOAc=10/to 3/1) to give benzyl 4-((3-hydroxycyclobutyl)methyl)piperidine-1-carboxylate. LRMS m/z (M+H) 304.3 found, 304.2 required.

tert-butyl 4-((3-hydroxycyclobutyl)methyl)piperidine-1-carboxylate

A mixture of benzyl 4-((3-hydroxycyclobutyl)methyl)piperidine-1-carboxylate, 20% Pd(OH)$_2$/C (88 mg), Boc$_2$O (1.26 g, 5.8 mmol) and t-BuOH (8 mL) was degassed and backfilled with H$_2$ via balloon (three times). The mixture was stirred at 30° C. overnight. The catalyst was filtered off and the filtrate was concentrated and the residue was purified by silica gel chromatography (PE/EtOAc=10/1 to 3/1) to afford tert-butyl 4-((3-hydroxycyclobutyl)methyl)piperidine-1-carboxylate. LRMS m/z (M-55) 214.2 found, 214.2 required.

tert-butyl 4-(((1s,3r)-3-(3-chloro-4-(dimethylcarbamoyl)phenoxy)cyclobutyl)methyl)piperidine-1-carboxylate To a solution of tert-butyl 4-((3-hydroxycyclobutyl)methyl)piperidine-1-carboxylate (423 mg, 1.570 mmol, 1.0 eq) and 2-chloro-4-fluoro-N,N-dimethylbenzamide (327 mg, 1.622 mmol, 1.03 eq) in DMF (20 mL) was added sodium hydride (628 mg, 15.70 mmol, 60% in oil, 10.0 eq) at ambient temperature. The reaction mixture was stirred at 90° C. for 90 min, then the reaction mixture was cooled to ambient temperature, diluted with ethyl acetate (200 mL), washed with water (20 mL×3), brine (20 mL), dried over anhydrous $Na_2SO_4$, filtered and concentrated under reduced pressure. The residue was purified by reverse phase chromatography (mobile phase: methanol/water (10 mM $NH_4HCO_3$)) to afford cis/trans isomers mixture. The product was resolved by Chiral HPLC (column: OJ-H (250*4.6 mm 5 um); mobile phase: n-hexane (0.1% DEA):EtOH (0.1% DEA)=90:10; flow: 1.0 mL/min; temperature: 40° C.) to afford the trans-isomer tert-butyl 4-(((1r,3s)-3-(3-chloro-4-(dimethylcarbamoyl)phenoxy)cyclobutyl)methyl)piperidine-1-carboxylate (RT=9.7 min) and cis-isomer tert-butyl 4-(((1s,3r)-3-(3-chloro-4-(dimethylcarbamoyl)phenoxy)cyclobutyl)methyl)piperidine-1-carboxylate (RT=12.8 min). Trans-isomer: LRMS m/z (M+Na) 473.0 found, 473.2 required. $^1$H NMR (400 MHz, $CDCl_3$): δ 7.16 (d, J=8.8 Hz, 1H), 6.77 (s, 1H), 6.70 (d, J=8.8 Hz, 1H), 4.71 (t, J=11.2 Hz, 1H), 4.07 (s, 2H), 3.10 (s, 3H), 2.85 (s, 3H), 2.68-2.62 (m, 2H), 2.49-2.47 (m, 1H), 2.31-2.25 (m, 2H), 2.15-2.09 (m, 2H), 1.76 (s, 1H), 1.62-1.59 (m, 2H), 1.46-1.40 (m, 11H), 1.13-1.03 (m, 2H); Cis-isomer: LRMS m/z (M+Na) 473.0 found, 473.2 required. $^1$H NMR (400 MHz, $CDCl_3$): δ 7.16 (d, J=6.8 Hz, 1H), 6.80 (s, 1H), 6.73 (d, J=6.8 Hz, 1H), 4.47 (t, J=11.6 Hz, 1H), 4.07 (s, 2H), 3.10 (s, 3H), 2.86 (s, 3H), 2.65-2.59 (m, 4H), 2.02-1.98 (m, 1H), 1.77-1.70 (m, 3H), 1.60-1.57 (m, 2H), 1.42-1.36 (m, 11H), 1.10-1.05 (m, 2H).

2-chloro-N,N-dimethyl-4-((1r,3s)-3-(piperidin-4-ylmethyl)cyclobutoxy)benzamide hydrochloride To a solution of tert-butyl 4-((4(1s,3r)-3-(3-chloro-4-(dimethylcarbamoyl)phenoxy)cyclobutyl)methyl)piperidine-1-carboxylate (30 mg, 0.067 mmol, 1.0 eq) in DCM (0.36 mL) was added 4M HCl/dioxane (0.36 mL, 1.44 mmol, 21.6 eq) at ambient temperature. After stirring for 3 h, the reaction mixture was concentrated to afford 2-chloro-N,N-dimethyl-4-((1r,3s)-3-(piperidin-4-ylmethyl)cyclobutoxy)benzamide hydrochloride, which was used in the next step without further purification. LRMS m/z (M+H) 351.0 found, 351.2 required.

2-chloro-N,N-dimethyl-4-((1r,3s)-3-((1-((R or S)-3,3,3-trifluoro-2-hydroxy-2-phenylpropanoyl)piperidin-4-yl)methyl)cyclobutoxy)benzamide To a solution of 2-chloro-N,N-dimethyl-4-((1r,3s)-3-(piperidin-4-ylmethyl)cyclobutoxy)benzamide hydrochloride (32 mg, 0.067 mmol, 1.0 eq), (R or S)-3,3,3-trifluoro-2-hydroxy-2-phenylpropanoic acid (15 mg, 0.068 mmol, 1.0 eq), and HATU (51 mg, 0.134 mmol, 2.0 eq) in THF (2 mL) was added DIEA (0.06 mL, 0.344 mmol, 5.1 eq) at ambient temperature. And the reaction mixture was stirred at 30° C. for 17 h. The mixture was directly purified by reverse phase chromatography (mobile phase: methanol/water (10 mM $NH_4HCO_3$)) to afford 2-chloro-N,N-dimethyl-4-((1r,3s)-3-((1-((R or S)-3,3,3-trifluoro-2-hydroxy-2-phenylpropanoyl)piperidin-4-yl)methyl)cyclobutoxy)benzamide. LRMS m/z (M+H) 553.2 found, 553.2 required. $^1$H NMR (400 MHz, $CDCl_3$): δ 7.41-7.37 (m, 5H), 7.16 (d, J=8.0 Hz, 1H), 6.80 (s, 1H), 6.72 (d, J=8.0 Hz, 1H), 5.77 (s, 1H), 4.44 (m, 1H), 3.11 (s, 3H), 2.86 (s, 3H), 2.70-2.54 (m, 4H), 1.92-1.89 (m, 1H), 1.71-1.07 (m, 11H).

Using the same procedure described in Example 70-1, the following examples were prepared using the appropriate intermediates.

TABLE 70

| Example | Structure | IUPAC Name | LRMS, found [M + H]+ |
|---|---|---|---|
| 37-2 | 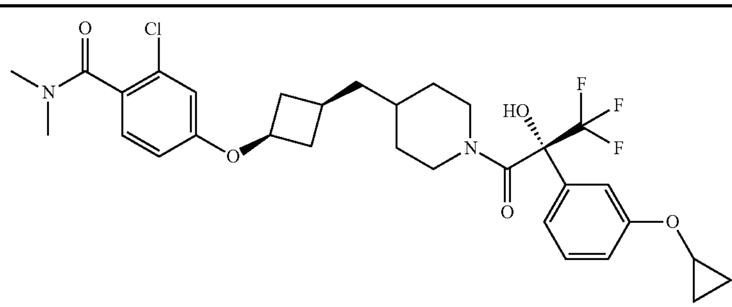 | 2-chloro-4-((1R,3s)-3-((1-((R or S)-2-(3-cyclopropoxyphenyl)-3,3,3-trifluoro-2-hydroxypropanoyl)piperidin-4-yl)methyl)cyclobutoxy)-N,N-dimethylbenzamide | 609.3 |
| 37-3 | 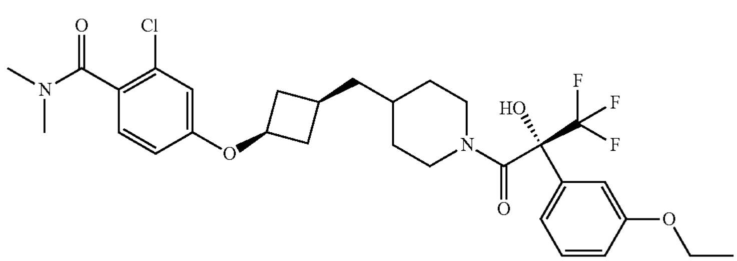 [SMILES: CCOc1cccc([C@@](O)(C(=O)N2CCC(C[C@H]3C[C@@H](Oc4ccc(C(=O)N(C)C)c(Cl)c4)C3)CC2)C(F)(F)F)c1] | 2-chloro-4-((1R,3s)-3-((1-((R or S)-2-(3-ethoxyphenyl)-3,3,3-trifluoro-2-hydroxypropanoyl)piperidin-4-yl)methyl)cyclobutoxy)-N,N-dimethylbenzamide | 597.3 |

TABLE 70-continued

| Example | Structure | IUPAC Name | LRMS, found [M + H]+ |
|---|---|---|---|
| 37-4 | 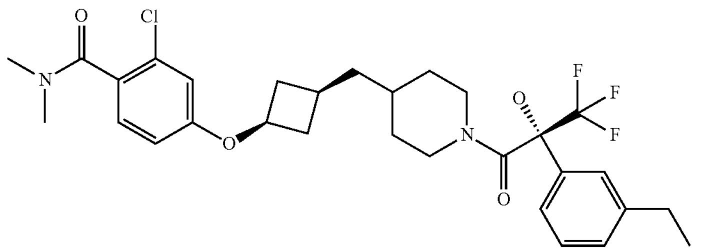 [SMILES: CCc1cccc([C@@](O)(C(=O)N2CCC(C[C@H]3C[C@@H](Oc4ccc(C(=O)N(C)C)c(Cl)c4)C3)CC2)C(F)(F)F)c1] | 2-chloro-4-((1R,3s)-3-((1-((R or S)-2-(3-ethylphenyl)-3,3,3-trifluoro-2-hydroxypropanoyl)piperidin-4-yl)methyl)cyclobutoxy)-N,N-dimethylbenzamide | 581.1 |
| 37-5 | 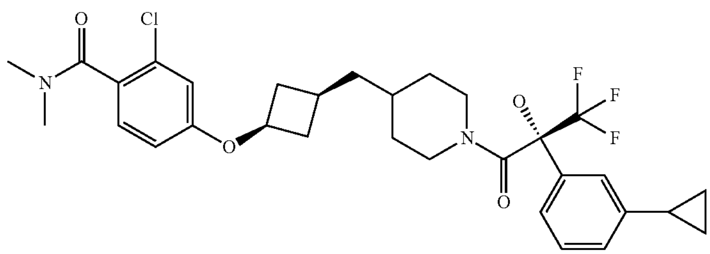 [SMILES: CN(C)C(=O)c1ccc(O[C@H]2C[C@@H](CC3CCN(C(=O)[C@](O)(c4cccc(C5CC5)c4)C(F)(F)F)CC3)C2)cc1Cl] | 2-chloro-4-((1R,3s)-3-((1-((R or S)-2-(3-cyclopropylphenyl)-3,3,3-trifluoro-2-hydroxypropanoyl)piperidin-4-yl)methyl)cyclobutoxy)-N,N-dimethylbenzamide | 593.0 |
| 37-6 | 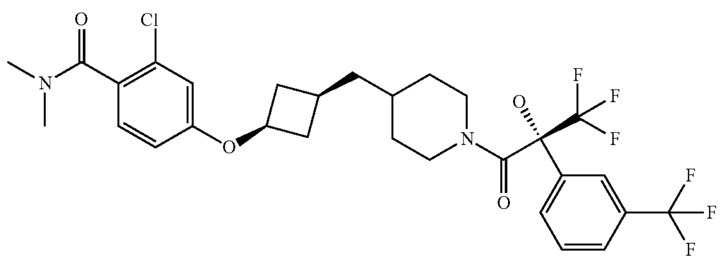 [SMILES: CN(C)C(=O)c1ccc(O[C@H]2C[C@@H](CC3CCN(C(=O)[C@](O)(c4cccc(C(F)(F)F)c4)C(F)(F)F)CC3)C2)cc1Cl] | 2-chloro-N,N-dimethyl-4-((1R,3s)-3-((1-((R or S)-3,3,3-trifluoro-2-hydroxy-2-(3-(trifluoromethyl)phenyl)propanoyl)piperidin-4-yl)methyl)cyclobutoxy)benzamide | 621.1 |
| 37-7 | 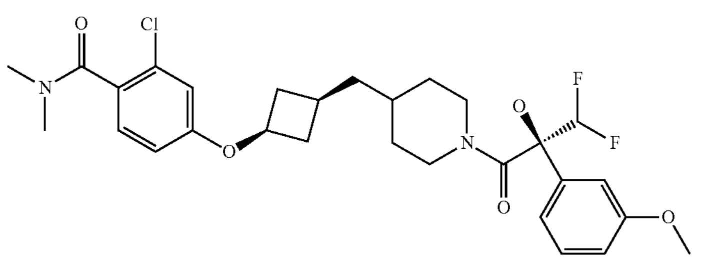 | 2-chloro-4-((1R,3s)-3-((1-((R or S)-3,3-difluoro-2-hydroxy-2-(3-methoxyphenyl)propanoyl)piperidin-4-yl)methyl)cyclobutoxy)-N,N-dimethylbenzamide | 565.2 |
| 37-8 | 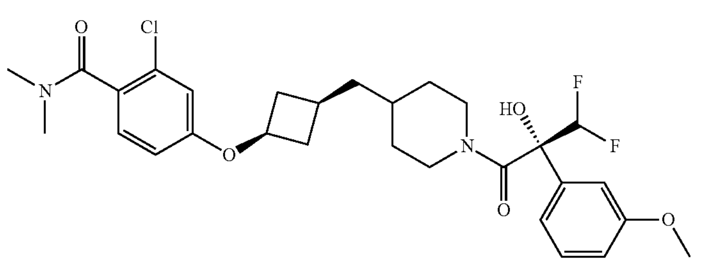 | 2-chloro-4-((1R,3s)-3-((1-((R or S)-3,3-difluoro-2-hydroxy-2-(3-methoxyphenyl)propanoyl)piperidin-4-yl)methyl)cyclobutoxy)-N,N-dimethylbenzamide | 565.2 |

TABLE 70-continued

| Example | Structure | IUPAC Name | LRMS, found [M + H]+ |
|---|---|---|---|
| 37-9 | 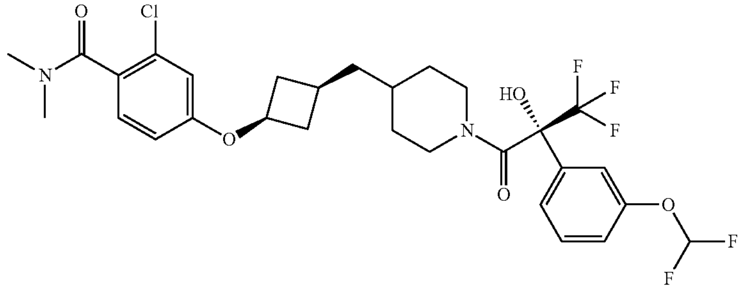 [SMILES: CN(C)C(=O)c1ccc(O[C@H]2C[C@@H](CC3CCN(C(=O)[C@](O)(c4cccc(OC(F)F)c4)C(F)(F)F)CC3)C2)cc1Cl] | 2-chloro-4-((1R,3s)-3-((1-((R or S)-2-(3-(difluoromethoxy)phenyl)-3,3,3-trifluoro-2-hydroxypropanoyl)piperidin-4-yl)methyl)cyclobutoxy)-N,N-dimethylbenzamide | 618.9 |
| 37-10 | 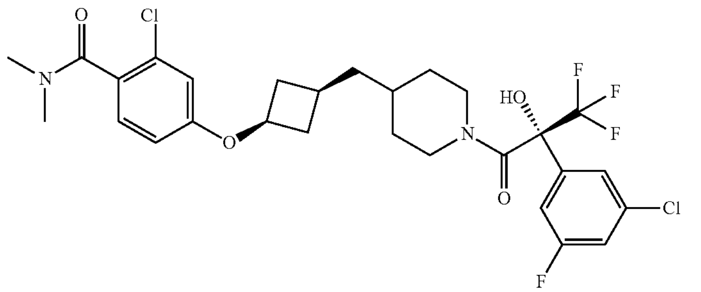 [SMILES: CN(C)C(=O)c1ccc(O[C@H]2C[C@@H](CC3CCN(C(=O)[C@](O)(c4cc(F)cc(Cl)c4)C(F)(F)F)CC3)C2)cc1Cl] | 2-chloro-4-((1R,3s)-3-((1-((R or S)-2-(3-chloro-5-fluorophenyl)-3,3,3-trifluoro-2-hydroxypropanoyl)piperidin-4-yl)methyl)cyclobutoxy)-N,N-dimethylbenzamide | 605.2 |
| 37-11 | 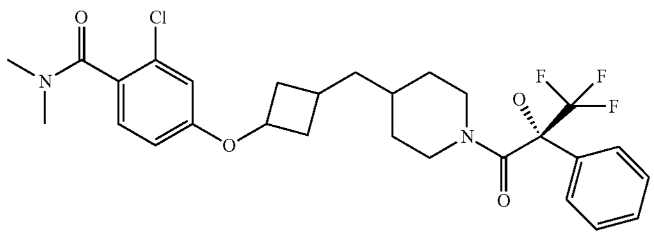 [SMILES: CN(C)C(=O)c1ccc(OC2CC(CC3CCN(C(=O)[C@](O)(c4ccccc4)C(F)(F)F)CC3)C2)cc1Cl] | (R or S)-2-chloro-N,N-dimethyl-4-(3-((1-(3,3,3-trifluoro-2-hydroxy-2-phenylpropanoyl)piperidin-4-yl)methyl)cyclobutoxy)benzamide | 553.1 |
| 37-12 | 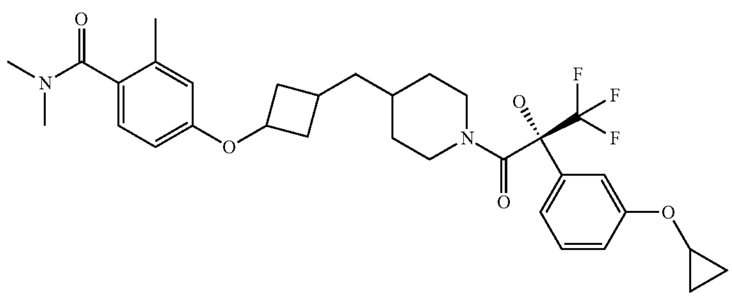 [SMILES: Cc1cc(OC2CC(CC3CCN(C(=O)[C@](O)(c4cccc(OC5CC5)c4)C(F)(F)F)CC3)C2)ccc1C(=O)N(C)C] | (R or S)-4-(3-((1-(2-(3-cyclopropoxyphenyl)-3,3,3-trifluoro-2-hydroxypropanoyl)piperidin-4-yl)methyl)cyclobutoxy)-N,N,2-trimethylbenzamide | 589.3 |

Example 38-1

2-chloro-N,N-dimethyl-4-((1S,4s)-4-(1-((R or S)-3,3,3-trifluoro-2-hydroxy-2-(3-methoxyphenyl)propanoyl)piperidin-4-yl)cyclohexyloxy)benzamid

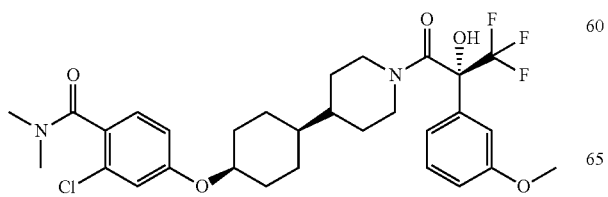

-continued

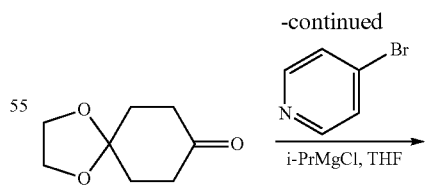

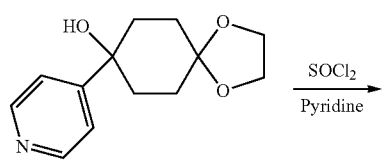

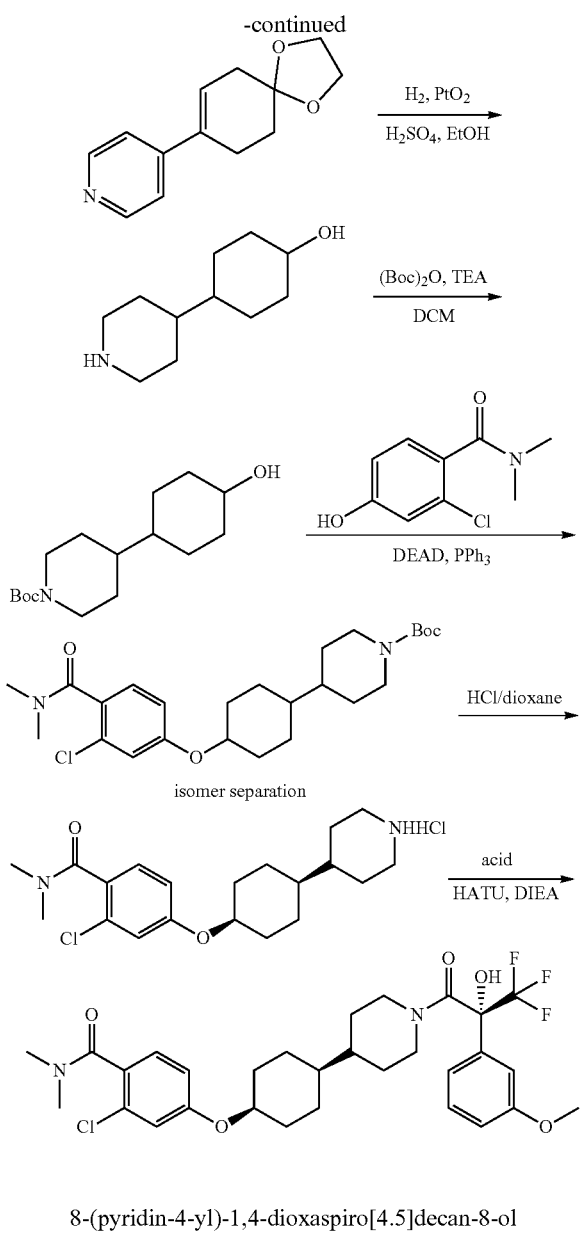

8-(pyridin-4-yl)-1,4-dioxaspiro[4.5]decan-8-ol

To a solution of 4-bromopyridine (15 g, 94.94 mmol) in THF (50 mL) was added $^{i}$-PrMgCl (50 mL, 100 mmol, 2M in THF) at 0° C. under nitrogen atmosphere. After stirring at 0° C. for 1 h, 1,4-dioxaspiro[4.5]decan-8-one (14.81 g, 94.94 mmol) in THF (40 mL) was added dropwise at 0° C. The resulting mixture was stirred at 0° C. to rt overnight, quenched by the addition of saturated ammonium chloride (50 mL), and extracted with EtOAc (400 mL). The organic phase was washed with water (40 mL×2) and dried over anhydrous $Na_2SO_4$, filtered and concentrated. The residue was purified by column chromatography (silica gel: 300-400 mesh, PE/EtOAc=2/1 to 1/2) to give 8-(pyridin-4-yl)-1,4-dioxaspiro[4.5]decan-8-ol. LRMS m/z (M+H) 236.1 found, 236.1 required.

4-(1,4-dioxaspiro[4.5]dec-7-en-8-yl)pyridine

To a solution of 8-(pyridin-4-yl)-1,4-dioxaspiro[4.5]decan-8-ol (10.5 g, 44.68 mmol) in pyridine (50 mL) was added dropwise $SOCl_2$ (15 mL) at −10° C. The mixture was stirred at −10° C. for 1 h, poured into ice (100 g) carefully and neutralized sat. $NaHCO_3$ (150 mL), extracted with DCM (300 mL×2). The combined organic phase was washed with water (50 mL), dried over anhydrous $Na_2SO_4$ and concentrated. The residue was purified by column chromatography (silica gel: 300-400 mesh, PE/EtOAc=1/1) to give 4-(1,4-dioxaspiro[4.5]dec-7-en-8-yl)pyridine. LRMS m/z (M+H) 218.1 found, 218.1 required 4-(piperidin-4-yl)cyclohexanol To a solution of 4-(1,4-dioxaspiro[4.5]dec-7-en-8-yl)pyridine (4.0 g, 18.44 mmol) in ethanol (40 mL) was added platinum(IV) oxide (400 mg, 1.76 mmol) and conc. $H_2SO_4$ (1.81 g, 18.44 mmol) at rt. The mixture was stirred at rt under $H_2$ balloon overnight. Then the catalyst was filtered off and the filtrate was concentrated in vacuo to afford the crude product 4-(piperidin-4-yl)cyclohexanol. LRMS m/z (M+H) 184.1 found, 184.2 required.

tert-butyl 4-(4-hydroxycyclohexyl)piperidine-1-carboxylate

To a solution of tert-butyl 4-(piperidin-4-yl)cyclohexanol (4 g, 21.73 mmol) in DCM (60 mL) was added TEA (6.59 g, 65.22 mmol) and $(Boc)_2O$ (7.11 g, 32.6 mmol) at 0° C. The mixture was stirred at 0° C. to rt for 4 h. Then the mixture was extracted with EtOAc (300 mL). The organic phase was washed with water (30 mL×2), dried over anhydrous $Na_2SO_4$ and concentrated. The residue was purified by column chromatography (silica gel: 300-400 mesh, PE/EtOAc=3/1) to give tert-butyl 4-(4-hydroxycyclohexyl)piperidine-1-carboxylate. LRMS m/z (M+H) 284.2 found, 284.2 required.

tert-butyl 4-(4-(3-chloro-4-(dimethylcarbamoyl)phenoxy)cyclohexyl)piperidine-1-carboxylate To a solution of tert-butyl 4-(4-hydroxycyclohexyl)piperidine-1-carboxylate (100 mg, 0.35 mmol) in THF (3 mL) was added 2-chloro-4-hydroxy-N,N-dimethylbenzamide (84 mg, 0.42 mmol), $PPh_3$ (139 mg, 0.53 mmol) and DEAD (123 mg, 0.71 mmol) at 0° C. under nitrogen atmosphere. The mixture was stirred at 0° C. to rt for 6 h. Then the mixture was directly purified by reverse phase chromatography (mobile phase: methanol/water (10 mM $NH_4HCO_3$)) to afford tert-butyl 4-(4-(3-chloro-4-(dimethylcarbamoyl)phenoxy)cyclohexyl)piperidine-1-carboxylate. The product was resolved by Chiral HPLC (column: OD-H (250*4.6 mm 5 um); mobile phase: SFC-$CO_2$:EtOH (0.1% DEA)=80:20; flow: 3 mL/min; temperature: 40.3° C.) to afford the isomer A (RT=4.39 min) and isomer B (RT=5.24 min). LRMS m/z (M+H) 465.2 found, 465.2 required.

2-chloro-N,N-dimethyl-4-((1s,4s)-4-(piperidin-4-yl)cyclohexyloxy)benzamide hydrochloride (7)

To a solution of tert-butyl 4-((1s,4s)-4-(3-chloro-4-(dimethylcarbamoyl)phenoxy)cyclohexyl)piperidine-1-carboxylate (isomer A) (33 mg, 0.071 mmol) in THF (1 mL) was added 4M HCl/1,4-dioxane (3 mL, 12 mmol) at 0° C. The mixture was stirred at rt for 2 h and concentrated in vacuo to afford the crude product 2-chloro-N,N-dimethyl-4-((1s,4s)-4-(piperidin-4-yl)cyclohexyloxy)benzamide hydrochloride. LRMS m/z (M+H) 365.2 found, 365.2 required.

2-chloro-N,N-dimethyl-4-((1S,4s)-4-(1-((R or S)-3,3,3-trifluoro-2-hydroxy-2-(3-methoxyphenyl)propanoyl)piperidin-4-yl)cyclohexyloxy)benzamide To a solution of 2-chloro-N,N-dimethyl-4-((1s,4s)-4-(piperidin-4-yl)cyclohexyloxy)benzamide hydrochloride (29 mg, 0.072 mmol) in THF (1 mL) was added (R or S)-3,3,3-trifluoro-2-hydroxy-2-(3-methoxyphenyl)propanoic acid (27 mg, 0.11 mmol), DIEA (28 mg, 0.22 mmol) and HATU (42 mg, 0.11 mmol). The mixture was stirred at rt overnight. Then the mixture was directly purified by reverse phase chromatography (mobile phase: methanol/water (10 mM $NH_4HCO_3$) to afford 2-chloro-N,N-dimethyl-4-((1S,4s)-4-(1-((R or S)-3,3,3-trifluoro-2-hydroxy-2-(3-methoxyphenyl)propanoyl)piperidin-4-yl)cyclohexyloxy)benzamide. LRMS m/z (M+H) 597.1 found, 597.2 required. $^1$H NMR (400 MHz, $CDCl_3$): δ 7.40-7.33 (m, 1H), 7.20 (d, J=8.4 Hz, 1H), 7.06-6.80 (m, 5H), 5.90 (s, 1H), 3.80 (s, 3H), 3.15 (s, 3H), 2.90 (s, 3H), 2.57-2.45 (t, 2H), 2.0 (d, J=12.4 Hz, 3H), 1.53-1.45 (m, 5H), 1.40-1.20 (m, 6H), 1.15-1.05 (m, 3H). Intermediate A-1

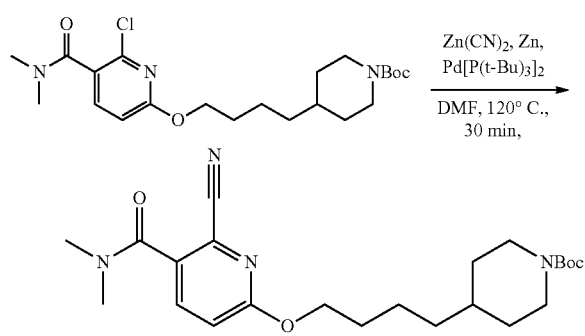

tert-butyl 4-(4-(6-cyano-5-(dimethylcarbamoyl)pyridin-2-yloxy)butyl)piperidine-1-carboxylate A 35 mL vial was charged with tert-butyl 4-(4-(6-chloro-5-(dimethylcarbamoyl)pyridin-2-yloxy)butyl)piperidine-1-carboxylate (438 mg, 1.0 mmol, 1.0 eq), $Zn(CN)_2$ (117 mg, 1.0 mmol, 1.0 eq), Zn (195 mg, 3.0 mmol, 3.0 eq), Pd[P(t-Bu)$_3$]$_2$ (51.1 mg, 0.1 mmol, 0.1 eq) in DMF (4 mL) under $N_2$ atmosphere. The sealed vial was irradiated under microwave on a CEM Synthesizer at 120° C. for 30 min. After the reaction was cooled down to room temperature, the solution was purified by reverse phase chromatography (mobile phase: methanol/water (10 mM $NH_4HCO_3$) to give tert-butyl 4-(4-(6-cyano-5-(dimethylcarbamoyl)pyridin-2-ylamino)butyl)piperidine-1-carboxylate. LRMS m/z (M-99) 331.2 found, 331.2 required.

Biological Assays

Potency (Inflection Point, IP) and efficacy (Emax) are evaluated via compound-induced co-activator recruitment to glutathione-S-transferase (GST) tagged LXRbeta and LXRalpha LBD (ligand binding domain) proteins in relation to reference dual agonist compound T0901317 (N-(2,2,2-Trifluoroethyl)-N-[4-[2,2,2-trifluoro-1-hydroxy-1-(trifluoromethyl)ethyl] phenyl] benzenesulfonamide) using the LanthaScreen™ TR-FRET Liver X Receptor Coactivator Assays according to manufacturer's instructions (Invitrogen catalog number pv4658.pps and pv4655). While running the LanthaScreen™ TR-FRET Liver X Receptor Coactivator Assay, LXR alpha-LBD or LXR beta-LBD was added to ligand test compounds followed by addition of a mixture of a fluorescein-labelled coactivator peptide and terbium-conjugated anti-GST antibody. After an incubation period at room temperature, TR-FRET (time-resolved fluorescence resonance energy transfer) was measured using a filter-based instrument capable of TR-FRET, e.g. PerkinElmer Envision. When the terbium label on the anti-GST antibody was excited at 340 nm, energy was transferred to the fluorescein label on the coactivator peptide and detected as emission at 520 nm, providing an indication of ligand binding that enables ligand-dependent recruitment of coactivator peptide, and the ratio of 520 nm:495 nm is calculated and is used to determine the ligand's potencies and efficacies from appropriate dose response curves of the compound. IP and % Emax values for each of the example compounds of the invention were measured in accordance with the above and are provided in the Table below.

| Example | LXR beta IP (nM) | LXR beta actiivty at max dose (%) | LXR alpha IP (nM) | LXR alpha actiivty at max dose (%) |
|---|---|---|---|---|
| 1-1 | 25 | 51 | 663 | 22 |
| 1-2 | 92 | 120 | 1881 | 35 |
| 1-3 | 75 | 84 | 1161 | 21 |
| 2-1 | 140 | 46 | No IP | 0 |
| 3-1 | 501 | 62 | No IP | 32 |
| 3-2 | 6 | 79 | 128 | 37 |
| 3-3 | 169 | 72 | 1374 | 17 |
| 3-4 | 7 | 73 | 126 | 41 |
| 3-5 | 91 | 54 | No IP | 0 |
| 3-6 | 77 | 64 | No IP | 8 |
| 3-7 | 57 | 54 | No IP | 0 |
| 3-8 | 5 | 85 | 173 | 30 |
| 3-9 | 15 | 64 | 289 | 17 |
| 3-10 | 353 | 55 | No IP | 5 |
| 3-11 | 9 | 80 | 614 | 21 |
| 3-12 | 16 | 76 | No IP | 15 |
| 3-13 | 394 | 61 | No IP | 0 |
| 3-14 | 160 | 77 | No IP | 46 |
| 3-15 | 328 | 80 | No IP | 14 |
| 3-16 | 259 | 83 | No IP | 5 |
| 3-17 | 8 | 74 | 334 | 41 |
| 3-18 | 17 | 75 | 498 | 33 |
| 3-19 | 124 | 24 | 1152 | 25 |
| 3-20 | 25 | 74 | 2287 | 28 |
| 4-1 | 30 | 77 | 419 | 37 |
| 4-2 | 12 | 81 | 488 | 28 |
| 5-1 | 36 | 66 | No IP | 7 |
| 5-2 | 63 | 77 | 2509 | 32 |
| 6-1 | 29 | 73 | 1326 | 28 |
| 6-2 | 8 | 90 | 1232 | 74 |
| 7-1 | 36 | 138 | 776 | 82 |
| 7-2 | 23 | 122 | 429 | 80 |
| 7-3 | 112 | 120 | 2926 | 57 |
| 8-1 | 33 | 55 | 328 | 10 |
| 8-2 | 13 | 68 | 527 | 29 |
| 8-3 | 17 | 39 | 1007 | 26 |
| 8-4 | 12 | 60 | 48 | 18 |
| 8-5 | 18 | 27 | No IP | 1 |
| 8-6 | 86 | 75 | 1051 | 35 |
| 8-7 | 7 | 48 | 131 | 42 |
| 8-8 | 21 | 44 | 653 | 27 |
| 8-9 | 94 | 82 | 856 | 34 |
| 8-10 | 30 | 76 | 719 | 28 |
| 8-11 | 18 | 56 | 520 | 32 |
| 8-12 | 16 | 64 | 351 | 7 |
| 8-13 | 22 | 73 | 412 | 29 |
| 8-14 | 38 | 48 | 227 | 19 |
| 8-15 | 64 | 36 | 410 | 9 |
| 8-16 | 10 | 71 | 116 | 32 |
| 8-17 | 17 | 50 | No IP | 10 |
| 8-18 | 14 | 91 | 742 | 31 |
| 8-19 | 33 | 53 | 1235 | 36 |
| 8-20 | 4407 | 25 | No IP | 4 |
| 9-1 | 51 | 88 | 411 | 13 |

| Example | LXR beta IP (nM) | LXR beta actiivty at max dose (%) | LXR alpha IP (nM) | LXR alpha actiivty at max dose (%) |
| --- | --- | --- | --- | --- |
| 10-1 | 5 | 66 | 117 | 14 |
| 10-2 | 106 | 69 | 1512 | 14 |
| 10-3 | 2 | 116 | 28 | 63 |
| 10-4 | 8 | 147 | 586 | 83 |
| 10-5 | 7 | 75 | 209 | 13 |
| 10-6 | 12 | 71 | 206 | 36 |
| 10-7 | 49 | 104 | 861 | 41 |
| 11-1 | 106 | 78 | 1420 | 23 |
| 12-1 | 24 | 58 | No IP | 1 |
| 12-2 | 661 | 57 | 10490 | 52 |
| 12-3 | 153 | 28 | No IP | 1 |
| 12-4 | 182 | 22 | No IP | 0 |
| 12-5 | 3 | 54 | 91 | 49 |
| 12-6 | 4 | 68 | 80 | 48 |
| 12-7 | 29 | 64 | 589 | 39 |
| 12-8 | 135 | 67 | 2234 | 23 |
| 12-9 | 50 | 65 | No IP | 0 |
| 12-10 | 608 | 61 | 3744 | 21 |
| 12-11 | 12 | 87 | 447 | 24 |
| 12-12 | 81 | 60 | No IP | 28 |
| 12-13 | 17 | 72 | 505 | 26 |
| 12-14 | 22 | 74 | 343 | 20 |
| 12-15 | 62 | 79 | 2091 | 37 |
| 12-16 | 26 | 33 | No IP | 8 |
| 12-17 | 9 | 79 | 166 | 35 |
| 12-18 | 80 | 26 | 1182 | 27 |
| 12-19 | 426 | 12 | No IP | 14 |
| 12-20 | 47 | 32 | No IP | 0 |
| 12-21 | 42 | 47 | 1396 | 23 |
| 13-1 | 87 | 110 | 762 | 25 |
| 14-1 | 65 | 99 | 765 | 9 |
| 14-2 | 28 | 86 | 424 | 17 |
| 14-3 | 41 | 81 | No IP | 6 |
| 14-4 | 83 | 80 | No IP | 0 |
| 14-5 | 10 | 118 | 231 | 50 |
| 14-6 | 6 | 116 | 162 | 23 |
| 14-7 | 9 | 100 | 186 | 46 |
| 15-1 | 19 | 88 | 506 | 28 |
| 15-2 | 65 | 115 | 654 | 32 |
| 15-3 | 5 | 102 | 202 | 67 |
| 16-1 | 66 | 84 | 955 | 18 |
| 17-1 | 188 | 77 | 1629 | 19 |
| 18-1 | 395 | 87 | No IP | 4 |
| 19-1 | 86 | 75 | 1174 | 23 |
| 20-1 | 80 | 72 | 1427 | 26 |
| 20-2 | 71 | 73 | 1491 | 25 |
| 21-1 | 9 | 75 | 422 | 27 |
| 22-1 | 7 | 67 | 212 | 32 |
| 23-1 | 24 | 74 | 436 | 23 |
| 23-2 | 19 | 53 | No IP | 0 |
| 23-3 | 12 | 89 | 150 | 42 |
| 23-4 | 60 | 53 | 717 | 9 |
| 24-1 | 33 | 54 | No IP | 14 |
| 25-1 | 101 | 91 | 1158 | 29 |
| 25-2 | 98 | 84 | 1359 | 12 |
| 26-1 | 8 | 65 | 236 | 12 |
| 26-2 | 6 | 71 | 103 | 41 |
| 26-3 | 6 | 77 | 125 | 48 |
| 26-4 | 41 | 114 | 669 | 35 |
| 27-1 | 5 | 70 | 74 | 23 |
| 28-1 | 65 | 62 | No IP | 0 |
| 29-1 | 173 | 48 | 911 | 27 |
| 30-1 | 99 | 84 | No IP | 8 |
| 31-1 | 25 | 56 | 284 | 27 |
| 31-2 | 19 | 38 | No IP | 3 |
| 32-1 | 319 | 82 | No IP | 0 |
| 32-2 | 206 | 73 | No IP | 8 |
| 32-3 | 105 | 125 | 1378 | 17 |
| 32-4 | 163 | 60 | No IP | 0 |
| 32-5 | 136 | 149 | 1537 | 33 |
| 32-6 | 42 | 75 | 631 | 33 |
| 33-1 | 9 | 69 | 329 | 42 |
| 33-2 | 220 | 60 | No IP | 8 |
| 34-1 | 16 | 113 | 551 | 46 |
| 34-2 | 26 | 90 | 268 | 25 |
| 34-3 | 70 | 65 | 292 | 13 |
| 35-1 | 69 | 61 | 546 | 27 |
| 36-1 | 66 | 52 | No IP | 3 |
| 37-1 | 10 | 131 | 381 | 42 |
| 37-2 | 40 | 109 | No IP | 2 |
| 37-3 | 17 | 124 | No IP | 9 |
| 37-4 | 16 | 120 | No IP | 13 |
| 37-5 | 6 | 134 | 401 | 30 |
| 37-6 | 15 | 119 | 602 | 31 |
| 37-7 | 32 | 95 | No IP | 4 |
| 37-8 | 354 | 51 | No IP | 0 |
| 37-9 | 16 | 111 | 1016 | 25 |
| 37-10 | 5 | 140 | 318 | 46 |
| 37-11 | 92 | 113 | 563 | 33 |
| 37-12 | 63 | 106 | No IP | 0 |
| 38-1 | 3 | 89 | 49 | 44 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A compound having the structural Formula (I):

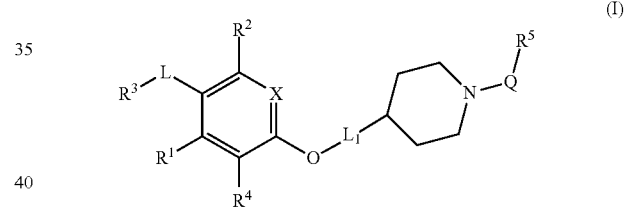

or a pharmaceutically acceptable salt thereof, wherein:

X is CH or N;

$R^1$ is selected from H, methyl, and halogen;

$R^2$ is selected from H, Cl, cyano, cyclopropyl, —$CH_3$, and —$OCH_3$;

$R^4$ is selected from H, Cl, and methyl;

-L- is a divalent moiety C(O)—;

$R^3$ is —N($R^{N1}$)($R^{N2}$), wherein $R^{N1}$ and $R^{N2}$ are taken together with the nitrogen atom to which they are shown attached to form a 4-, 5-, or 6-membered fully saturated heterocyclic ring wherein said heterocyclic ring having 1, 2, or 3 ring heteroatoms selected from N, N-oxide, O, S, and S-oxide, wherein said heterocyclic ring is unsubstituted or substituted with 1, 2, or 3 substituents independently selected from halogen, —OH, oxo, CN, —($C_1$-$C_6$)alkyl, amino-substituted —($C_1$-$C_6$)alkyl, —O—($C_1$-$C_6$)alkyl, —($C_1$-$C_6$)alkyl-OH, —($C_1$-$C_6$)haloalkyl, —C(O)O—($C_1$-$C_6$)alkyl, cyclopropyl, spirocyclopropyl, —$CH_2$—NHC(O)O—($C_1$-$C_6$)alkyl, —$CH_2$—N($CH_3$)C(O)O—($C_1$-$C_6$)alkyl, phenyl, benzyl, —NHC(O)-phenyl, heteroaryl, —($C_1$-$C_4$)alkylheteroaryl, and heterocycloalkyl, wherein 1, 2, or 3 groups of said amino substituent on the amino-substituted —($C_1$-

$C_6$)alkyl is independently selected from —NH$_2$, —N(C$_1$-C$_4$alkyl)$_2$, and —NH(C$_1$-C$_4$alkyl);

-L$_1$- is a divalent moiety selected from:

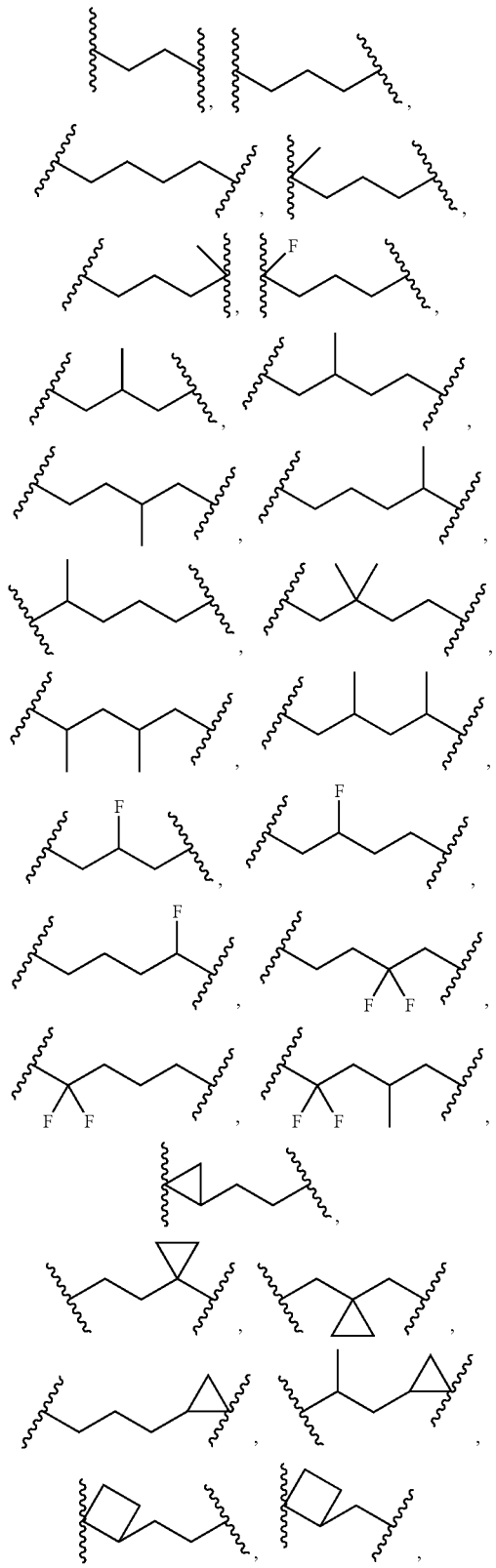

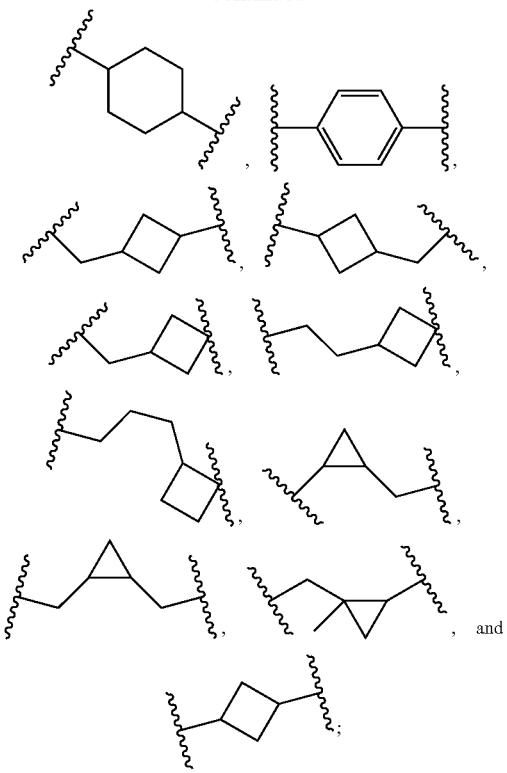

Q is a bond or a divalent moiety selected from —C(O)—, and —S(O)$_2$—; and

R$^5$ is selected from:

1) —C(R$^{5A}$)(R$^{5B}$)(R$^{5C}$), wherein:

R$^{5A}$ is OH;

R$^{5B}$ is —(C$_1$-C$_3$)fluoroalkyl; and

R$^{5C}$ is selected from NH$_2$, NHCH$_3$, —(C$_1$-C$_6$)alkyl, —(C$_1$-C$_4$)fluoroalkyl, thiadiazolyl, thienyl, thiazolyl, ethenyl, ethynyl, phenyl, cyclopropyl, and cyclobutyl; wherein said phenyl is substituted with from 1-3 groups independently selected from halogen —(C$_1$-C$_6$)alkyl, and —(C$_1$-C$_6$)alkoxy; wherein said cyclopropyl or cyclobutyl is optionally substituted with —(C$_1$-C$_6$)alkyl;

2)

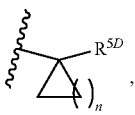

wherein n is an integer from 1 to 4;

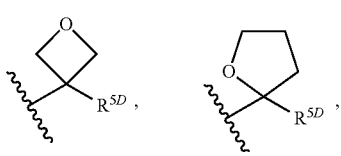

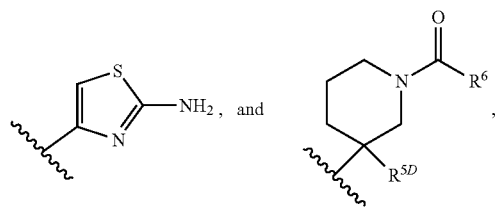

wherein $R^{5D}$ is selected from H, —(C$_1$-C$_6$)alkyl, —(C$_1$-C$_6$)haloalkyl, pyrimidinyl, phenyl, and said phenyl substituted with from 1 to 3 groups independently selected from OH, halogen, —(C$_1$-C$_6$)alkyl, and —O—(C$_1$-C$_6$)alkyl; and R$^6$ is H or CH$_3$, —O—(C$_1$-C$_6$)alkyl; and 3) unsubstituted phenyl or phenyl substituted with 1, 2, or 3 groups independently selected from halogen, CN, —(C$_1$-C$_6$)alkyl, —(C$_1$-C$_6$)haloalkyl, and pyrrolidinyl.

2. The compound of claim 1, or a pharmaceutically acceptable salt thereof, wherein X is N.

3. The compound of claim 1, or a pharmaceutically acceptable salt thereof, wherein X is CH.

4. The compound of claim 3, or a pharmaceutically acceptable salt thereof, wherein R$^1$ is selected from H, methyl, F, and Cl.

5. The compound of claim 1, or a pharmaceutically acceptable salt thereof, wherein: Q is selected from a bond, and —C(O)—.

6. A compound or a pharmaceutically acceptable salt thereof, said compound selected from:

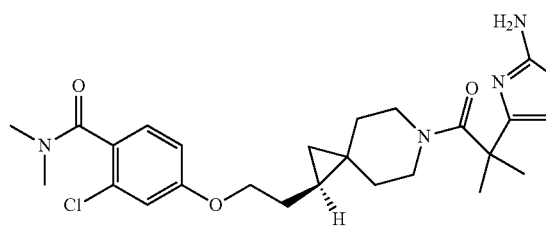

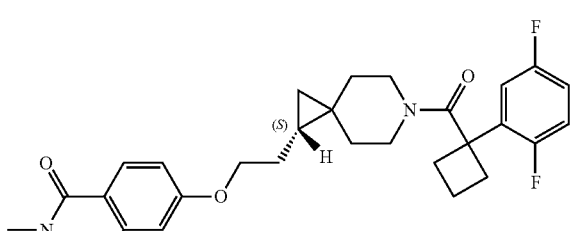

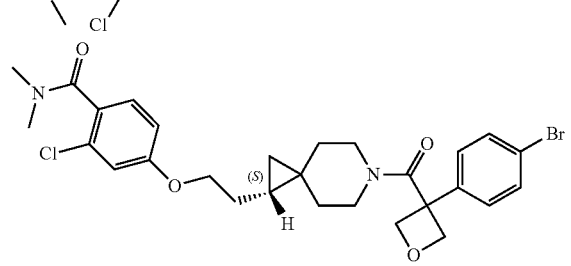

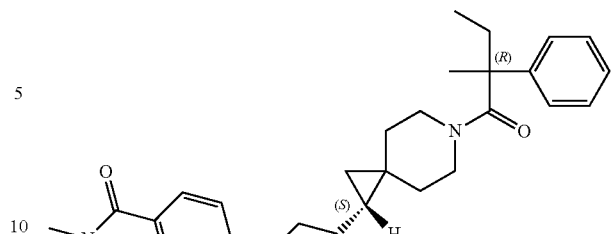

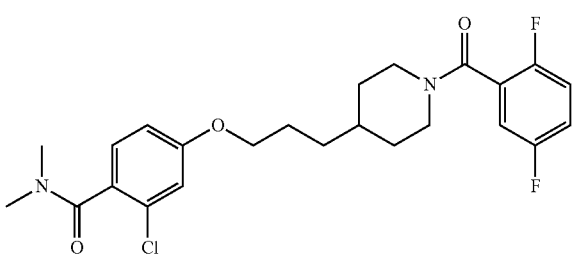

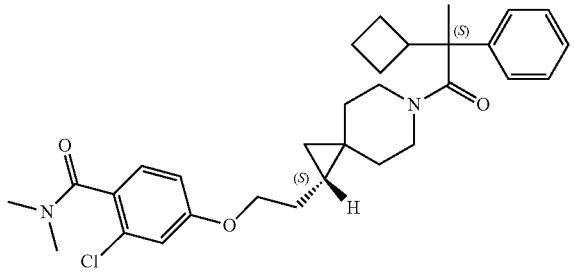

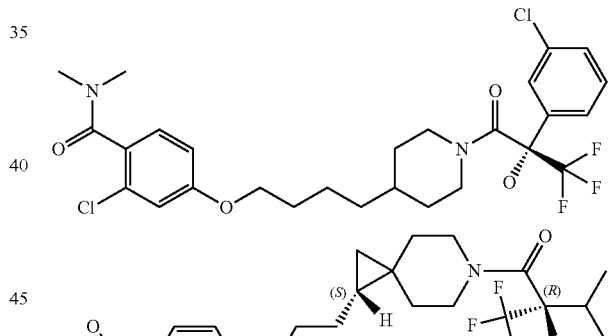

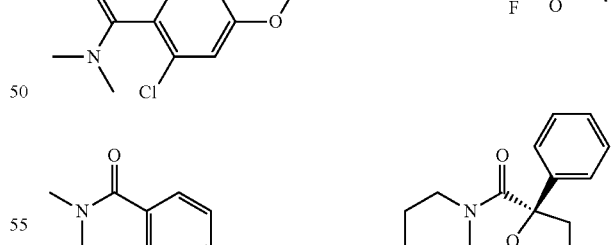

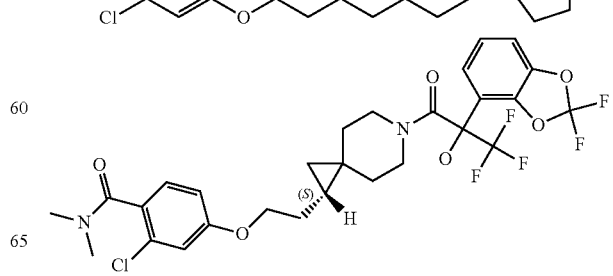

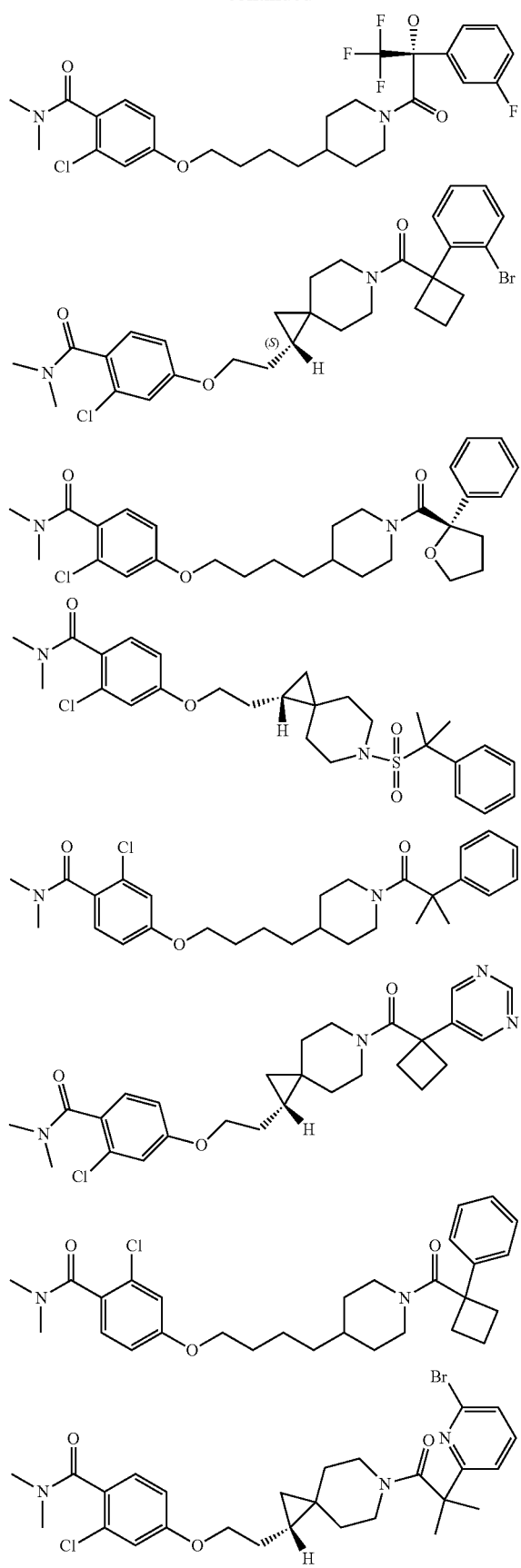
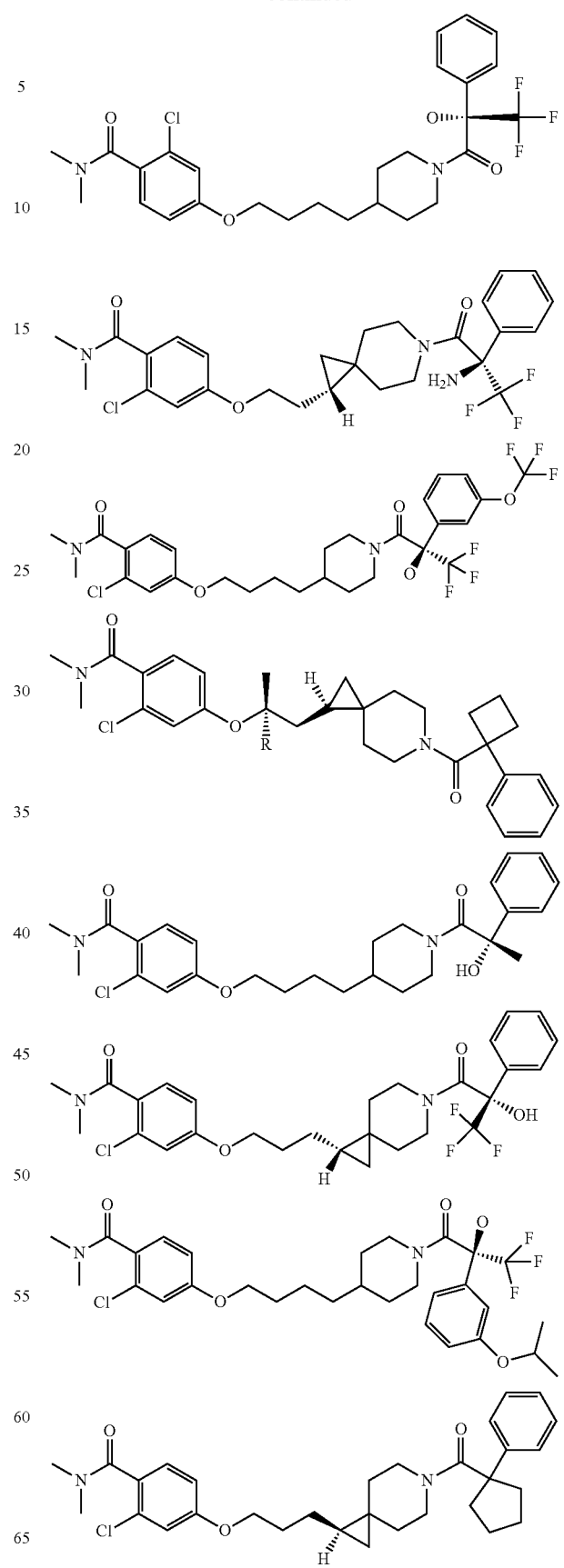

187
-continued
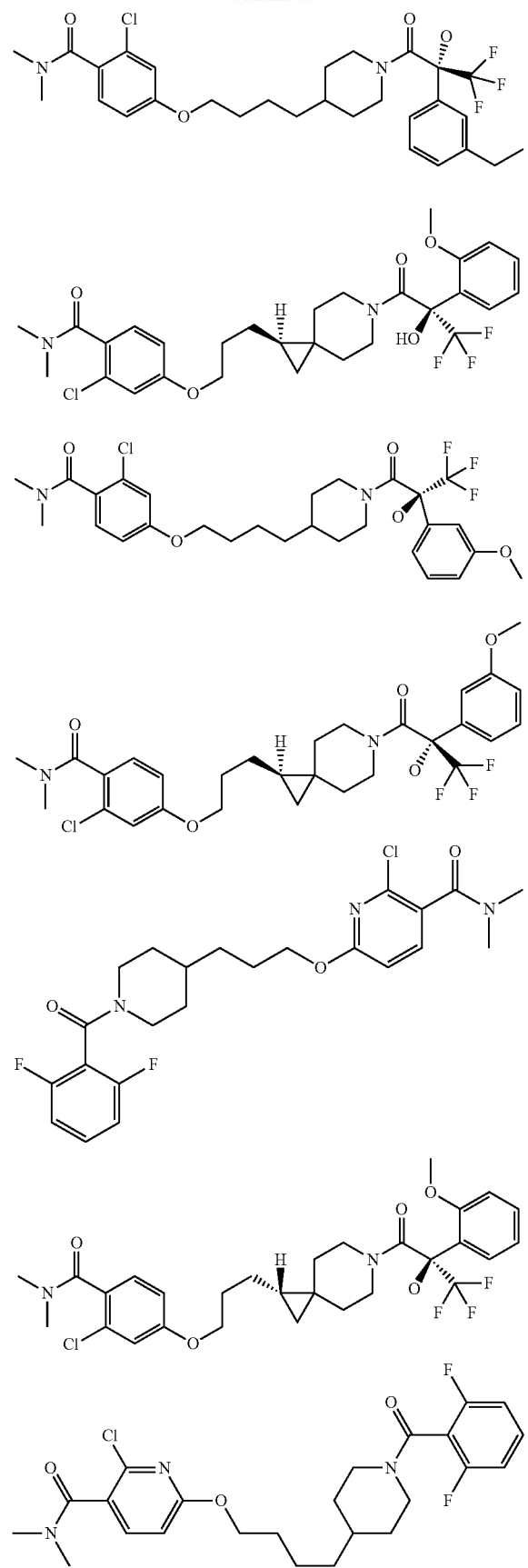
188
-continued
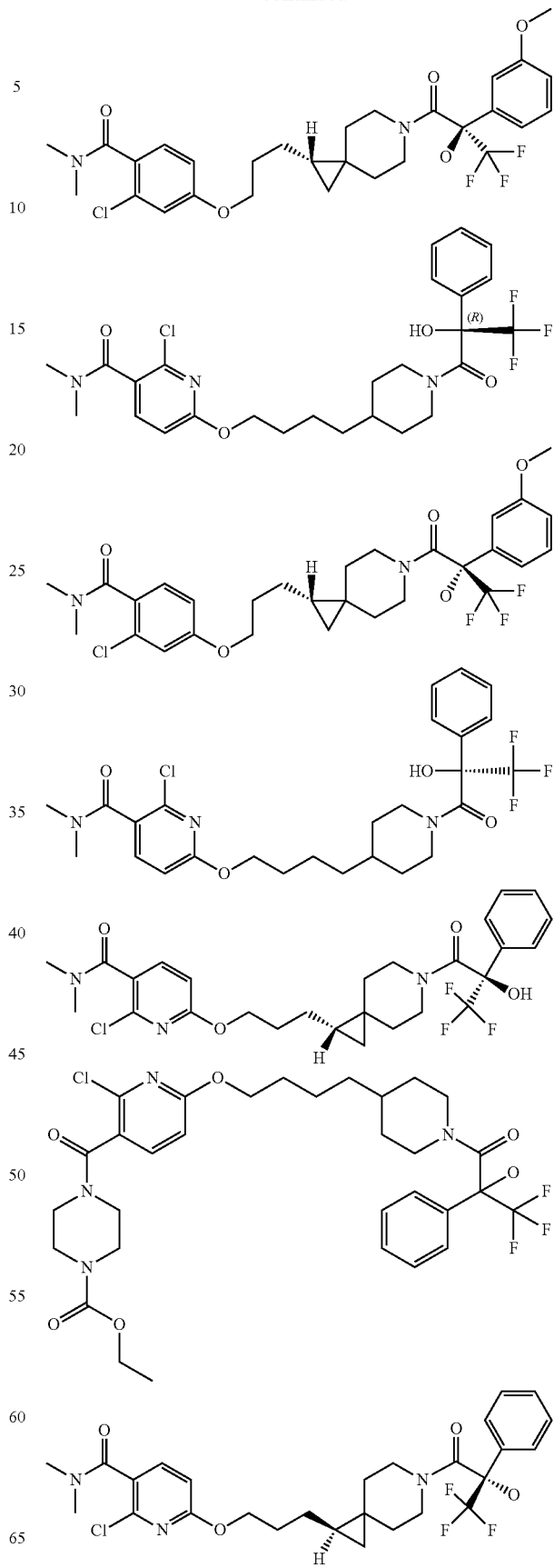

189
-continued
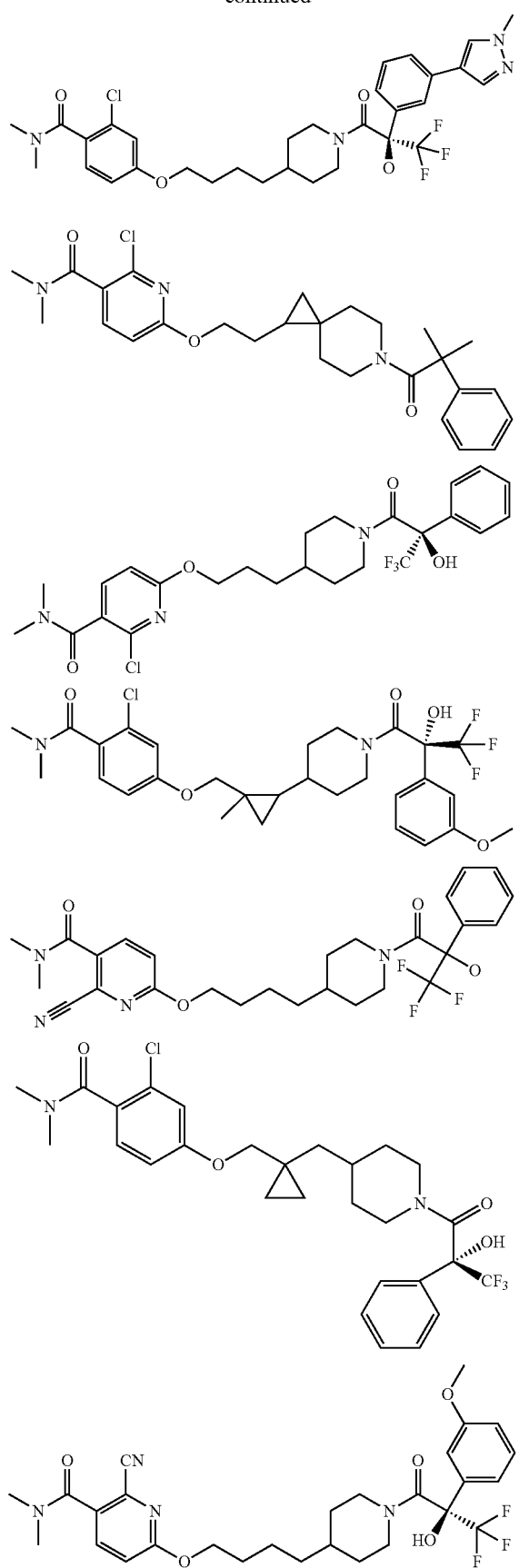
190
-continued
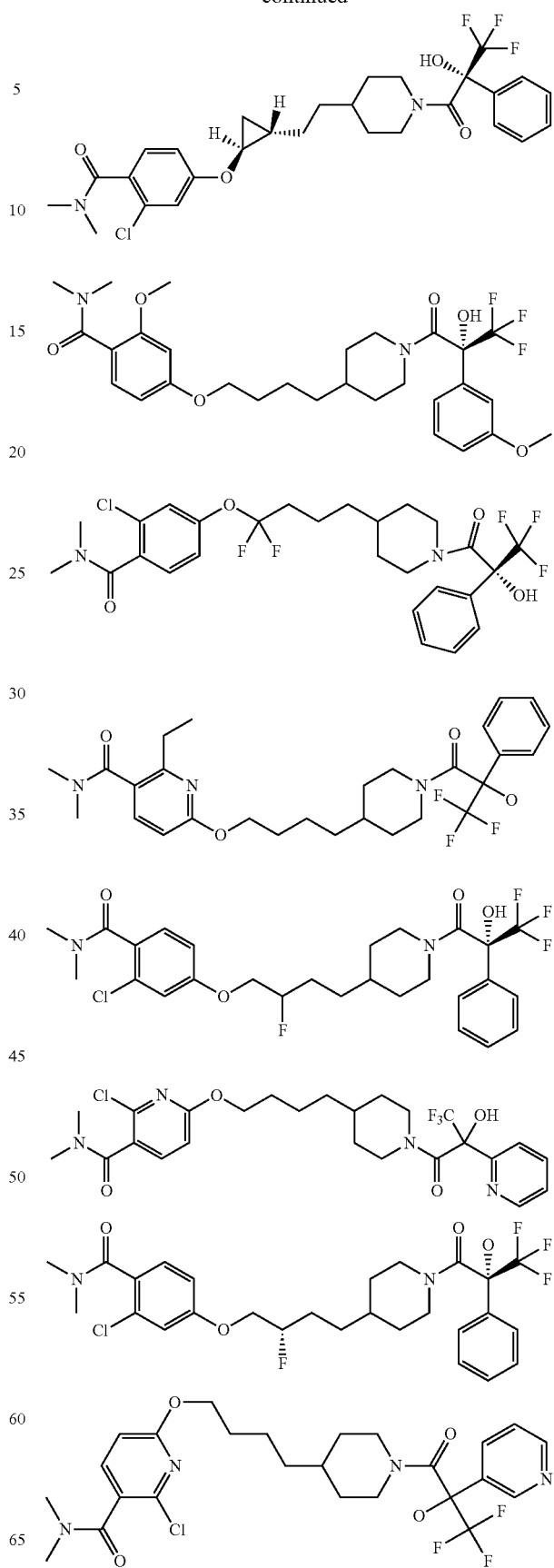

191
-continued
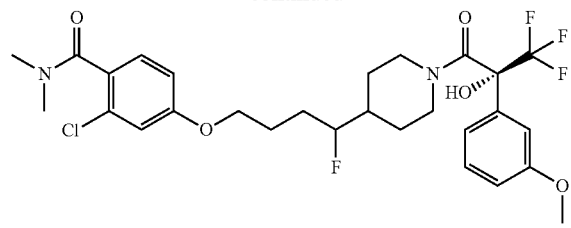
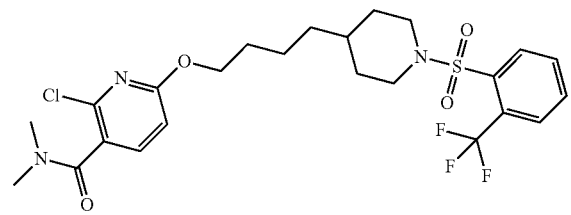
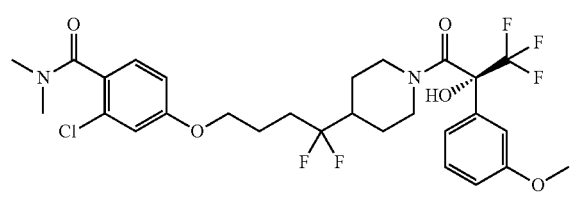
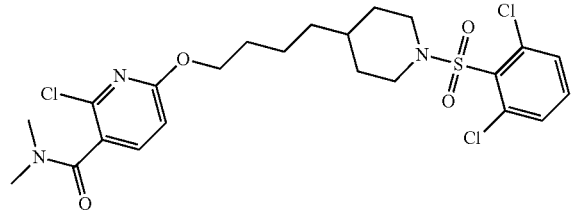
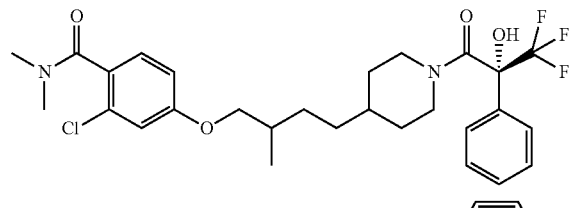
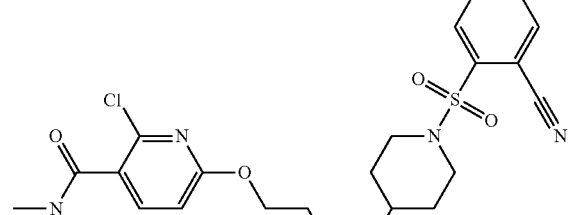
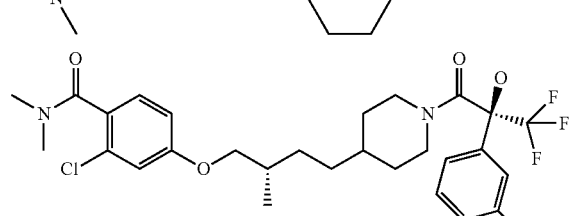
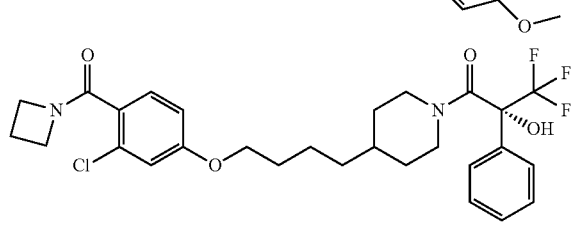
192
-continued
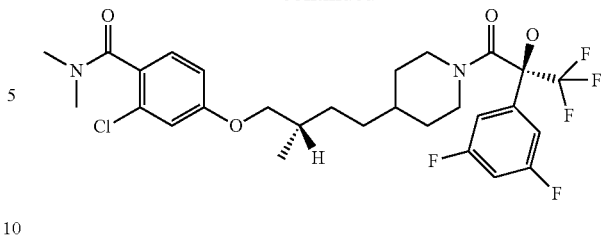
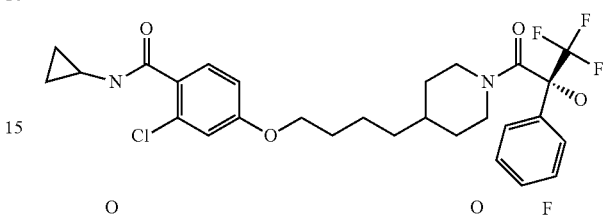
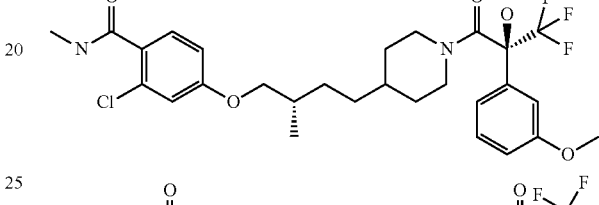
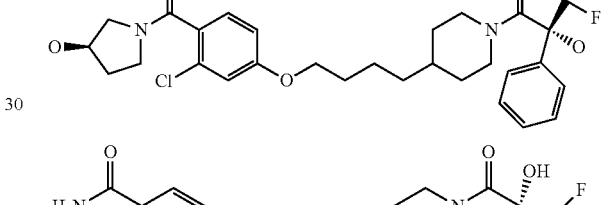
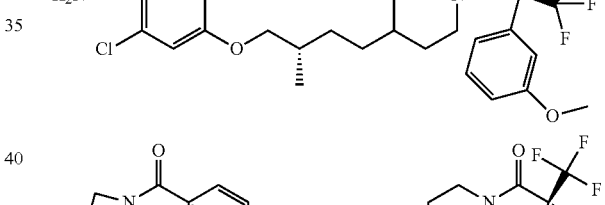
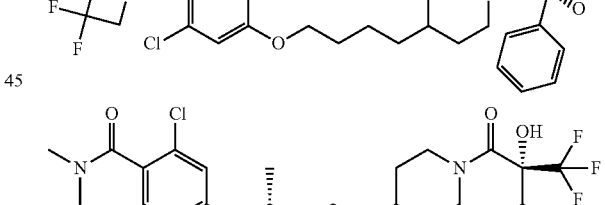
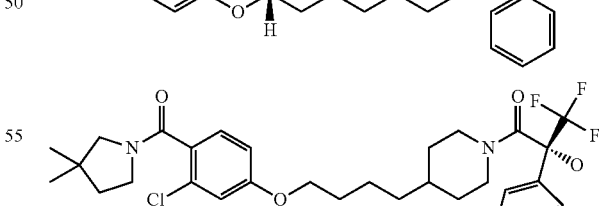
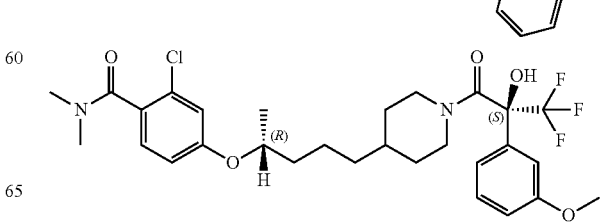

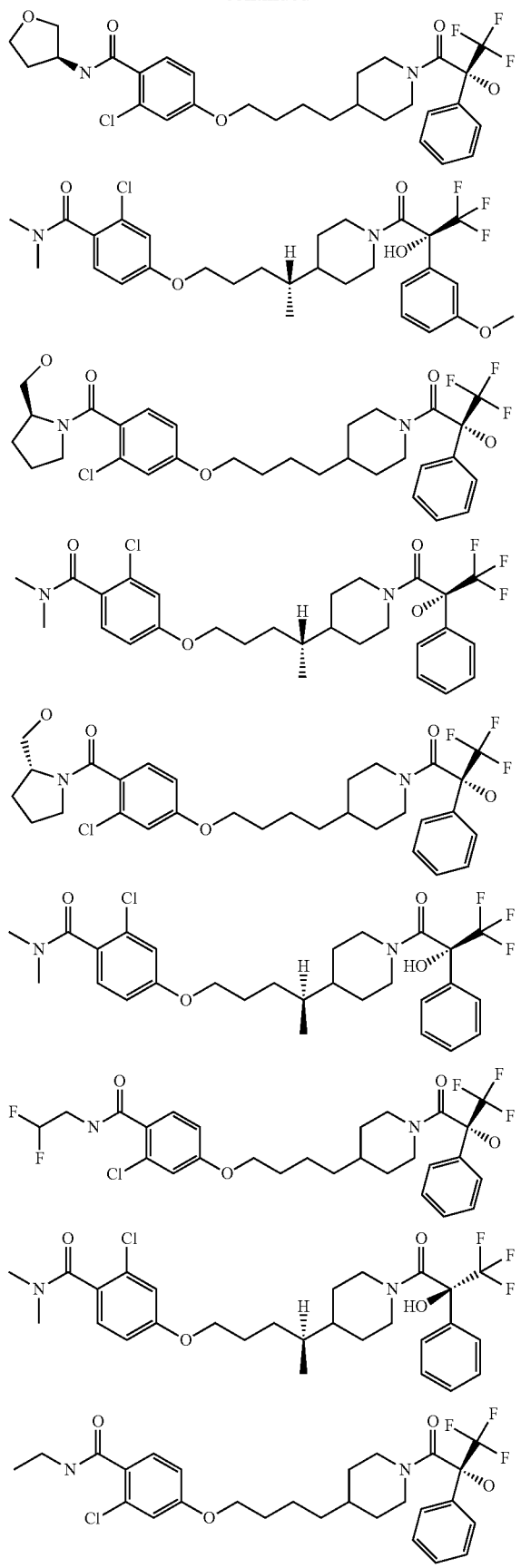
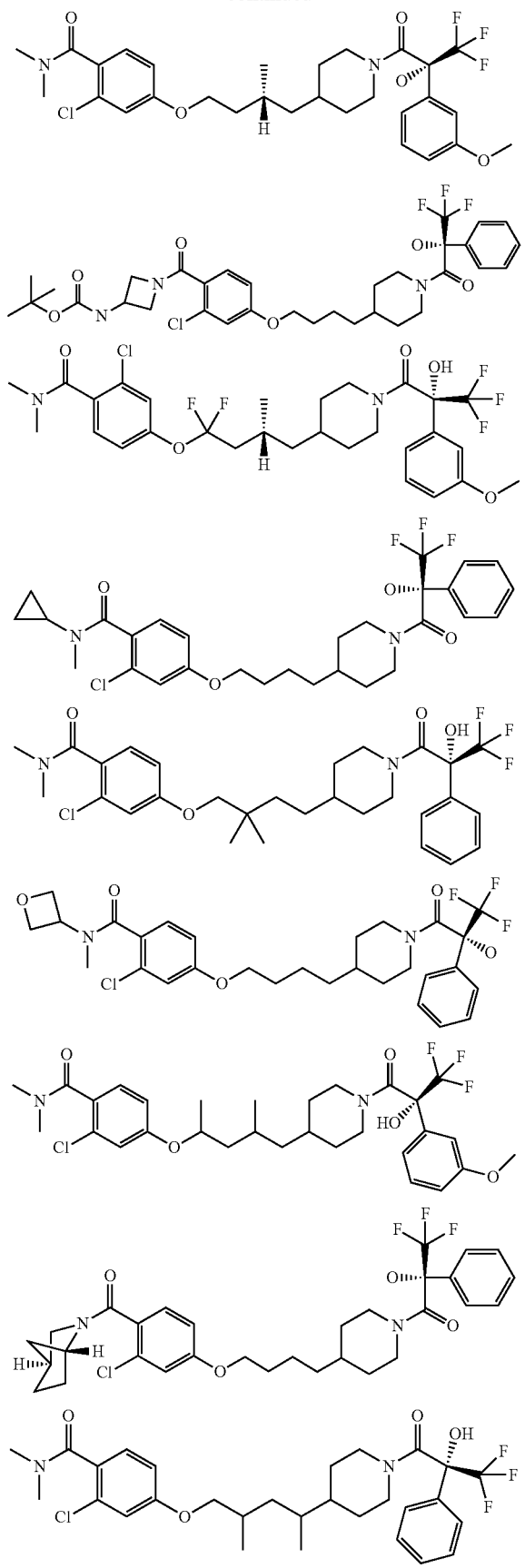

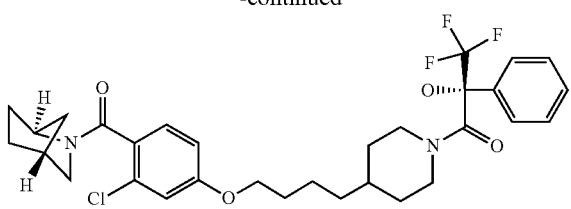
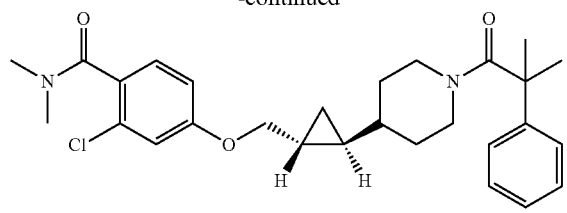
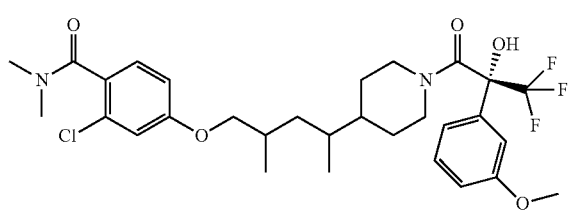
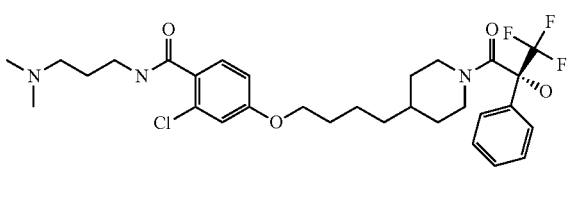
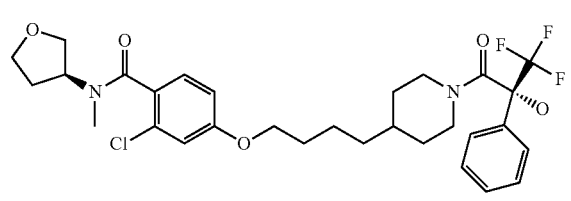
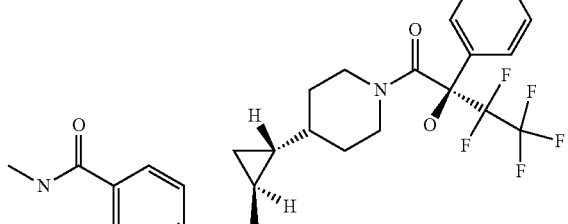
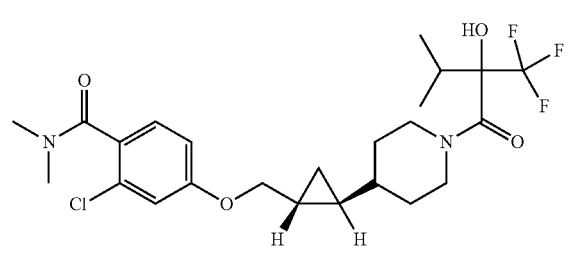
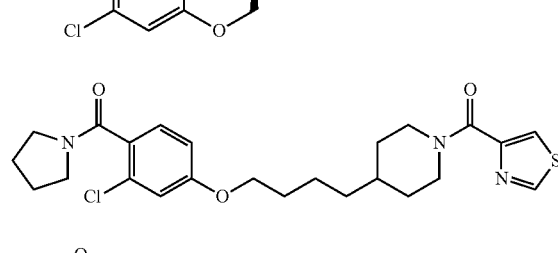
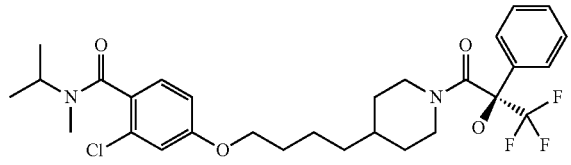
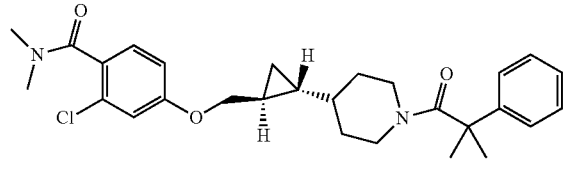
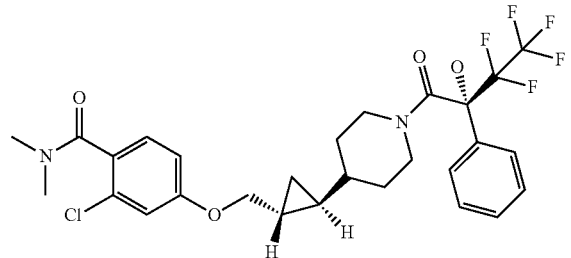
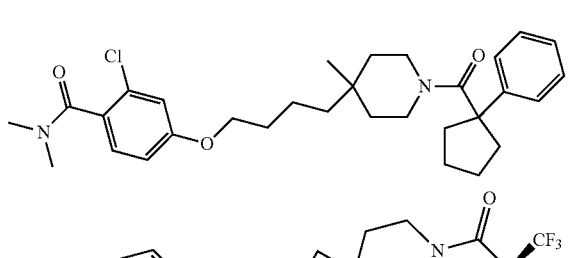
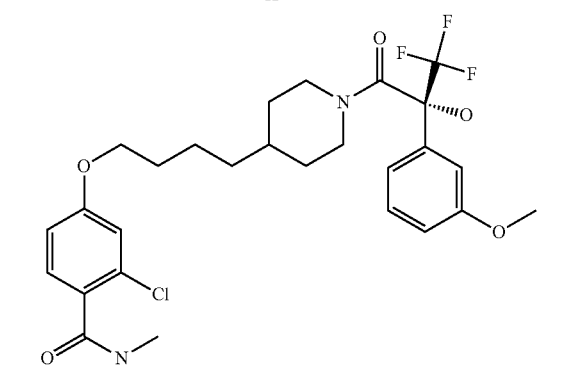
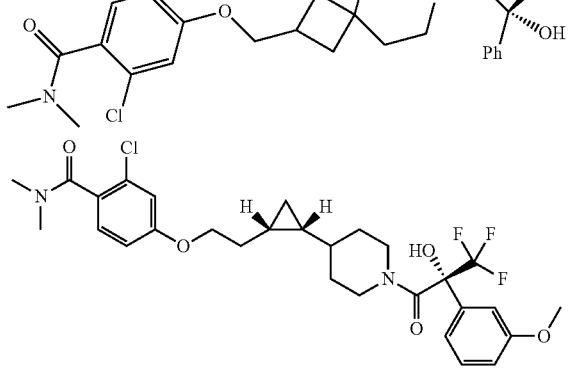

197
-continued
198
-continued
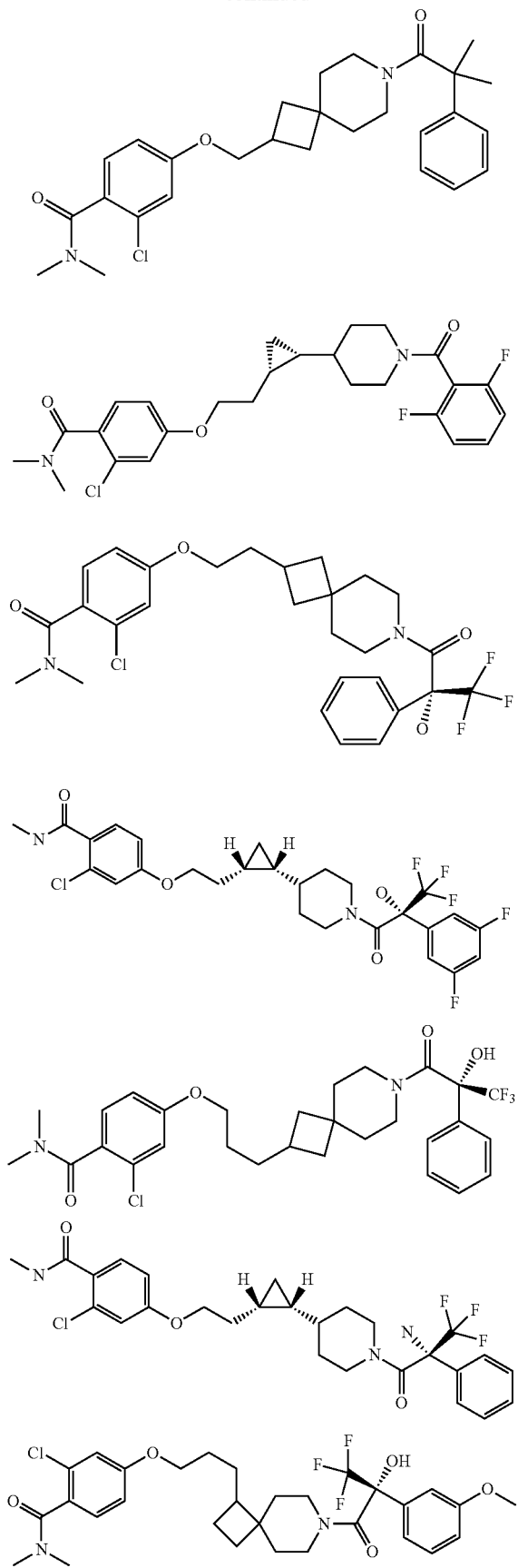
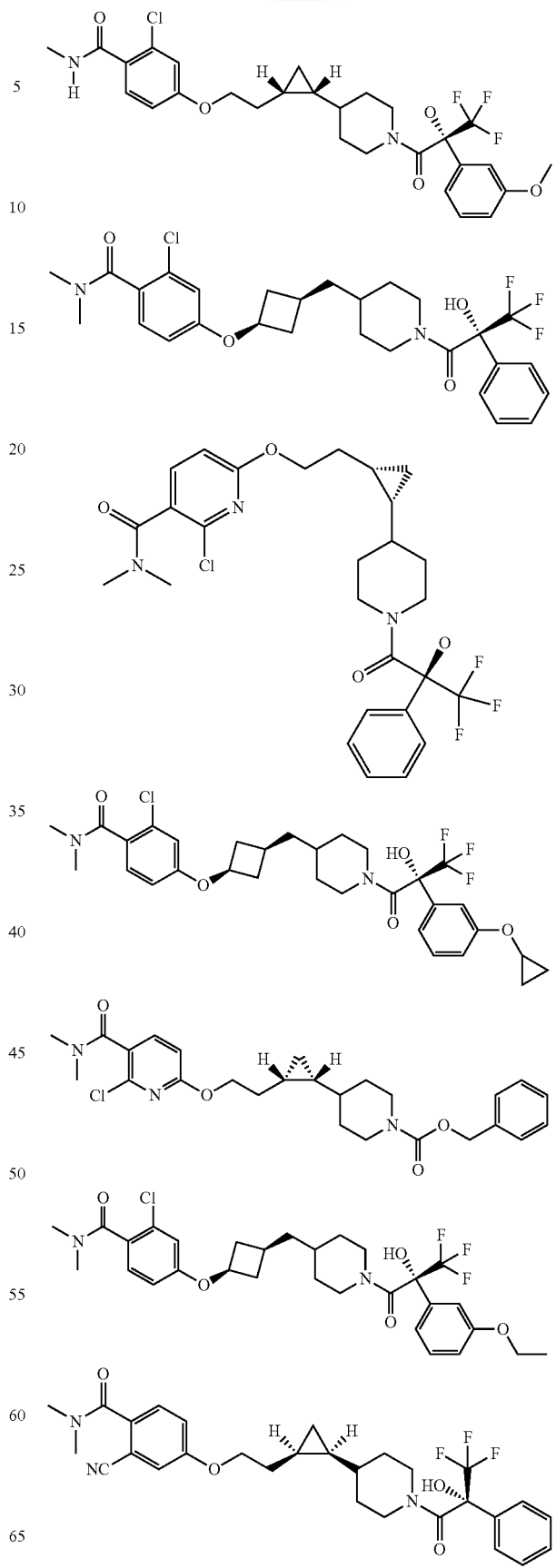

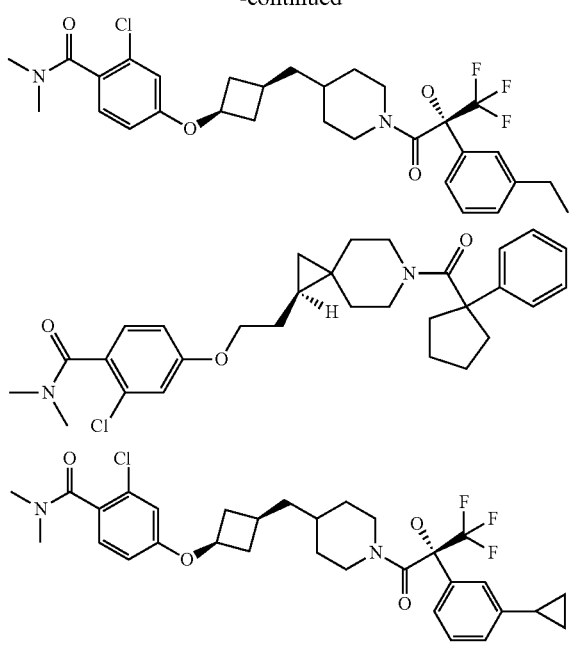
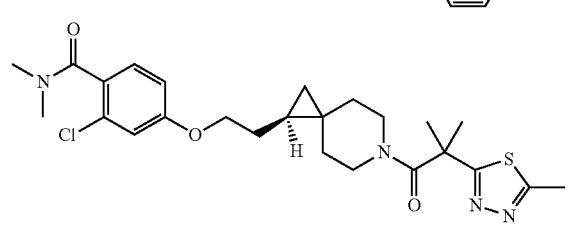
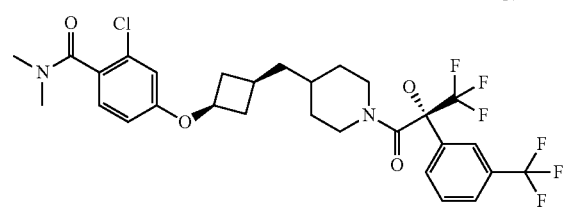
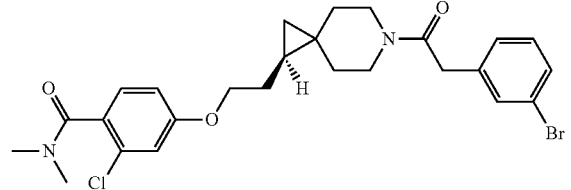
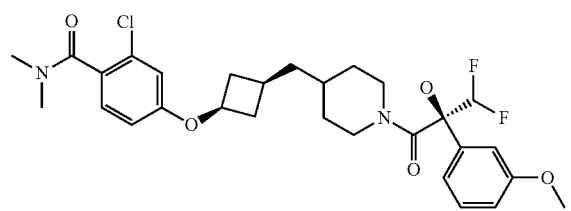
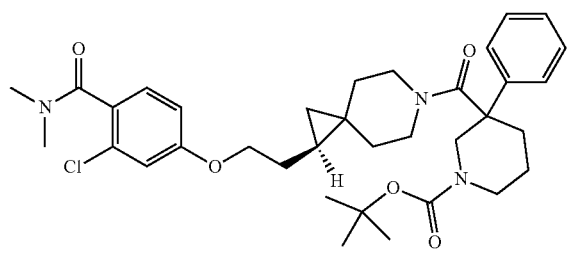
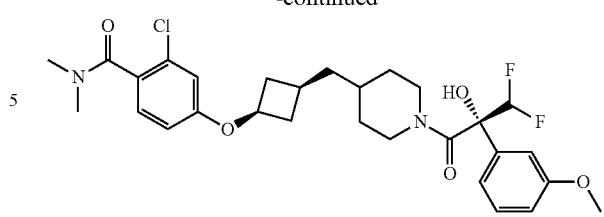
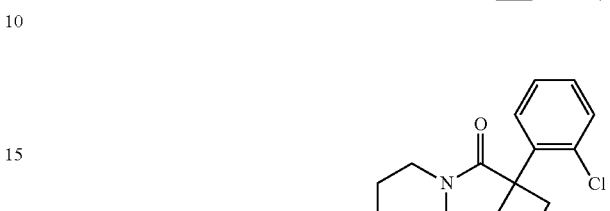
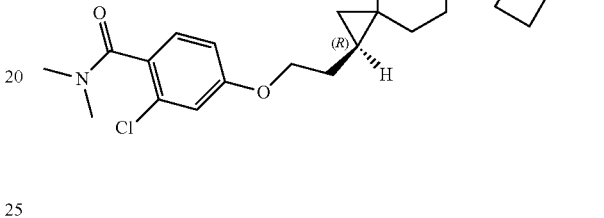
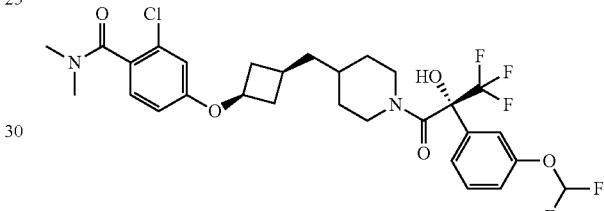
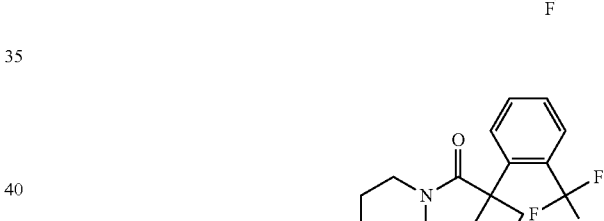
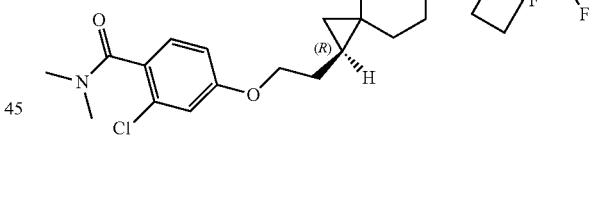
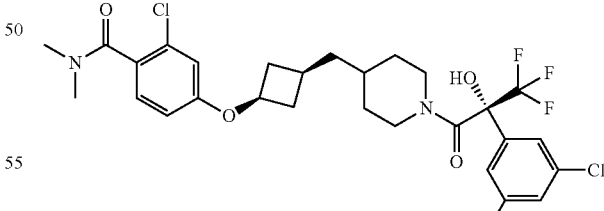
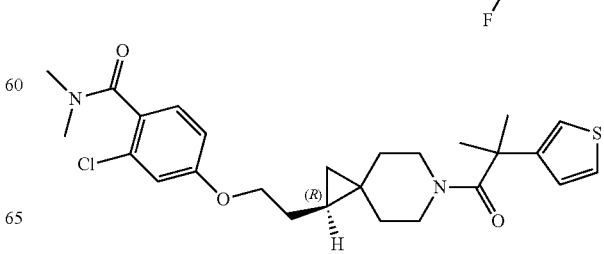

-continued

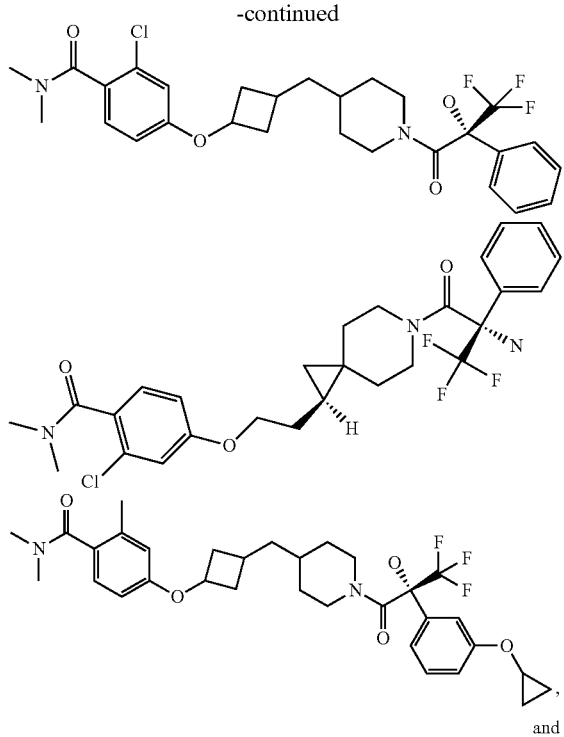
and

-continued

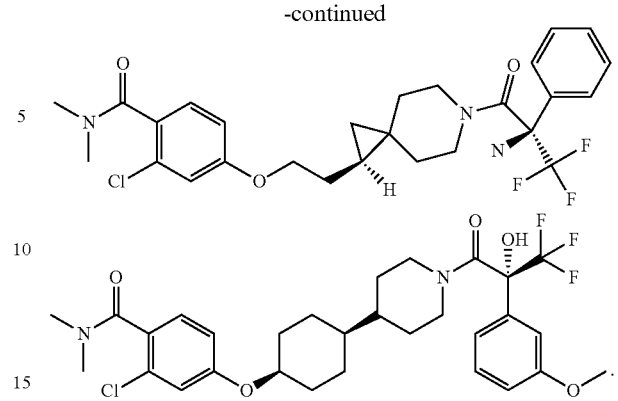

7. A pharmaceutical composition comprising a compound according to claim 1, or a pharmaceutically acceptable salt thereof, and a pharmaceutically acceptable carrier or diluent.

8. A method for the treatment of Alzheimer's Disease, Neimann-Pick disease type C1, Parkinson's Disease, amyotrophic lateral sclerosis, stroke, age-related macular degeneration, schizophrenia, depression, cardiovascular disease, obesity, or diabetes, said method comprising administering an effective amount of a compound according to claim 1 to a patient in need thereof.

* * * * *

UNITED STATES PATENT AND TRADEMARK OFFICE
CERTIFICATE OF CORRECTION

| | |
|---|---|
| PATENT NO. | : 11,655,216 B2 |
| APPLICATION NO. | : 16/341595 |
| DATED | : May 23, 2023 |
| INVENTOR(S) | : Michael T. Rudd et al. |

It is certified that error appears in the above-identified patent and that said Letters Patent is hereby corrected as shown below:

On the Title Page

At Item (71), Applicant delete:
"Merck Sharp & Dohme Corp.
Michael T. Rudd
Zhaoyang Meng
Jenny Wai
David Jonathan Bennett
Edward J. Brnardic
Nigel J. Liverton
Shawn J. Stachel
Yongxin Han
Paul Tempest
Jiuxiang Zhu
Xuewang Xu
Bin Zhu"

Insert:
--Merck Sharp & Dohme LLC--

Signed and Sealed this
Nineteenth Day of March, 2024

Katherine Kelly Vidal
*Director of the United States Patent and Trademark Office*